US012258634B2

(12) United States Patent
Lo et al.

(10) Patent No.: US 12,258,634 B2
(45) Date of Patent: *Mar. 25, 2025

(54) FRAGMENTATION FOR MEASURING METHYLATION AND DISEASE

(71) Applicant: Centre for Novostics, New Territories (HK)

(72) Inventors: Yuk-Ming Dennis Lo, Hong Kong (CN); Rossa Wai Kwun Chiu, Hong Kong (CN); Kwan Chee Chan, Hong Kong (CN); Peiyong Jiang, Hong Kong (CN); Qing Zhou, Hong Kong (CN); Guannan Kang, Hong Kong (CN); Rong Qiao, Hong Kong (CN); Lu Ji, Hong Kong (CN)

(73) Assignee: Centre for Novostics, New Territories (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/117,992

(22) Filed: Mar. 6, 2023

(65) Prior Publication Data

US 2023/0374601 A1 Nov. 23, 2023

Related U.S. Application Data

(63) Continuation of application No. 18/106,793, filed on Feb. 7, 2023.

(60) Provisional application No. 63/400,244, filed on Aug. 23, 2022, provisional application No. 63/328,710, filed on Apr. 7, 2022, provisional application No. 63/307,622, filed on Feb. 7, 2022.

(51) Int. Cl.
*C12Q 1/6886* (2018.01)
*C12Q 1/6806* (2018.01)
*C12Q 1/6851* (2018.01)
*G16B 20/00* (2019.01)
*G16B 20/30* (2019.01)
*G16B 30/10* (2019.01)
*G16B 40/00* (2019.01)
*G16B 40/20* (2019.01)
*G16B 50/00* (2019.01)

(52) U.S. Cl.
CPC ......... *C12Q 1/6886* (2013.01); *C12Q 1/6851* (2013.01); *G16B 20/00* (2019.02); *G16B 20/30* (2019.02); *G16B 30/10* (2019.02); *G16B 40/00* (2019.02); *G16B 40/20* (2019.02); *G16B 50/00* (2019.02); *C12Q 1/6806* (2013.01); *C12Q 2600/154* (2013.01)

(58) Field of Classification Search
CPC ......... G16B 20/30; G16B 40/00; G16B 20/20
See application file for complete search history.

(56) References Cited

U.S. PATENT DOCUMENTS

| | | |
|---|---|---|
| 2014/0080715 A1 | 3/2014 | Lo et al. |
| 2018/0237863 A1 | 8/2018 | Namsaraev et al. |
| 2020/0005899 A1 | 1/2020 | Nicula et al. |
| 2020/0199656 A1 | 6/2020 | Lo et al. |
| 2021/0189494 A1 | 6/2021 | Lo et al. |
| 2021/0238668 A1 | 8/2021 | Lo et al. |
| 2021/0254142 A1 | 8/2021 | Lo et al. |
| 2022/0010353 A1 | 1/2022 | Lo et al. |
| 2022/0396838 A1 | 12/2022 | Lo et al. |

FOREIGN PATENT DOCUMENTS

| | | |
|---|---|---|
| CN | 112735531 A | 4/2021 |
| WO | 2018027176 A1 | 2/2018 |
| WO | 2021032060 A1 | 2/2021 |

OTHER PUBLICATIONS

Cervena et al., Diagnostic and prognostic impact of cell-free DNA in human cancers: Systemic Review, 2019, Mutation Research-Reviews in Mutation Research, 781, p. 100-129 (Year: 2019).*
Ehrlich, DNA hypomethylation in cancer cells, 2009, Epigenomics, 1(2), p. 239-259 (Year: 2009).*
Song et al., Limitations and opportunities of technologies for the analysis of cell-free DNA in cancer diagnostics, Jan. 2022 (online); 6(3), p. 232-245 (Year: 2022).*
Genome Research, CSH Press, vol. 31, No. 11, Nov. 2021, 1 page.
U.S. Appl. No. 17/993,845, Molecular Analyses Using Long Cell-Free Dna Molecules for Disease Classification filed Nov. 23, 2022.
An et al., DNA Methylation Analysis Explores the Molecular Basis of Plasma Cell-Free DNA Fragmentation, Nature Communications, vol. 14, Article No. 287, Jan. 18, 2023, pp. 1-12.
Brukner et al., Sequence-Dependent Bending Propensity of DNA as Revealed by DNase I: Parameters for Trinucleotides, The European Molecular Biology Organization Journal, vol. 14, No. 8, Apr. 18, 1995, pp. 1812-1818.
Han et al., Nuclease Deficiencies Alter Plasma Cell-Free DNA Methylation Profiles, Genome Research, vol. 31, No. 11, Sep. 1, 2021, pp. 2008-2021.

(Continued)

*Primary Examiner* — Kaitlyn L Minchella
(74) *Attorney, Agent, or Firm* — Kilpatrick Townsend & Stockton LLP

(57) ABSTRACT

Fragmentation of cell-free DNA molecules is measured and used for various purposes, including determining methylation, e.g., at a particular site of a DNA molecule, at a particular genomic site in a reference genome for a biological sample (e.g., plasma, serum, urine, saliva) of cell-free DNA of a subject, or for a particular region in the reference genome for the biological sample (also just referred to as a sample). Various types of fragmentation measurements can be used, e.g., end motifs and cleavage profiles. Another purpose is determining a fractional concentration of DNA of a particular tissue type (e.g., clinically-relevant DNA). Another purpose is determining a pathology of a subject using a biological sample including cell-free DNA. The cell-free DNA can be of the subject or of a pathogen (e.g., a virus) in the subject's sample. Sites/regions that are hypermethylated, hypomethylated, 5hmC-enriched, and 5hmC-depleted for a particular tissue type can be used.

26 Claims, 128 Drawing Sheets

Specification includes a Sequence Listing.

(56) References Cited

OTHER PUBLICATIONS

Kim et al., Determination of Fetal DNA Fraction from the Plasma of Pregnant Women Using Sequence Read Counts, Prenatal Diagnosis, vol. 35, No. 8, Aug. 3, 2015, pp. 810-815.
Lazarovici et al., Probing DNA Shape and Methylation State on a Genomic Scale with DNase I, Proceedings of the National Academy of Sciences of the United States of America, vol. 110, No. 16, Apr. 16, 2013, pp. 6376-6381.
Lazarovici et al., Supporting Information: Probing DNA Shape and Methylation State on a Genomic Scale with DNase I, Proceedings of the National Academy of Sciences of the United States of America, vol. 110, No. 16, Apr. 16, 2013, pp. 1-12.
Liu et al., Abstract 5689: Identify Tissue-of-Origin in Cancer cfDNA by Whole Genome Sequencing, Cancer Research, vol. 77, Suppl. 13, Jul. 1, 2017, 1 page.
Liu , At the dawn: Cell-Free DNA Fragmentomics and Gene Regulation, British Journal of Cancer, vol. 126, No. 3, Feb. 2022, pp. 379-390.
International Search Report and Written Opinion of the International Searching Authority mailed May 10, 2023 in International Patent Application No. PCT/CN2023/074730. 7 pages.
U.S. Appl. No. 18/106,793, Non-Final Office Action mailed on Nov. 13, 2023, 23 pages.
Brunner et al., Distinct DNA Methylation Patterns Characterize Differentiated Human Embryonic Stem Cells and Developing Human Fetal Liver, Genome Research, vol. 19, No. 6, Jun. 2009, pp. 1044-1056.
Mair et al., Cell-free DNA Technologies for the Analysis of Brain Cancer, British Journal of Cancer, vol. 126, Nov. 22, 2021, pp. 371-378.
Peng et al., Identifying the Tissues-of-Origin of Circulating Cell-Free DNAs is a Promising Way in Noninvasive Diagnostics, Briefings in Bioinformatics, vol. 22, No. 3, May 2021, pp. 1-20.
Valencia et al., Analytical Performance Assessment of Two Clinical Exome Pipelines: The CCHMC Experience, Journal of Molecular Diagnostics, vol. 16, No. 6, Nov. 2014, p. 702.
Zheng et al., Prediction of Genome-wide DNA Methylation in Repetitive Elements, Nucleic Acids Research, vol. 45, No. 15, Jul. 7, 2017, pp. 8697-8711.
Final Office Action mailed Feb. 22, 2024 in U.S. Appl. No. 18/106,793, filed Feb. 7, 2020. 21 pages.
Galardi, Francesca et al.; "Cell-Free DNA-Methylation-Based Methods and Applications in Oncology"; Biomolecules; 2020; vol. 10, No. 12; 1677; pp. 1-23.
Non-Final Office Action mailed Mar. 21, 2024 in U.S. Appl. No. 18/118,024, filed Mar. 6, 2023. 47 pages.
Non-Final Office Action mailed Oct. 9, 2024 in U.S. Appl. No. 18/106,793, filed Feb. 7, 2020. 22 pages.
Final Office Action mailed Oct. 18, 2024 in U.S. Appl. No. 18/118,024, filed Mar. 6, 2023. 55 pages.
Leal, Alessandro et al.; "Tissue and Cell-Free DNA-Based Epigenomic Approaches for Cancer Detection"; Clinical Chemistry; 2020; vol. 66, No. 1; pp. 105-116.
Office Action dated Dec. 2, 2024 in MX Patent Application No. MX/a/2024/009647, with English translation. 13 pages.
Substantive Examination Adverse Report mailed Dec. 13, 2024 in MY Patent Application PI2024004348. 4 pages.
Examination Report under Section 18(3) dated Dec. 2, 2024 in GB Patent Application No. 2411921.6. 6 pages.

* cited by examiner

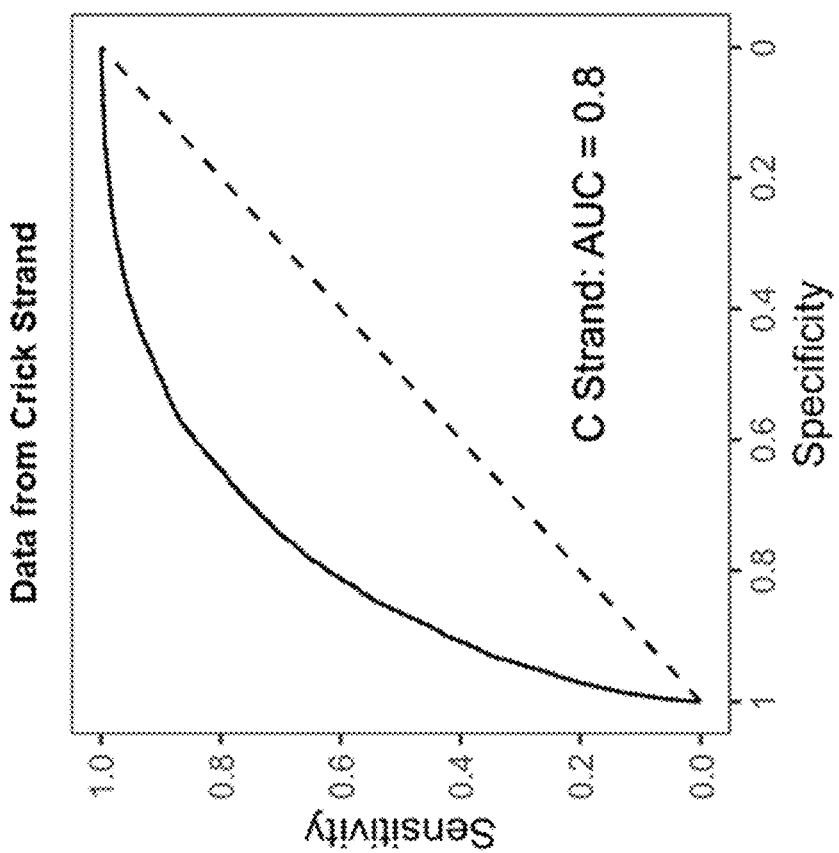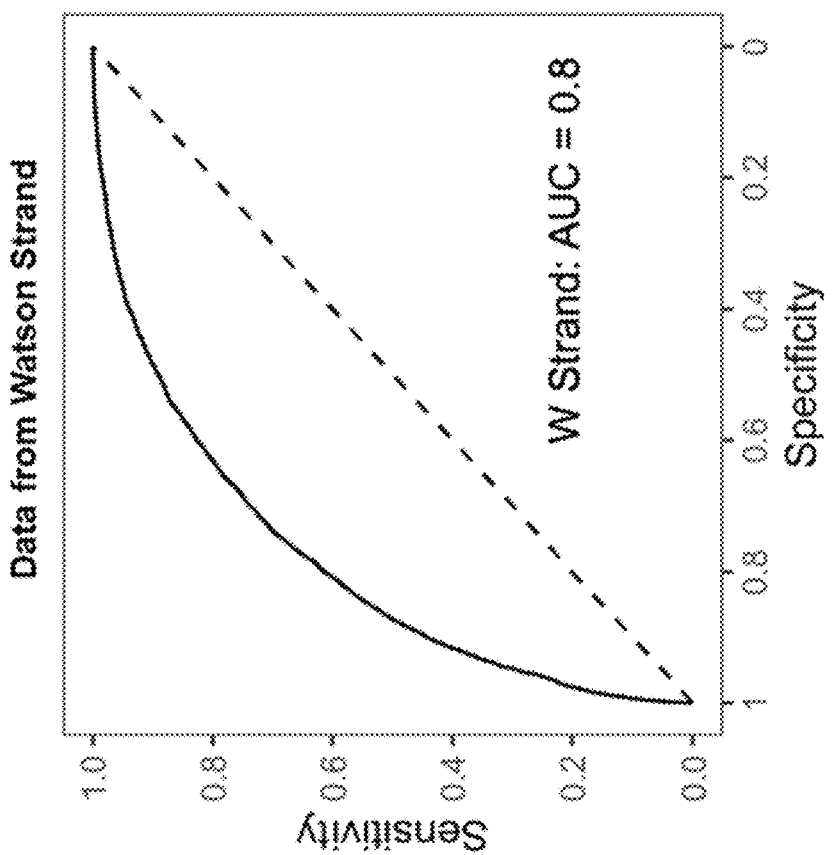
FIG. 19

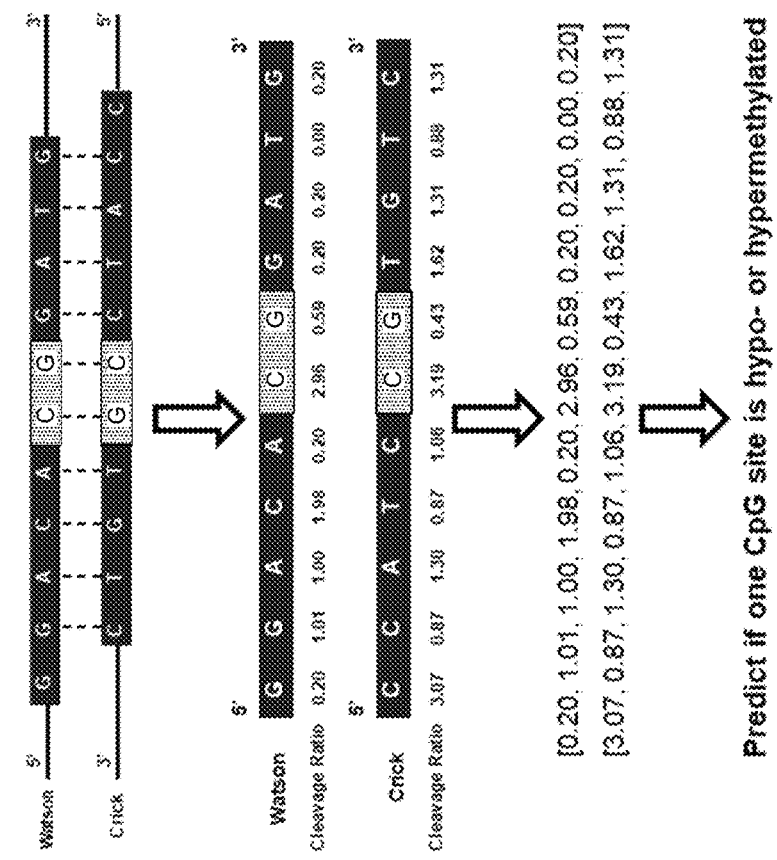
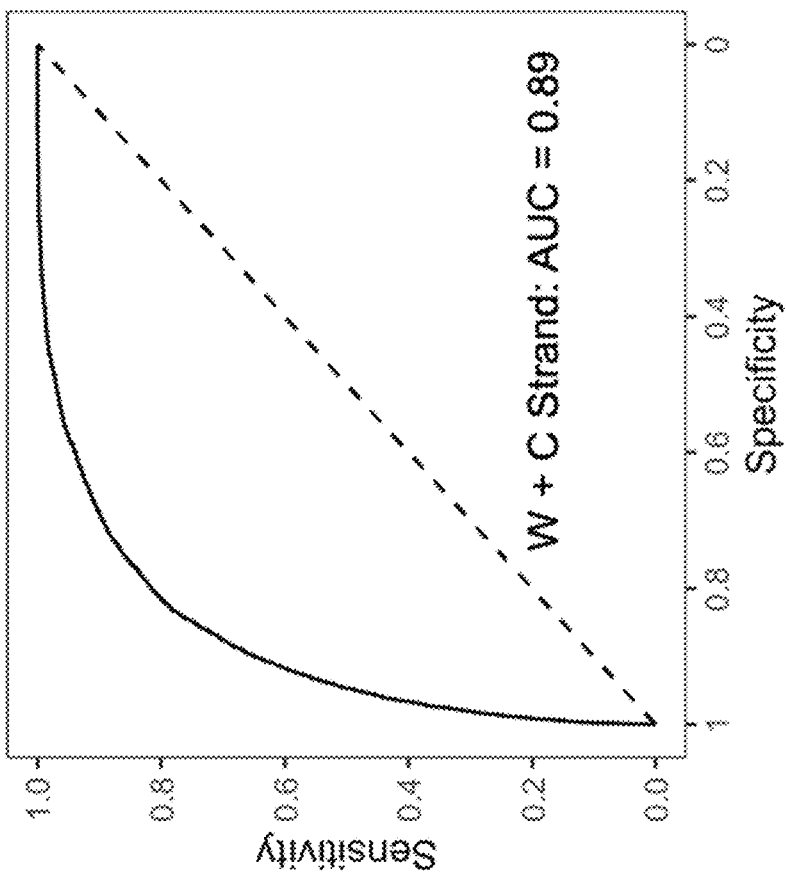
FIG. 20

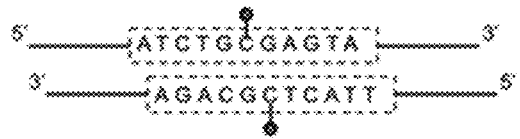
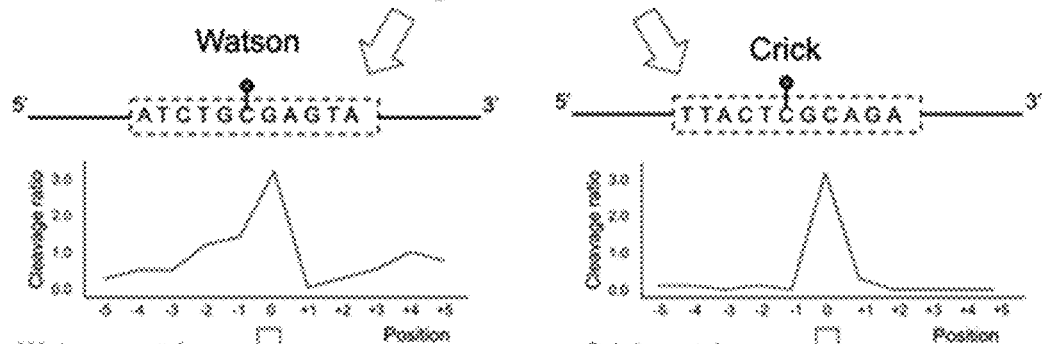
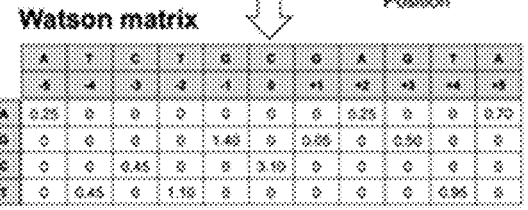
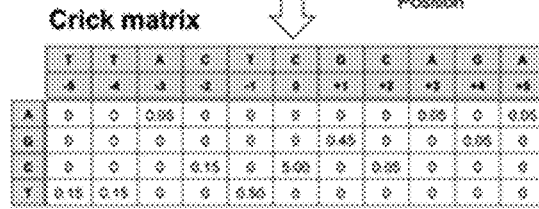
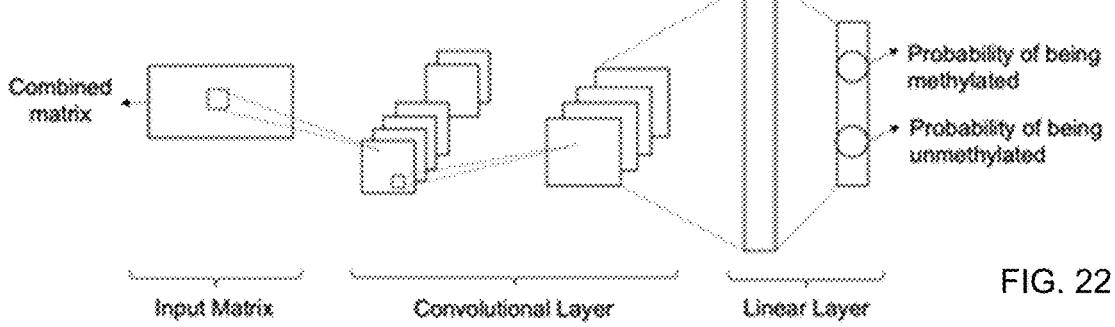
FIG. 22

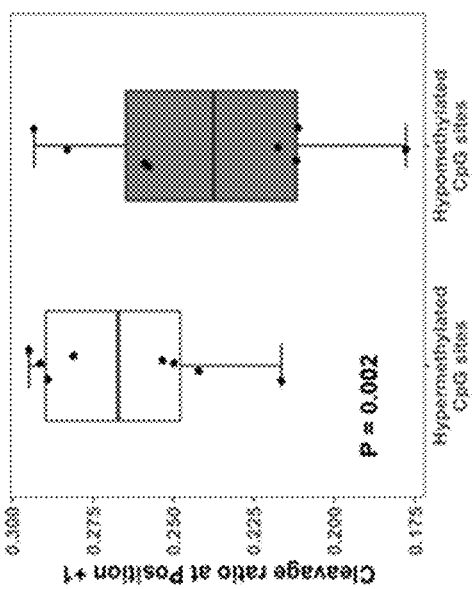
FIG. 25A  FIG. 25B  FIG. 25C
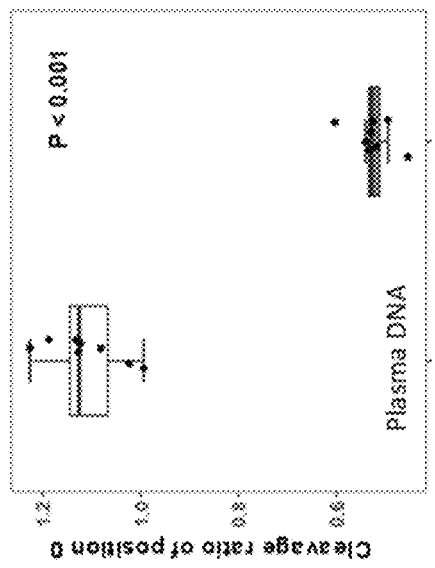
FIG. 25D  FIG. 25E  FIG. 25F
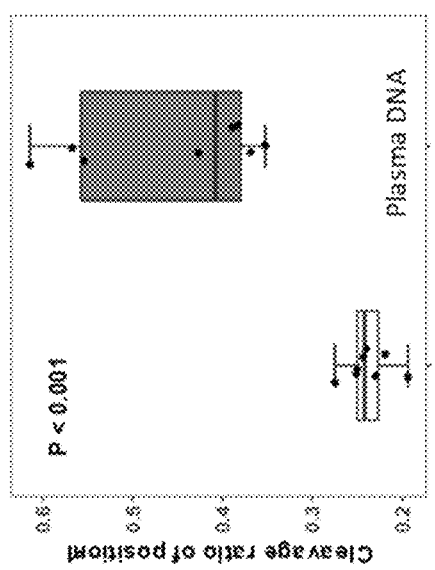
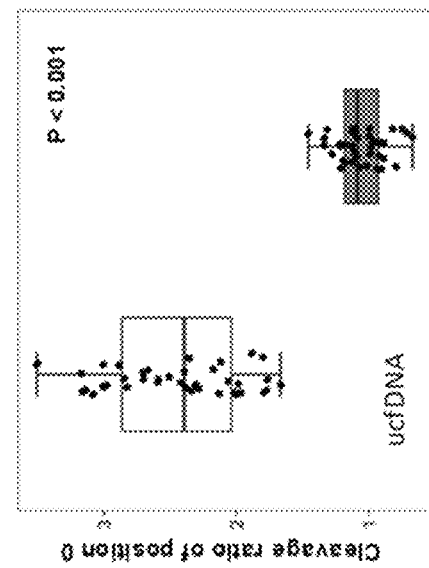
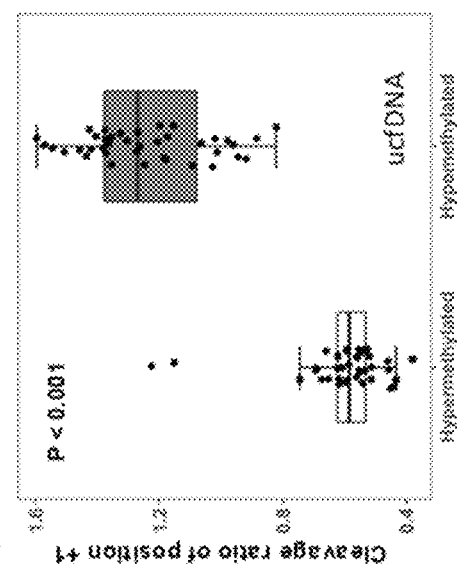
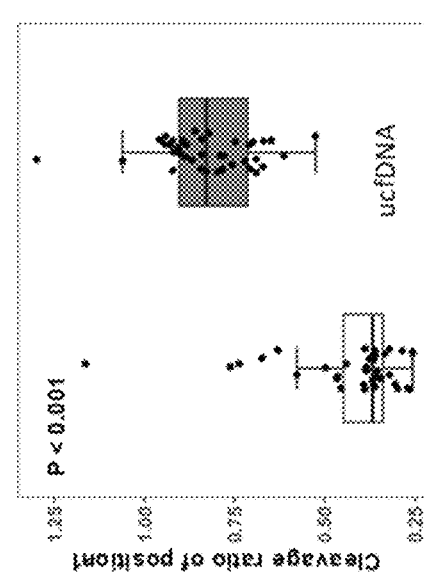

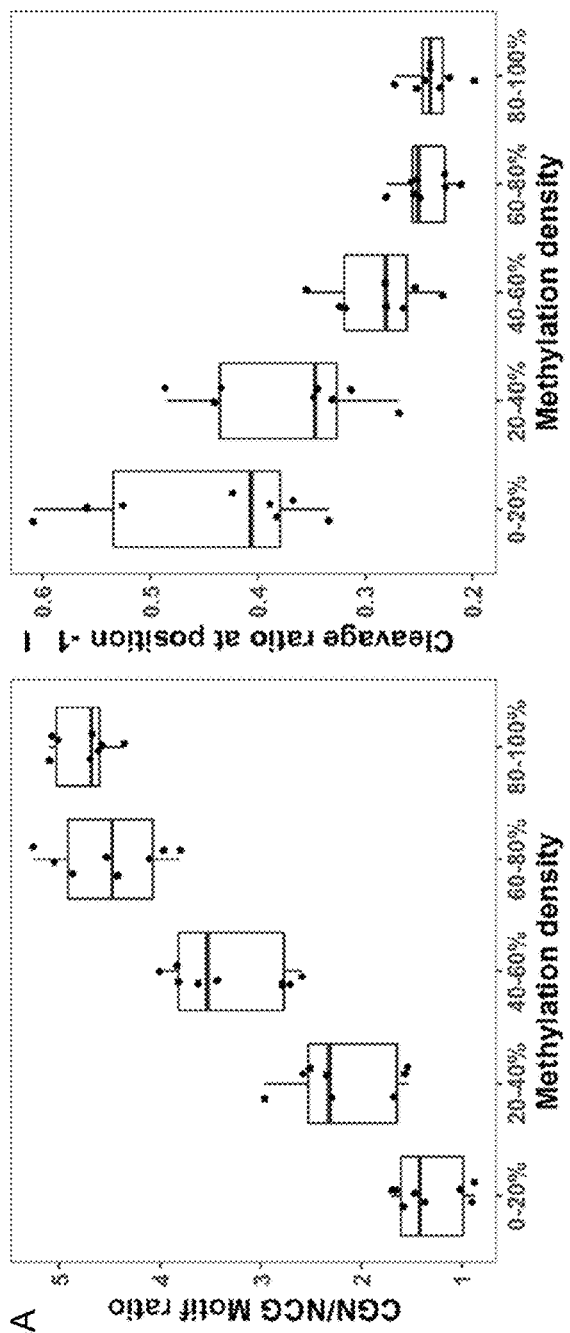
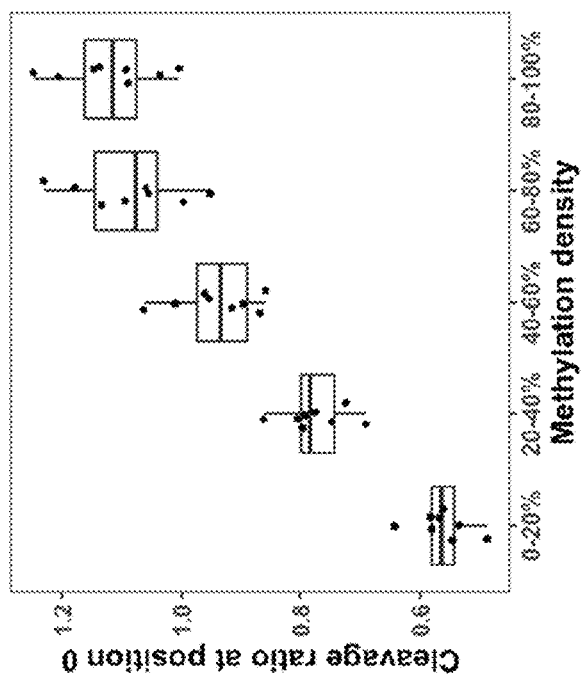
FIG. 26A
FIG. 26B
FIG. 26C

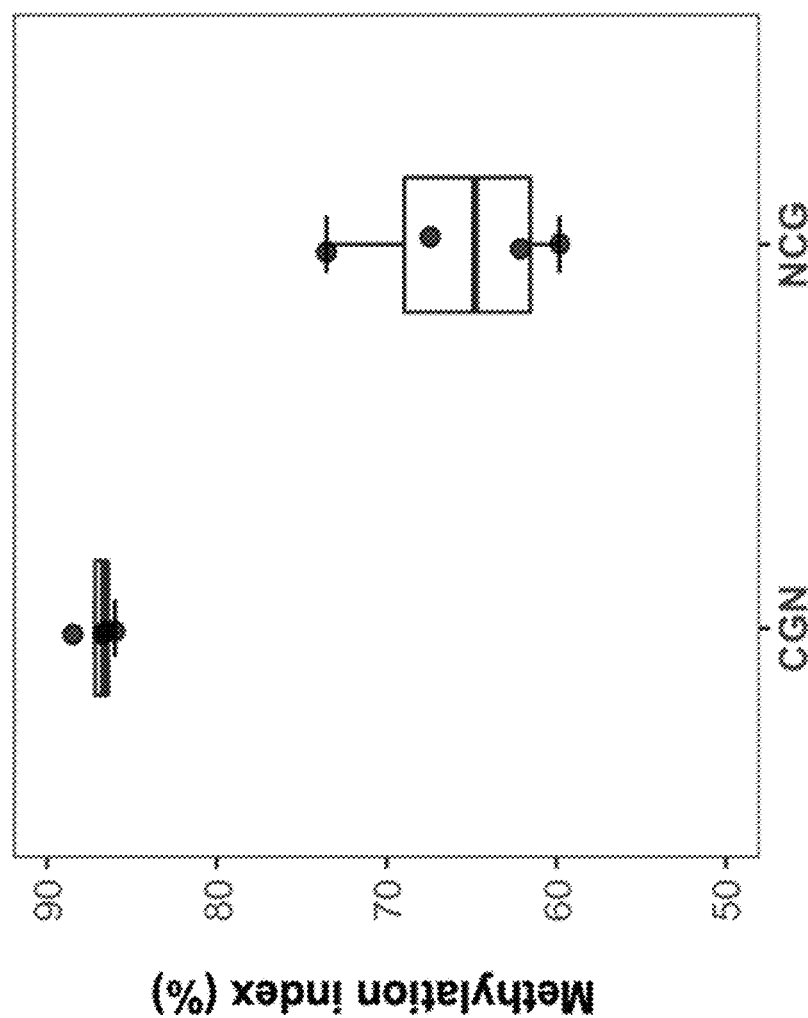
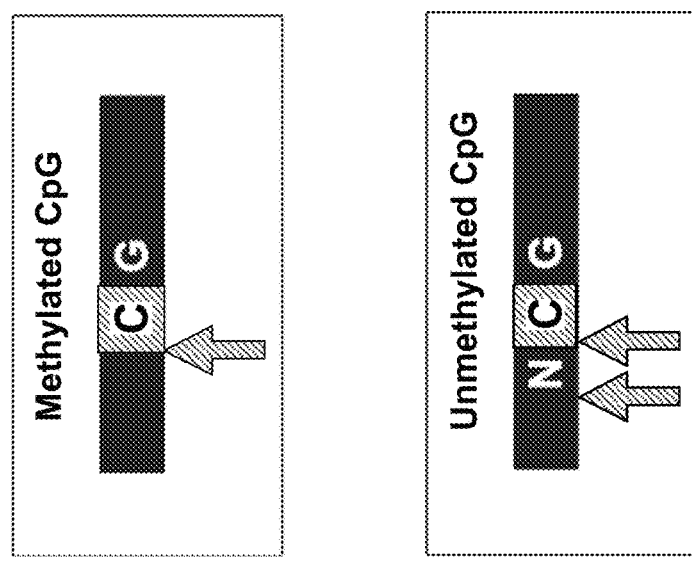
FIG. 28

FIG. 49A Placenta-specific hypermethylated CpGs
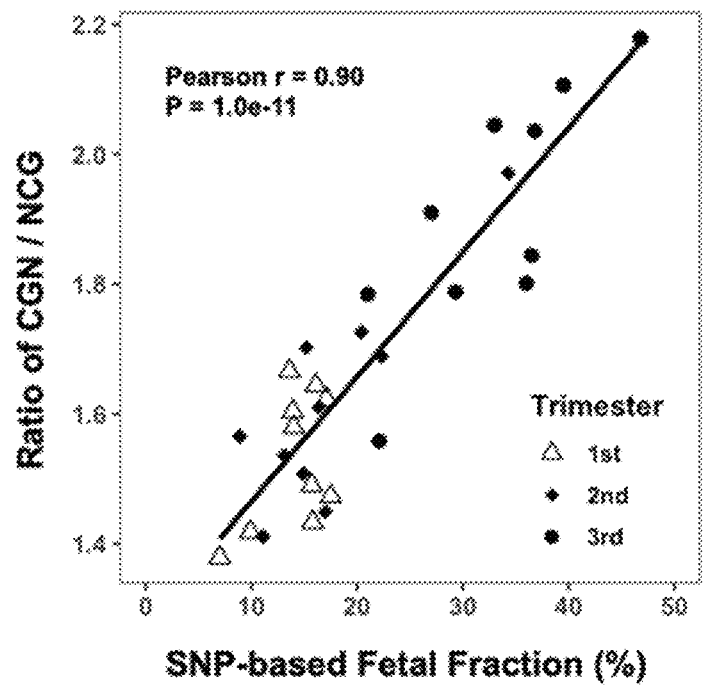
FIG. 49B Placenta-specific hypomethylated CpGs
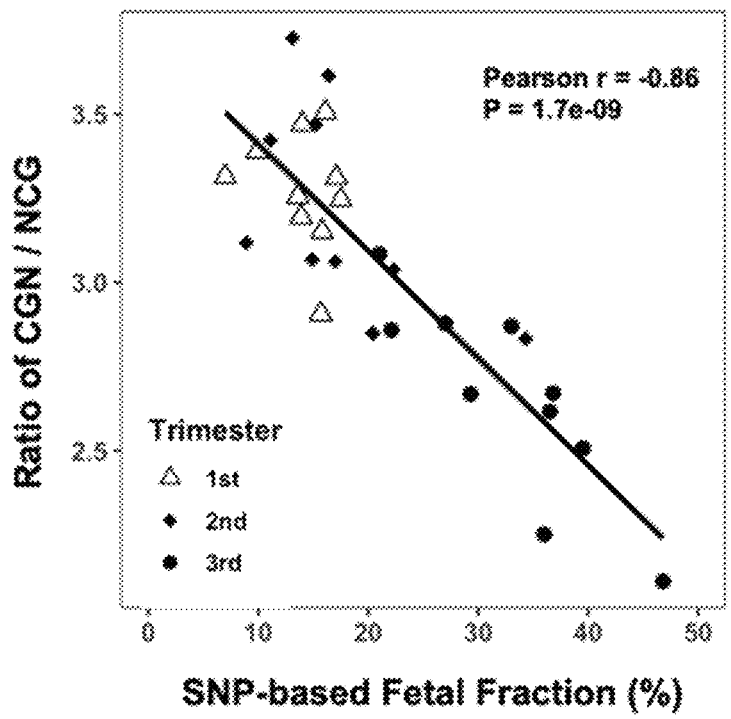

FIG. 54A Placenta Specific Hypermethylated CpG Sites
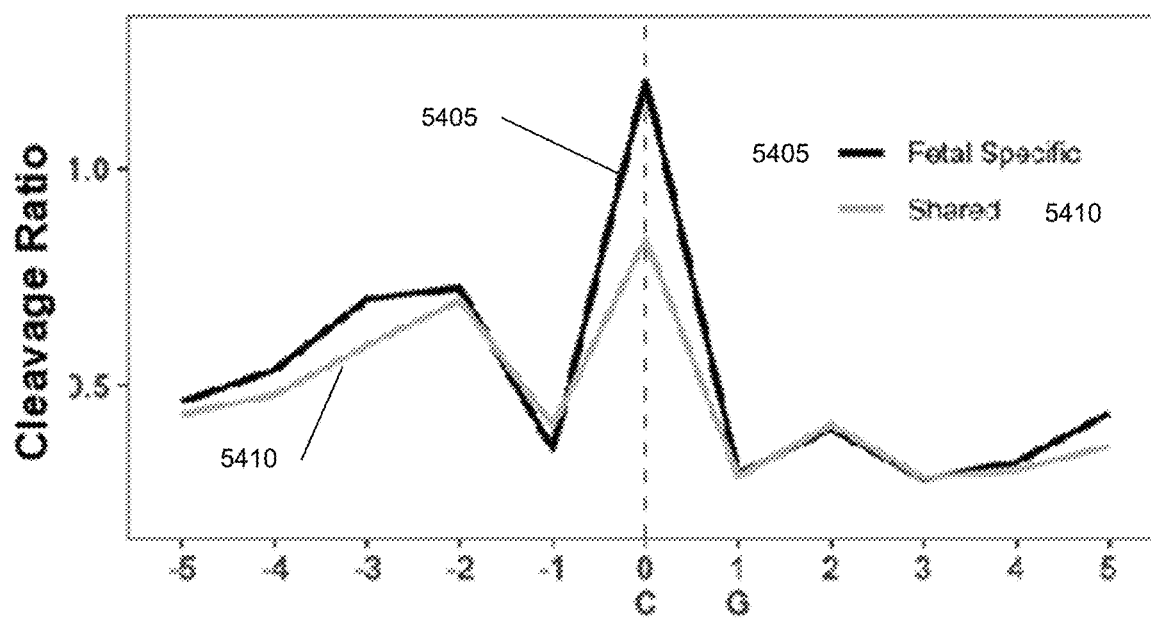
FIG. 54B Placenta Specific Hypomethylated CpG Sites
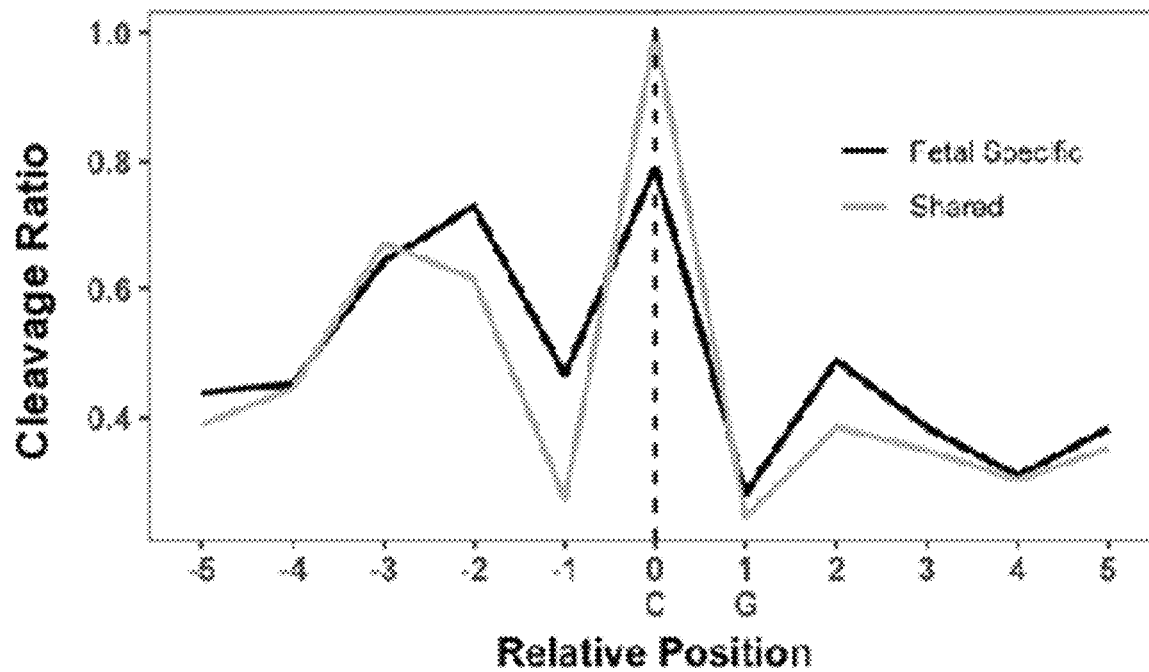

Alu region     CGNNNNN          NCGNNNN

Top 10 CG Probe

| Top 10 CG Probe | Repeat Number | Percentage (%) |
|---|---|---|
| CGCCTGT | 192262 | 2.85 |
| CGGGAGG | 183039 | 2.71 |
| CGGCCTC | 135438 | 2.00 |
| CGAGACC | 134954 | 2.00 |
| CGCCCAG | 129710 | 1.92 |
| CGTGAGC | 125941 | 1.86 |
| CGTGGTG | 125270 | 1.85 |
| CGGCTCA | 124114 | 1.84 |
| CGATCTC | 113899 | 1.69 |
| CGGTGGC | 109759 | 1.62 |

FIG. 63A

Top 10 NCG Probe

| Top 10 NCG Probe | Repeat Number | Percentage (%) |
|---|---|---|
| ACGCCTGT | 127759 | 1.89 |
| TCGGCCTC | 121832 | 1.80 |
| TCGAGACC | 120433 | 1.78 |
| GCGTGAGC | 115403 | 1.71 |
| TCGGCTCA | 110687 | 1.64 |
| GCGTGGTG | 108286 | 1.60 |
| CCGTCTCT | 97133 | 1.44 |
| TCGGGAGG | 95934 | 1.42 |
| TCGCTTGA | 93254 | 1.38 |
| CCGCCTCC | 92330 | 1.37 |

FIG. 63B

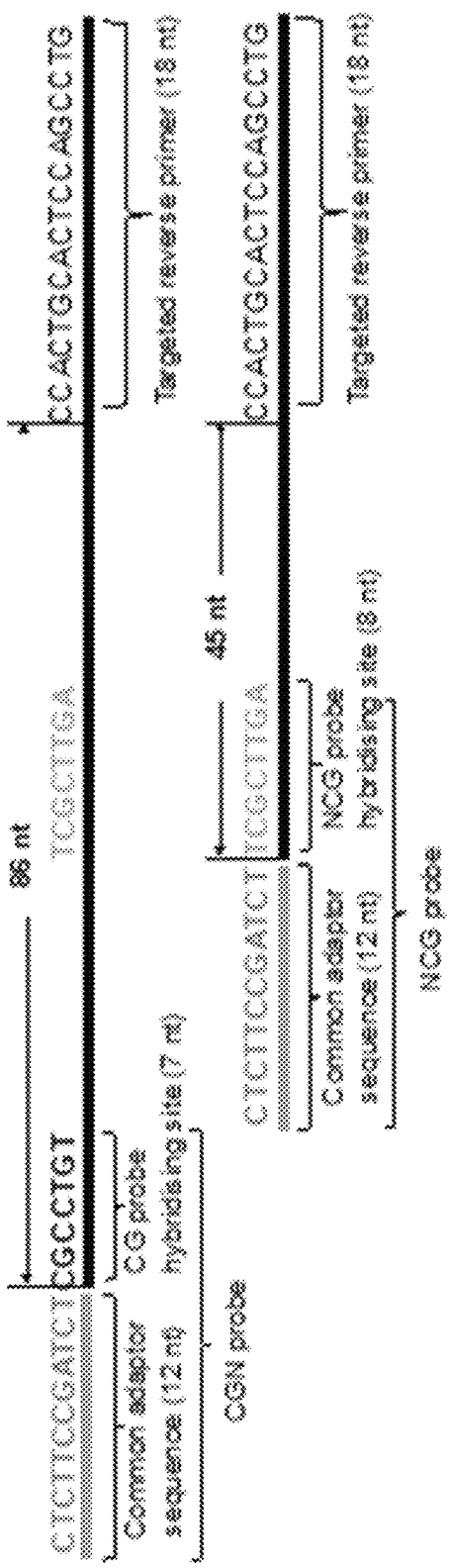

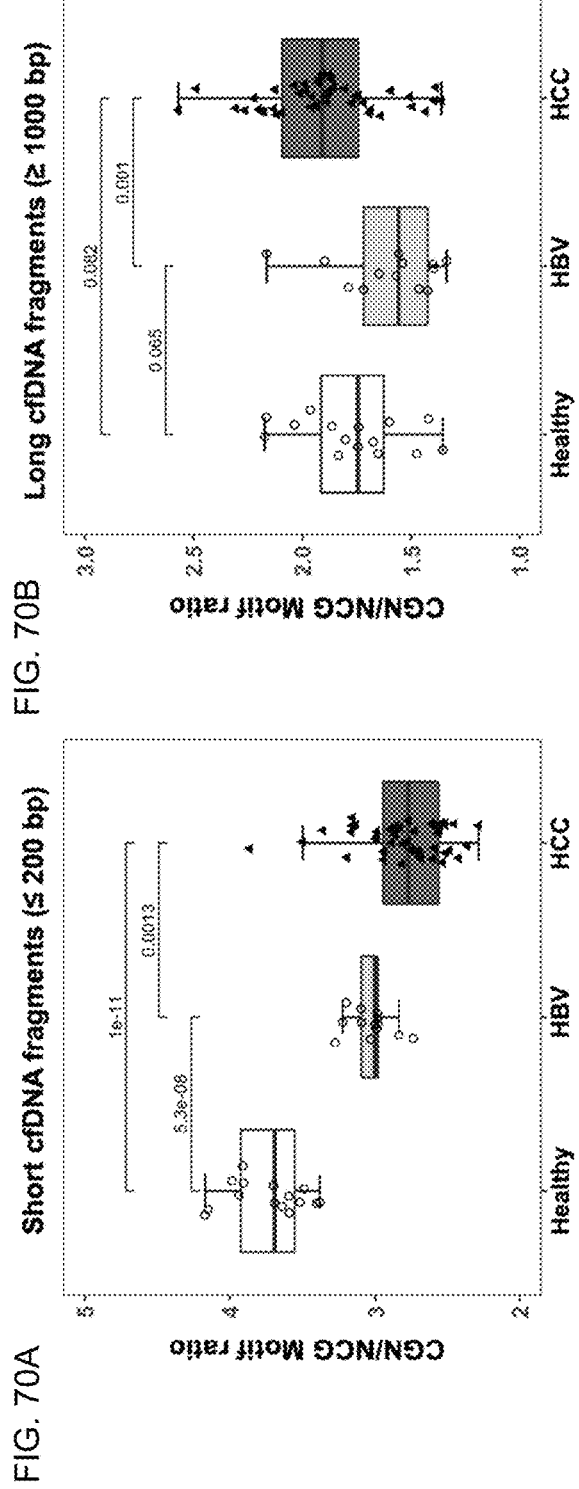
FIG. 70A
FIG. 70B
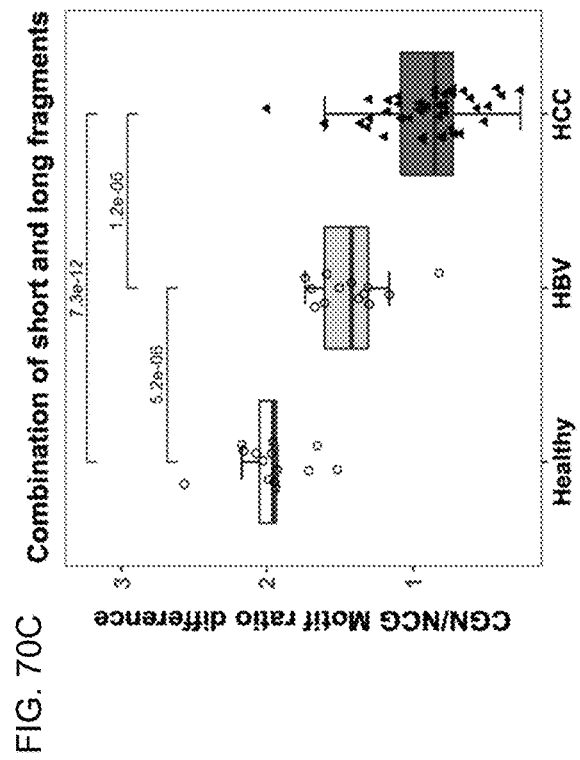
FIG. 70C

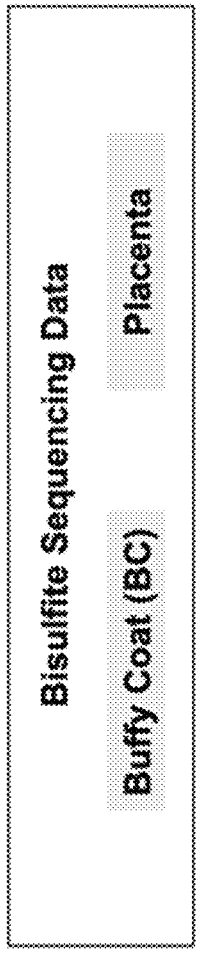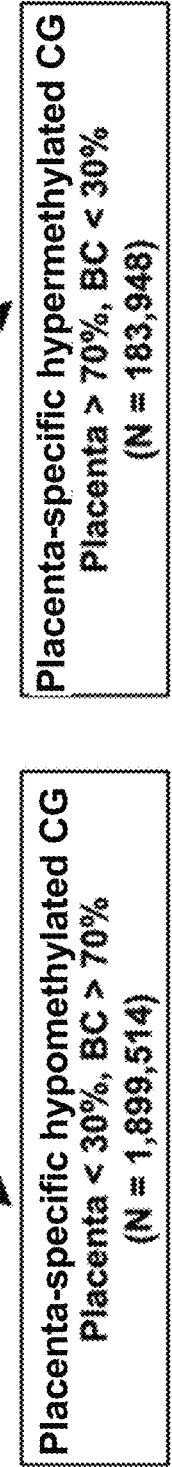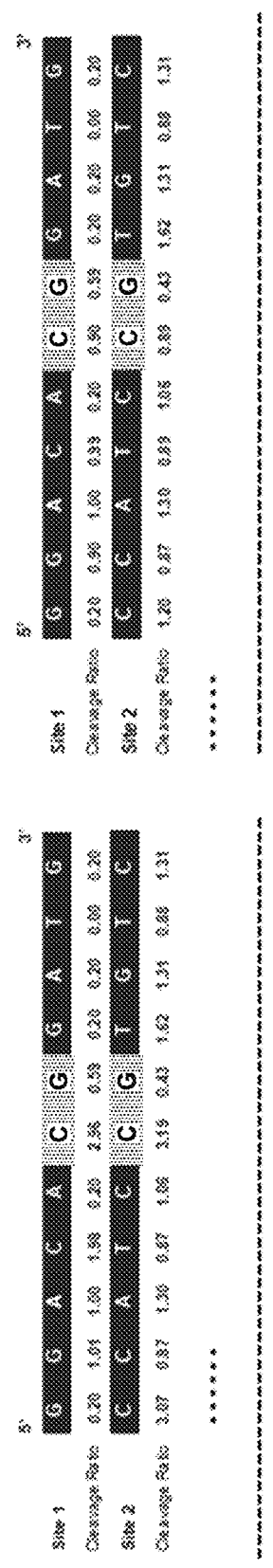
FIG. 77

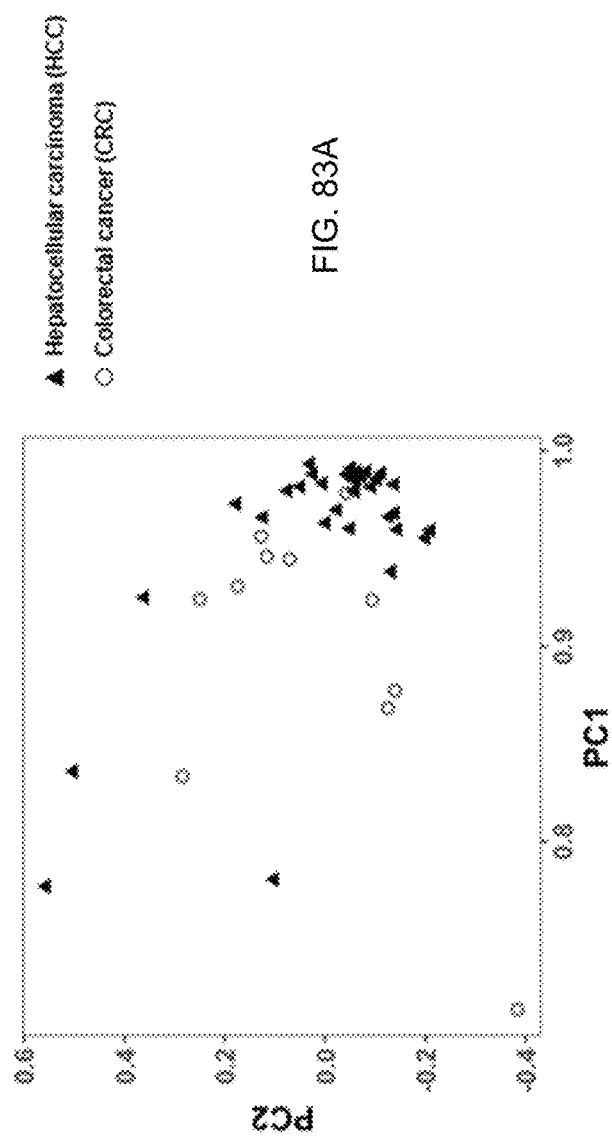
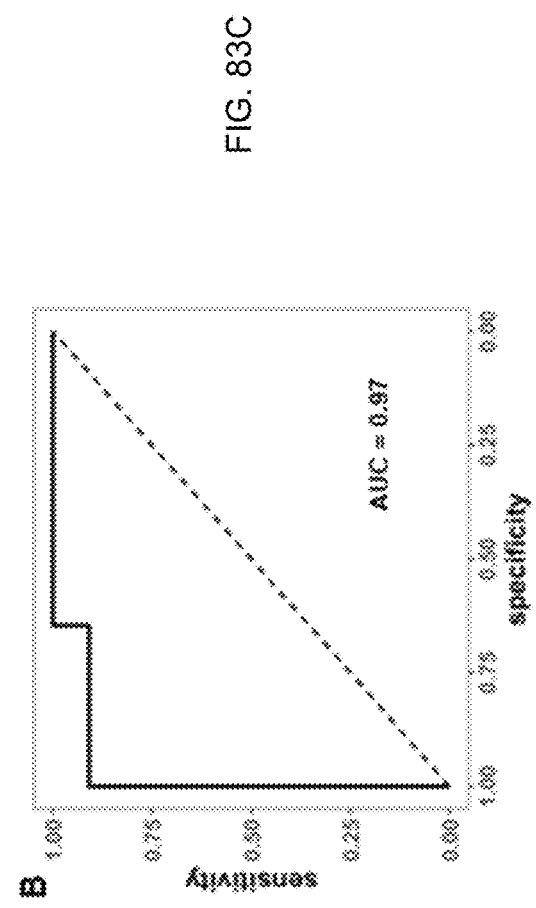
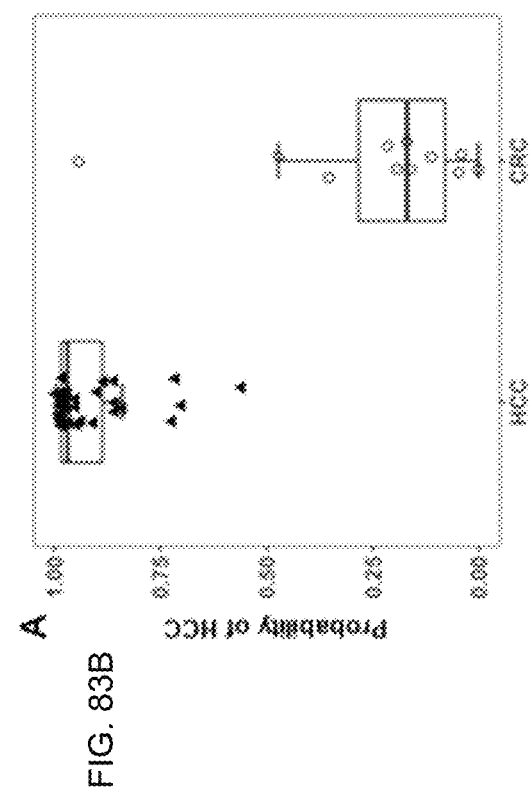
FIG. 83A
FIG. 83B
FIG. 83C

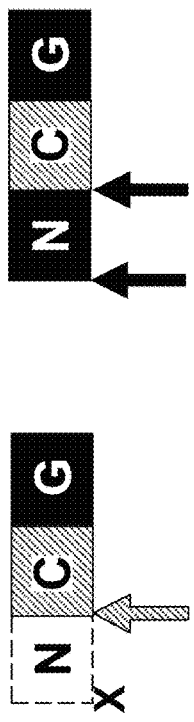
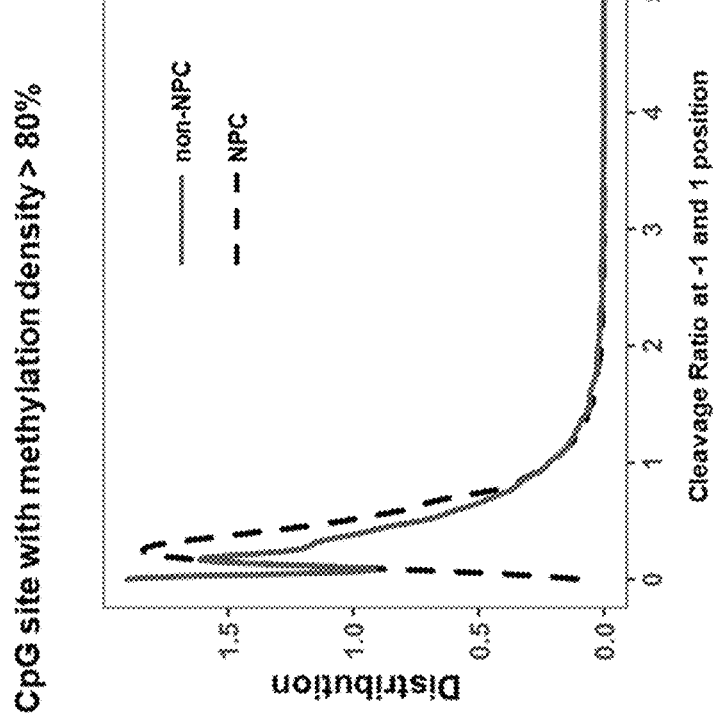
FIG. 91A
FIG. 91B

| Method | Sensitivity (Training Set) | Specificity (Training Set) | Sensitivity (Testing Set) | Specificity (Testing Set) |
|---|---|---|---|---|
| Count | 100% (37/37) | 73.6% (95/129) | 100% (10/10) | 74.2% (23/31) |
| Size | 100% (37/37) | 34.9% (45/129) | 100% (10/10) | 38.7% (12/31) |
| Cleavage Ratio | 100% (37/37) | 73.6% (95/129) | 100% (10/10) | 61.3% (19/31) |
| Count + Size | 100% (37/37) | 80.6% (104/129) | 100% (10/10) | 87.1% (27/31) |
| Count + Cleavage Ratio | 100% (37/37) | 94.6% (122/129) | 100% (10/10) | 90.3% (28/31) |
| Count + Size + Cleavage Ratio | 100% (37/37) | 96.9% (125/129) | 100% (10/10) | 96.8% (30/31) |

FIG. 95

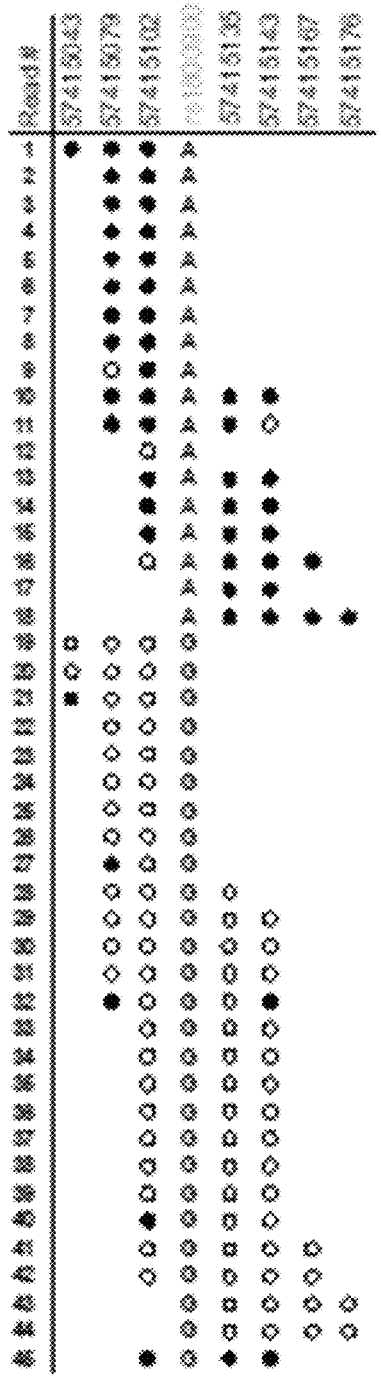
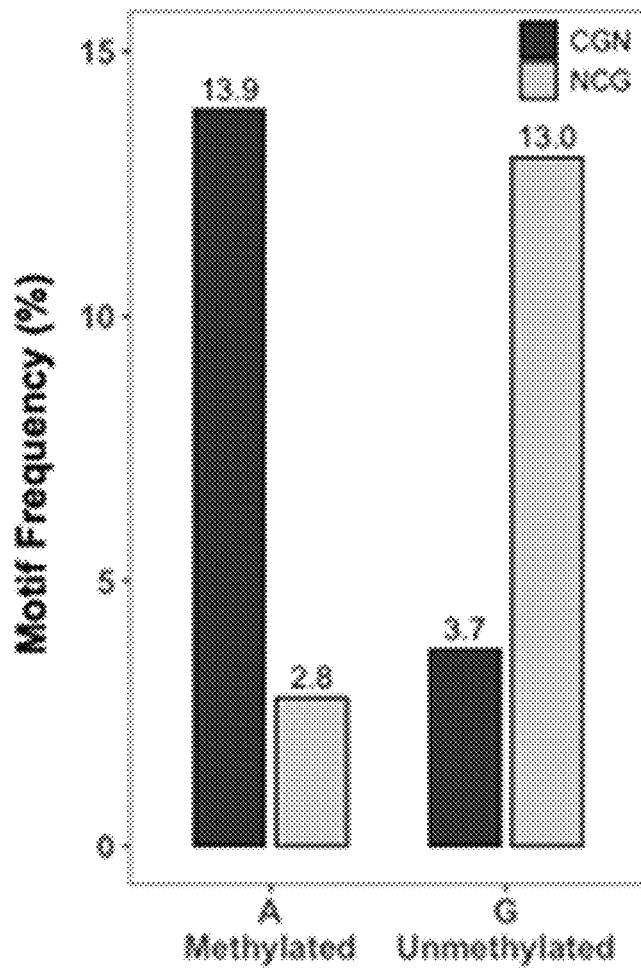
FIG. 100A
FIG. 100B

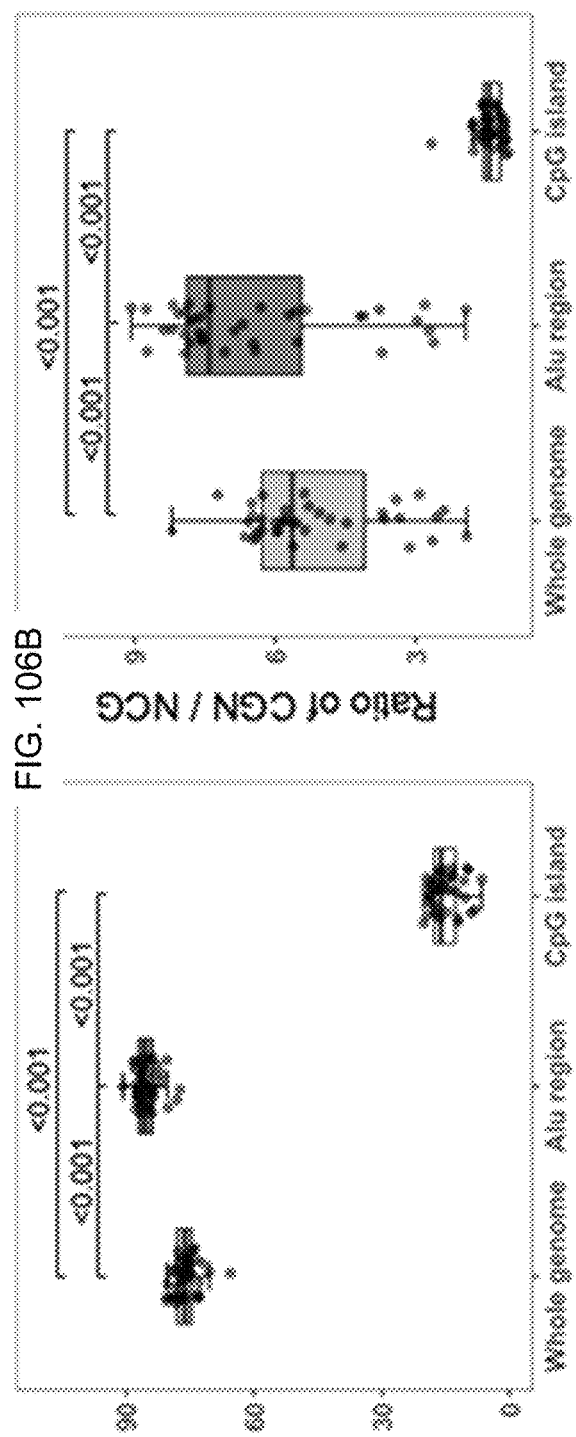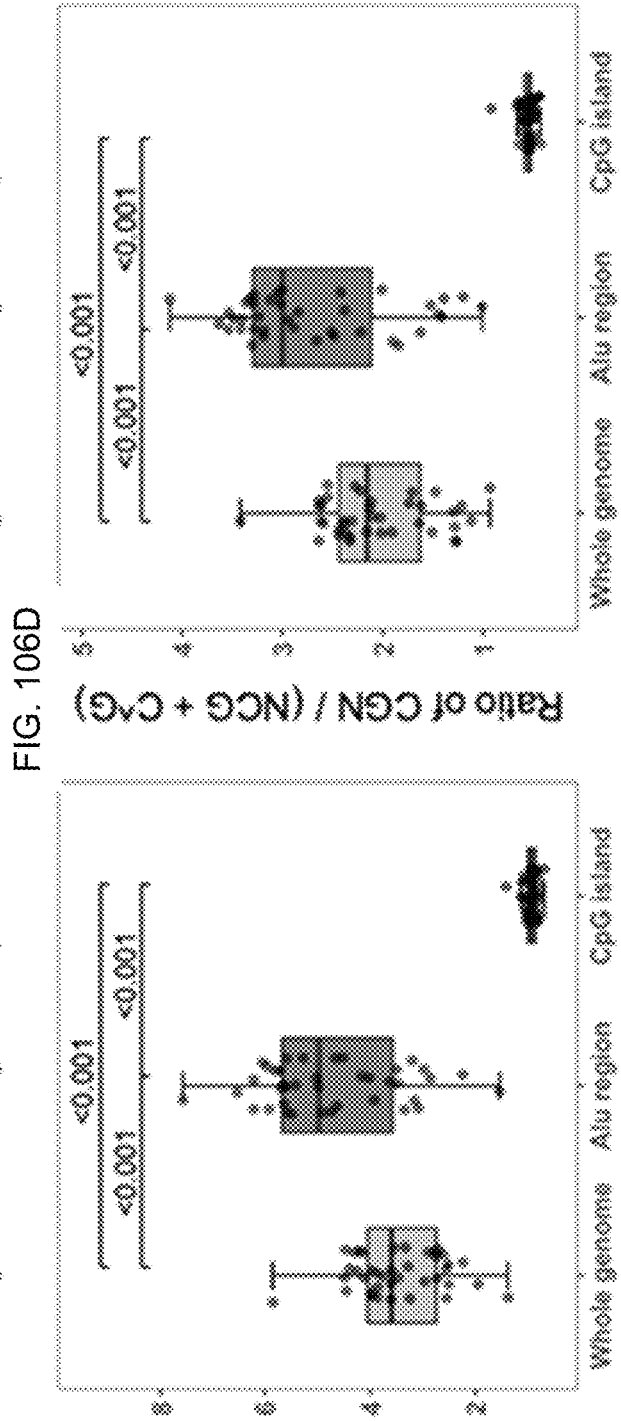
FIG. 106A  FIG. 106B  FIG. 106C  FIG. 106D

| | ACG | TCG | CCG | GCG | CGA | CGT | CGC | CGG |
|---|---|---|---|---|---|---|---|---|
| Bladder cancer-informative Hypermethylation | 13.21 | 0.00 | 18.87 | 4.72 | 12.26 | 21.70 | 13.21 | 16.04 |
| Bladder cancer-informative Hypomethylation | 9.77 | 2.34 | 10.56 | 3.11 | 25.57 | 27.74 | 6.15 | 14.75 |
| Kidney cancer-informative Hypermethylation | 9.18 | 5.65 | 18.35 | 3.29 | 27.06 | 14.59 | 10.12 | 11.76 |
| Kidney cancer-informative Hypomethylation | 11.76 | 1.68 | 13.03 | 2.94 | 22.90 | 26.26 | 6.09 | 15.34 |
| Prostate cancer-informative Hypermethylation | 8.40 | 2.78 | 17.78 | 4.69 | 19.96 | 19.74 | 10.41 | 19.25 |
| Prostate cancer-informative Hypomethylation | 8.25 | 2.10 | 10.90 | 2.99 | 29.45 | 24.19 | 6.61 | 15.52 |
| Tissue-shared Hypermethylation | 8.31 | 1.21 | 10.07 | 4.56 | 20.10 | 27.24 | 11.14 | 17.38 |
| Tissue-shared Hypomethylation | 9.78 | 2.55 | 16.42 | 4.23 | 18.63 | 21.89 | 6.95 | 19.55 |

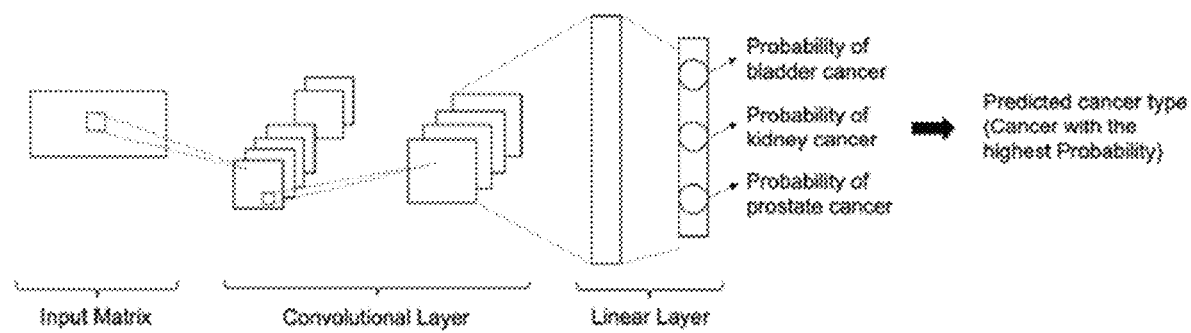

FIG. 126B

FRAGMENTATION FOR MEASURING METHYLATION AND DISEASE

CROSS-REFERENCES TO RELATED APPLICATIONS

The present application is a continuation application of U.S. patent application Ser. No. 18/106,793, entitled "FRAGMENTATION FOR MEASURING METHYLATION AND DISEASE" filed Feb. 7, 2023, which claims priority from and is a non-provisional application of U.S. Provisional Application No. 63/307,622, entitled "Fragmentation For Measuring Methylation And Disease" filed Feb. 7, 2022; U.S. Provisional Application No. 63/328,710, entitled "Fragmentation For Measuring Methylation And Disease" filed Apr. 7, 2022; and U.S. Provisional Application No. 63/400,244, entitled "Fragmentation For Measuring Methylation And Disease" filed Aug. 23, 2022, the entire contents of which are herein incorporated by reference for all purposes.

SEQUENCE LISTING

The instant application contains a Sequence Listing which has been submitted electronically in XML format and is hereby incorporated by reference in its entirety. Said XML copy, created on Jun. 21, 2023, is named 108473-8004US2-1374811_SL.xml and is 13,471 bytes in size.

BACKGROUND

Cell-free DNA (cfDNA) molecules are nonrandomly fragmented. The association between cfDNA fragmentation patterns and nucleosome structures has been demonstrated in a number of studies (Sun et al. Proc Natl Acad Sci UAS. 2018; 115:E5106; Snyder et al. Cell. 2016; 164:57-68). For example, the characteristic size profile of cfDNA shows a modal frequency at approximately 166 bp, with smaller molecules forming a series of peaks in a 10-bp periodicity (Lo et al. Sci Transl Med. 2010; 2:61ra91). Such size patterns of plasma DNA fragments suggest the presence of both inter- and intra-nucleosome cleavages during the release of DNA molecules into the blood circulation upon cell death (e.g., via apoptosis) or other mechanisms. Moreover, our group has reported previously that a subset of genomic locations was found to be preferentially cut during the generation of plasma DNA molecules (Chan et al. Proc Natl Acad Sci USA. 2016; 113:E8159-E8168; Jiang et al. Proc Natl Acad Sci USA. 2018; 115:E10925-E10933), such preferred cutting could reflect the tissue of origin of cfDNA (Jiang et al. Proc Natl Acad Sci USA. 2018; 115:E10925-E10933; Sun et al. Proc Natl Acad Sci USA. 2018; 115: E5106-E5114).

Currently, a widely used strategy for methylation analysis is based on the bisulfite or enzymatic conversion followed by sequencing. Such conversions involving extra steps of DNA purification or DNA degradation in harsh conditions result in the information loss of DNA molecules.

BRIEF SUMMARY

Various embodiments are provided for using fragmentation of cell-free DNA molecules for various purposes. One example purpose is determining methylation, e.g., at a particular site of a DNA molecule, at a particular genomic site in a reference genome for a biological sample (e.g., plasma, serum, urine, saliva) of cell-free DNA of a subject, or for a particular region in the reference genome for the biological sample (also just referred to as a sample). Various types of fragmentation measurements can be used for this purpose, e.g., end motifs and cleavage profiles, which may include cleavage information at one or more positions around a site, such as a CpG site.

Another example purpose is determining a fractional concentration of DNA of a particular tissue type (e.g., clinically-relevant DNA). Various types of fragmentation measurements can be used for this purpose, e.g., end motifs and cleavage profiles. Certain sites may be selected for using fragmentation measurements. For example, sites/regions that are hypermethylated and/or hypomethylated for the particular tissue type can be used. As another example, sites that are 5hmC-enriched or -depleted for the particular tissue type can be used. In addition, techniques can use fragmentation measurements (e.g., end motifs and cleavage profiles) to identify regions that are 5hmC-enriched and 5hmC-depleted for a particular tissue.

Another example purpose is determining a pathology of a subject using a biological sample including cell-free DNA. The cell-free DNA can be of the subject or of a pathogen (e.g., a virus) in the subject's sample. Various types of fragmentation measurements can be used for this purpose, e.g., end motifs and cleavage profiles. Certain sites may be selected for using fragmentation measurements. For example, sites/regions that are hypermethylated and/or hypomethylated for a particular tissue type can be used, e.g., to identify a pathology for the particular tissue type. As another example, sites/regions that are similarly methylated can be used, but that have different cleavage profiles between subjects that have the pathology and those subjects that do not. As yet another example, sites/regions that are 5hmC-enriched or -depleted for the particular tissue type can be used, e.g., to identify a pathology for the particular tissue type. Machine learning models can use such tissue-specific methylation patterns (e.g., hyper- and hypo-methylated as well as 5hmC-enriched and -depleted) to differentiate among different types of cancers. The cell-free DNA fragments used for the fragmentation measurements can be filtered, e.g., based on size. Thus, a pathology can be detected based on an amount of end motifs of cell-free DNA fragments having a particular size.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

FIG. 19 shows the performance of single CpG site methylation status prediction using support vector machine (SVM) on the basis of cleavage profiles according to embodiments of the present disclosure.

FIG. 20 shows the performance of single CpG site methylation status prediction using support vector machine (SVM) on the basis of cleavage profiles from both strands according to embodiments of the present disclosure. Figure discloses SEQ ID NOS 9-10, 9, and 11, respectively, in order of appearance.

FIG. 22 shows a schematic illustration for methylation status prediction using a CNN model on the basis of cleavage profiles and sequence context according to embodiments of the present disclosure. Figure discloses SEQ ID NOS 1, 12, 1-2, 1-2, and 1-2, respectively, in order of appearance.

FIGS. 25A-25F are boxplots illustrated the difference of mean cleavage ratio of various positions for plasma and urine (ucfDNA) between hypermethylated and hypomethylated CpGs.

FIGS. 26A-26C show a comparison of various techniques for determining a quantitative value for a methylation level (e.g., a density) for CpGs having different methylation levels in 8 plasma DNA samples.

FIG. 28 shows the methylation index for CGN and NCG end motif according to embodiments of the present disclosure.

FIGS. 49A-49B show a correlation between the fetal DNA fraction and the CGN/NCG ratio based on plasma DNA molecules originating from placenta-specific hypermethylated CpG sites (FIG. 49A), and placenta-specific hypomethylated CpG sites (FIG. 49B) according to embodiments of the present disclosure.

FIGS. 54A-54B show fetal-specific methylation is reflected in cleavage profiles of cfDNA fragmentation according to embodiments of the present disclosure.

FIG. 55 discloses SEQ ID NOS 9, 11, 9, and 11, respectively, in order of appearance.

FIGS. 63A-63B show the top 10 CG probe and top 10 NCG probes for the potential experiment design according to embodiments of the present disclosure.

FIGS. 67A-67C show an example for the designs of primers and probes. FIG. 67A discloses SEQ ID NO: 14, and FIG. 67B discloses SEQ ID NOS 4, 3, 5, and 3, respectively, in order of appearance.

FIGS. 70A-70C are boxplots showing the overall CGN/NCG motif ratios of short cfDNA fragments (<=200 bp; 70A) and long cfDNA fragments (>=1000 bp; 70B), and the difference in CGN/NCG motif ratio (70C) between short (<=200 bp) and long cfDNA fragments (>=1000 bp) across healthy subjects (Healthy), HBV carriers (HBV), and HCC cases.

FIG. 77 shows an example marker selection and data collection according to embodiments of the present disclosure. Figure discloses SEQ ID NOS 9, 11, 9, and 11, respectively, in order of appearance.

FIG. 83A shows an unsupervised clustering analysis for patients with HCC and CRC on the basis of 5' 3-mer CG containing end motifs related to tissue-informative and tissue-shared CpG sites. FIGS. 83B-83C show performance of HCC classifier on the basis of 5' 3-mer CG containing end motifs related to tissue-informative and tissue-shared CpG sites.

FIG. 91A shows the distribution for both −1 and 1 positions. FIG. 91B shows the preference for cutting when an enzyme deficiency exists.

FIG. 95 shows the diagnosis power of distinguishing NPC cases from non-NPC cases by using different metrics in training and testing dataset.

FIGS. 100A and 100B show CGN and NCG end motif frequencies could be used for predicting genomic imprinting according to embodiments of the present disclosure.

FIGS. 106A-106D show boxplots illustrating the difference of methylation density (FIG. 106A), CGN/NCG motif ratio (FIG. 106B), CGN/C^G motif ratio (FIG. 106C), CGN/(NCG+C^G) motif ratio (FIG. 106D) across genome-wide regions, Alu regions and CpG islands in urinary cfDNA of healthy controls. Each dot represents a urinary cfDNA sample.

FIG. 123 shows a schematic for classification of multiple cancer types with multiple binary classifications.

FIGS. 124A-124B show performance of bladder cancer classifier on the basis of 5' 3-mer CG containing end motifs related to tissue-informative and tissue-shared CpG sites.

FIGS. 125A-125D show performance of kidney cancer and prostate cancer classifiers on the basis of 5' 3-mer CG containing end motifs related to tissue-informative CpG sites together with tissue-shared CpG sites.

FIGS. 126A-126B show a schematic illustration for multiple cancer classification using a CNN model on the basis of CG-containing motifs.

FIG. 127 illustrates a measurement system according to an embodiment of the present invention.

FIG. 128 shows a block diagram of an example computer system usable with systems and methods according to embodiments of the present invention.

TERMS

Figure 1:
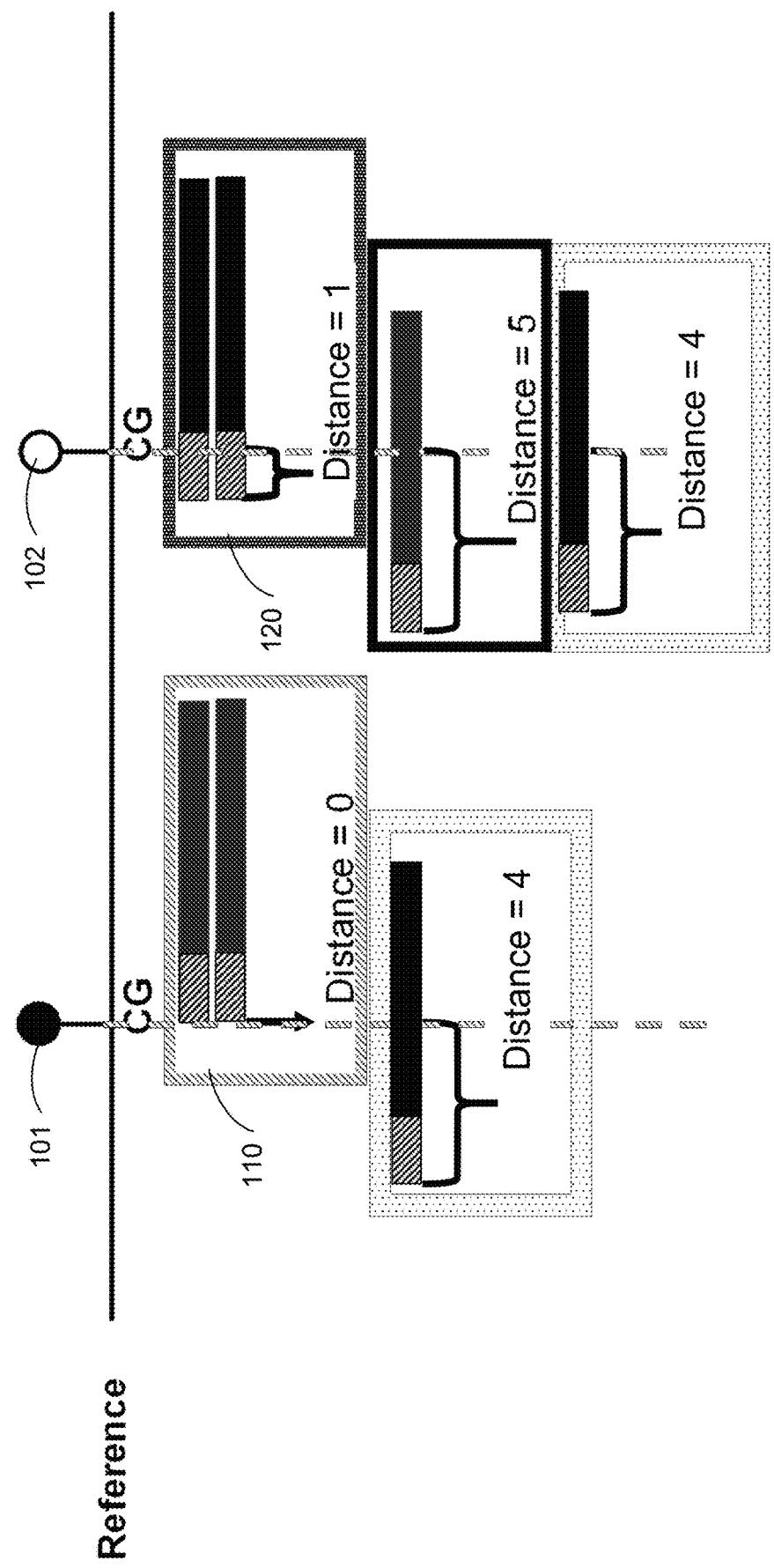
FIG. 1 illustrates cutting positions relative to CpG sites (also referred to as CG sites) according to embodiments of the present disclosure.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" can correspond to tissues used to determine tissue-specific methylation levels or tissue-specific fragmentation patterns. Multiple samples of a same tissue type from different individuals may be used to determine a tissue-specific methylation level for that tissue type.

A "biological sample" refers to any sample that is taken from a subject (e.g., a human (or other animal), such as a pregnant woman, a person with cancer or other disorder, or a person suspected of having cancer or other disorder, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), intraocular fluids (e.g., the aqueous humor), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. As part of an analysis of a biological sample, a statistically significant number of cell-free DNA molecules can be analyzed (e.g., to provide an accurate measurement) for a biological sample. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed. At least a same number of sequence reads can be analyzed.

"Clinically-relevant DNA" can refer to DNA of a particular tissue source that is to be measured, e.g., to determine a fractional concentration of such DNA or to classify a phenotype of a sample (e.g., plasma). Examples of clinically-relevant DNA are fetal DNA in maternal plasma or tumor DNA in a patient's plasma or other sample with cell-free DNA. Another example includes the measurement of the amount of graft-associated DNA in the plasma, serum, or urine of a transplant patient. A further example includes the measurement of the fractional concentrations of hematopoietic and nonhematopoietic DNA in the plasma of a subject, or fractional concentration of a liver DNA fragments (or other tissue) in a sample or fractional concentration of brain DNA fragments in cerebrospinal fluid.

A "sequence read" refers to a string of nucleotides sequenced from any part or all of a nucleic acid molecule.

For example, a sequence read may be a short string of nucleotides (e.g., 20-150 nucleotides) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes as may be used in microarrays, or amplification techniques, such as the polymerase chain reaction (PCR) or linear amplification using a single primer or isothermal amplification. Example sequencing techniques include massively parallel sequencing, targeted sequencing, Sanger sequencing, sequencing by ligation, ion semiconductor sequencing, and single molecule sequencing (e.g., using a nanopore, or single-molecule real-time sequencing (e.g. from Pacific Biosciences)). Example PCR techniques include real-time PCR and digital PCR (e.g. droplet digital PCR). As part of an analysis of a biological sample, a statistically significant number of sequence reads can be analyzed, e.g., at least 1,000 sequence reads can be analyzed. As other examples, at least 10,000 or 50,000 or 100,000 or 500,000 or 1,000,000 or 5,000,000 sequence reads, or more, can be analyzed.

A sequence read can include an "ending sequence" associated with an end of a fragment. The ending sequence can correspond to the outermost N bases of the fragment, e.g., 1-30 bases at the end of the fragment. If a sequence read corresponds to an entire fragment, then the sequence read can include two ending sequences. When paired-end sequencing provides two sequence reads that correspond to the ends of the fragments, each sequence read can include one ending sequence.

A "sequence motif" may refer to a short, recurring pattern of bases in DNA fragments (e.g., cell-free DNA fragments). A sequence motif can occur at an end of a fragment, and thus be part of or include an ending sequence. An "end motif" (also referred to as a "end sequence motif") can refer to a sequence motif for an ending sequence that preferentially occurs at ends of DNA fragments, potentially for a particular type of tissue. An end motif may also occur just before or just after ends of a fragment, thereby still corresponding to an ending sequence. A nuclease can have a specific cutting preference for a particular end motif, as well as a second most preferred cutting preference for a second end motif. The number of nucleotides (nt) at the fragment ends used for analysis could be, for example, but not limited to, 1 nt, 2 nt, 3 nt, 4 nt, 5 nt, 6 nt, 7 nt, 8 nt, 9 nt, and 10 nt or above. In some embodiments, the fragment end motif could be defined by one or more nucleotides across positions nearby the end of a fragment. The fragment end motif could be defined by one or more nucleotides in a reference genome surrounding the genomic locus to which the end of a fragment is aligned.

A "site" (also called a "genomic site") corresponds to a single site, which may be a single base position or a group of correlated base positions, e.g., a CpG site, TSS site, DNase hypersensitivity site, or larger group of correlated base positions. A "locus" may correspond to a region that includes multiple sites. A locus can include just one site, which would make the locus equivalent to a site in that context. Various number of regions, sites, or loci can be analyzed, e.g., 50, 100, 200, 500, 1,000, 5,000, 10,000, 50,000, 100,000, 500,000, one million, or more. Various techniques can determine a DNA molecule is located at one or more genomic positions in a reference genome, e.g., alignment of a sequence read to the reference genome or using position-specific probes. The position determination can be to some or all of the reference genome, e.g., if only part of the genome is being analyzed. As examples, the amount of the genome analyzed can be greater than 0.01%, 0.1%, 1%, 5%, 10%, or 50%. A "cutting site" can refer to a location where DNA was cut by a nuclease, thereby resulting in a DNA fragment.

A "cleavage profile" can refer to amounts of fragments that end at two or more positions that occur in a window around a site (e.g., a CpG site). The amounts of fragments may correspond to different categories according to end motifs (e.g., CGN and NCG for positions 0 and −1, respectively). The amounts can be normalized, e.g., as using a sequencing depth at each position, depth in a region, or number of fragments ending in a region. Such a normalized amount at a single position can be referred to as a cleavage ratio, cleavage amount, or a cleavage density. In one example, a cleavage profile could be defined as patterns of the ratios between fragment ends and the sequencing depth across genomic coordinates within a window related to a CpG site, which could be used to deduce the methylation patterns of that CpG site. Various types of normalization can be used, as are described herein. The window could include, but not limited to, X nucleotides (i.e., X-nt) upstream and Y nucleotides (i.e., Y-nt) downstream of a CpG site. The values of X and Y could be 1, 2, 3, 4, 5, 6, 7, 8, 9, 10, 15, 20, 30, 40, 50, 100, 1000, 5000, etc. The window can cover a nucleosome size range upstream and downstream of CpG site, e.g., −160 nt to 160 nt.

The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically include multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations. The term "haplotype" as used herein refers to a combination of alleles at multiple loci that are transmitted together on the same chromosome or chromosomal region. A haplotype may refer to as few as one pair of loci or to a chromosomal region, or to an entire chromosome or chromosome arm.

The term "sequence context" can refer to the base compositions (A, C, G, or T) and the base orders in a stretch of DNA. Such a stretch of DNA could be surrounding a CpG site that is subjected to or the target of methylation analysis. For example, the sequence context can refer to bases upstream and/or downstream of a CpG site that is subjected to methylation analysis. For instance, the sequence context can include a K-mer matrix specifying a number of instances of each K-mer in the test cell-free DNA molecule, wherein K is an integer. When K equals 2, the K-mer matrix is a di-nucleotide matrix specifying a number of instances of di-nucleotide pairs in the test cell-free DNA molecule. As another example, the sequence context can include sequence information from each nucleotide of the test cell-free DNA molecule (i.e., the entire sequence). One-hot encoding may be used for the sequence, thereby generating a matrix of 0s and 1s with a dimension of 4×N, where N is the number of bases in the sequence.

Various types of methylation exists. Methylation has been found on cytosines, adenines, thymines and guanines, such as 5mC (5-methylcytosine), 4mC (N4-methylcytosine), 5hmC (5-hydroxymethylcytosine), 5fC (5-formylcytosine), 5caC (5-carboxylcytosine), 1 mA (N1-methyladenine), 3 mA (N3-methyladenine), 7 mA (N7-methyladenine), 3mC (N3-methylcytosine), 2mG (N2-methylguanine), 6mG (O6-methylguanine), 7mG (N7-methylguanine), 3mT (N3-methylthymine), and 4mT (O4-methylthymine). In vertebrate genomes, 5mC is the most common type of base methylation, followed by that for guanine (i.e., in the CpG context).

The "methylation index" or "methylation status" for each genomic site (e.g., a CpG site) can refer to the proportion of DNA fragments (e.g., as determined from sequence reads or probes) showing methylation at the site over the total number of reads covering that site. A methylation status can refer to whether a particular site is methylated at a particular site of a DNA fragment. A "read" can correspond to information (e.g., methylation status at a site) obtained from a DNA fragment. A read can be obtained using reagents (e.g., primers or probes) that preferentially hybridize to DNA fragments of a particular methylation status. Typically, such reagents are applied after treatment with a process that differentially modifies or differentially recognizes DNA molecules depending on their methylation status, e.g., bisulfite conversion, or methylation-sensitive restriction enzyme, or methylation binding proteins, or anti-methylcytosine antibodies, or single molecule sequencing techniques that recognize methylcytosines and hydroxymethylcytosines.

The "methylation density" of a region or a set of sites can refer to the number of reads at site(s) within the region (also referred to as a bin) or the set of sites showing methylation divided by the total number of reads covering the site(s) in the region or the set of sites. A region can include one or more sites of interest, including at least 1, 2, 3, 4, 5, 10, 20, 50, 100, 200, 500, and 1,000 sites. The site(s) may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g., 500 bp, 5 kb, 10 kb, 50-kb or 1-Mb, etc. A region could be the entire genome or a chromosome or part of a chromosome (e.g., a chromosomal arm). The methylation index of a CpG site is the same as the methylation density for a region when the region only includes that CpG site. The "proportion of methylated cytosines" can refer to the number of cytosine sites, "C's", that are shown to be methylated (for example unconverted after bisulfite conversion) over the total number of analyzed cytosine residues, i.e., including cytosines outside of the CpG context, in the region. The methylation index, methylation density and proportion of methylated cytosines are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci USA 2013; 110: 18910-18915) and by the Pacific Biosciences single molecule real time analysis (Tse et al. Proc Natl Acad Sci USA 2021; 118: e2019768118).

The term "hypomethylation" can refer to a site or set of sites (e.g., a region) that has below a specified threshold for a methylation level, e.g., at or below 50%, 45%, 40%, 35%, 30%, 25%, or 20% for the methylation level. A site in a genome may be considered unmethylated if the methylation level is below a threshold. The term "hypermethylation" can refer to a site or set of sites (e.g., a region) that has above a specified value for a methylation level, e.g., at or above 95%, 90%, 80%, 75%, 70%, 65%, or 60% for the methylation level. A site in a genome may be considered methylated if the methylation level is greater than a threshold.

A differentially methylated region (DMR) is a genomic region with different DNA methylation status across two or more biological samples. The different DNA methylation status may be defined by the certain difference in methylation index or density, such as but not limited to 1%, 5%, 10%, 20%, 30%, 40%, 50%, 60%, 70%, 80%, 90%, 95%, 99%, etc.

The term "5hmC-enriched" can refer to a site or set of sites (e.g., a region) that has relative higher proportion of 5hmC methylation molecules relative to other types of methylation. The term "5hmC-depleted" can refer to a site or set of sites (e.g., a region) that has relative lower proportion of 5hmC methylation molecules relative to other types of methylation.

A "relativefrequency" (also referred to just as "frequency") may refer to a proportion (e.g., a percentage, fraction, or concentration). In particular, a relative frequency of a particular end motif (e.g., CCGA or just a single base) or a group of end motifs (e.g., CGN or NCG) can provide a proportion of cell-free DNA fragments in a sample that are associated with a set of one or more end motifs.

An "aggregate value" may refer to a collective property, e.g., of relative frequencies of a set of end motifs. Examples include a mean, a median, a sum of relative frequencies, a variation among the relative frequencies (e.g., entropy, standard deviation (SD), the coefficient of variation (CV), interquartile range (IQR) or a certain percentile cutoff (e.g., $95^{th}$ or $99^{th}$ percentile) among different relative frequencies), or a difference (e.g., a distance) from a reference pattern of relative frequencies, as may be implemented in clustering. As another example, an aggregate value can comprise an array/vector of relative frequencies, which can be compared to a reference vector (e.g., representing a multidimensional data point).

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "x" refers to the number of times a locus is covered with a sequence read. Sequencing depth can also be applied to multiple loci, or the whole genome, in which case x can refer to the mean number of times the loci or the haploid genome, or the whole genome, respectively, is sequenced. Ultra-deep sequencing can refer to at least 100× in sequencing depth.

A "calibration sample" can correspond to a biological sample having a property (measure value) that is known. Example properties include a methylation level or a fraction concentration of clinically-relevant DNA. A fractional concentration of clinically-relevant DNA (e.g., tissue-specific DNA fraction) can be known or determined via a calibration method, e.g., using an allele specific to the tissue, such as in transplantation whereby an allele present in the donor's genome but absent in the recipient's genome can be used as a marker for the transplanted organ. As examples, the methylation level can be of a region, genome, or a site in a genome or on a fragment. A methylation level can be determined using a methylation-aware assay such as methylation-aware sequencing or PCR. Example methylation-aware sequencing can include bisulfite sequencing or single molecule techniques, e.g., using nanopores. A calibration sample can have separate measured values (e.g., an amount of fragments with a particular end motif or cleavage profile) can be determined to which the desired measure value can be correlated.

A "calibration data point" includes a "calibration value" (e.g., an amount of fragments with a particular end motif or cleavage profile) and a measured or known value that is desired to be determined for other test samples. The calibration value can be determined from various types of data measured from DNA molecules of the sample. The calibration value corresponds to a parameter that correlates to the desired property, e.g., classification of a genetic disorder or a methylation level. For example, a calibration value can be determined from measured values as determined for a calibration sample, for which the desired property is known. The calibration data points may be defined in a variety of ways, e.g., as discrete points or as a calibration function (also called a calibration curve or calibration surface). The calibration function could be derived from additional mathematical transformation of the calibration data points.

A "separation value" corresponds to a difference or a ratio involving two values, e.g., two fractional contributions or two methylation levels. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and a ratio. A separation value can be compared to a threshold to determine whether the separation between the two values is statistically significant.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter. The parameter can be used to determine any classification described herein, e.g., with respect to fetal, cancer, or transplant analysis. A "separation value" and an "aggregate value" (e.g., of relative frequencies) are two examples of a parameter (also called a metric) that provides a measure of a sample that varies between different classifications (states), and thus can be used to determine different classifications. An aggregate value can be a separation value, e.g., when a difference is taken between a set of relative frequencies of a sample and a reference set of relative frequencies, as may be done in clustering.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts. A cutoff or threshold may be "a reference value" or derived from a reference value that is representative of a particular classification or discriminates between two or more classifications. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical simulations of samples. A particular value for a cutoff, threshold, reference, etc. can be determined based on a desired accuracy (e.g., a sensitivity and specificity).

The term "level of cancer" can refer to whether cancer exists (i.e., presence or absence), a stage of a cancer, a size of tumor, whether there is metastasis, the total tumor burden of the body, the cancer's response to treatment, and/or other measure of a severity of a cancer (e.g., recurrence of cancer). The level of cancer may be a number or other indicia, such as symbols, alphabet letters, and colors. The level may be zero. The level of cancer may also include premalignant or precancerous conditions (states). The level of cancer can be used in various ways. For example, screening can check if cancer is present in someone who is not previously known to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance or extent of cancer metastasizing. Detection can mean 'screening' or can mean checking if someone, with suggestive features of cancer (e.g., symptoms or other positive tests), has cancer.

A "level of pathology" can refer to the amount, degree, or severity of pathology associated with an organism, where the level can be as described above for cancer. Another example of pathology is a rejection of a transplanted organ. Other example pathologies can include autoimmune attack (e.g., lupus nephritis damaging the kidney or multiple sclerosis damaging the central nervous system), inflammatory diseases (e.g., hepatitis), fibrotic processes (e.g., cirrhosis), fatty infiltration (e.g., fatty liver diseases), degenerative processes (e.g., Alzheimer's disease) and ischemic tissue damage (e.g., myocardial infarction or stroke). A heathy state of a subject can be considered a classification of no pathology.

A "machine learning model" can refer to a software module configured to be run on one or more processors to provide a classification or numerical value of a property of one or more samples. An example type of model is supervised learning that can be used with embodiments of the present disclosure. Example supervised learning models may include different approaches and algorithms including analytical learning, artificial neural network, backpropagation, boosting (meta-algorithm), Bayesian statistics, case-based reasoning, decision tree learning, inductive logic programming, Gaussian process regression, genetic programming, group method of data handling, kernel estimators, learning automata, learning classifier systems, minimum message length (decision trees, decision graphs, etc.), multilinear subspace learning, naive Bayes classifier, maximum entropy classifier, conditional random field, nearest neighbor algorithm, probably approximately correct learning (PAC) learning, ripple down rules, a knowledge acquisition methodology, symbolic machine learning algorithms, subsymbolic machine learning algorithms, minimum complexity machines (MCM), random forests, ensembles of classifiers, ordinal classification, data pre-processing, handling imbalanced datasets, statistical relational learning, or Proaftn, a multicriteria classification algorithm. The model may include linear regression, logistic regression, deep recurrent neural network (e.g., long short term memory, LSTM), hidden Markov model (HMM), linear discriminant analysis (LDA), k-means clustering, density-based spatial clustering of applications with noise (DBSCAN), random forest algorithm, support vector machine (SVM), or any model described herein. Supervised learning models can be trained in various ways using various cost/loss functions that define the error from the known label (e.g., least squares and absolute difference from known classification) and various optimization techniques, e.g., using backpropagation, steepest descent, conjugate gradient, and Newton and quasi-Newton techniques.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to +10%. The term "about" can refer to ±5%.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

Standard abbreviations may be used, e.g., bp, base pair(s); kb, kilobase(s); pi, picoliter(s); s or sec, second(s); min, minute(s); h or hr, hour(s); aa, amino acid(s); nt, nucleotide(s); and the like.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments of the present disclosure, some potential and exemplary methods and materials may now be described.

DETAILED DESCRIPTION

We herein develop approaches to deduce the methylation status of cfDNA molecules based on utilizing cfDNA fragmentation patterns. The fragmentation patterns herein can involve, but not limited to, fragment ends, cleavage profiles, fragment end motifs, genomic coordinates of fragment ends, and fragment sizes.

We found cleavage profiles associated with CpG methylation status. The cleavage profiles could be used for predicting methylation for a region, at single base resolution, or on a per fragment basis. Additionally, we found cfDNA end motifs (e.g., 3-mers or higher) are useful for predicting regional methylation. Accordingly, a cleavage profile measuring fragments ending in a window around a site can be used to deduce a methylation of a region, a site in a genome, or of one or more sites in a fragment. As another example, the fragment end motifs could be used for deducing the methylation levels of a genomic region of interest (e.g., regional methylation levels). The fragment end motifs could be defined by one or more nucleotides at the ends of cell-free DNA fragments. As a further example, cfDNA fragmentomic features can be used to deduce methylation status at single-molecule resolution (i.e., methylation patterns across CpG sites present in a DNA molecule). For instance, the end motifs from one DNA molecule can be used to predict the methylation status of the whole fragment.

Further aspects of the disclosure provide for determining a fractional concentration of clinically-relevant DNA using cleavage profiles. For instance, methylation associated cfDNA fragmentomic features could be used for, but not limited to, performing a tissue-of-origin analysis of plasma DNA. Various fragmentomic features can be used, such as cleavage profiles and end motifs, as are described herein. Certain sites may be selected for using fragmentation measurements for determining such a fractional concentration. For example, sites/regions that are hypermethylated and/or hypomethylated for the particular tissue type can be used. As another example, sites that are 5hmC-enriched or -depleted for the particular tissue type can be used. In addition, techniques can use fragmentation measurements (e.g., end motifs and cleavage profiles) to identify regions that are 5hmC-enriched and 5hmC-depleted for a particular tissue.

Yet further aspects of the disclosure provide for pathology detection. As an example, CG-containing motifs genome-wide or from tissue-specific (e.g., liver specific) hypomethylated or hypermethylated sites/regions can provide a cancer (e.g., HCC) diagnosis/classification or other diseases, e.g., which may relate to a particular tissue. DNA of the subject and/or of a pathogen (e.g., a virus) can be used. For either type of DNA, sites that have similar methylation levels across different subjects (with or without the pathology) can be used, but where the subjects have different cleavage profiles. As yet another example, sites/regions that are 5hmC-enriched or -depleted for the particular tissue type can be used, e.g., to identify a pathology for the particular tissue type. Machine learning models can use such tissue-specific methylation patterns (e.g., hyper- and hypo-methylated as well as 5hmC-enriched and -depleted) to differentiate among different types of cancers. The cell-free DNA fragments used for the fragmentation measurements can be filtered, e.g., based on size. Thus, a pathology can be detected based on an amount of end motifs of cell-free DNA fragments having a particular size.

The fragmentation information (fragmentomic features) can be measured in various ways. As examples, massively parallel sequencing or genome-wide sequencing can be used. As another example, targeted sequencing approaches could be used to determine cfDNA fragmentomic features from regions of interest that are used for methylation pattern prediction. As additional examples, cfDNA fragmentomic features could be detected by using non-sequencing based approaches, such as quantitative polymerase chain reaction (qPCR), real-time PCR, digital PCR (dPCR), droplet digital PCR (ddPCR), mass spectrometry, etc.

Examples use of 5' end motifs as just one example. The 3' end motifs could be used in addition or instead for any embodiments described herein.

I. Relation of Fragmentation to Methylation

The present disclosure shows a relation between where DNA is cut (e.g., as part of forming cell-free DNA) and a methylation index (status) of a site in a genome. Where the DNA is cut can be defined as a cleavage profile. In another example, where the DNA is cut can be represented by end motifs.

A. Definitions for Cutting Positions

FIG. 1 illustrates cutting positions relative to CpG sites (also referred to as CG sites) according to embodiments of the present disclosure. The horizontal line refers to a reference sequence, e.g., part of a reference genome, which contains two CpG sites. After sequencing, the resulting reads can be mapped to this region. The distance between the fragment ends and the position relative to the CpG sites can be calculated. For example, the fragments 110 ended exactly at the CG position, and thus have a distance of 0 (also referred to as position 0).

The fragments 120 end one position to the left of CpG site 102. Since the fragment was cut one base before the CpG site, the distance is considered one. In this manner, we can calculate the distance between the cutting ends and the CpG sites and group the fragments with the same distance together. As shown below, this distance is associated with the methylation level.

Figure 2A:
FIGS. 2A-2B show the methylation index differs depending on the distance between the 5' ends and CpG sites according to embodiments of the present disclosure.

FIG. 2A shows how DNA fragments can be grouped depending on distance from the 5' ends to the CpG site. If the first two nucleotides at the 5' end of a fragment are CG, the aforementioned distance is 0. If there is one nucleotide at the 5' end immediately preceding the CG, the aforementioned distance is 1, which corresponds to fragments having an NCG motif, where N is any one of the 4 bases. The sequenced CpG sites could be grouped into different categories according to their distances relative to 5' ends. The maximum distance shown in FIG. 2A is eight, but further distances can be used.

B. Cutting Positions are Correlated with Cutting CpG Methylation

To explore whether cfDNA fragmentation patterns could be used for methylation prediction, we investigated the relationship between the methylation index and CpG positions relative to the 5' end of a fragment (i.e., nucleotide distance between CpG sites to the 5' end). We analyzed bisulfite sequencing reads from 8 plasma DNA samples of healthy subjects (median paired-end sequencing reads: 381 million (interquartile range: 353-404 million)). The sequences were then aligned to the reference genome. A methylation density for each CpG site was determined using the methylation values of the sequence reads at that CpG site.

The methylation index for each distance can be determined in various ways. For example, the number of methylated CpG sites covered by DNA fragments in a group divided by the total number of sequenced CpG sites on DNA fragments for each group may be used. If there are 100 CpG sites on the fragments and 90 of them are methylated, then the index will be 90. As another example, the methylation index can be determined as how many fragments in a group occur at a site that is hypermethylated (e.g., a methylation density at the site greater than a specified percentage, such as 60%, 70%, 80% etc.).

Figure 2B:
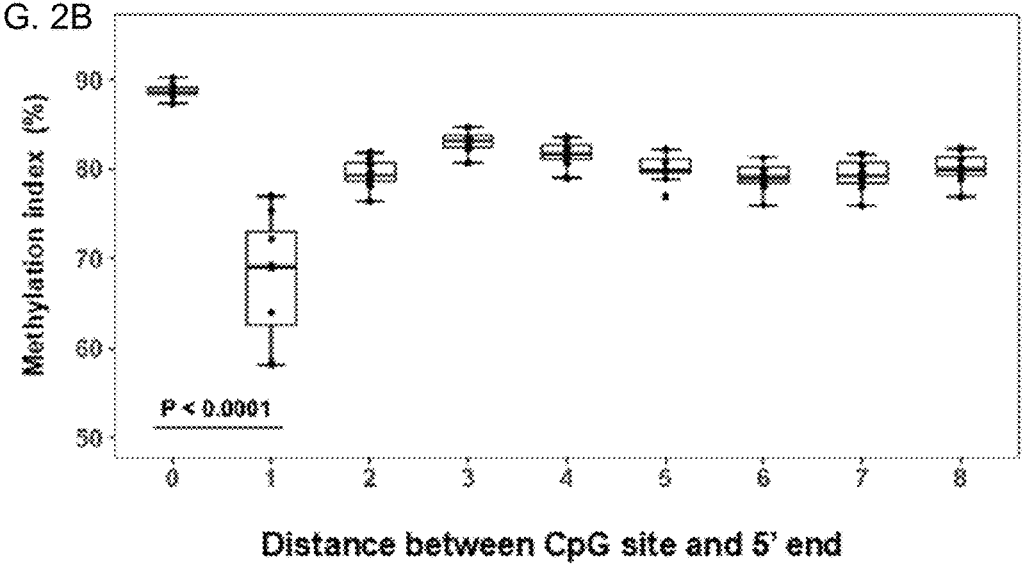

FIG. 2B provides methylation level for CpG sites each with a given downstream distance from the cutting edge of a plasma DNA molecule (e.g., methylation level for CpG sites with a 5-nt distance to the 5' end). FIG. 2B show the methylation index differs depending on the distance between the 5' ends and CpG sites. There is a correlation between the methylation index of CpG sites and their distance to the 5' end. As one can see, if the distance is 0, the methylation level is the highest in the CpG. If the distance is 1, then the methylation level is the lowest. As the distance further increases, the methylation level became rather stable. When a CpG site is methylated, the cutting will happen more at methylated C, whereas if the CpG site is unmethylated, there will be more random cutting.

Accordingly, CpG sites with a distance of 0 have higher chances of being methylated than those with a distance of 1 [mean methylation index: 88.7% (range: 87.3-90.3) vs 69.1% (range: 58.2-76.9%)]. As the methylation index differs depending on the distance between the 5' end and the CpG sites, the fragmentation patterns could be used for predicting the methylation levels of those CpG sites.

The cutting position is also associated with the motif types. For example, if the fragment is cut exactly at the CG position, then the end motif is CGN**** (where * represents a base and N is any of the 4 bases). If the fragment is cut one base before this CG, the end motif is NCG*** (where * represents a base) and so on. Thus, there is a relation between motif types and methylation level of a CpG site around which the fragment was cut.

To validate our observation, we further looked into the methylation levels in different types of 4-mer motifs, i.e., the 256 possible sequences at the four positions at the end of a fragment.

Figure 3:
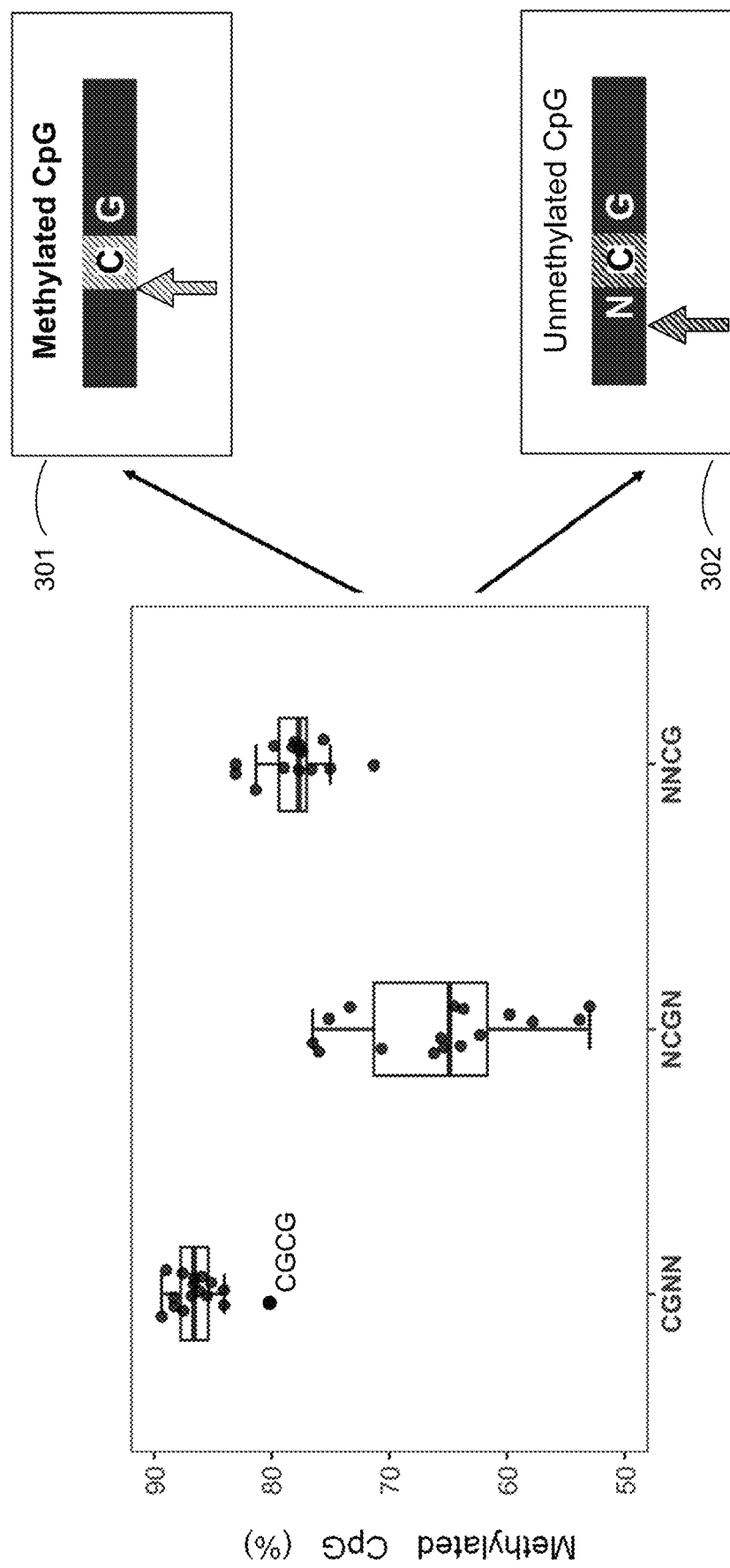
FIG. 3 shows a plurality of 4-mer end motifs and the percentage of methylated CpG sites covered by fragments having the particular 4-mer end motif according to embodiments of the present disclosure.

FIG. 3 shows a plurality of 4-mer end motifs and the percentage of methylated CpG sites covered by fragments having the particular 4-mer end motif according to embodiments of the present disclosure. In FIG. 3, each point represents a specific 4-mer motif. The individual motifs are grouped based on the distance of the cutting position from the CG. As one can see, the CGNN motif still revealed the highest methylation level, and the NCGN motif revealed the lowest methylation level, with NNCG between them.

As illustrated in 301, if CpG site is methylated, then it might be highly preferred to cut exactly at this CG. At 302, if it is unmethylated, it might be cut at one base before this CpG site. This is why we observed that many fragments started with CG are methylated, but many fragments started with NCG are unmethylated.

Accordingly, some embodiments can use an amount of CGN motifs and/or NCG motifs to determine a methylation index of a site or a region that includes multiple sites. Other examples use a cleavage profile (described in more detail below) and the relation of the distances to methylation to determine methylation. The CGN and NCG end motifs can be used to determine a cleavage profile, and a cleavage profile can include counts of CGN and NCG end motifs (also just referred to as motifs).

C. Probe-Based Counting of Certain Ends

In the example above, sequencing was used to determine the amount of fragments ending at certain distances from a CpG site or to determine the end motifs of the fragments. Instead of sequencing, one can used probe-based techniques to measure the amount of CGN (or longer motifs, such as CGNN) relative to NCG. Thus, CGN and NCG frequency from specific regions could be detected through other methods such as qPCR, digital PCR, digital droplet PCR, etc.

Figure 4:
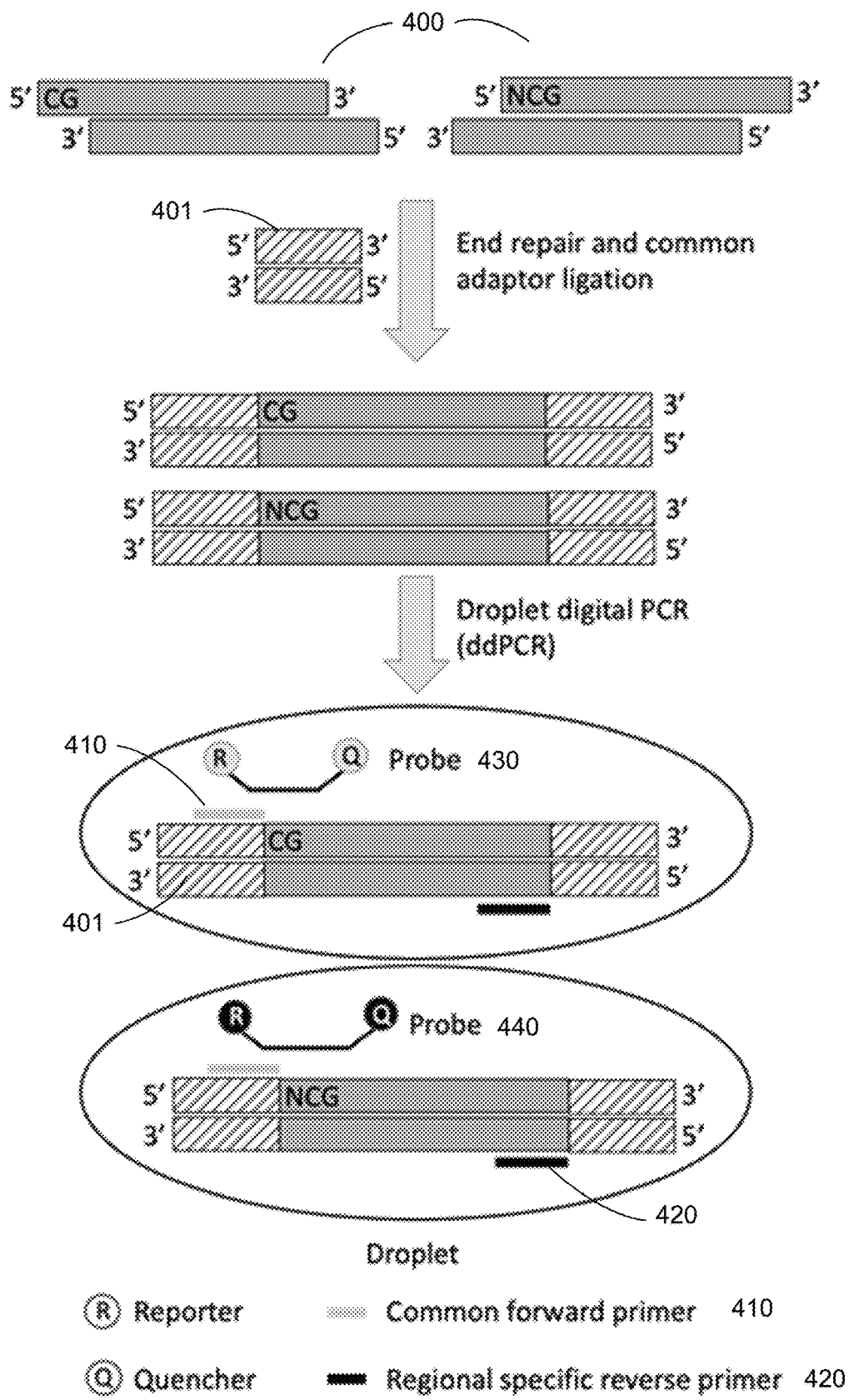
FIG. 4 shows an example for a method using droplet PCR to determine NCG and CGN motifs in regions of interest according to embodiments of the present disclosure.

FIG. 4 shows an example for a method using droplet PCR to determine NCG and CGN motifs in regions of interest according to embodiments of the present disclosure. As shown, cfDNA molecules 400 can be subjected to the process of DNA end pair, A-tailing (adding an A at the end of the fragment), and common adaptor ligation as optional steps. The DNA end repair can make the ends blunted so there is no overhang between the two strands. A common adaptor 401 can be added to the end of the fragments.

The adaptor-ligated molecules can be partitioned, e.g., into different reactions, such as droplets. A pair of PCR primers can be designed in a way that one primer (e.g., common forward primer 410) could bind to the common adaptor 401 and the other (e.g., regional specific reverse primer 420) could bind to the specific region of interest.

DNA molecules would be amplified inside a reaction (e.g., droplet) by the pair of PCR primers. Two different fluorescent probes can be used, e.g., a probe 430 to detect CN ending fragments and a probe 440 for detecting NCG ending fragments. The fluorescent probe specific to a certain end motif (such as CGN or NCG end motif) can be hydrolyzed and emit fluorescent signals, thus enabling the detection of the presence of a specific motif as well as the quantification of a specific motif. For digital PCR, the number of reactions positive for a particular end motif can be counted and used to determine the amount of DNA fragments with that end motif in the region analyzed. For real-time PCR, the intensity of each signal can be used as a measure of an amount of DNA fragments ending with a particular motif. The two intensities can be compared to each other D. Targeted Sequencing for CGN and NCG Another example technique for analyzing fragmentation is targeted sequencing, e.g., by amplifying DNA fragments having a sequence corresponding at least partly from one or more regions of interest and/or using capture probes that select such DNA fragments. Certain DNA molecules having particular end motifs corresponding to particular distances from the CpG site to the end of the fragment can be amplified. The targeted sequencing approach can be utilized to determine cfDNA fragmentomic features from regions of interest in a cost-effective manner. Targeted sequencing approach could increase the depth of regions of interest, thus improving the accuracy for methylation analysis. The CGN and NCG motif-containing DNA fragments can be enriched during sequencing library preparation. This amplification makes the sequencing more efficient, since most of the sequence reads would include CGN and/or NCG motifs.

Figure 5:
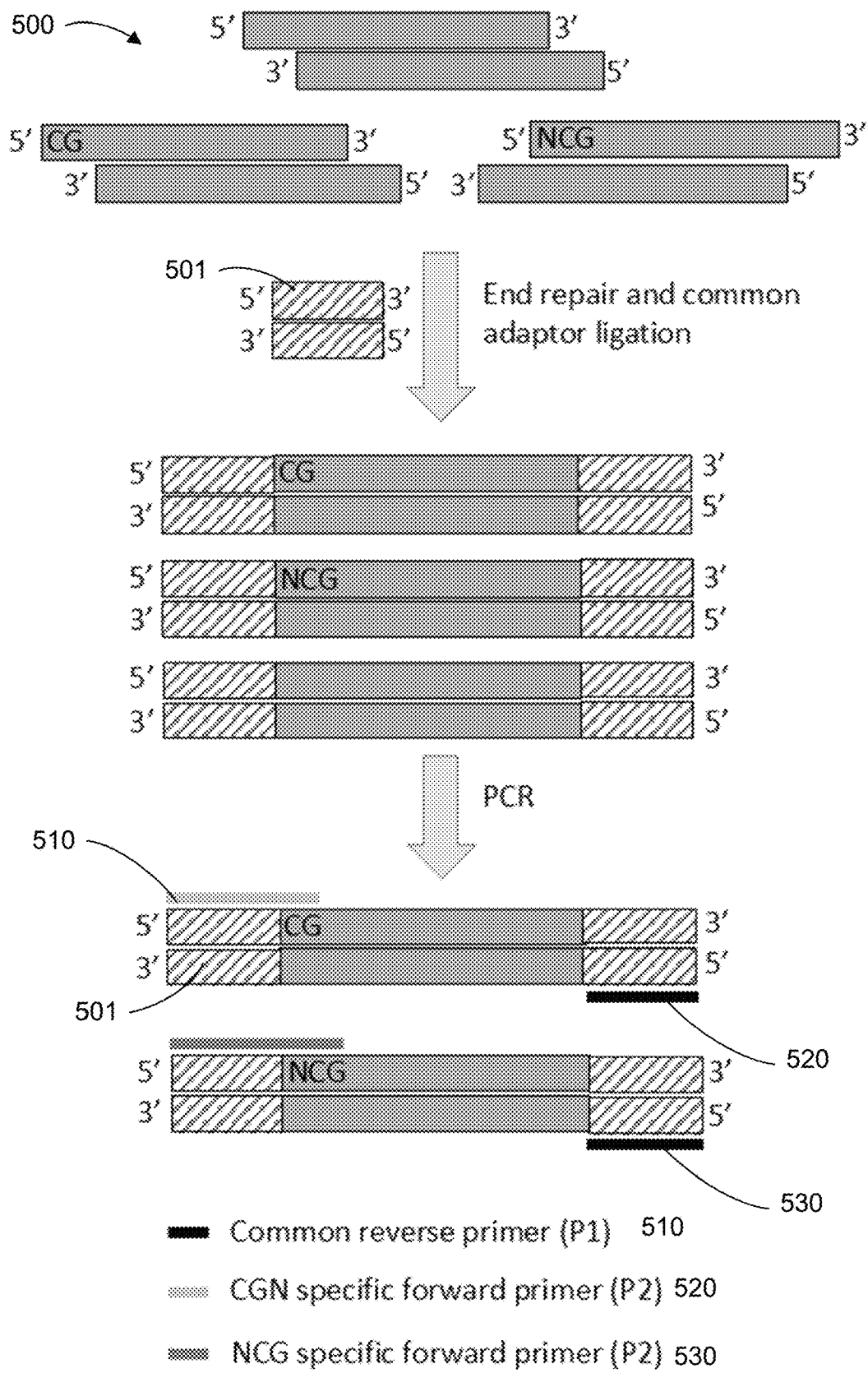
FIG. 5 is an example workflow for the sequencing library preparation by selectively amplifying DNA containing NCG or CGN end motifs according to embodiments of the present disclosure.

FIG. 5 shows an example workflow for the sequencing library preparation by selectively amplifying DNA containing NCG or CGN end motifs according to embodiments of the present disclosure. As shown, the cfDNA molecules 500 can be subjected to the process of DNA end pair, A-tailing, and common adaptor ligation as optional steps, as described above. A pair of PCR primers can be designed in a way that one primer 510 could bind to the common adaptor region 501 (P1), and the other primer 520 or 530 could bind to the junctional region between the DNA and the common adaptor (P2). By controlling the last bases in the 3'-end of the P2 to be CG (primer 520) or NCG (primer 530), i.e., ACG, CCG, TCG, GCG, one can selectively amplify DNA fragments containing CG- or NCG-end motifs.

Those libraries would be subsequently sequenced. Such sequenced reads would be used for performing the analysis of CGN and NCG end motifs, allowing the determining of methylation levels, patterns (e.g., levels at different sites or regions), as well as differences. Moreover, selective amplification of DNA fragments containing CGN or NCG end motif might enrich reads mapping to regions with different methylation levels, e.g., from different tissues within the body, from tumoral versus non-tumoral origin, or from fetus versus maternal in pregnancy.

II. Example Use Cases of Using Cleavage Profiles and End Motifs cfDNA is a mixture containing DNA molecules derived from different origins, which could have different methylation statuses in one or more CpG sites. Different methylation statuses would affect plasma DNA fragmentation patterns during the release of DNA molecules into plasma due to cell death (e.g., via apoptosis) or other mechanisms (e.g., active secretion). Different methylation statuses might also affect the clearance of cell-free DNA molecules. Therefore, the use of cfDNA fragmentation patterns will allow for deducing the methylation status of CpG sites. The influence on cfDNA fragmentation patterns due to methylation status on a CpG would involve plasma DNA cleavages across a series of genomic positions nearby or distal to that CpG site, which could be mediated by one or more DNA nucleases such as DNASE1 and DNASE1L3.

Figure 6:
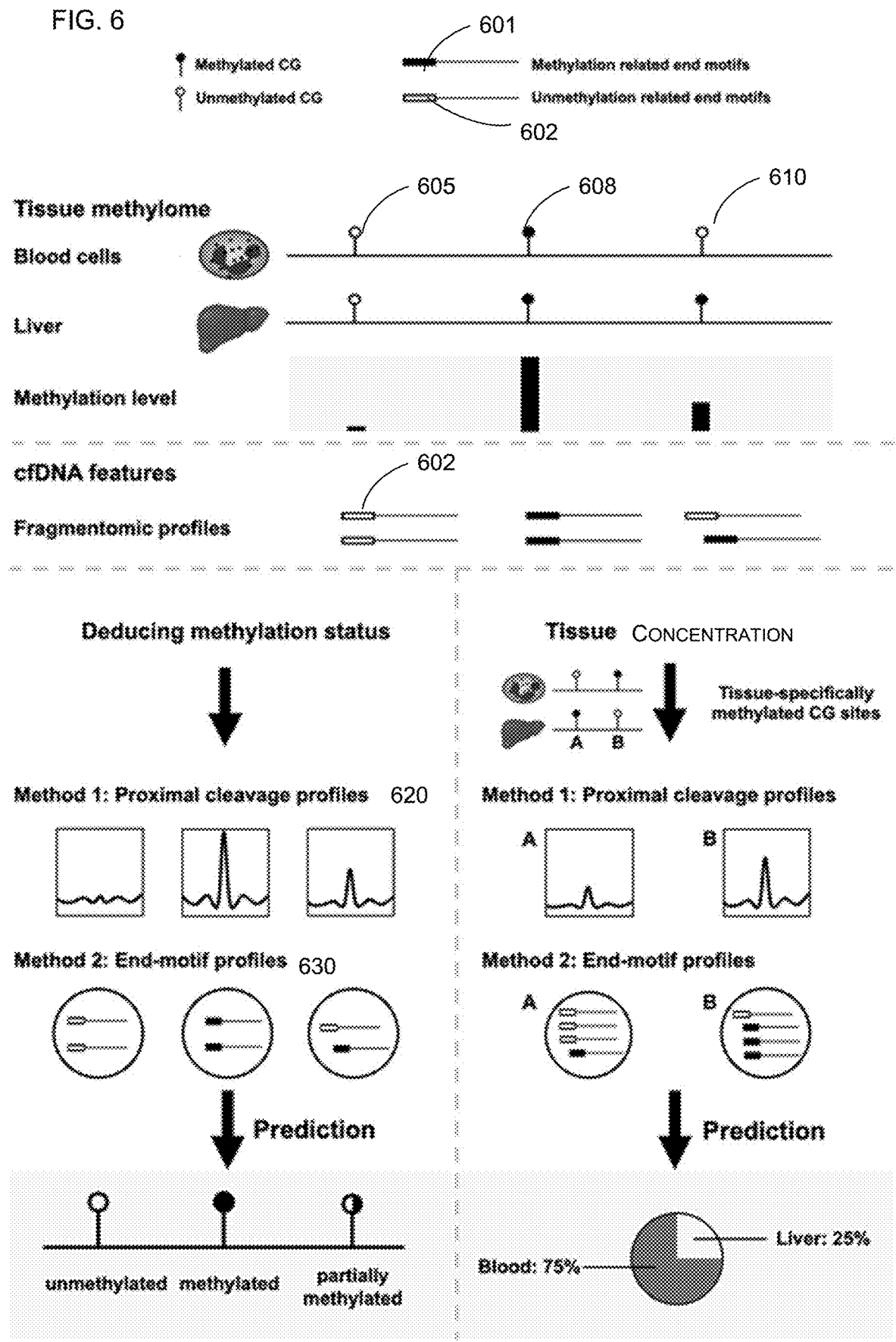
FIG. 6 shows a schematic illustration for the methylation status deduction based on fragmentation patterns according to embodiments of the present disclosure.

FIG. 6 shows a schematic illustration for the methylation status deduction based on fragmentation patterns according to embodiments of the present disclosure. DNA from different tissues will have different methylomes. For example, blood cells will have different methylation at sites than liver, as shown for site 610. In these three CpG sites, blood cells have different levels of methylation and liver tissues will have different methylation levels, namely UMU for blood and UMM for liver.

Both tissues will contribute cell-free DNA in plasma, which will make a cell-free DNA methylation level different in each site. For example, if the first site is hypomethylated in both tissues, then in the cell-free DNA, the methylation level will be quite low. Whereas if they are both methylated, then the cell-free DNA methylation level will be high. And if one is methylated and one is not, then you will get a CpG site which is partially-methylated. Such a scenario is shown for the methylation levels in FIG. 6. The methylation level shows an aggregate level as may be measured in plasma in light of the example methylation patterns depicted for blood cells and liver.

In the meantime, both tissues (and other tissues in the body) also contribute their cell-free fragmentomic features into the plasma. So, if the first site is hypomethylated, there will be more unmethylated motifs (e.g., NCG) and the cutting will be more random; whereas in the second site, if they are both hypermethylated, there will be more methylated motifs (CGN). Thus, the end motifs and the cleavage profile will be a mixture of the tissues, and this information can actually deduce the methylation status of each site based on their profiling. This is shown in the section on cfDNA features where site 605 has unmethylation related end motifs 602, and site 608 has methylation related end motifs 601.

FIG. 6 also shows two methods to deduce methylation status. A method 620 uses the cleavage profiles, and a method 630 uses end motif profiles.

The cleavage profile can correspond to an amount of DNA fragment ending at positions around the CpG site. Using the methylation pattern in this example, the site that is methylated in both tissues has the highest peak. For unmethylated sites, there is no peak. For highly-methylated sites, there is a high peak. For partially-methylated sites (e.g., only methylated in some tissues), there is a lower peak. As shown, one could use the cleavage profile related to a CpG site to predict its aggregated methylation index of plasma DNA molecules derived from different tissues such as the liver, lung, colon, small intestines, lymphocytes, neutrophils etc. The cleavage profile could be defined as, but not limited to, the amount of fragment ends at each position across a number of genomic positions surrounding a CpG site being analyzed (also referred to as cleavage measurement window). The number of genomic positions (referred to as window size) could be, but not limited to, 1 nt, 2 nt, 3 nt, 4 nt, 5 nt, 6 nt, 7 nt, 8 nt, 9 nt and 10 nt or above. The amount of fragment ends could be normalized values such as but not limited to the number of fragment ends divided by the sequencing depth at each position.

Method 630 can use end-motif profiles to predict the methylation levels in plasma. If the methylation level is lower (e.g., first site shown), there will be more unmethylated-related end motifs. If the methylation level is higher, there will be more methylated-related end motifs. Using these two signals, one can predict whether a CpG site or a region is unmethylated, highly methylated, or is partially methylated. The end motif profiles of a genomic region of interest (i.e., regional end motif profiles) could be used to deduce its corresponding methylation density (e.g., the percentage of sequenced CpGs determined to be methylated).

Because methylation is tissue-specific and because the fragmentomic features reflect methylation, the methylation can further reflect the tissue of origin. The fragmentomic features can be used directly (or used to determine methylation that in turn is used) to determine a fractional concentration of a particular tissue type (e.g., using tissue deconvolution if determining multiple tissue concentration), which can provide a fractional concentration of DNA from a particular tissue (e.g., of clinically-relevant DNA). The cleavage profiles and the end motif profiles can be used to estimate the fraction for a particular tissue. Accordingly, methylation associated cfDNA fragmentomic features, such as the cleavage profile and the motif profile, can be used to deduce the contribution (fractional concentration) of cfDNA from different tissues of origin.

Some embodiments can also use the fragmentomic features to deduce whether a pathology (e.g., a disease such as cancer) is present or not.

III. Predicting Methylation at a Site Based on Fragmentation

This section describes techniques to predict a methylation index at a single CpG resolution in a genome using the cleavage profile. A cleavage profile can be determined in various ways, including using certain end motifs, such as CGN end motifs. Example definitions and results are provided below. The results are consistent regardless of how the cleavage profile is defined, e.g., type of normalization used.

A. Normalization by Total Reads Covering the Position

The cleavage profile was constructed according to the cleavage ratio across genomic coordinates within a measurement window related to a CpG site. The cleavage ratio at a position within the measurement window of interest could be calculated by the below formula:

$$\text{cleavage ratio} = \frac{\text{the } no. \text{ of fragment ends}}{\text{sequencing depth}} \times 100\%.$$

Thus, in this example, the cleavage ratio is defined as the number of ends at a position over a number of reads covering that site (sequencing depth).

Figure 7:
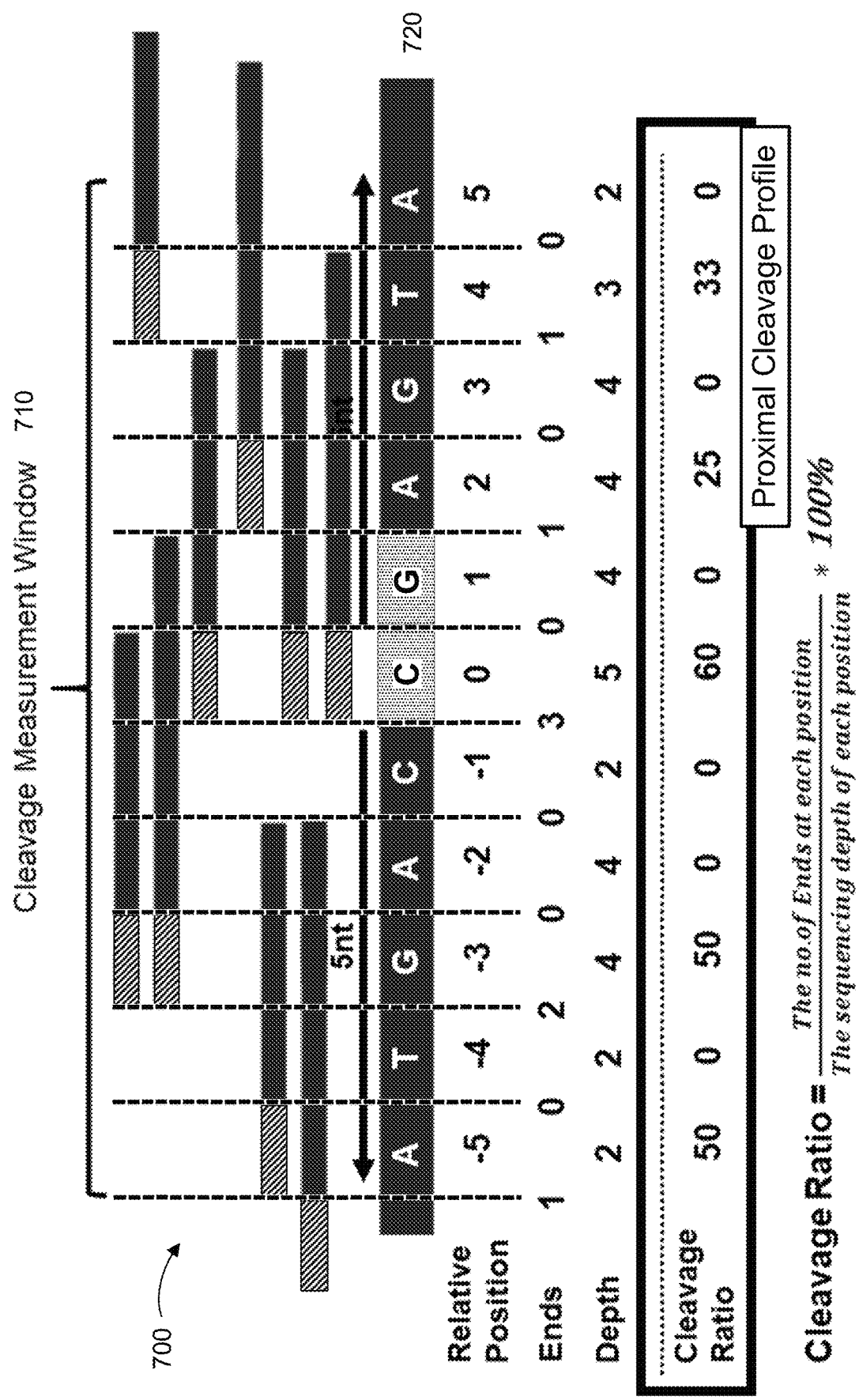
FIG. 7 illustrates a definition of a cleavage profile using a cleavage ratio according to embodiments of the present disclosure. Figure discloses SEQ ID NO: 6.

FIG. 7 illustrates a definition of a cleavage profile using a cleavage ratio according to embodiments of the present disclosure. A cleavage measurement window 710 of width 11 is shown, but other widths can be used. A set of cell-free DNA fragments 700 is shown above a reference sequence 720. The relative positions are with respective the C of the CpG site. The row marked "Ends" shows the number of cell-free DNA fragments that end at that particular base position. The row marked "Depth" shows the number of the cell-free DNA fragments that overlap with that base position. The cleavage ratio is provided using the equation shown.

The C of the CpG site is at the 0 position, which corresponds to the CGN end motif. The positions −5 to −1 are upstream. The −1 position corresponds to the NCG end motif. The G is at position 1 and the other four are downstream, up to 5. These positions are the cleavage measurement window 710. Within the window, we map all the cell-free fragments inside. For each position, we calculate how many fragments end at that position. This is shown in the row labeled as "Ends."

We then calculate the depth for each position. For the A at position −5, there are two fragments mapped to that position, so the depth is two. Since position −5 A has one fragment ending at that position and a depth of two, then the cleavage ratio will be 0.5 (or 50%).

1. Cleavage Profile for CG

A cleavage profile is analyzed for two sets of CG sites: putative unmethylated and putative methylated. As most of the cfDNA molecules in healthy participants is derived from leukocytes (Sun et al. Proc Natl Acad Sci USA. 2015; 112:E5503-5512), 1,000 putative methylated CpG sites (beta value >0.8) and 1000 putative unmethylated CpG sites (beta value <0.1) were identified based on a publicly available Illumina HumanMethylation450 BeadChip data of leukocytes (GSE40279). If a site was methylated in the leukocytes, then it was assumed to be putatively unmethylated. To investigate how methylation affected cfDNA fragmentation, the cleavage profile of the 1,000 putative unmethylated CpG sites and 1,000 putative methylated CpG sites were analyzed for 8 healthy control cfDNA samples, with a median number of 381 million paired-end sequencing reads (interquartile range: 353-404 million). One can also use the probe-based techniques mentioned herein, including targeted sequencing. The "putative" means that methylation is derived from the loci array data, which is from a publicly available database.

Figure 8:
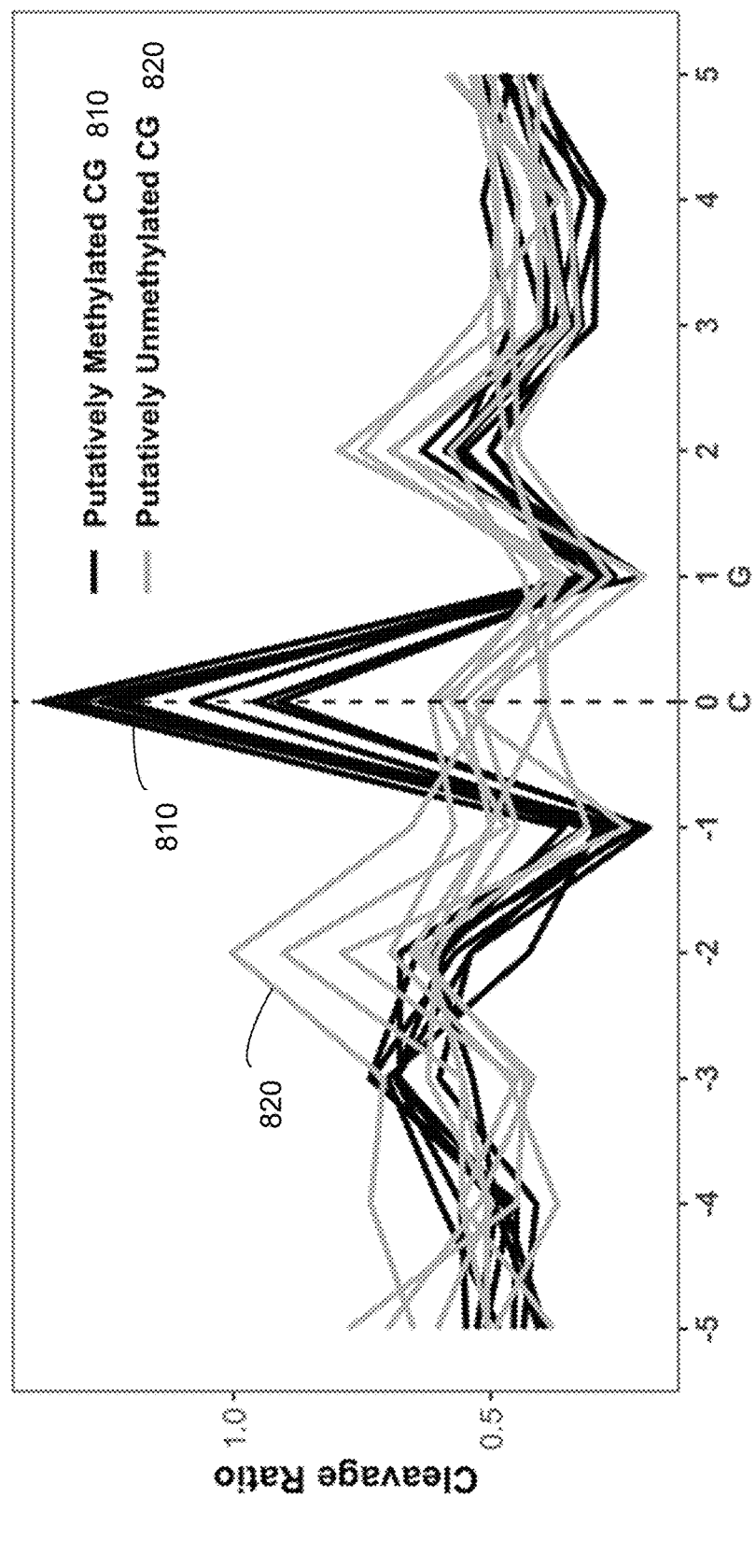
FIG. 8 shows a comparison of cleavage profiles between methylated and unmethylated CpG sites according to embodiments of the present disclosure.

FIG. 8 shows a comparison of cleavage profiles between methylated CpG sites 810 and unmethylated CpG sites 820 according to embodiments of the present disclosure. The x-axis represents the nucleotide positions relative to a CpG site within a measurement window. As an example, the window herein was defined as 5 nucleotides (i.e., 5-nt) upstream and downstream of the C base in a CpG site (i.e., window size was 11 nt).

The y-axis represents the mean cleavage ratio. For each sample, the cleavage profile from putative methylated CpG sites or putative unmethylated CpG sites were merged by calculating the mean cleavage ratio of each position within the 11-nt window. As shown, the merged cleavage profiles of putative methylated CpG sites showed a higher cutting preference at the position '0' (i.e., the cytosine nucleotide of the CpG site in question) (median cleavage ratio: 1.24; range: 0.91-1.37) than putative unmethylated CpG sites (median cleavage ratio: 0.54; range: 0.39-0.62) (P value=0.00016, Mann-Whitney U test). Thus, once the C is methylated, the cutting is quite preferred at C; whereas when the C is unmethylated, the cutting is not preferred at the C.

2. Cleavage Profile for Other Sequence Contexts

In addition to the methylation status, the sequence context might affect the cleavage profile. To study the influence of the sequence context, the merged cleavage profiles related to methylated and unmethylated CpG sites were determined from a set of cleavage measurement windows for which the position '–1' corresponded to the cytosine nucleotide, namely, "CCG" subsequence (a total of 6,928,652 measurement windows).

Figure 9:
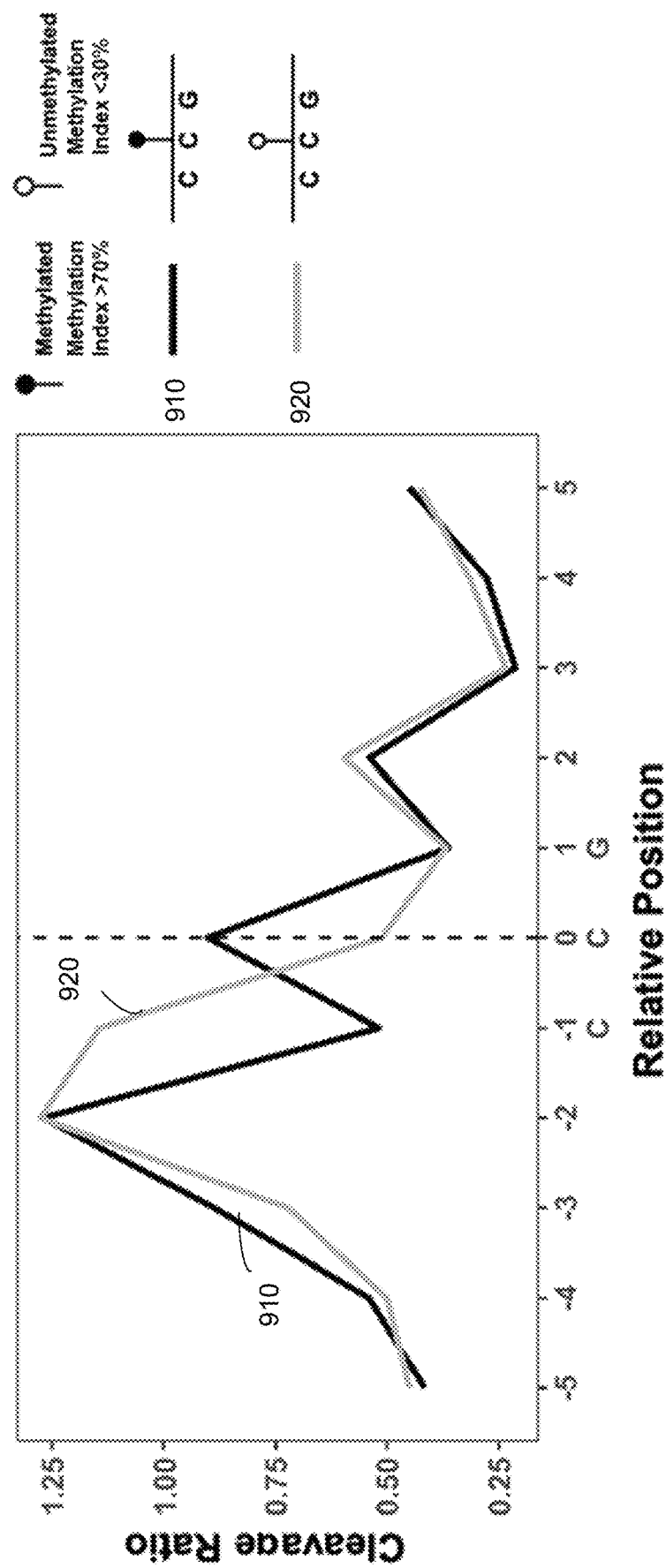
FIGS. 9-10 show cleavage profiles of windows associated with different sequence contexts including CCG and methylation status according to embodiments of the present disclosure.
Figure 10:
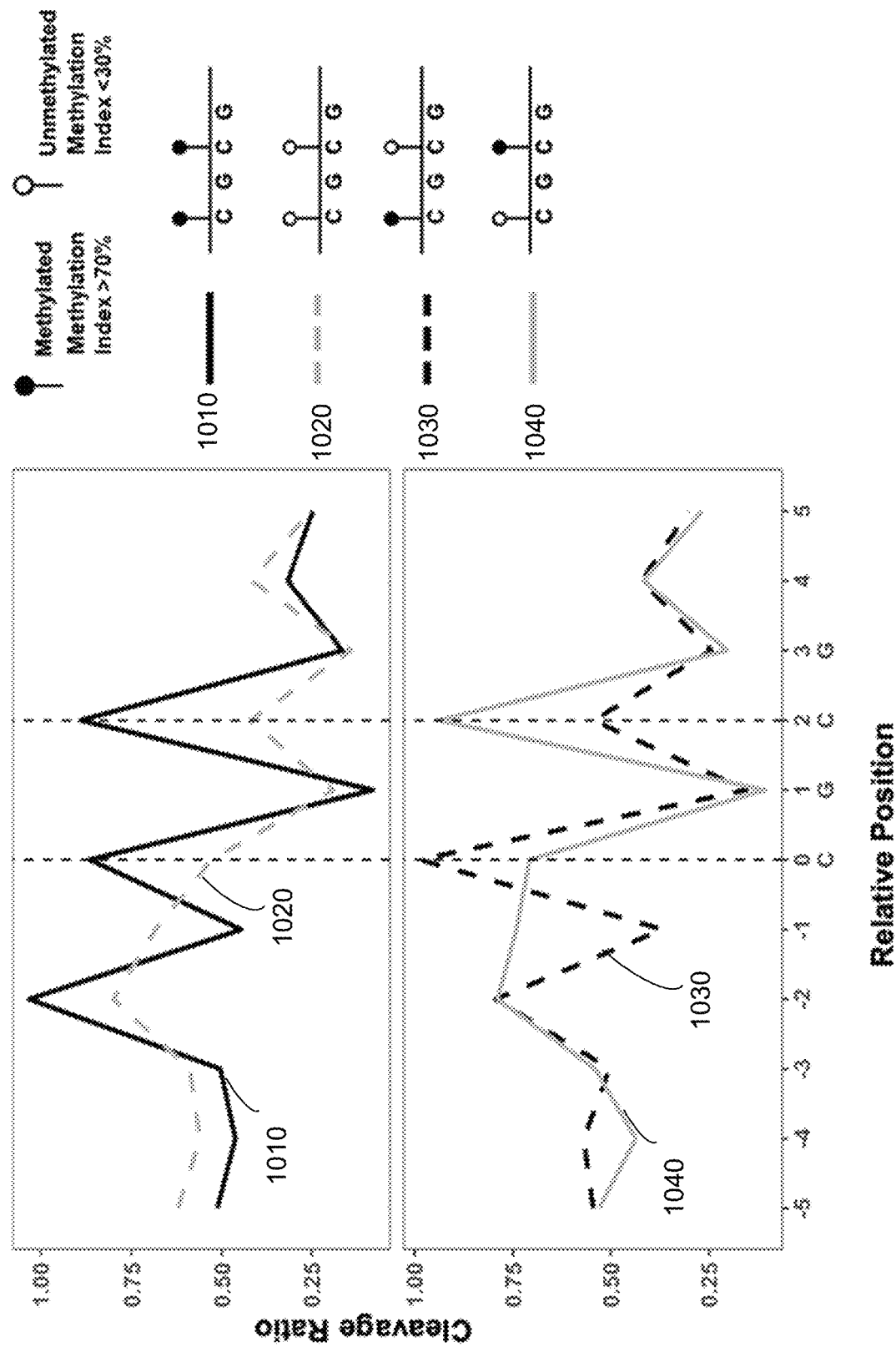

FIGS. 9-10 shows cleavage profiles of windows associated with different sequence contexts including CCG and methylation status according to embodiments of the present disclosure. This data is generated using bisulfite sequencing results from one healthy control sample as an example (391 million paired-end sequencing reads).

FIG. 9 shows the merged cleavage profiles of windows contain C, C, and G nucleotide at the positions of –1, 0 and 1. The black line 910 represents the merged cleavage profiles of windows contain methylated C at the position 0, and the grey line 920 represents those of windows containing unmethylated C at the position 0. In this example, the methylated status (denoted by M) was defined by those CpG sites whose methylation index was greater than 70%, whereas the unmethylated status was defined by those CpG sites whose methylation index was less than 30% (denoted by U).

The cleavage ratio at the position of '0' appeared to be much higher at methylated CpG sites (0.90%) than those unmethylated (0.51%). When the C is methylated, the cutting is preferred at the C; while the C is unmethylated, the cutting is not preferred at that C.

FIG. 10 shows the merged cleavage profiles of 615,465 windows containing C, G, C, and G nucleotide at the positions 0, 1, 2 and 3 (i.e., CGCG subsequence). The cleavage profiles were classified into four groups according to the methylation patterns of the two CpG sites regarding the CGCG subsequence, namely "MM", "MU", "UM", and "UU". The black solid line 1010 represents the merged cleavage profiles of windows containing methylated C at positions 0 and 2, and the grey dash line 1020 represents those of windows containing unmethylated C at positions 0 and 2. The black dash line 1030 represents the merged cleavage profiles of windows containing methylated C at position 0 and unmethylated C at position 2, and the grey solid line 1040 represents those of windows containing unmethylated C at position 0 and methylated C at position 2.

A relatively high cleavage ratio was observed in both cytosine positions of CGCG subsequence for the group of "MM" (cleavage ratios of 0.86 and 0.89, respectively) compared with the group of "UU" (cleavage ratios of 0.53 and 0.42, respectively). When the methylation status of those 2 CpG sites were different (i.e., the groups of "MU" and "UM"), the relative high cleavages tended to occur at the methylated cytosine. These data suggested that the cleavage profile was related to the methylation patterns across a series of different CpG sites. Accordingly, the cleavage profile can be used for deducing the methylation patterns across a series of different CpG sites.

3. CGN/NCG Ratio for Different Sequence Contexts

We have showed that the CGN and NCG motifs can be used to reflect the methylation status of the CpG that was immediately adjacent to the cleavage site of interest, e.g., in FIGS. 2-3. And FIG. 10 shows cleavage patterns for two CpGs that are next to each other (i.e., in tandem).

To understand the relationship between the cfDNA cleavage patterns and the methylation states across adjacent several CpGs, we analyzed the CGN/NCG motif ratios across different combinations of methylation states for those molecules multiple adjacent CpG sites. The CGN/NCG motif ratio corresponds to a ratio of an amount of DNA fragments with the CGN motif and an amount of DNA fragments with the NCG motif. Here we defined adjacent CpGs as those CpG sites located within a range of 75 bp in size but not in tandem. In other embodiment, adjacent CpGs can be defined as CpG sites located within a range of but not limited to 5 bp, 10 bp, 20 bp, 30 bp, 40 bp, 50 bp, 100 bp, 200 bp, 500 bp, 600 bp, 1000 bp and so on. In yet another embodiment, tandem CpGs can be used. As the majority of cfDNA molecules (~93.5%) contain the number of CpG sites no more than 3 in each molecule within the 75-bp range, we analyzed the CGN/NCG motif ratios across different combinations of methylation states for those molecules with 2 and 3 CpG sites, respectively.

Figure 11:
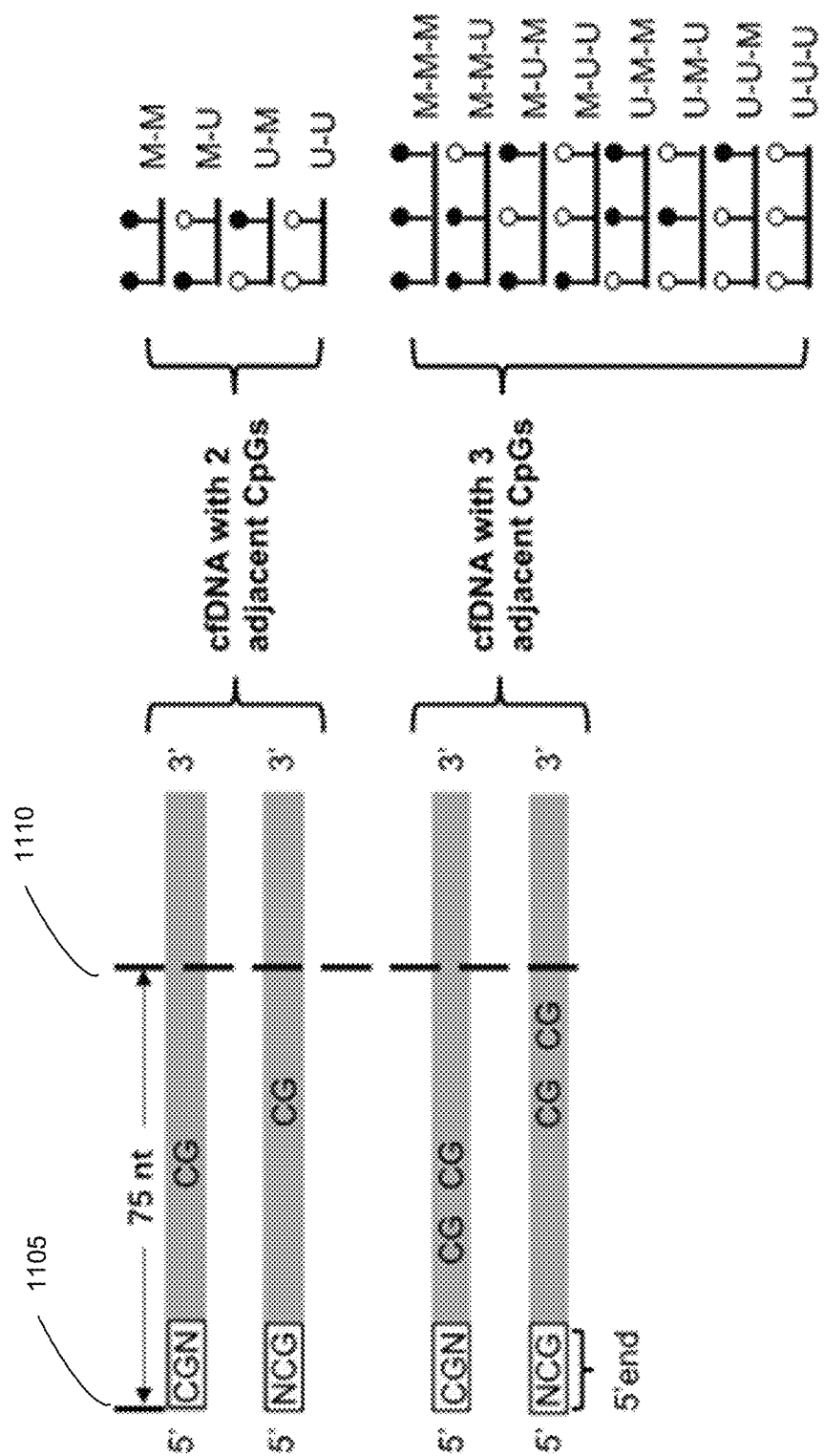
FIG. 11 shows a schematic for a cfDNA grouping at nearby CpG sites.

FIG. 11 shows a schematic for a cfDNA grouping at adjacent CpG sites. The cleavage site 1105 is on the left at the 5' end. In this example, the range 1110 is 75 nt. The first two examples show DNA fragments with two CpG sites. The last two examples show DNA fragments with three CpG sites. The right side shows the different combinations of methylation statuses.

For cfDNA molecules with 2 CpGs, there were a total of 4 combinations of methylation states. One combination could be the situation where the methylated CpG at 5' end was followed by a methylated CpG (denoted by "M-M", where 'M' represents the methylated CpG and '-' represents any one or more nucleotides). The other combinations could be "M-U", "U-M", "U-U", where 'U' represents the unmethylated CpG. For cfDNA molecules with 3 CpGs, there were a total of 8 combinations of methylation states, namely, "M-M-M", "M-M-U", "M-U-M", "M-U-U", "U-M-M", "U-M-U", "U-U-M", and "U-U-U."

Figure 12B:
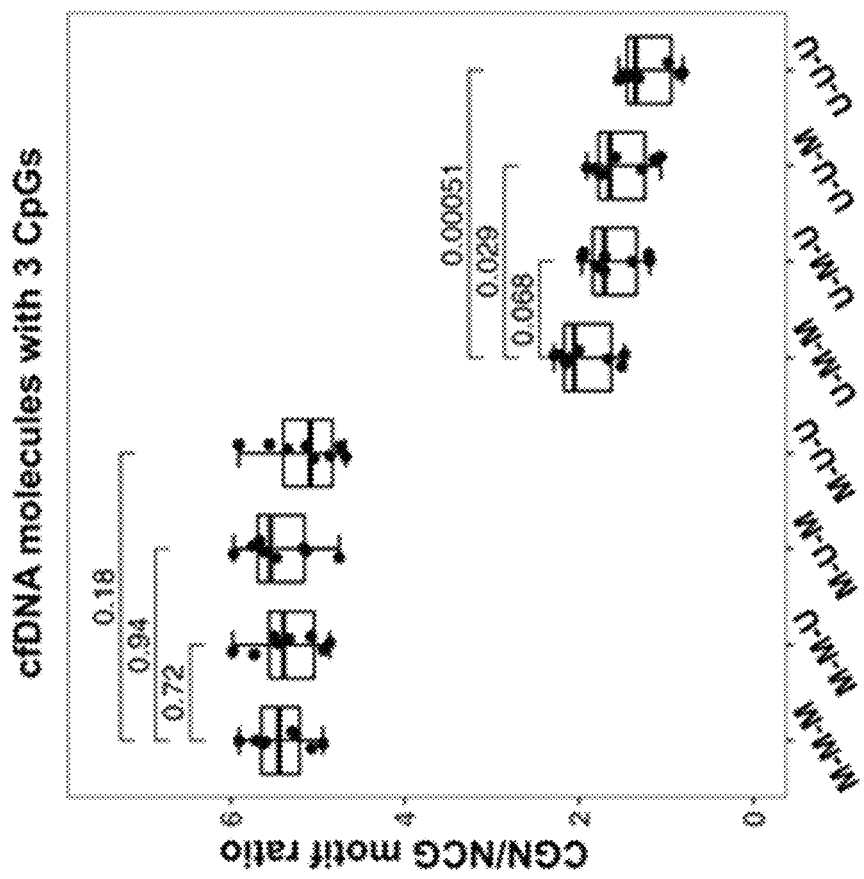
FIGS. 12A-12B show the impact of methylation patterns with multiple adjacent CpGs on CGN/NCG motif ratio.
Figure 12A:
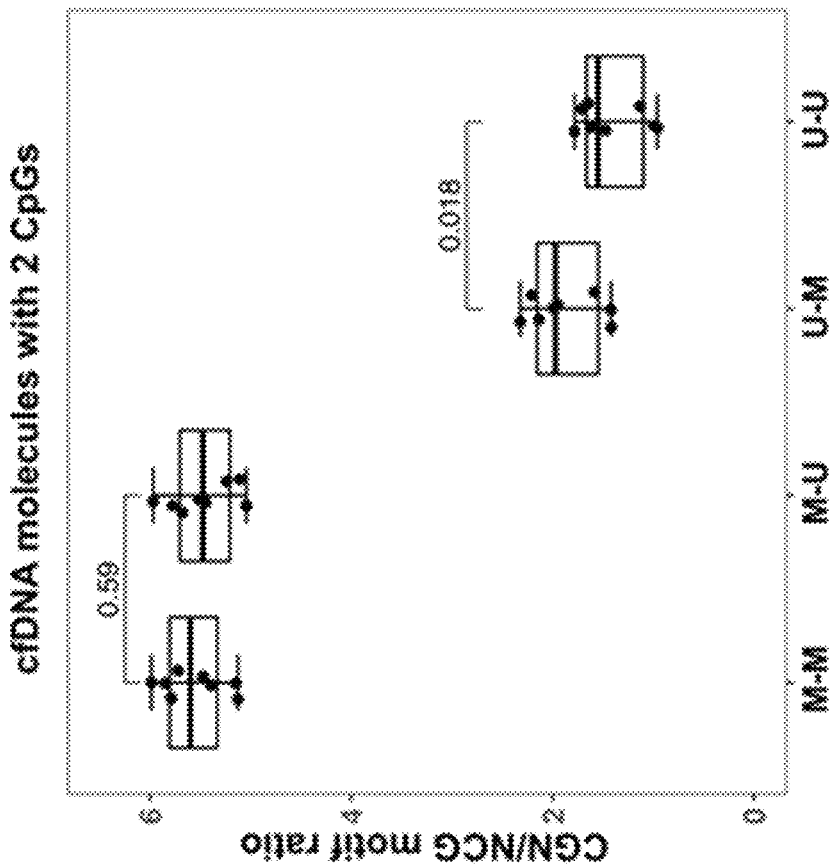

FIGS. 12A-12B show the impact of methylation patterns with multiple adjacent CpGs on the CGN/NCG motif ratio. As shown in FIGS. 12A-12B, the CGN/NCG motif ratio was significantly higher in those cfDNA molecules starting with the methylated CpG at 5' end (i.e., "M-M", "M-U", "M-M-M", "M-M-U", "M-U-M", and "M-U-U"), compared with molecules starting with the unmethylated CpG at 5' end (i.e., "U-M", "U-U", "U-M-M", "U-M-U", "U-U-M", and "U-U-U"). This is similar to the behavior for a single CpG site, which indicates the dominant effect is the end motif at the cleavage site of interest.

Interestingly, the cleavage of molecules starting with the unmethylated CpG at 5' end seemingly was relatively enhanced by the presence of methylation of the adjacent CpGs. For instance, for those molecules with 2 CpG sites, the "U-M" group showed an increase of ~27.9% in the CGN/NCG motif ratio than the "U-U" group (P value=0.018) (FIG. 12A).

Additionally, for those cfDNA molecules with 3 CpGs starting with the unmethylated CpG at 5' end, there was a gradually decreasing trend of the CGN/NCG motif ratio as the more adjacent CpGs turned unmethylated. The "U-M-M" group showed an increase of ~20.6%, ~25.0% and ~52.2% in the CGN/NCG motif ratio, when compared with "U-M-U", "U-U-M", and "U-U-U" group, respectively (FIG. 12B).

Thus, the methylation status of the CpG that was immediately adjacent to the cleavage site of interest showed more pronounced impact on the cfDNA cleavages than those CpG sites away from the cleavage site. Additionally, the data also suggested that the cleavage of the CpG at the 5' end might at least in part be affected by the methylation status of adjacent CpGs. This finding may have some potential applications.

In one embodiment, one could use 5'end CGN and NCG motif to deduce the methylation index of several adjacent CpGs in a reference genome. Although using the end motifs at the cleavage site of interest is optimal, there may be insufficient number of DNA fragments ending at that site, e.g., as the CpG site might be within a nucleosome so the DNase might have less opportunity to cut at such a site. In such a case, one infer the methylation status based on the CGN/NCG at a CpG site that is upstream. For instance, as shown, a motif ratio around 2 would indicate that the next CpG site is methylated, whereas a motif ratio of around 1.7 would indicate that the next CpG site is unmethylated. Thus, the motif ratio at the cleavage site can determine the methylation index at the cleavage site but also the methylation index at one or two CpG sites that are downstream.

In another embodiment, the cfDNA cleavage patterns associated with one or more adjacent CpGs can be used to enhance the power of the diagnosis of pathological conditions. For example, one could use cfDNA cleavage patterns associated with a number of CpGs within a certain nucleotide distance that showed identical methylation patterns to facilitate the diagnostic marker selection. As another example, the fragmentomic features derived from cancer-specific hypomethylated markers can be used for cancer diagnosis. In some instances, the use of cleavage patterns across CpG sites with adjacent hypomethylated CpGs can outperform the use of CpGs with adjacent hypermethylated CpGs B. Normalization by Total Ends in Region Another example for normalization uses the number of fragments ending in a region around the site. The region can be the same or different than the window used to determine the cleavage profile.

Figure 13:
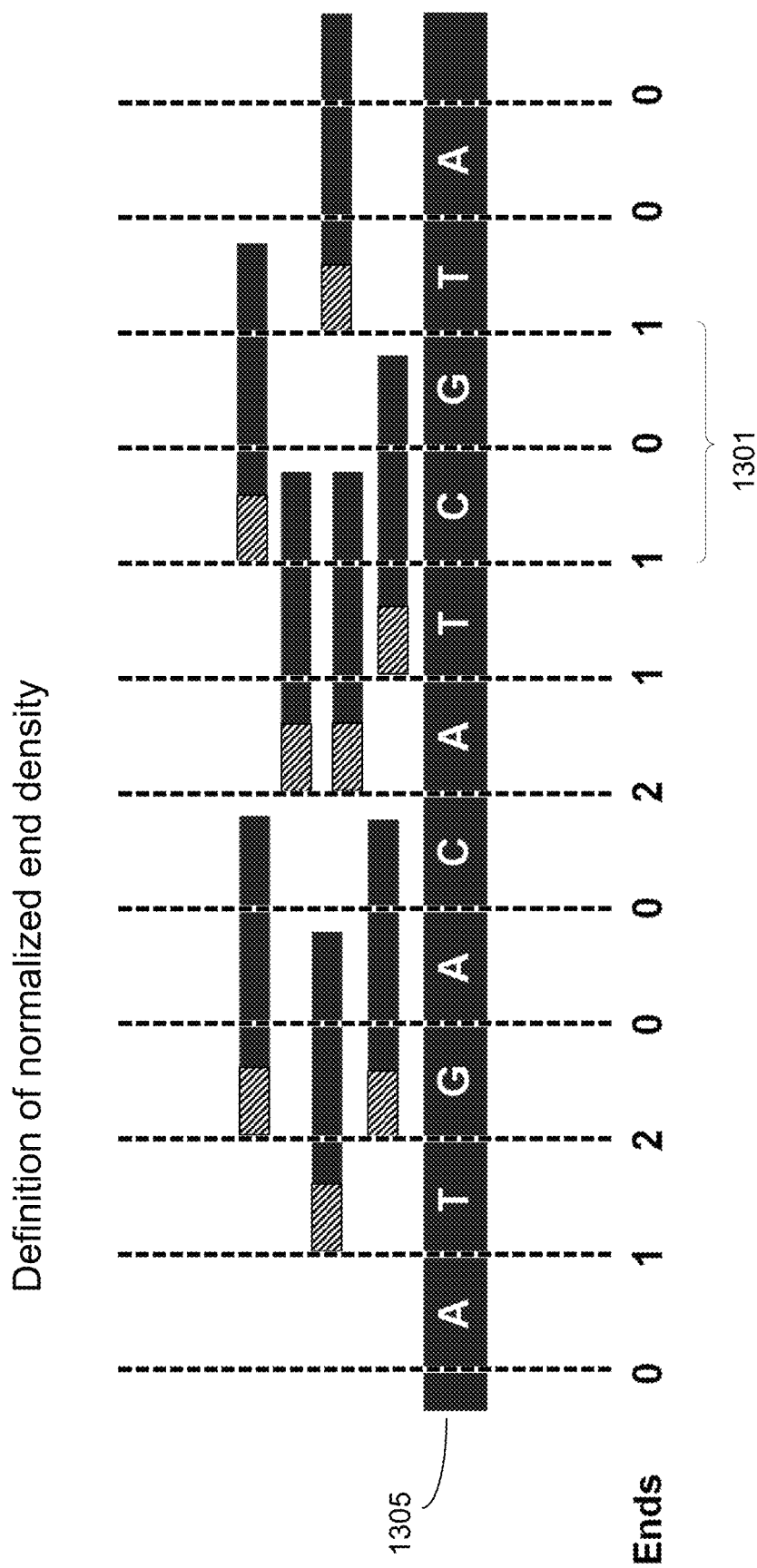
FIG. 13 illustrates a normalization for a cleavage profile using a normalized cleavage density according to embodiments of the present disclosure. Figure discloses SEQ ID NO: 7.

FIG. 13 illustrates a normalization for a cleavage profile using a cleavage density according to embodiments of the present disclosure. The black bar 1305 shows a reference genome that contains a CG 1301. As with the example using the cleavage ratio, to deduce the methylation status of the CpG site, we can calculate how many fragments ended at this CpG site. For the normalization, we divided the numbers of ends at each position divided by the total ends in this whole region. This is another example technique that may be used to normalize amount of DNA fragments with a particular end motif or end at a particular position.

A similar analysis is performed to determine profiles for various CpG sites for the cleavage density as was done for the cleavage ratio. For example, an analysis of one CG, 2 CGs, and 3 CGs is performed. The sequencing analysis uses merged data from multiple samples to obtain higher sequencing depths. A site is methylated if the methylation index is greater than a first threshold (80% in this example), and a site is unmethylated if the methylation index is less than a second threshold (30% in this example). If the methylation index for a site is in between the threshold, then it is not used for this example. In other implementations, a middle classification can be used.

Figure 14:
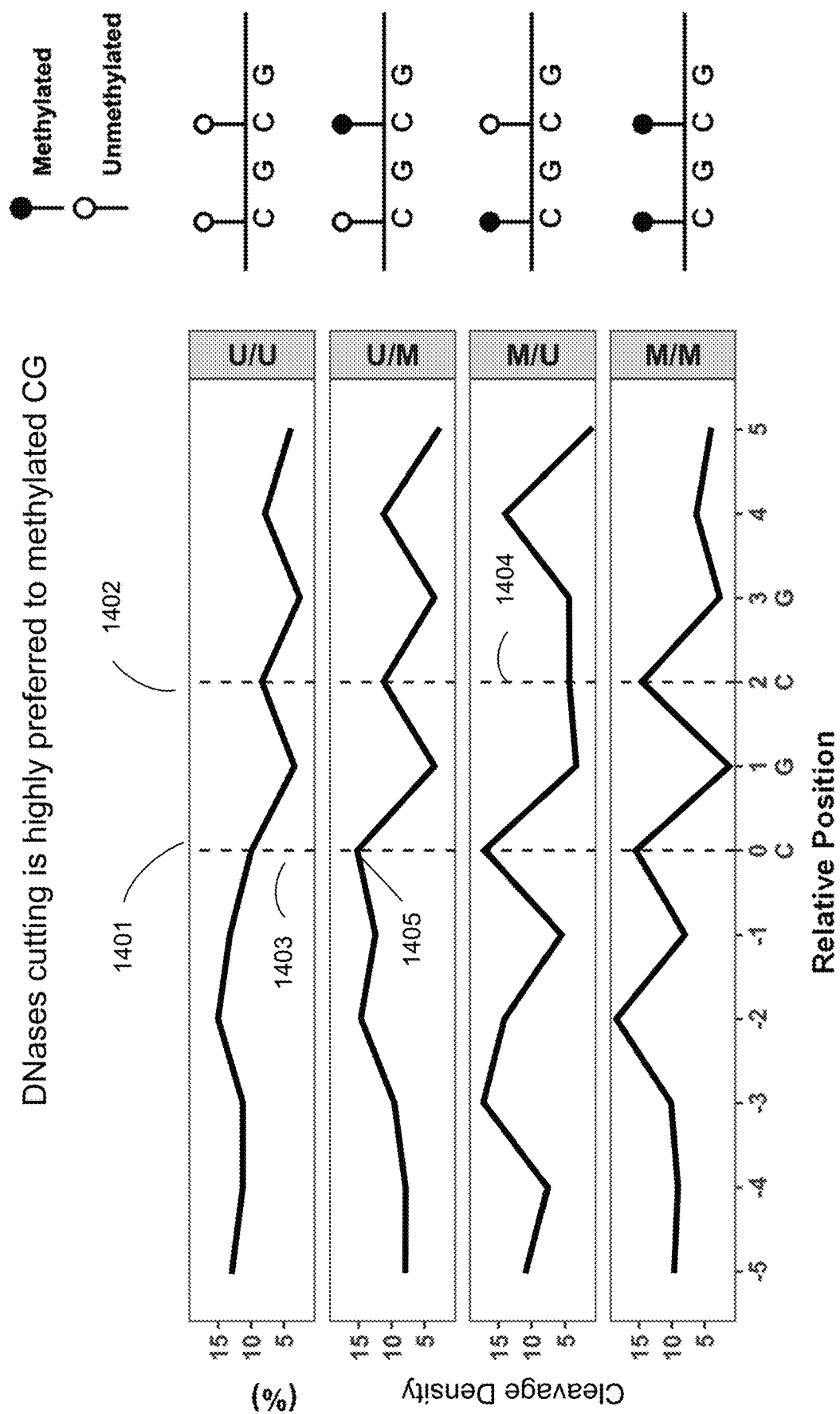
FIG. 14 provides cleavage profiles using a cleavage density for various methylation combination of two CpG sites according to embodiments of the present disclosure.

FIG. 14 provides cleavage profiles using a cleavage density for various methylation combination of two CpG sites according to embodiments of the present disclosure. The CpG sites are tandem in this example, like in FIG. 10. There are four groups by the methylation status of the first CG and the second CG. There two dashed lines 1403 and 1404 represent the positions of these two cytosines.

As one can see, in the upper two profiles, the first C 1401 is unmethylated and there is no peak at C 1201. But in the bottom two profiles, the first C is methylated, and there is a dramatic increase from −1 to the 0 position. The second CG is methylated for the second profile and the fourth profile. In these profiles, there is a peak for the second C 1402. The second CG is unmethylated for the first profile and the third profile and the peak is low or disappeared. As to the cleavage density 1405, it has a high value. But there is no relative increase. The relative increase is more important to deduce the methylation status, rather than the exact number at a position. These results are consistent with the results in FIG. 10 using the cleavage ratio.

Figure 15:
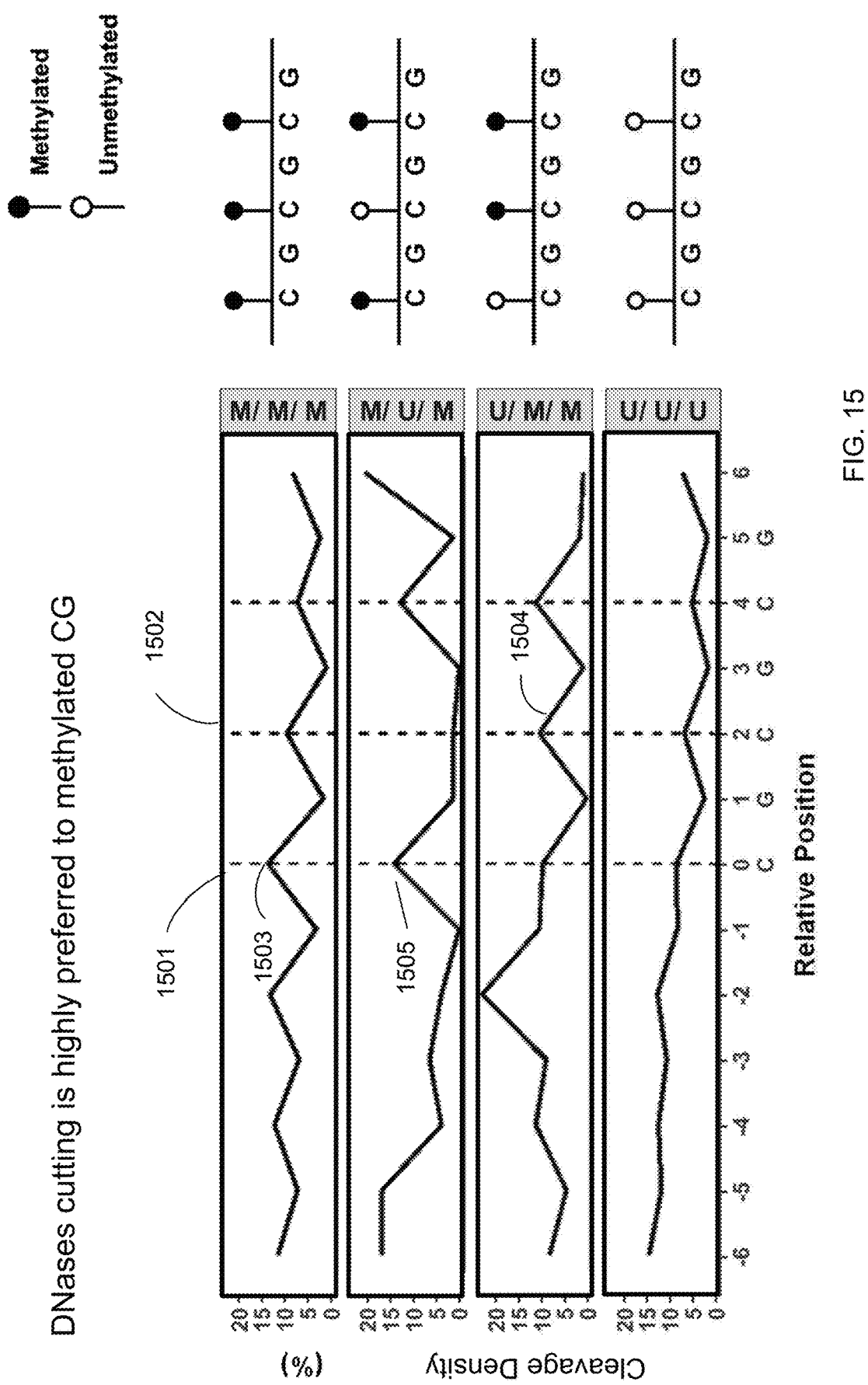
FIG. 15 provides cleavage profiles using a cleavage density for various methylation combination of three CpG sites according to embodiments of the present disclosure.

FIG. 15 provides cleavage profiles using a cleavage density for various methylation combination of three CpG sites according to embodiments of the present disclosure. The different profiles correspond to different combinations of methylation statuses for the different sites. As we can see, the upper two profiles have the first CG methylated and unmethylated in the bottom two profiles. We also observed significant peaks 1503 and 1505 for the upper two profiles at the first C 1501. But the peak disappears in the bottom two profiles for the first C 1501.

The second CG is methylated for the first profile and the third profile. We observe a peak 1504 for the second C 1502. The second CG is unmethylated for the second profile and the fourth profile, and the peak has decreased or disappeared.

The third CG is methylated in the first three profiles, and we observe a peak. The third CG is unmethylated in the fourth profile, and the peak is very weak.

Figure 16:
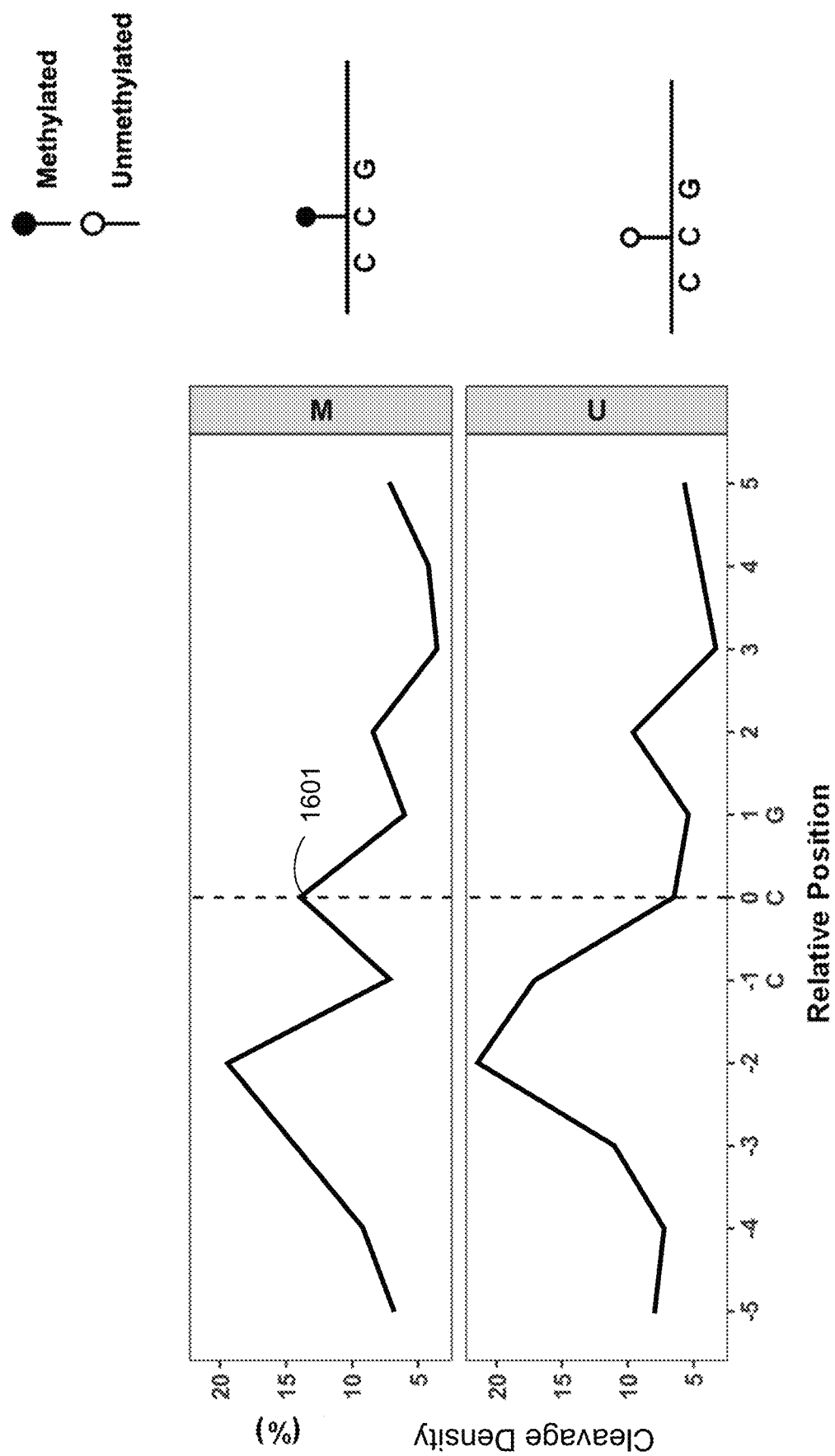
FIG. 16 shows cleavage density of windows including CCG and methylation status according to embodiments of the present disclosure.

FIG. 16 shows cleavage density of windows including CCG and methylation status according to embodiments of the present disclosure. We analyzed regions that contain CCG because DNASE1L3 prefers to cut at CC or at CCC ends. But if the CG is methylated, we hypothesize that it would prefer to cut exactly before this CG (between Cs). And if it is methylated, we do observe a peak 1601. Thus, if the CG is methylated, then it is more preferred to cut between the two Cs. If the CG is unmethylated, the peak disappears. These results are consistent with the results in FIG. 9 using the cleavage ratio.

Figure 17:
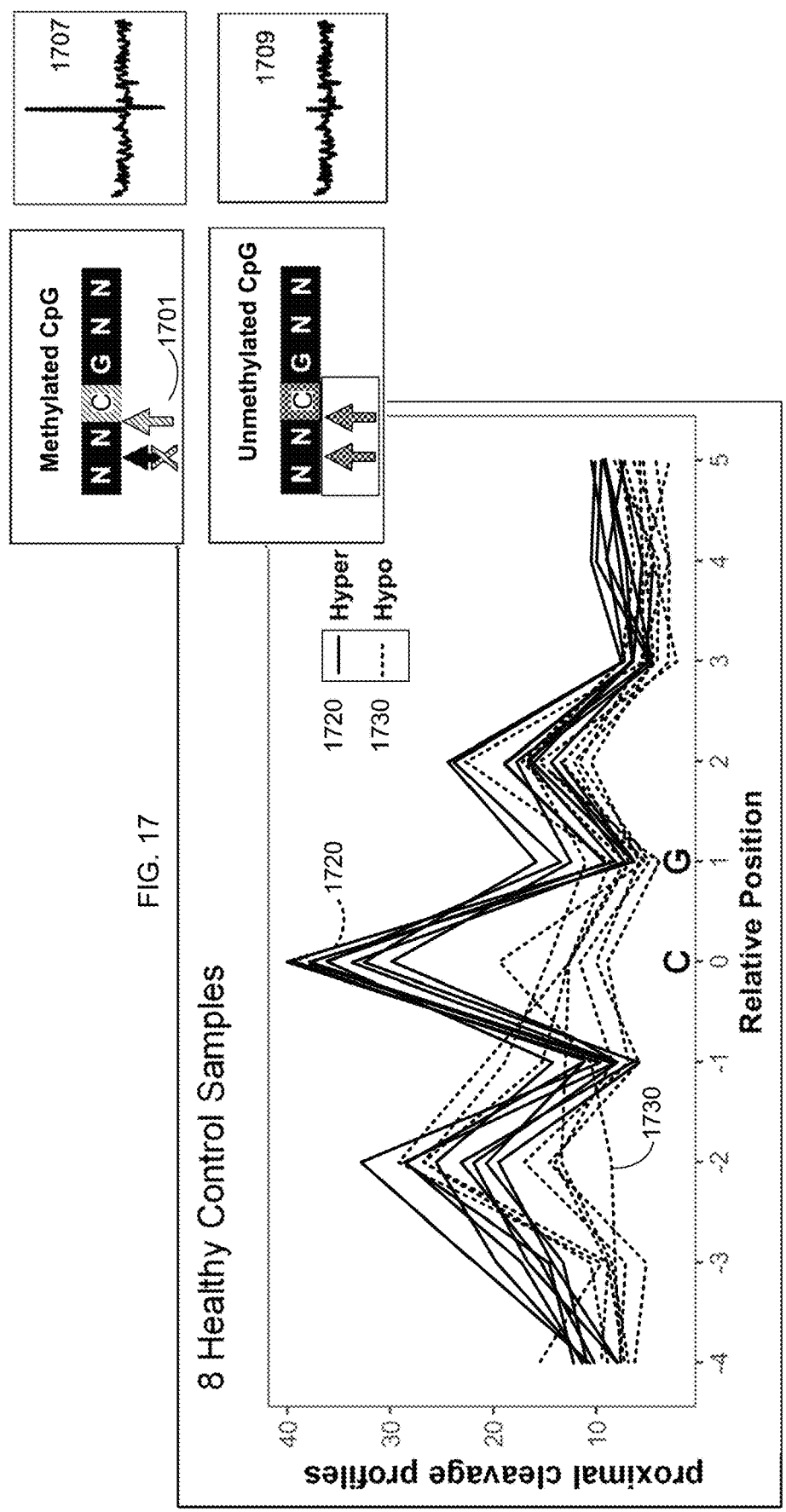
FIG. 17 shows a comparison of cleavage profiles between methylated and unmethylated CpG sites using cleavage density according to embodiments of the present disclosure.

FIG. 17 shows a comparison of cleavage profiles between methylated and unmethylated CpG sites using cleavage density according to embodiments of the present disclosure. FIG. 17 is comparable to FIG. 8 and shows similar results but using a different definition for the cleavage profile, namely using cleavage density as opposed to a cleavage ratio. As with FIG. 8, we selected putatively hyper-methylated, or putatively hypomethylated CpG status from the published leukocyte methylation array data. We randomly selected one thousand CpG sets that are methylated in leukocytes (beta-value >0.8) and one thousand CpG sites that are unmethylated in leukocytes (beta-vale <0.1).

Each red line 1720 represents a sample with the one thousand methylated CpG regions, and each blue line 1730 represents a sample with one thousand unmethylated CpG sites. We observed a dramatic peak in the red line, which means in the hyper-methylated region, we can deduce the methylation status by this peak. And for the blue line, this peak decreased or even disappeared here. Accordingly, if a CpG is methylated, then there would be a spike of fragments that ended at position 1701. The spike would be seen in schematic graph 1707 representing a cleavage profile. When the C is unmethylated, this preference of CG ends would disappear, as shown in schematic graph 1709. The results show we can predict the methylation status at single CpG resolution, by the cleavage profiles.

C. Results Using Support Vector Machines

In some embodiments, machine learning (ML) techniques can be used. Such techniques can use two or more amounts within the cleavage measurement window and may include a full cleavage profile in the window around the CpG site. The machine learning techniques may also use sequence context, e.g., the entire sequence or instances of k-mers, which can be tracked in various ways. The use of sequence contexts can also be used outside of machine learning, e.g., the other relative increase from −1 to 0 position may be different depending on the base before the C. Machine learning can identify such patterns in any of the positions used in the feature vector input to the ML model. Various ML models can be used. This section provides results using support vector machine (SVM) to classify a site as hyper-methylated or hypomethylated.

1. Using Just Cleavage Profile

In some embodiments, cleavage profiles were constructed using the cleavage ratio from 11-nt cleavage measurement window centering on a CpG site. The cleavage profiles from the Watson and Crick strands were used to train a machine learning model that was used for deducing the methylation status of the CpG site in the center of the window. In one embodiment, the support vector machine (SVM) was used to predict whether the aggregated methylation index at a CpG site was over 95% or below 20% on the basis of the cleavage profile associated with that CpG site.

Figure 18:
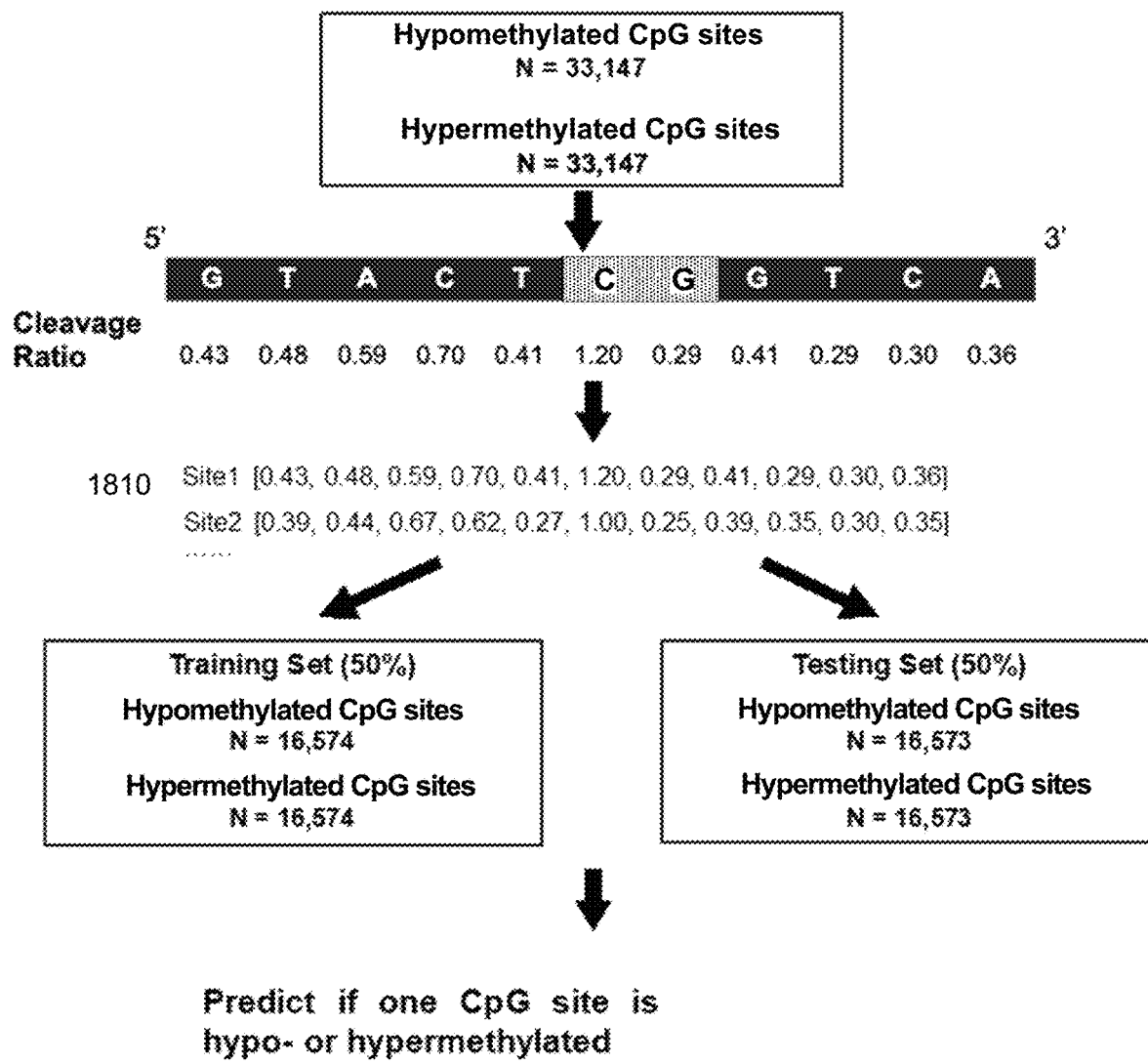
FIG. 18 shows a workflow for using SVM to classify CpG sites as hypermethylated or hypomethylated according to embodiments of the present disclosure. Figure discloses SEQ ID NO: 8.

FIG. 18 shows a workflow for using an SVM to classify CpG sites as hypermethylated or hypomethylated according to embodiments of the present disclosure. For a training set, 33,147 hypomethylated CpG sites and 33,147 hypermethylated CpG sites in a reference genome are used. The actual classification of each site was determined using bisulfite sequencing. In this example, hypomethylated is more than 20 percent for the methylation index, and hypermethylated is higher than 95 percent for the methylation index. Half of the sites were used for training and the other half is used for testing. The trained model can predict if a CpG site is hypomethylated or hypermethylated based on the cleavage profile. The input feature vector is the cleavage ratio at the 11 positions, as is shown at each site. Feature vector 1810 is an example of such a feature vector.

FIG. 19 shows the performance of single CpG site methylation status prediction using support vector machine (SVM) on the basis of cleavage profiles according to embodiments of the present disclosure. The two plots show data from the Watson strand and the Crick strand. When only using the data from the Watson or Crick strand, one can achieve an AUC of around 0.8. In this example, the cleavage ratios in the cleavage profiles were normalized using sequencing depth at each position.

Typically, the methylation patterns at a CpG site in the Watson strand and the corresponding site in the complementary Crick strand would be symmetrical. Cleavage profiles from both the Watson and Crick strands could be merged to train a machine learning model for deducing the methylation status of the CpG site at the center of a window. Accordingly, in some embodiments, a cleavage profile from each strand is used. Thus, the feature vector can have 22 values in this example of 11 positions in the measurement window. In most cases, the two strands share the same methylation status. Thus, one can use both of the strands to deduce the methylation status of both CpG sites.

FIG. 20 shows the performance of single CpG site methylation status prediction using support vector machine (SVM) on the basis of cleavage profiles from both strands according to embodiments of the present disclosure. An AUC of around 0.89 was achieved in a testing dataset, which appeared to be superior to either model based on the data from the Watson or Crick strand alone (P value <0.0001, DeLong test). If one sets a cutoff of an SVM-based output probability as 0.5 for determining whether a CpG site was methylated or not. A sensitivity of 83.8%, with a specificity of 77.2%, could be achieved. If one sets a cutoff of an SVM-based output probability as 0.55 for determining whether a CpG site was methylated or not. A sensitivity of 81.4%, with a specificity of 80.2%, could be achieved. These data suggested that it was feasible to use the cleavage profile to predict methylation status using machine learning algorithms.

The sequencing depth used for the training samples (e.g., 10×) can be higher than used for test samples.

2. Using Sequence Context

The use of sequencing context around a CpG site can be analyzed to improve the model performance. For example, the training datasets comprising the cleavage profiles associated with methylated and unmethylated CpG sites could be divided into four categories, according to the nucleotide types at the position of '−1' of the Watson strand. The sequence context can be used by training different models: one for each of the four sequence contexts.

Figure 21A:
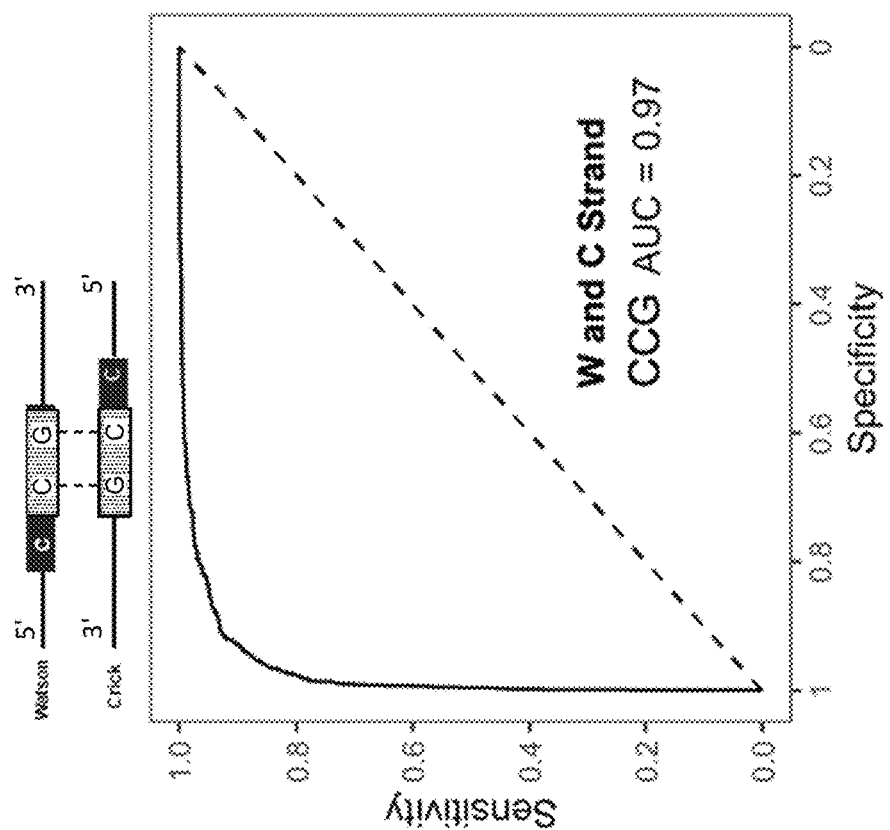
FIGS. 21A-21B show performance of single CpG site methylation status prediction using support vector machine (SVM) on the basis of cleavage profiles conditioned on different sequence contexts according to embodiments of the present disclosure.
Figure 21B:
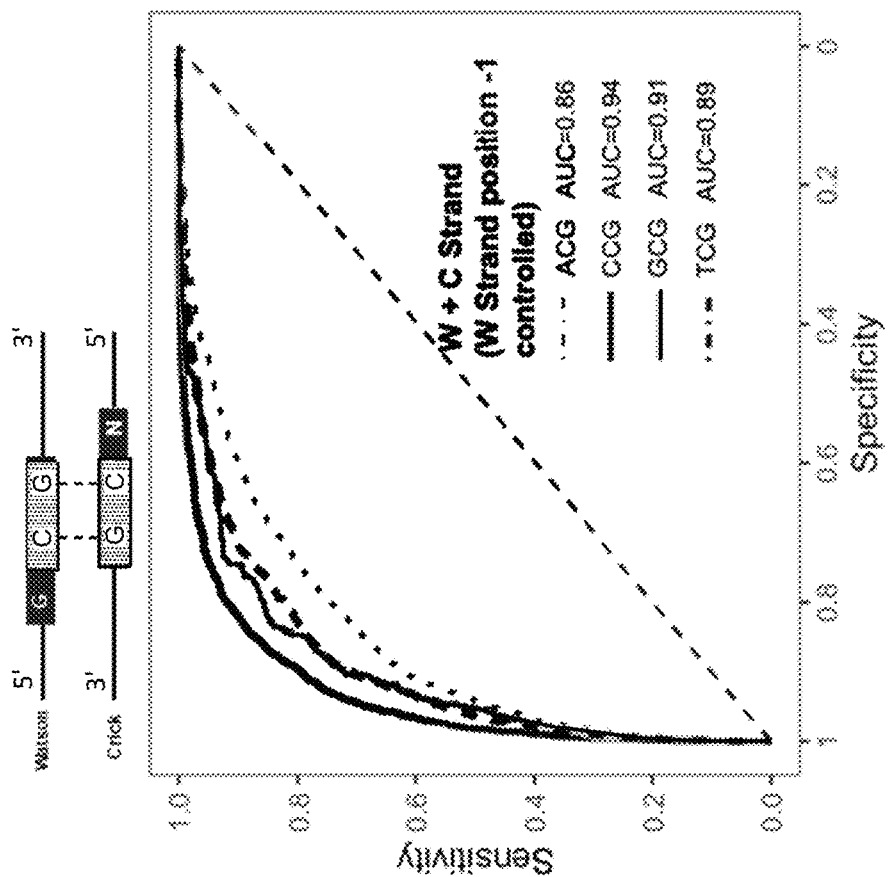

FIGS. 21A-21B show performance of single CpG site methylation status prediction using support vector machine (SVM) on the basis of cleavage profiles conditioned on different sequence contexts according to embodiments of the present disclosure. Using the sequence context can improve accuracy.

FIG. 21A shows data combined from the Watson (W) and Crick (C) strands. Different lines represent ROC curves when using different subsequences at the positions of −1, 0, and 1 within a measurement window for the Watson strand. Having the C at the −1 position provides the greatest accuracy. For this implementation, there essentially would be four different models: a model for A, C, G, and T on the Watson strand.

As shown in FIG. 21A, the model performance would be improved, as evidenced by an increase of the AUC from 0.89 to 0.94 (P value <0.0001, DeLong test), when one focused on the cleavage measurement window with C, C, and G nucleotides (i.e., the CCG subsequence) at the positions of −1, 0, and 1 in the Watson strand. The use of cleavage measurement windows with ACG, GCG and TCG subsequences at the positions of −1, 0, and 1 in the Watson strand would give AUC values of 0.86, 0.91 and 0.89, respectively. Thus, there was an improvement over the results of FIG. 20 for two the sequence contexts (CCG and GCG) and was the same for TCG, although lower for ACG.

FIG. 21B shows data combined from the Watson (W) and Crick (C) strand with a CCG subsequence at the positions of −1, 0, and 1 within a measurement window for both strands. Thus, using the sequence context from both strands improves the AUC from 0.94 to 0.97. If this was extended for both strands and all four bases, then there would be 16 different models.

Accordingly, in some embodiments, the use of cleavage profiles from windows with CCG subsequence at the positions of −1, 0, and 1 in both the Watson strand and Crick strand would further enhance the model performance up to an AUC of 0.97. These results suggested that to selectively analyze cleavage profiles according to the sequence context and the combination of Watson and Crick strand data would synergistically improve the model performance in differentiating methylated and unmethylated CpG sites.

3. Windows of Varying Width

In the example of FIG. 20, a measurement window of 11 bp was used to determine whether a given site in the genome was hypermethylated or hypomethylated. Windows of various widths can be used, e.g., 2, 3, 4, 6, 7, 8, 9, 10, 11, and 20, for any of the embodiments described herein. Results for such widths are shown in table 1. Table 1 summarizes the AUC for methylation prediction by SVM models with different window sizes. AUC (overall) is analyzed by the method used in FIG. 20, and the remaining four are analyzed by the method used in FIG. 21A using a sequence context of the reference genome at position −1. The measurements use fragments from both the Watson (W) strand and the Crick (C) strand, although measurements can use just one strand. The sequence context is defined with respective to the Watson strand but could be defined with respect to the Crick strand, as well as both. In addition or alternatively, other sequence contexts (besides −1 position) can be used, e.g., at positions −3, −2, 1, 2, and 3.

ylated, and a second cutoff/threshold value can be used to differentiate between hypomethylated and not hypomethylated. When additional cleavage ratios are used (e.g., as part of a cleavage profile), additional cutoff/threshold values can be used. The cleavage ratio can take various forms as described herein, such as a normalization by number of DNA fragments covering a position, a number of DNA fragments in a region around the site, or a number of DNA fragments ending at one or more particular positions around the site. Any of such normalizations can be used for a cleavage profile.

For 1 bp at position −1, the cleavage ratio is determined at position −1 to the left of the CpG site. Such a position corresponds to the NCG end motif. For the column of AUC using ACG, the DNA fragments would have ACG at the end, and so on for the other AUC values using the respective sequence contexts.

For 1 bp at position 1, the cleavage ratio is determined at position 1 to the right of the CpG site. For each of the remaining measurement windows, the specific positions used are identified in the column for window size.

The data in table 1 is generated using the 33,147 hypomethylated CpG sites and 33,147 hypermethylated CpG sites described above. In this example, hypomethylated is lower than 20 percent for the methylation index and hypermethylated is higher than 95 percent for the methylation index D. Results Using Convolutional Neural Network, with Sequence Context In some embodiments, the machine learning model (e.g., a neural network) can consider the sequencing content and the cleavage profile (e.g., more than one cleavage density or cleavage ratio) around the CG site to predict the methylation. In one embodiment, to synergistically use the sequence context and cleavage profiles present in the measurement window, a convolutional neural network (CNN)

TABLE 1

AUC for methylation prediction by SVM models with different window sizes.

| Window Size | AUC (Overall) | AUC (ACG in W strand) | AUC (CCG in W strand) | AUC (GCG in W strand) | AUC (TCG in W strand) |
|---|---|---|---|---|---|
| 1 bp (Position 0) | 0.77 | 0.73 | 0.81 | 0.73 | 0.74 |
| 1 bp (Position −1) | 0.82 | 0.75 | 0.88 | 0.83 | 0.78 |
| 1 bp (Position +1) | 0.59 | 0.57 | 0.57 | 0.56 | 0.64 |
| 2 bp (Position −1, 0) | 0.84 | 0.81 | 0.93 | 0.88 | 0.86 |
| 3 bp (Position −1, 0, +1) | 0.85 | 0.82 | 0.93 | 0.89 | 0.86 |
| 4 bp (Position −2 ~ +1) | 0.85 | 0.83 | 0.93 | 0.89 | 0.87 |
| 5 bp (Position −2 ~ +2) | 0.86 | 0.83 | 0.94 | 0.89 | 0.88 |
| 6 bp (Position −3 ~ +2) | 0.86 | 0.84 | 0.94 | 0.90 | 0.89 |
| 7 bp (Position −3 ~ +3) | 0.88 | 0.85 | 0.94 | 0.90 | 0.88 |
| 8 bp (Position −4 ~ +3) | 0.88 | 0.86 | 0.94 | 0.91 | 0.89 |
| 9 bp (Position −4 ~ +4) | 0.89 | 0.87 | 0.94 | 0.91 | 0.89 |
| 10 bp (Position −5 ~ +4) | 0.89 | 0.87 | 0.94 | 0.91 | 0.90 |
| 11 bp (Position −5 ~ +5) | 0.89 | 0.86 | 0.94 | 0.91 | 0.89 |
| 20 bp (Position −10 ~ +9) | 0.89 | 0.88 | 0.95 | 0.91 | 0.90 |

For 1 bp at position 0, the cleavage ratio is determined at the CpG site, i.e., using the number of DNA fragments that end at the C of the CpG site. For this example, the cleavage ratio is determined using the sequencing depth, as described in section III.A. The SVM model can receive as input a cleavage ratio for the Watson strand and/or a cleavage ratio for the Crick strand. Other machine learning models can be used, such as decision trees or neural networks.

When just one cleavage ratio is determined (e.g., for just one strand), a first cutoff/threshold value can be used to differentiate between hypermethylated and not hypermethwas implemented to determine whether a CpG site in a genome was methylated or not.

FIG. 22 shows a schematic illustration for methylation status prediction using a CNN model on the basis of cleavage profiles and sequence context according to embodiments of the present disclosure. A methylated status can be defined by a methylation index over 95% (or other value, e.g., as mentioned herein), whereas an unmethylated status could be defined by a methylation index below 20% (or other value, e.g., as mentioned herein). For illustration purposes, the 5-nt upstream (e.g., ATCTG) and 5-nt downstream (e.g., GAGTA) of the cytosine at a CpG site being analyzed were presented as 5'-[ATCTG]C[GAGTA]-3' (SEQ ID NO: 1) for the Watson strand. The relative positions of this sequence corresponded to −5, −4, −3, −2, −1, 0, +1, +2, +3, +4 and +5, respectively. The center position of "0" corresponded to the cytosine at the CpG site that was subjected to methylation status analysis.

The fragment cleavage ratio for each individual position can be constructed into a 2-dimensional (2-D) matrix 2220 according to the sequence context. For instance, for a position of −1 corresponding to the base of guanine ("G"), the cleavage ratio associated with "G" (1.40) was filled in the corresponding cell between a column of "−1" and a row of "G". The remaining rows corresponding to "A", "C", and "T" in the Watson strand were filled by "0". The cleavage profiles and sequence context originating from the Crick strand ('5-[TTACT]C[GCAGA]-3' (SEQ ID NO: 2)) were also processed similarly. The data matrices from the Watson and Crick strand can be combined for downstream analysis. Thus, such a data matrix could contain both the sequence context and the cleavage profile information. A number of those data matrices associated with known methylated status, namely methylated CpG sites (output value as "1") and unmethylated CpG sites (output value as "0"), were used for training a CNN model.

As shown, the cleavage ratio was calculated for both strands. The matrix includes the base (nucleotide), the position, and the cleavage ratio (using one-hot encoding in this example). For example, at −5 in the W strand, the first base is A, and the cleavage ratio is of around 0.25. The two matrices can be combined into a combined matrix 2230. This combined matrix can be the input metric of the CNN model, which has a convolutional layout to extract the features of these matrices. The extracted features can be combined into a linear level to calculate the possibility of whether the CpG site is methylated or unmethylated. We can achieve an AUC of around 0.96.

In one embodiment, the CNN model made use of two one-dimensional (1D)-convolutional layers, each having 64 filters with a kernel size of 4, although other hyperparameters may be used, such as between 50-100 filters or kernel sizes of 3-6. The activation function of the rectified linear unit (ReLU) was used for those convolutional layers. A batch normalization layer was applied subsequently, followed by a dropout layer with a dropout rate of 0.5. A flattened layer was further added, followed by a fully connected layer comprising 128 neurons with the use of the ReLU activation function. The output layer with one neuron was finally applied, with a sigmoid activation function to yield the probabilistic score for a CpG site of being methylated (i.e., methylation score). The program for the CNN model was implemented on the basis of PyTorch machine learning framework (pytorch.org/). In various embodiments, the number of convolutional layers can be 1, 3, 4, 5, 6, 7, 8, 9, from 10 to 20, from 30 to 40, from 40 to 50, or more. The number of filters for each convolutional layer may be from 1 to 10, from 10 to 20, 20 to 30, 30 to 40, 40 to 50, 50 to 60, 60 to 70, 70 to 80, 80 to 90, 90 to 100, 100 to 150, 150 to 200, or more. The kernel size for the filters can be 2, 3, 4, 5, 6, 7, 8, 9, 10, from 10 to 20 or more. The CNN may also include a plurality of hidden layers including a plurality of nodes. The first layer of the plurality of hidden layers coupled to the input layer. The CNN may further include an output layer coupled to a last layer of the plurality of hidden layers and configured to output an output data structure.

The optimal parameters of the CNN model were obtained when the overall prediction error between the output scores by the sigmoid function and desired targeted outputs (binary values: 0 or 1) reached a minimum by iteratively adjusting model parameters. The overall prediction error was measured by the cross-entropy loss function in deep learning algorithms (pytorch.org). The model parameters learned from the training datasets were used for analyzing the testing dataset to output a probabilistic score (referred to as the methylation score in this study) which would indicate the likelihood of a CpG site being methylated.

The methylation score may range from 0 to 1. In one embodiment, a methylation score of 1 indicates that a CpG site may be deemed as methylated. A methylation score of 0 can indicate that a CpG site may be deemed as unmethylated. In some embodiments, a cutoff value can be used to classify if a particular CpG site is classified as "methylated" or "unmethylated" based on the cutoff of methylation score. The possible values of the cutoff include 5%, 10%, 15%, 20%, 25%, 30%, 35%, 40%, 45%, %, 55%, 60%, 65%, 70%, 75%, 80%, 85%, 90%, or 95%. The methylation score for a CpG site greater than a predefined cutoff may be classified as "methylated," while the probability of being methylated for a CpG site not greater than a predefined cutoff may be classified as "unmethylated." A desired cutoff can be obtained from training dataset using, for example, receiver operating characteristics (ROC) curve analysis.

Figure 23A:
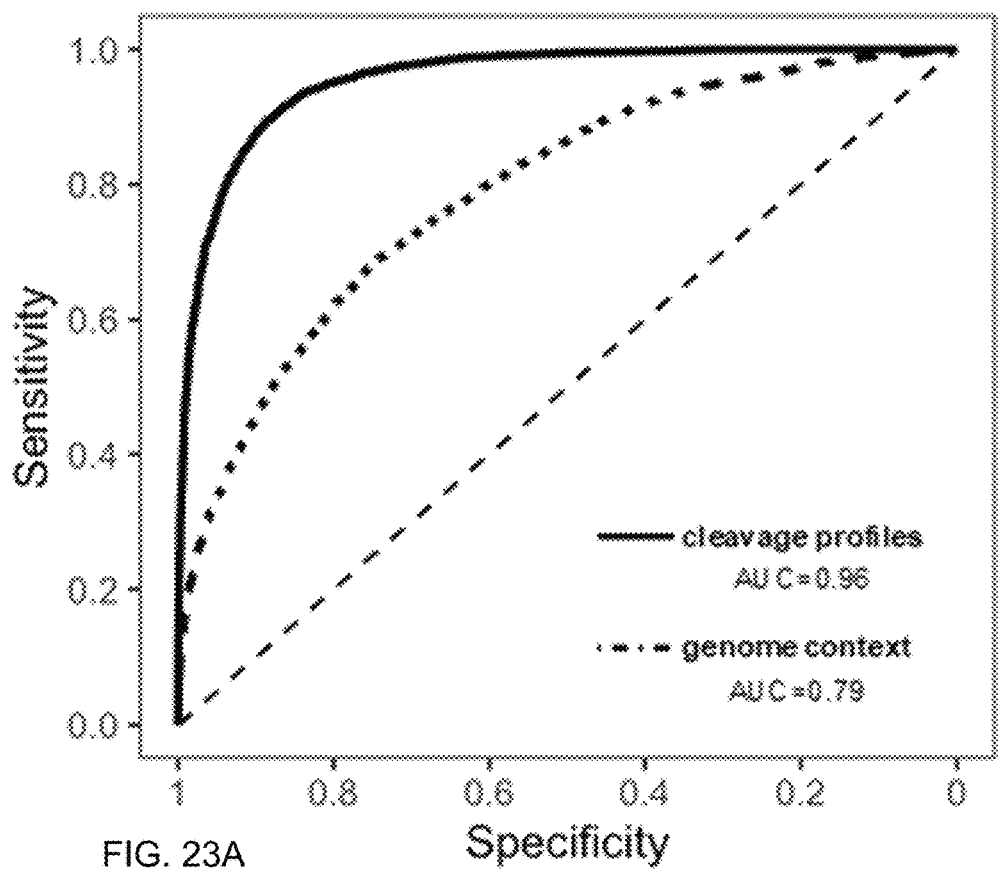
FIG. 23A shows a performance of methylation status prediction of a single CpG site using CNN on the basis of cleavage profiles and sequence context according to embodiments of the present disclosure.

FIG. 23A shows a performance of methylation status prediction of a single CpG site using CNN on the basis of cleavage profiles and sequence context according to embodiments of the present disclosure. The solid line represents the performance of the model trained with cleavage profiles and sequence context, and the dash line represents the performance of the model trained with genome context only. The genome context only is just trained on the sequence pattern in reference, without any fragmentation information.

Based on the methylation score, the CNN model could achieve an AUC of 0.96, which was superior to the SVM-based model that did not contain sequence context (0.89) (P value <0.0001, DeLong test). And this AUC is for all sequence contexts. If one only used sequence context but without cleavage patterns in this model, the performance would decline to an AUC of 0.79. These results suggested that the combined use of cleavage profile and sequence context would significantly improve the model performance in determining the methylation status. In other embodiment, cleavage profiles and sequence context could be used to deduce the methylation indices (e.g., specific percentages or range of percentages) instead of the binary values of hypermethylated or hypomethylated.

In some embodiments, the machine learning models could include, but not limited to, convolutional neural network (CNN), linear regression, logistic regression, deep recurrent neural network (e.g., fully-connected recurrent neural network (RNN), Gated Recurrent Unit (GRU), long short-term memory, (LSTM)), transformed-based methods (e.g. XLNet, BERT, XLM, RoBERTa), Bayes' classifier, hidden Markov model (HMM), linear discriminant analysis (LDA), k-means clustering, density-based spatial clustering of applications with noise (DBSCAN), random forest algorithm, adaptive boosting (AdaBoost), eXtreme Gradient Boosting (XGBoost), support vector machine (SVM), or a composite model comprising one or more models proposed above.

E. Results Using Various Positions

As shown above, the cutting distance is reflective of the methylation index, e.g., as shown in FIGS. 2A-2B and 3, particularly distances 0 (corresponding to end motif CGN) and 1, where distance 1 corresponds to positions −1 (corresponding to end motif NCG) and +1 (corresponding to cutting site between the C and G). The cleavage ratio (e.g., determined using an amount at a particular position) at various positions also shows differences between methylation levels, e.g., as shown in FIGS. 8-10 and 17. Additional data is provided in this section showing the discrimination among difference methylation levels using an amount of cell-free DNA molecules ending at a first position of the CpG site, where the first position is one of −1 to +1 position. As shown, the −1 position, the 0 position, or the +1 positions can be used.

Figure 23B:
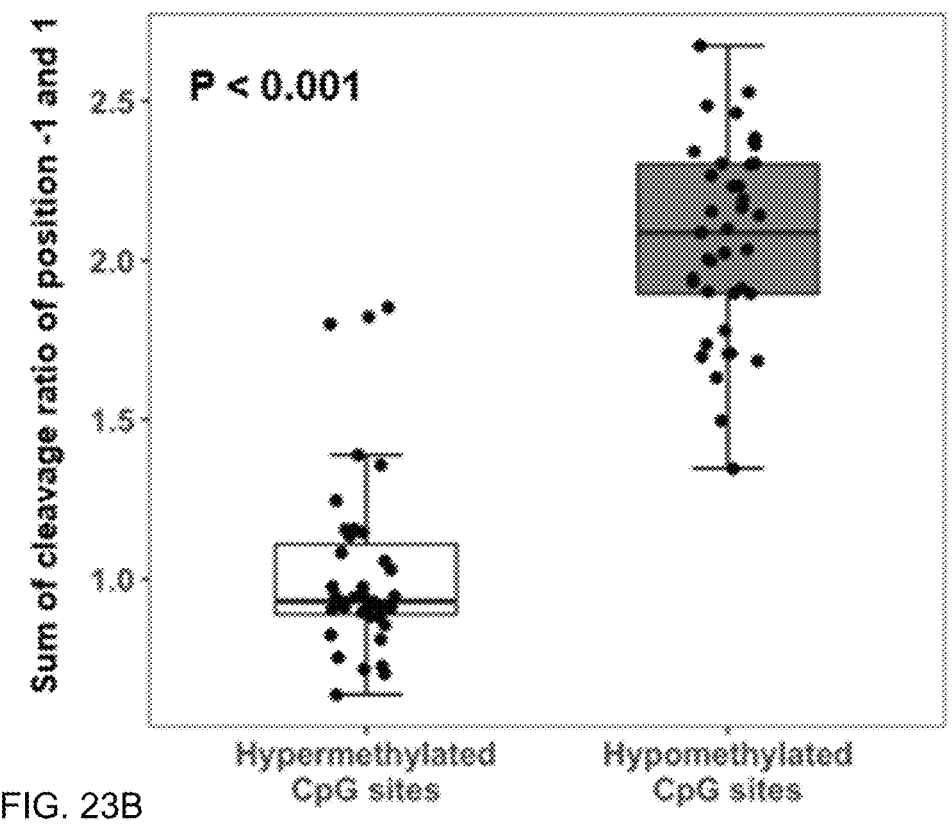
FIG. 23B shows a comparison of the sum of mean cleavage ratios at positions −1 and +1 between hypermethylated and hypomethylated CpGs for 39 ucfDNA samples.

FIG. 23B shows a comparison of the sum of mean cleavage ratios at positions −1 and +1 between hypermethylated and hypomethylated CpGs for 39 ucfDNA samples. The sum of mean cleavage ratios of 18,280,640 hypermethylated CpG sites and 2,576,102 hypomethylated CpG sites were analyzed for 39 healthy control urinary cfDNA samples, with a median number of 75.8 million paired-end sequencing reads (interquartile range: 60.5-155 million). Each dot represents one subject. As shown, the cleavage ratio at positions −1 and +1 is different between hypermethylated sites and hypomethylated sites. Such data shows that the methylation can be predicted without the use of fragment information for the 0 position.

Figure 24A:
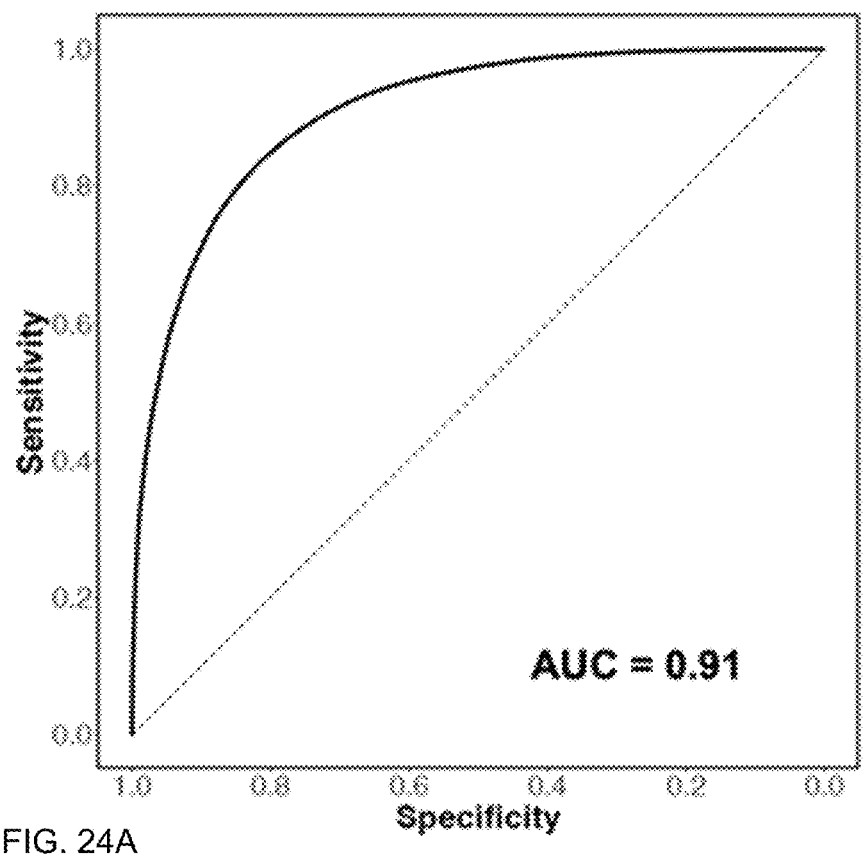
FIG. 24A shows performance of methylation status prediction of a single CpG site using a CNN model on the basis of proximal cleavage profiles and sequence context with the exclusion of position 0.

FIG. 24A shows performance of methylation status prediction of a single CpG site using a CNN model on the basis of proximal cleavage profiles and sequence context with the exclusion of position 0. The sequence context was used as described above. Without the 0 position, the combined matrix for a +/−5 base window would have 10 columns instead of 11, as was used in FIG. 22. An AUC of 0.91 was achieved, a bit lower than the 0.96 achieved using the 0 position but still much higher than using sequence context alone (AUC=0.79). The same data set was used as for FIG. 23B.

As mentioned above, any of the positions −1 to +1 can be used alone. While some embodiments can use a ratio (e.g., a CGN/NCG ratio) or others can use a vector of cleavage ratios at multiple positions, an amount of fragments ending at a particular position relative to the CpG site can be used.

Figure 24B:
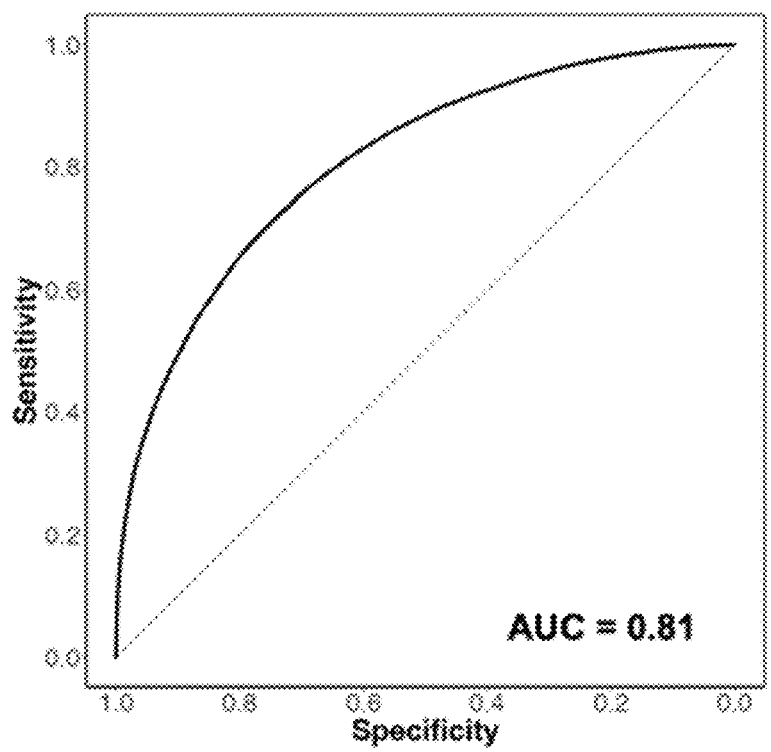
FIG. 24B shows performance of methylation status prediction of a single CpG site using a CNN model on the basis of proximal cleavage profiles and sequence context with the exclusion of position −1, 0, and 1.

FIG. 24B shows performance of methylation status prediction of a single CpG site using CNN on the basis of proximal cleavage profiles and sequence context with the exclusion of position −1, 0, and 1. FIG. 24B shows it is feasible to use a set of continuous or not continuous positions within cleavage profile window to form the data structure that is input to machine learning model for training. However, the performance may be reduced if some positions that have significant contribution to classification, such as −1, 0 and +1.

FIGS. 25A-25F are boxplots illustrated the difference of mean cleavage ratio of various positions for plasma and urine (ucfDNA) between hypermethylated and hypomethylated CpGs. FIG. 25A shows the difference for position −1 in plasma between hypermethylated and hypomethylated CpGs. FIG. 25B shows the difference for position 0 in plasma. FIG. 25C shows the difference for position +1 in plasma. The bottom boxplots illustrated the difference of the mean cleavage ratio of position −1 (FIG. 25D), position 0 (FIG. 25E), and position −1 (FIG. 25F) in ucfDNA. The separation is quite clear, providing p<0.001. Position 0 provides the best discrimination. Position −1 obtained better discrimination for plasma than for urine, while position +1 obtained better discrimination for urine than plasma.

F. Determining Quantitative Methylation Density

Above, the examples were a classification of hypermethylated, e.g., methylation density is greater than X % (e.g., 80%), or hypomethylated, e.g., less than Y % (e.g., less than 30%). Some embodiments can use a calibration function (e.g., as described in the Terms section) to determine a more narrow range or estimate a specific value. For example, a methylation level of a site can be determined using a methylation-aware assay. Cleavage information can also be determined, such as any cleavage parameter described herein, such as a cleavage density or a cleavage ratio.

This measured methylation level for a site and the corresponding cleavage information/parameter (e.g., a cleavage ratio or cleavage density) can form a calibration data point, with the cleavage parameter being a calibration value corresponding to a known/measured methylation level. Given the relationship between cleavage and methylation, when the cleavage parameter changes, the methylation level will also change. The calibration function can define the proportional change of the methylation level when the cleavage parameter changes. In this manner, when the cleavage parameter for a new sample (e.g., sequenced without methylation-aware assay) is measured, this cleavage parameter can be compared to the calibration function (e.g., to a calibration value corresponding to a known methylation level). In one implementation, cleavage information/parameter (e.g., a cleavage profile or end motifs) can be combined with a methylation-aware assay (e.g., using a holistic kinetic model on data generated by single-molecule real-time sequencing, such as in U.S. Publication No. 2021/0047679) so as to improve the final classification accuracy for determining a DNA methylation profile.

The calibration data points can be used to train a model, e.g., a regression model. The regression model can be used to determine a quantitative value, which can be a range, e.g., a 5% (such as a density of between 40-45%), 10%, 15%, 20%, 25%, or 30% range. The regression can provide a calibration function. In some implementations, the likelihood from ML model (e.g., a neural network) can be used as the methylation index.

FIGS. 26A-26C show a comparison of various techniques for determining a quantitative value for a methylation level (e.g., a density) for CpGs having different methylation levels in 8 plasma DNA samples. FIG. 26A shows the mean CGN/NCG motif ratio for various ranges of the methylation density. Specifically, ranges that are 20% in width are shown: 0-20%, 20-40%, 40-60%, 60-80%, and 80-100%. FIG. 26B shows the mean cleavage ratio at position −1 relative to CpG sites. FIG. 26C shows a mean cleavage ratio at position 0 for CpG sites.

In WGBS data of plasma DNA sample, CpGs were separated into 5 groups according to a certain range of methylation index, i.e., 0-20%, 20-40%, 40-60%, 60-80%, and 80-100%. In the same sample, mean CGN/NCG motif ratio (FIG. 26A), mean cleavage ratio at position −1 (FIG. 26B), and mean cleavage ratio at position 0 (FIG. 26C) of each set of CpGs were calculated and plotted. Each dot represents one subject.

All three parameters show a consistent relation (increasing or decreasing) with methylation density. CGN/NCG motif ratio gradually increases as the methylation density is increased. The cleavage ratio at position −1 and 0 are negatively and positively correlated with different groups of methylation density range. These results reflected that CGN/NCG motif ratio and cleavage ratio can distinguish hypermethylated and hypomethylated CpGs. Furthermore CGN/NCG motif ratio and cleavage ratio can be used to predict ranges for the methylation levels. Each plot shows a calibration curve that can be used to determine a quantitative value (at least within a range) using an amount of cell-free DNA fragments that end at a position of 0 or −1.

We also tested SVM regression using cleavage profiles from 11 bp windows (e.g., from −5 to 5). SVM models were trained with cleavage profiles from CpGs corresponding to different methylation index ranges. For example, we trained a SVM regression model based on ranges 0-5% (group 1), 50-55% (group 2), and 95-100% (group 3), namely SVR 1. We trained another SVM regression model for 0-10% (group 1), 45-55% (group 2), and 90-100% (group 3), namely SVR 2. We trained another SVM regression model for 0-20% (group 1), 40-60% (group 2), 80-100% (group 3), namely SVR 3.

Table 2 shows performance of methylation status prediction of a single CpG site within different methylation index ranges using SVM regression models on the basis of proximal cleavage profiles. As shown in the 2nd column (Pearson r), the predicted methylation score showed a good correlation with the methylation index of the tested CpGs (i.e., Pearson's r=0.73, 0.77, and 0.74). For each SVM regression model, the methylation index of each predicted group fit well to the actual methylation index ranges. In some embodiments, one could express the predicted values together with other confidence intervals at, but not limited to, 99%, 95%, 90%, 85%, 80%, 75%, 70%, 65%, 60%, 55%, 50% confidence level.

TABLE 2

Performance of methylation status prediction of a single CpG site within different methylation index ranges using SVM on the basis of proximal cleavage profiles.

| Regression model | Pearson r | Median methylation index (interquartile range) | | |
|---|---|---|---|---|
| | | Predicted group 1 | Predicted group 2 | Predicted group 3 |
| SVR1 | 0.73 | 0.8(0-2.1) | 52.7(51.6-53.7) | 96.7(95.8-97.4) |
| SVR2 | 0.77 | 1.5(0.4-4.6) | 50.4(48.0-53.0) | 95.0(93.0-96.2) |
| SVR3 | 0.74 | 4.7(0.7-10.5) | 51.5(46.5-55.5) | 93.3(89.4-95.7) |

G. Methods for Determining Methylation at Site in a Genome

Methods are provided for using cleavage information to determine methylation at a site in a genome. The methylation can be a property of the sample at a position in the genome, e.g., as defined relative to a reference genome. The cleavage information can be of various types, as described herein. Various normalizations can be used, and cleavage information for more than one position can be used.

Figure 27:
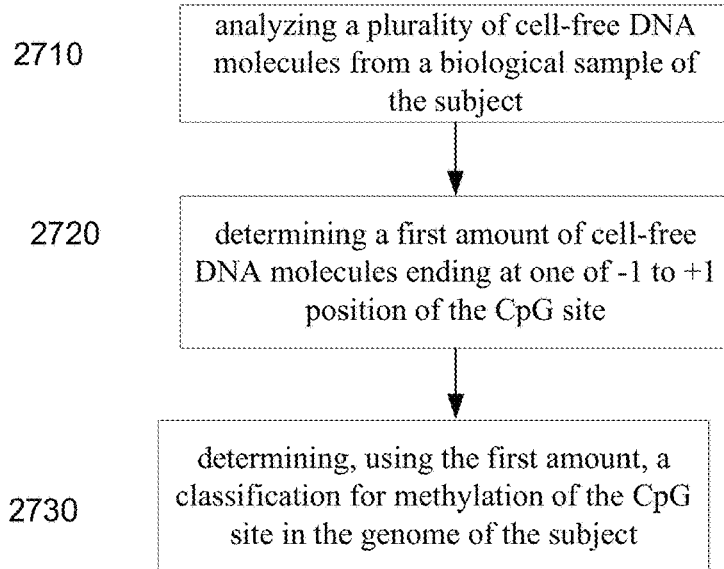
FIG. 27 is a flowchart of a method for determining methylation at a site based on fragmentation according to embodiments of the present disclosure.

FIG. 27 is a flowchart of a method 2700 for determining methylation at a site based on fragmentation according to embodiments of the present disclosure. Various examples of method 2700 are described above Method 2700 can be performed partially or entirely using a computer system.

At block 2710, a plurality of cell-free DNA molecules from a biological sample of the subject are analyzed. Various techniques can be used for such analysis in any of the methods described in the present disclosure. For example, the analysis can be performed using sequencing, such as massively parallel sequencing, targeted sequencing, and single molecule sequencing (e.g., using a nanopore or using real-time single molecule sequencing (e.g., from Pacific Biosciences)). Example PCR techniques include real-time PCR and digital PCR (e.g., droplet digital PCR). The analysis can include the physical steps of performing such assays and receiving the measurement data obtained from such assays, or may just include receiving the measurement data.

Analyzing a cell-free DNA molecule can includes determining a genomic position in a reference genome corresponding to at least one end of the cell-free DNA molecule. For example, one or more sequence reads of a DNA molecule (e.g., paired reads at the ends or a read for the entire molecule) can be aligned to the reference genome using any of various alignments techniques as will be appreciated by the skilled person. The alignment can be to some or all of the reference genome. As another example, probe-based techniques can identify a DNA molecule as being from a particular position, e.g., by emitting a particular color for a particular probe that corresponds to a particular genomic position. The position determination can be to some or all of the reference genome, e.g., if only part of the genome is being analyzed. As examples, the amount of the genome analyzed can be greater than 0.01%, 0.1%, 1%, 5%, 10%, or 50%. Such an analysis may be performed for other methods described herein.

As with other methods described herein, analyzing the plurality of cell-free DNA molecules can includes measuring a size of the cell-free DNA molecule. The measurement can be performed in various ways, e.g., using physical separation (such as electrophoresis) and/or sequencing (such as whole molecule sequencing or alignment using paired-end reads).

At block 2720, a first amount of cell-free DNA molecules ending at a first position within a window around the CpG site is determined. The first position can be between −1 to +1 position of the window. For example, the first amount can be the cell-free DNA at the −1 position, the first amount can be the cell-free DNA at the 0 position, or the first amount can be the cell-free DNA at the +1 position.

The first amount can be determined in various ways. For example, when the analysis uses sequence reads, block 2720 can determine a number of reads that align to the CpG site in a reference genome and end with CG (with the 5' end at the left on the Watson strand) or end with GC (with the 5' end at the right on the Crick strand). Thus, the amount can be a count of DNA molecules. As another example (e.g., as depicted in FIG. 4), probe-based techniques can be used. For example, a number of reactions positive for a particular probe can be used. As yet another example, an intensity (e.g., electrical or optical) of a signal (e.g., from real-time PCR) from a particular probe can be used.

A second amount of cell-free DNA molecules ending at a second position (different than the first position) within a window around the CpG site can optionally be determined at block 2720. The second amount can be determined in similar ways as the first amount. The amounts can be a raw number (e.g., no normalization) since they are compared to each other. In other examples, a relative frequency can be used. Examples of a relative frequency include a cleavage ratio and a cleavage density, as may be determined using normalization techniques described herein. The two amounts may be used to determine a relative frequency, which is used in later steps. As further examples, such normalization or any other normalization mentioned herein can be performed by analyzing a same number of DNA molecules, producing a same number of reads, or using a same sized sample (e.g., specified volume (e.g., number of milliliters)).

The second amount can be part of a larger amount. For example, a total number of DNA molecules covering the first position (e.g., the CpG site) can be determined (also referred to as depth). At least some of these DNA molecules end at different positions other than the first position. Thus, the total number covering the first position can include the second amount that end at the second position around the CpG site. Techniques that use such a total number for normalization use the second amount. Accordingly, when the first amount is normalized, the normalization can use a number of cell-free DNA molecules covering the CpG site. As another example, the normalization can use a number of cell-free DNA molecules ending within a region including the CpG site. As yet another example, the normalization can use an average or median depth of cell-free DNA molecules in a region including the CpG site.

The second position can be any position within a measurement window, for which example windows are described herein. For example, the first position can be at +1 or −1 from the CpG site, if the first position is the 0 position. As another example, the measurement window can be at least −2 to +2 from the CpG site, and thus larger than 5 bases in width.

At block 2740, a classification for methylation of the CpG site in the genome of the subject is determined using the first amount. Optionally, the second amount may also be used. Various methylation classifications of a site can be determined. For example, it can be determined whether a site is hypomethylated or hypermethylated in the sample and the subject. Thus, the classification for methylation can be whether the CpG site is in a hypermethylated state (also referred to as a methylated state) or a hypomethylated state (also referred to as an unmethylated state) in the genome of the subject, as determined by analyzing the plurality of cell-free DNA molecules in the sample. The methylated state can have a methylation density above a first threshold that is at least 70%. The unmethylated state can have the methylation density below a second threshold that is 30% or less. The classification can be any methylation level, which may be provided qualitatively (e.g., high, medium, or low, as may be defined using certain percentage thresholds) or quantitatively (e.g., a particular amount, such as a percentage, which may be provided with a given resolution/range).

The classification can be determined in various ways. For example, a separation value can be determined using the first amount and the second amount. The separation value can be compared to a calibration value. The calibration value can be determined using cell-free DNA molecules that are from one or more calibration samples and that are located at CpG sites having known classifications. The known classifications can be determined using a methylation-aware assay or from the results of others that use a methylation-aware assay. The calibration value can be a threshold/cutoff above which or below which a particular classification is determined. For example, in FIG. 17, a calibration value of about 22 for the cleavage ratio at position 0 discriminates between hypermethylated sites and hypomethylated sites.

As another example for classification, a site can be identified as having a methylation level of a particular percentage or percentage range (e.g., 5%, 10%, 15%, 20%, 25%, 30% or less). An example of a 20% range is 40%-60%. Thus, the classification can be a quantitative value. Comparing the separation value to the calibration value can include comparing the separation value to a calibration function, e.g., as described above in Section E.

The classification can use at least two positions other than the first position, e.g., other than the CpG site if the first position is position 0. For each position of the at least two positions within the window, a respective amount of cell-free DNA molecules ending at the position can be determined. The first amount of cell-free DNA molecules ending at the first position can be compared to the respective amount of cell-free DNA molecules ending at the position as part of determining the classification. Such a comparison could be of determining a difference between the amount at position −1 to position 0 and the difference between the amount at position 1 to position 0. For instance, FIGS. 8 and 17 both have different amounts of increase from −1 to 0 and decrease from 0 to 1. Additionally, such use of two or more positions can include machine learning techniques, such as those described in sections C and D above.

When machine learning techniques are used, a feature vector can include the respective amounts and the first amount and be input into the machine learning model as part of determining the classification. Any such machine learning model described herein can be trained using cell-free DNA molecules located at CpG sites having known classifications. The first positions and the at least two positions can include all positions within a window of at least +5 to −5 from the CpG site. As described in sections C.2 and D, the machine learning model can use a sequence context within the window. In one example, the machine learning model is trained for the sequence context within the window (e.g., as shown in FIG. 21A).

In another example, the feature vector can include the sequence context (e.g., as shown in FIG. 22). In such an example, the feature vector can form a matrix with each row corresponding to a base of a strand (potentially of both strands, Watson and Crick). As shown in FIG. 22, a column can include a non-zero amount in the row corresponding to the base at a respective position. A CNN model can be used when the feature vector forms a matric.

More than one CpG site can be within a measurement window (e.g., as described in FIGS. 10, 14, and 15) and both can be classified. In such a situation, the CpG site can be a first CpG site that has a first classification. The window can include a second CpG site and can include at least two positions other than the first CpG site (e.g., if first position is position 0) and the second CpG site. A third amount of cell-free DNA molecules ending at the second CpG site can be determined. For each position of the at least two positions within the window, a respective amount of cell-free DNA molecules ending at the position can be determined, e.g., as described above. When using machine learning, a feature vector can include the respective amounts, the first amount, and the third amount. The feature vector can be input into a machine learning model as part of determining the classification for the first CpG site and determining a second classification of the second CpG site.

The methylation classification for more than one CpG site can be determined using the first amount and the second amount for a first CpG site that is at the cleavage site, e.g., as described in section II.A.3. Thus, some embodiments can determine, using the first amount and the second amount, a classification for methylation of a different CpG site in the genome of the subject. The different CpG site can be downstream from the 5' end of the CpG site, e.g., within a specified range such as 50 nt, 75 nt, or 100 nt.

IV. Predicting Methylation in a Region Based on End Motifs

In some embodiments, the methylation of a region can be predicted. The classification of the methylation can be similar as for sites, e.g., into classifications of hypo- or hyper-methylated, or a specific methylation level, which could be a range of values (e.g., within 1%, 2%, 3%, 4%, or 5%. Various techniques, including machine learning, can be used.

A. Size of Region to be Analyzed

The region can be the entire genome or a particular part of the genome, which can be on one chromosome or span multiple chromosomes. The region can be composed of different windows that are separated from each other, i.e., disjoint. Thus, a methylation level can be determined in aggregate for multiple regions (e.g., 2, 3, 4, 5, 10, 20, 50, etc.), which may be on multiple chromosomes (e.g., 2, 3, 4, 5, etc.). The first section below analyzes the entire genome, and the following section looks at particular parts of the genome.

1. Global

FIG. 28 shows the methylation index for CGN and NCG end motif according to embodiments of the present disclosure. Each dot represents the mean methylation index for each of the 4 motifs within the groups of CGN and NCG end motifs. N represents A, C, G, or T. FIG. 28 is similar to distances 0 and 1 of FIG. 2B. CGN corresponds to position 0 in FIG. 7, and NCG corresponds to position −1 in FIG. 7.

The plot shows that the highest methylation index (median: 88%) was observed at the CpG sites related to the 5'-CGN end motifs (i.e., CGA, CGT, CGC, CGG). In contrast, the lowest methylation index (median: 69%) was present at the CpG sites related to the 5'-NCG end motifs (i.e., ACG, TCG, GCG, CCG). Cutting at the methylated C or the unmethylated C is very different: if methylated, the cutting would more likely happen at C, while as unmethylated, the cutting is less likely at the C. If it is cut at C, the end-motif will be the CGN. If it is cut one base before, the end-motif will be NCG.

Given this difference, some embodiments can use the end motifs to predict a regional methylation density. For example, a region with more CGN would have a higher methylation density. A region with more NCG would have a lower methylation density.

For example, one or more calibration samples can have a methylation level measured as well as an amount of CGN end motifs and/or an amount of NCG end motifs. The amount of each end motif can be used separately or used together, e.g., as a ratio of the two amounts. If used separately, the amounts can be normalized, e.g., using normalization techniques described herein. The measured methylation level (known classification) and a parameter of the one or more amounts can comprise a calibration data point, where the parameter can be considered a calibration value. Such calibration is described in more detail in other sections, e.g., in the Terms section and section III.E.

The cell-free DNA molecules in a new biological sample can be analyzed to determine a parameter of the amount of CGN end motifs and/or the amount NCG end motifs. This parameter can then be compared to the calibration data points from the one or more calibration samples, which may be done using a calibration function (e.g., a regression function fit to the calibration data points of a set of calibration samples). If the measured parameter is similar to a calibration value of a calibration data point, then the new sample and the previous calibration sample would have similar methylation levels. The calibration data points can be used to train a model, e.g., a linear model, non-linear model, or other analogous, or more complex machine learning models.

2. Selecting Regions

Based on the data in FIG. 28, we hypothesized that the number of CGN and NCG motifs present in a particular genomic region could be used for predicting the regional methylation density. To this end, we determined the methylation densities and the frequencies of CGN and NCG motifs for those plasma DNA molecules overlapping to the regions nearby the transcription start sites (i.e., ±1000 bp of TSSs, referred to be as TSS regions) as an example. The overlapping of the molecules was determined by mapping sequence reads to those regions. Each TSS region did overlap with another TSS region. An average depth for each CpG was over 2. Each region had over 100 DNA fragments mapped.

TSS regions with a methylation density of over 70% were defined as hypermethylated regions (although other percentage ranges could be used), and regions with a methylation density of below 30% were defined as hypomethylated regions. Regions in between were excluded, but can be included in other embodiments, e.g., to identify regions that are partially methylated. More than three classifications can also be used. CGN and NCG end motif frequencies were calculated for all hypo- and hypermethylated regions and normalized by the expected motif frequencies from 8 healthy control samples (median paired-end sequencing reads of 381 million (IQR: 353-404 million)).

The regions can be of various size (e.g., 100 kb, 200 kb, 500 kb, 1 Mb, 2 Mb, 3 Mb, and 5 Mb), with 1 Mb regions just being an example.

B. Example Classification Techniques

One example technique uses amounts for CGN or NCG, or a ratio of the two, possibly with normalization for either. Another example technique uses amounts for each motif, e.g., each 3-mer motif. Higher k values for the k-mer motifs can be used.

1. CGN or NCG

In some embodiments, an amount of CGN and/or NCG can be used. The amount can be a relative frequency of the motifs within the group of 3-mers for the end motifs of the cell-free DNA molecules analyzed, e.g., the DNA molecules from the region (possibly entire genome) being analyzed. For example, the sum of the individual percentages of end motifs CGA, CGC, CGG, and CGT out of all of the 3-mer end motifs for all of the DNA fragments analyzed can be determined. The same can be done for NCG. Each value can be used individually or the values for CGN and NCG can be used together to determine a parameter, e.g., a ratio. Such percentages are a type of normalization. Another example of a normalization is a ratio of the amounts of CGN and NCG, e.g., CGN/NCG, NCG/CGN, CGN/(CGN+NCG), and so on. Such various ratios can be used in any embodiment disclosed herein that uses a ratio of CGN and NCG. In some embodiments, such normalized values can also be scaled, e.g., using an expected frequency.

In some implementations, an expected frequency of the end motifs can be determined based on the reference sequence within the region for a reference genome, e.g., how many times a particular end motif appears in the region of the reference genome. The exact expected frequency would depend on the sequence of the region and may be normalized, e.g., the size of the region as may be defined as the total number of k-mer end motifs in the region. The expected frequency can provide information about whether the measured frequency is higher than expected, since certain regions may have more CpG sites than other regions.

In this analysis, an expected frequency of a certain end motif can be determined in silico for adjusting the weight of an observed frequency of the corresponding end motif. A 3-nt interval (i.e., a 3-nt sliding window) was used to scan a region of interest with a step size of 1 nt. In other words, a 3-nt sliding window was moved along a region of interest with a shifting of 1 nt each time. Thus, a number of 3-mer motifs could be generated based on the movement of 3-nt sliding window. The frequencies of those 3-mer motifs generated in silico was deemed as expected frequencies of end motifs related to a region of interest. Thus, the expected frequency is what would occur for random cutting.

In one example embodiment, the ratio of observed to expected frequency of a certain end motif (O/E ratio) can be used for downstream analysis. In the O/E ratio, the O is the observed frequency (i.e., normalized amount) of a particular set of one or more k-mer end motifs. The frequency can be determined via any normalization technique described herein. For example, the observed frequency can be determined as the percentage of fragments having one of the particular set of k-mer end motifs out of all of the k-mer end motifs (e.g., 3-mer end motifs).

Figure 29:
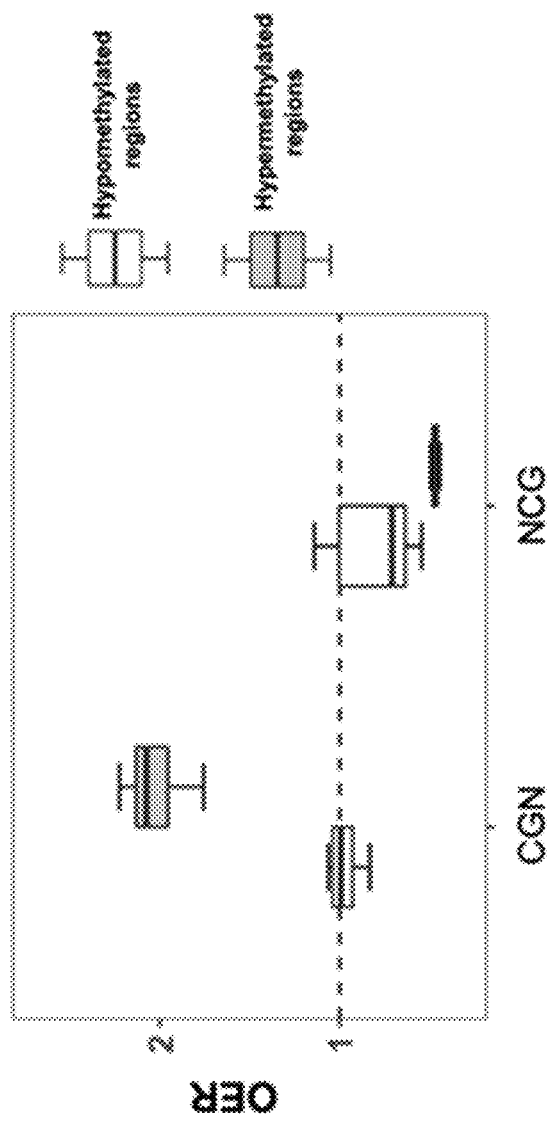
FIG. 29 shows the O/E ratio of CGN and NCG end motifs in hyper- and hypomethylated regions from 8 healthy control samples according to embodiments of the present disclosure.

FIG. 29 shows the O/E ratio of CGN and NCG end motifs in hyper- and hypomethylated regions from 8 healthy control samples according to embodiments of the present disclosure. As shown, the O/E ratio of CGN was substantially higher in hypermethylated regions (median=2.07) than hypomethylated regions (median=0.99) (P value: 0.00016, Mann-Whitney U test). In contrast, the O/E ratio of NCG was higher in hypomethylated regions (median=0.71) than hypermethylated regions (median=0.47) (P value: 0.00016, Mann-Whitney U test). These data suggested that the use of CGN and NCG motifs would allow for informing the hypomethylation or hypermethylation.

Such data can be used to train a model, e.g., to determine a calibration value (such as a cutoff/threshold value for making binary classifications or values used to determine narrower quantitative values, as described herein). For example, when using the O/E ratio determined from the CGN frequency, values above a cutoff of about 1.7 can indicate hypermethylation, as can be determined from FIG. 29. And values below about 1.1 can indicate hypomethylation. When using NCG, values above about 0.6 can indicate hypomethylation, and values below about 0.6 can indicate hypermethylation.

If such training data points (calibration data points) had specific values for the methylation levels (not just hypermethylation or hypomethylation status) in addition to the calibration levels (i.e., the O/E ratio), then such training data points can be used to determine a calibration function (e.g., using regression) that can provide a methylation level for an input O/E ratio. Such use of calibration data points is described throughout the disclosure. The skilled person will appreciate the applicability of such descriptions for one technique can apply to other techniques.

In other embodiments, a ratio can be taken of CGN/NCG, and this ratio can be normalized by an expected ratio of the expected frequencies. Although written as CGN/NCG, such a ratio can have various forms, such as the CGN/NCG motif ratio, or NCG/CGN motif ratio, or CGN/(CGN+NCG), or NCG/(CGN+NCG)). Such a ratio can also include a ratio of the functions of such values. Such variations can be used in any of the embodiments described herein.

2. Feature Vector of k-Mers

Some examples above used amounts of only some end motifs, e.g., only the CGN end motifs of all of the 3-mer end motifs (other values of k for the k-mers can be used). This section describes using amounts for all of the k-mers. Such amounts can form a feature vector that is input to a machine learning model, which as examples can determine a binary classification or provide a numerical value, such as a particular percentage (or equivalently a decimal value). Regression can provide such numerical values.

Figure 30:
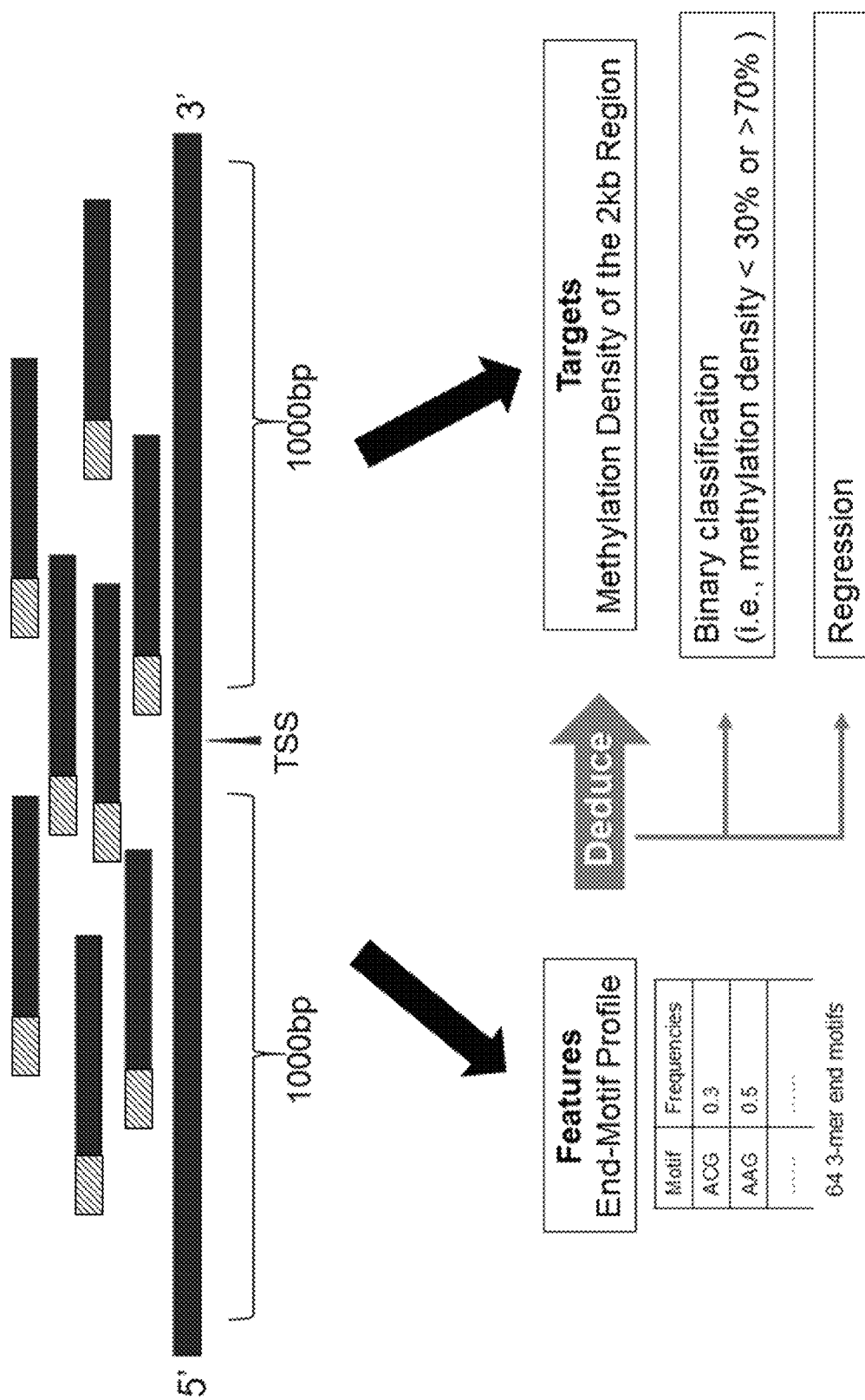
FIG. 30 illustrates the use of 3-mer end motifs for TSS regions to determine binary classification or regression according to embodiments of the present disclosure.

FIG. 30 illustrates the use of 3-mer end motifs for TSS regions to determine binary classification or regression according to embodiments of the present disclosure. The end motifs are shown to the lower left. As shown, 3-mer end motifs are used, but other values for k can be used, such as 1, 2, 4, etc. For a 3-mer motif, there are 64 values in the feature vector. For the 4-mer motif, there is a 256-value frequency vector, which can be input to the machine learning model.

The target determination is a classification of the methylation density of the regions. Two methods are listed. The first one is binary classification, which differentiates a hypermethylated region from a hypo-methylated region. We defined the hypo and hyper as the methylation density less than 30% or over 70%. The regions that have methylation density between these two numbers were excluded in this analysis. We also use a regression model to quantitatively predict the exact methylation density, which can include regions that have a methylation density between the thresholds used to define hyper-methylated and hypo-methylated regions.

Figure 31A:
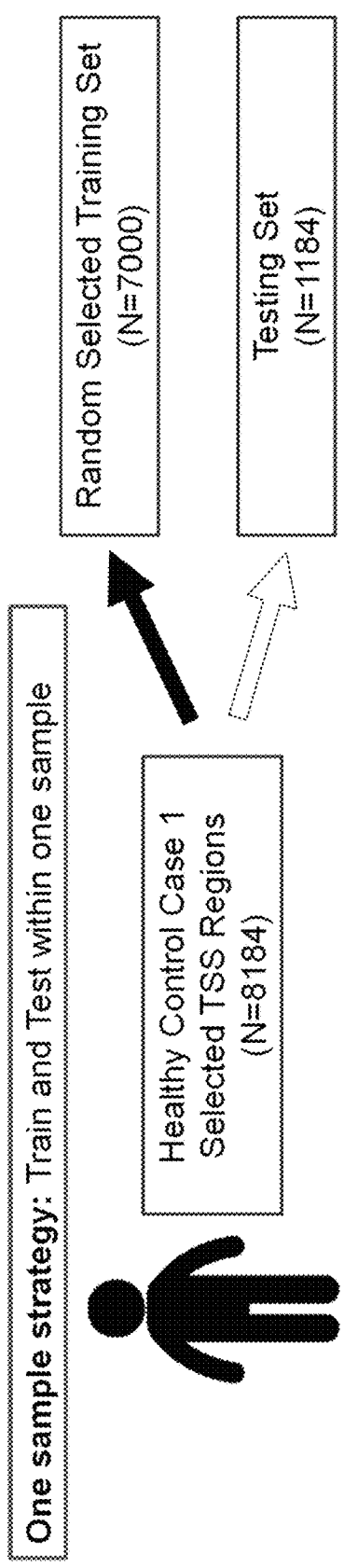
FIGS. 31A-31B show example training procedures according to embodiments of the present disclosure.
Figure 31B:
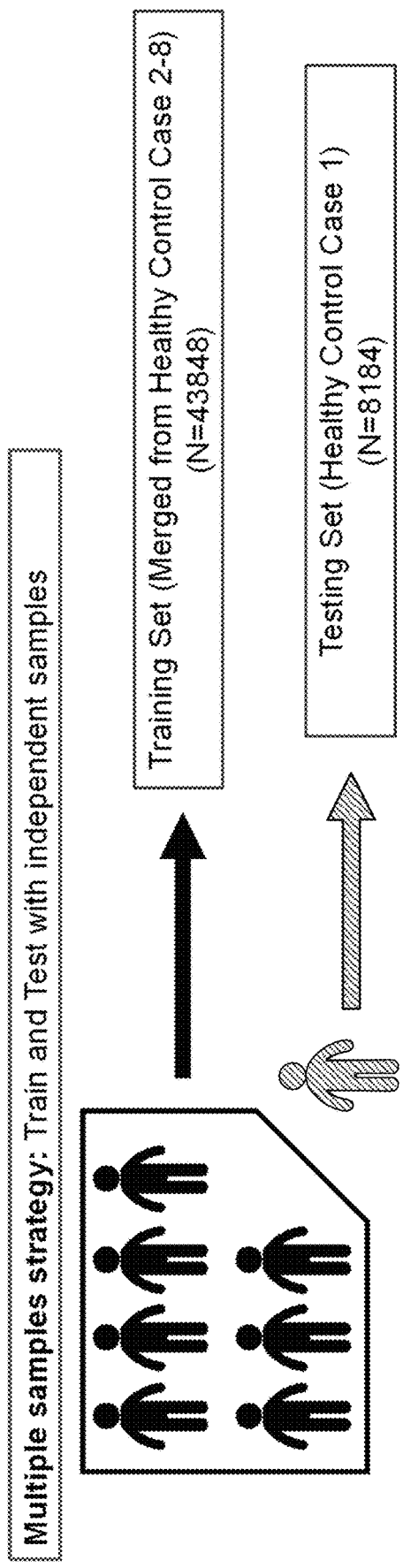
Figure 32A:
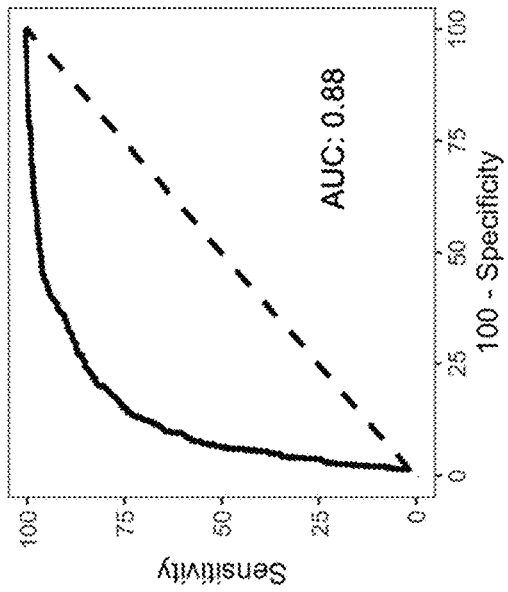
FIGS. 32A-32B and 33A-33B show the results of the binary classification for different k-mer motifs according to embodiments of the present disclosure.
Figure 32B:
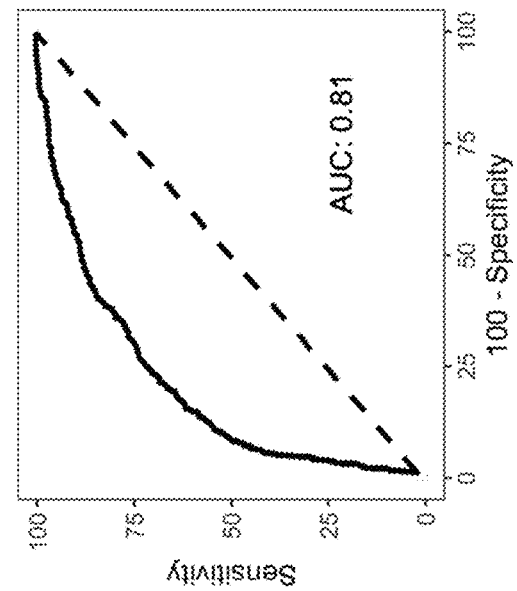
Figures 33A, 33B:
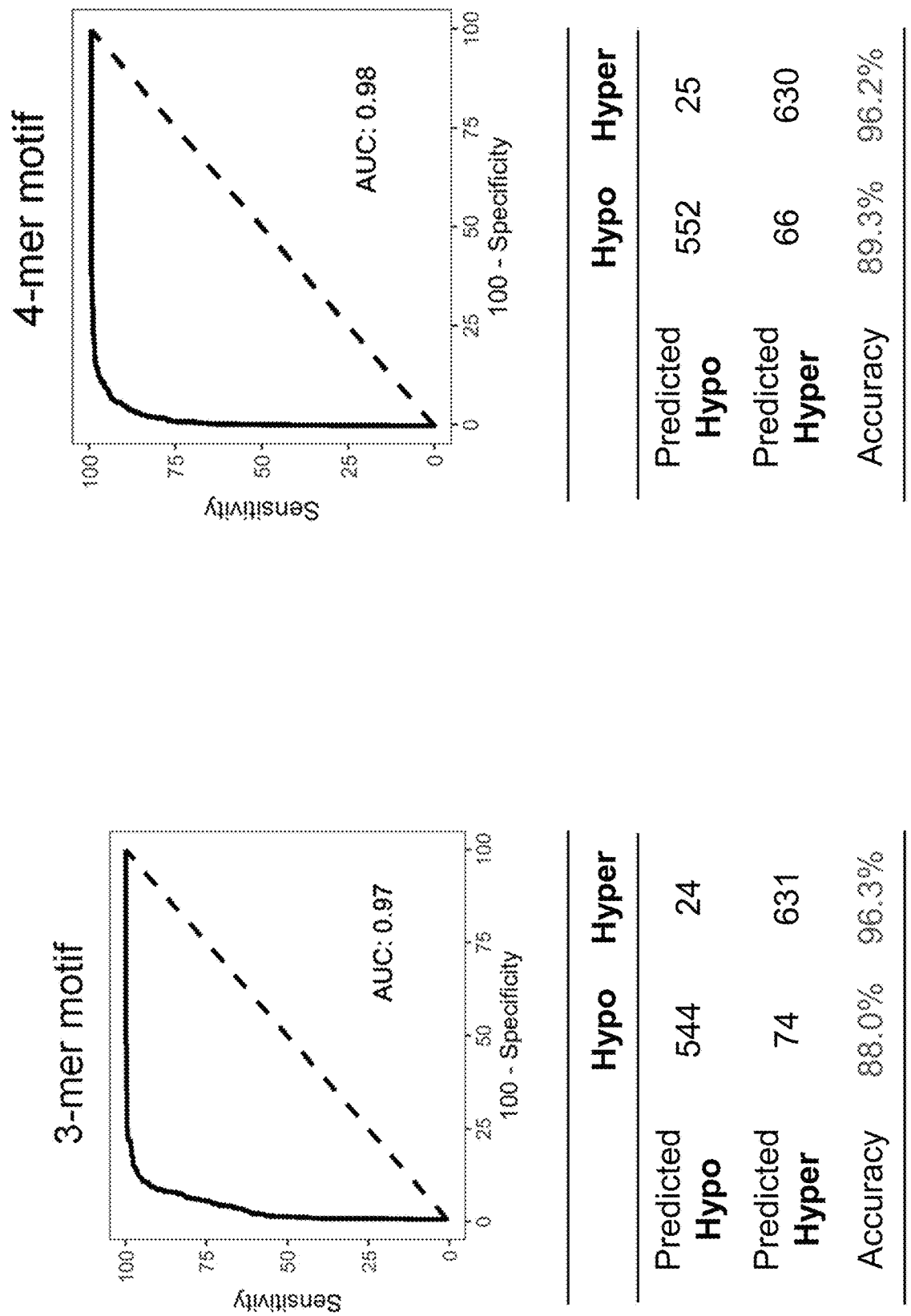

FIGS. 31A-31B show example training procedures according to embodiments of the present disclosure. FIG. 31A shows the training for a single subject and is labeled as the one sample strategy. We train and test the regions within one sample. We selected over 8,000 regions that meet the criteria. We divided the regions into randomly selected training sets, and the remaining regions were used as testing set. There is no overlap between these two sets. The technique in FIG. 31A is used to generate data in FIGS. 32A, 32B, 33A, 33B, and 36.

FIG. 31B shows the training where multiple subjects are used and is labeled as the multiple samples strategy. We merge the seven healthy control cases and got over 43 thousand regions. We tested the model using an individual, which has about 8,000 regions. The technique in FIG. 31B is used to generate data in FIGS. 34A, 34B, and 38.

We implemented the SVM to predict whether a TSS region had a methylation density over 70% or below 30% by using regional 5' k-mer end motif frequencies (e.g., the first three nucleotides at the 5' ends of cfDNA fragments and a total of 64 types of 3-mer motifs).

FIGS. 32A-32B and 33A-33B show the results of the binary classification for different k-mer motifs according to embodiments of the present disclosure. These results used the one sample strategy. We observed the prediction accuracy increased from 1-mer motif to 4-mer motif. The increase is most significant from 2-mer motif to 3-mer motif. The AUC for 3-mer end motifs could achieve of around 0.97 to predict the regional methylation density from the end-motif profiles.

Figure 34B:
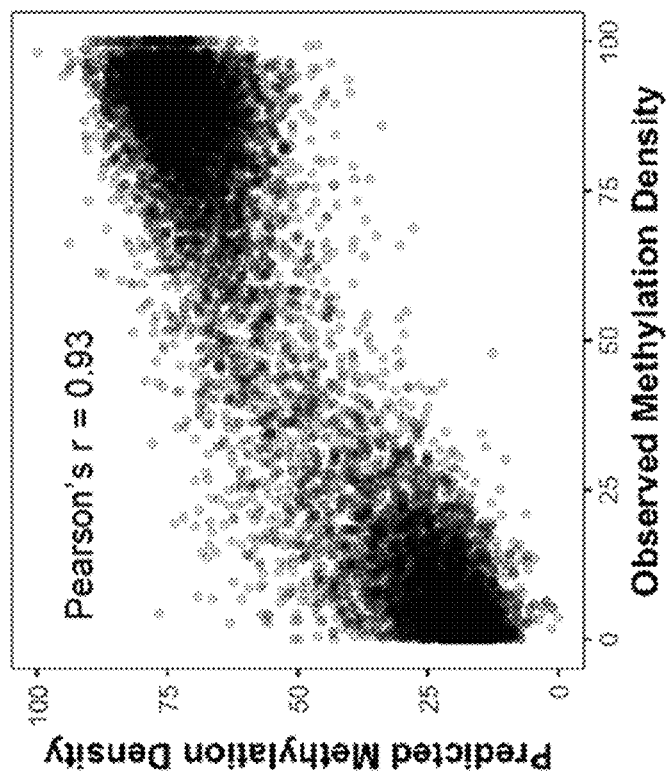
FIG. 34B shows the performance of regional methylation density estimation using SVR on the basis of regional end motif frequencies according to embodiments of the present disclosure.
Figure 34A:
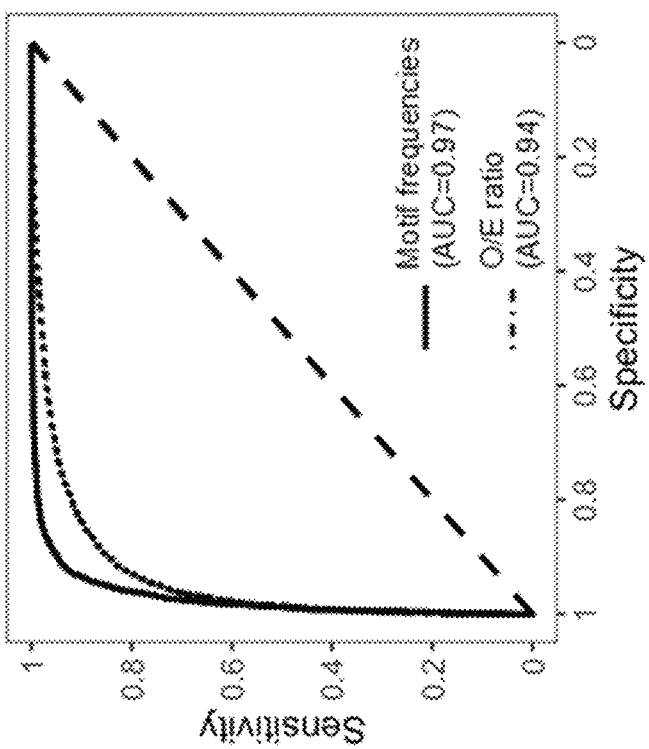
FIG. 34A shows the performance of regional methylation status prediction using SVM on the basis of regional end motif frequencies or O/E ratios of end motifs according to embodiments of the present disclosure.

FIG. 34A shows the performance of regional methylation status prediction using SVM on the basis of regional end motif frequencies or O/E ratios of end motifs according to embodiments of the present disclosure. Regional end motif frequencies or O/E ratios of end motifs from TSS regions (i.e., ±1000 bp of TSSs) with methylation density over 70% and below 30% from 7 healthy control samples were used to train the model. TSS regions from one independent healthy control sample were used for performing the ROC analysis regarding differentiating the methylated and unmethylated status of a genomic region. The solid and dashed line represents the model performance based on end motif frequencies and O/E ratios of end motifs, respectively.

The SVM models trained by 5' 3-mer end motif frequencies and O/E ratio of 5' 3-mer end motifs reached an AUC of 0.97 and 0.94, respectively. These data suggested that the use of 5' end motifs were informative for methylation density prediction in a particular region of interest. Note that the use of 5' end motifs is just one example. The 3' end motifs could be used in addition or instead for any embodiments described herein.

In another embodiment, we implemented the support vector regression (SVR) to predict the methylation density of TSS regions based on regional 5' 3-mer end motif frequencies. The SVR can perform a multi-dimensional linear regression. We trained the model use the exact number of the methylation density, and we predict the percentage of the methylation density.

FIG. 34B shows the performance of regional methylation density estimation using SVR on the basis of regional end motif frequencies according to embodiments of the present disclosure. Regional end motif frequencies from TSS regions (i.e., ±1000 bp of TSSs) from 7 healthy control samples were used to train the model to predict the methylation densities of TSS regions from one independent healthy control sample. The scatter plot shows the correlation between predicted methylation densities and observed methylation densities detected by using bisulfite sequencing for a testing sample.

The predicted methylation densities was well correlated with methylation densities deduced by bisulfite sequencing (Pearson's r: 0.93). Thus, the data suggested that the 3-mer end motif profiles allowed for deducing the methylation density of a genomic region of interest. In another embodiment, regional end motif frequencies could be used to predict the methylation density of other regions such as CpG islands (CGI), long interspersed nuclear elements (LINEs), Alu repeats, microsatellites, tandem repeats, enhancers, transposons, transcription factor binding sites, etc. In another embodiment, end motifs could involve, but not limited to, 1 nt, 2 nt, 3 nt, 4 nt, 5 nt, 6 nt, 7 nt, 8 nt, 9 nt, and 10 nt or above at each end of cell-free DNA molecules. In yet another embodiment, other machine learning models can be implemented, such as decision tree, Bayes classifier, support vector regression, recurrent neural network, other neural network-based models, and so on as will be appreciated by the skilled person.

In some embodiments, only certain end motifs are used, e.g., those corresponding to CGN or NCG, or only those including CG (i.e., including CGN and NCG, and even larger motifs depending on the value of k).

C. Normalization

The sequence context itself may play a role to predict the methylation status. Various types of normalization can be performed using sequence context for a region. Example types of normalization can use expected frequency per region (as described above) or a normalization that is per fragment.

1. Normalized Motif Frequency by Region

Figure 35:
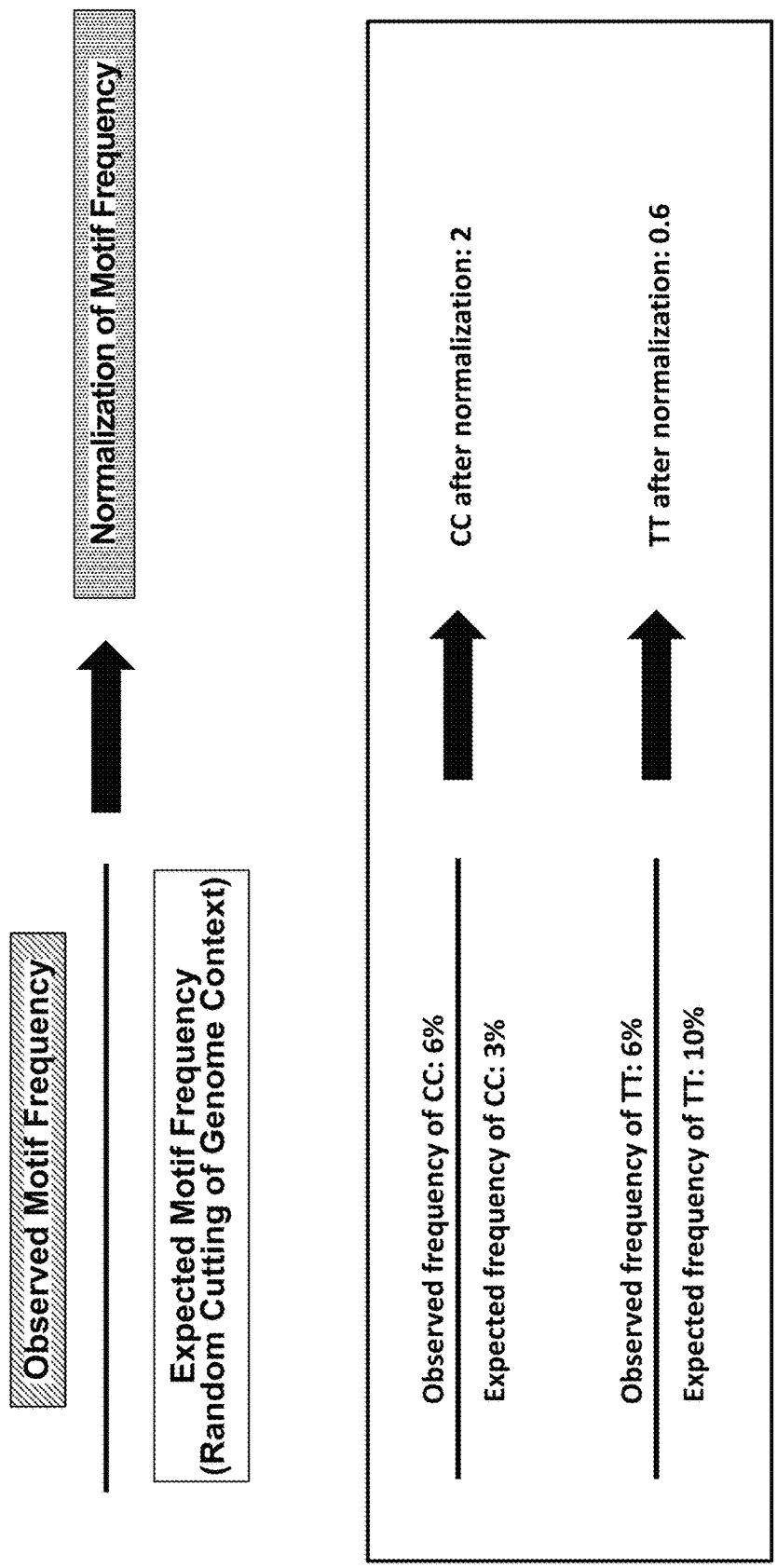
FIG. 35 illustrates a normalization using an expected frequency of a region (regional normalization) for each motif according to embodiments of the present disclosure.

FIG. 35 illustrates a normalization using an expected frequency of a region (regional normalization) for each motif according to embodiments of the present disclosure. The normalized motif frequencies for different motifs can then be used to generate a feature vector that is input to a ML model.

The expected frequency for a given motif in a region can be computed using a sliding window, e.g., as described above. The expected frequency can provide a measure of what frequency would be expected if the cutting were random. As shown, the observed frequency is divided by the expected frequency for a given region, and the normalized value for CC is 2, indicating a higher frequency than expected. The normalized frequency for TT is lower than expected. This normalization can remove the effects caused by the sequence context. In this way, we only keep the effects from the cutting preference.

Figure 36:
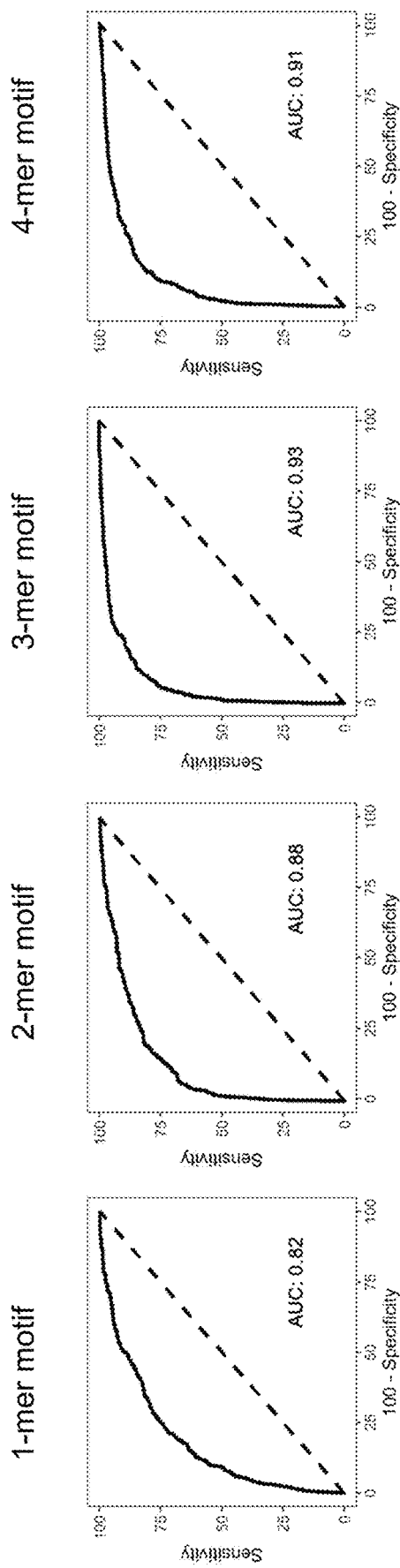
FIG. 36 shows result of binary classification using an SVM model that uses context normalized (regional normalization) end-motifs according to embodiments of the present disclosure.

FIG. 36 shows result of binary classification using an SVM model that uses context normalized end-motifs (regional normalization) according to embodiments of the present disclosure. The results are worse relative to the no normalization as shown in FIGS. 32A-33B. For the 3-mer motif and 4-mer motif, we observe a decreased prediction accuracy. This decrease may be because the sequence context has some information, and by the normalization we actually lose this part of the information. Another cause may be that, for the 4-mer motif, it has a diversity of 256 different types. But most regions only have mapped ends between 100 and 200 types. Thus, the features of 4-mer motif is relatively sparse. Larger regions may resolve such issues as there would be more motifs seen.

2. Normalized Motif Frequency Per Molecule

We also investigated a normalization per molecule.

Figure 37:
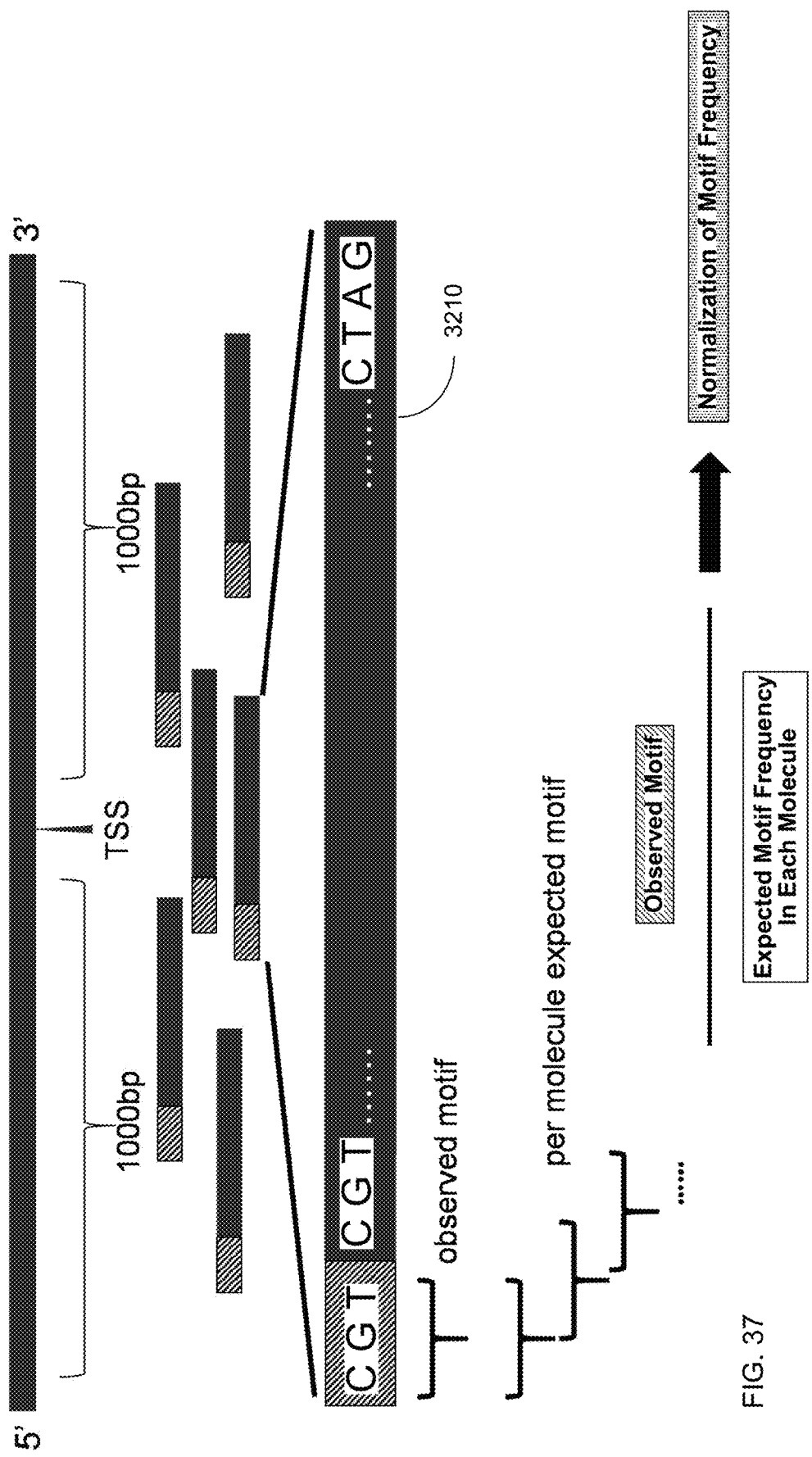
FIG. 37 shows a normalization on a per molecule context using an expected motif frequency in the molecule according to embodiments of the present disclosure.

FIG. 37 shows a normalization on a per molecule context using an expected motif frequency in the molecule according to embodiments of the present disclosure. The fragments are shown relative to a reference genome, but the normalization is done using the sequence of the respective molecules. The sequence of the respective molecule can be determined using the reference though, e.g., when the entire fragment is not sequenced and the two ends of a fragment are mapped to the reference. The reference sequence can be used to fill in the parts of the molecule that are not sequenced.

The example fragment shown has an end motif of CGT. The observed motif occurs so can be considered 1. The expected motif frequency can be determined using the 3-base sliding window over the fragment, e.g., as described herein. For instance, if the fragment is 150 bp, then there are 148 possibilities for cutting. If just one of those possibilities is CGT, then the expected frequency is 1/148, thereby providing a normalized motif frequency of 148. However, if there were five instances of CGT, then the expected frequency is 5/148, and the normalized frequency would be 29.6. In this manner, the expected frequency can act as a weight for each fragment for how much the fragment can contribute to normalized motif frequency.

Figure 38:
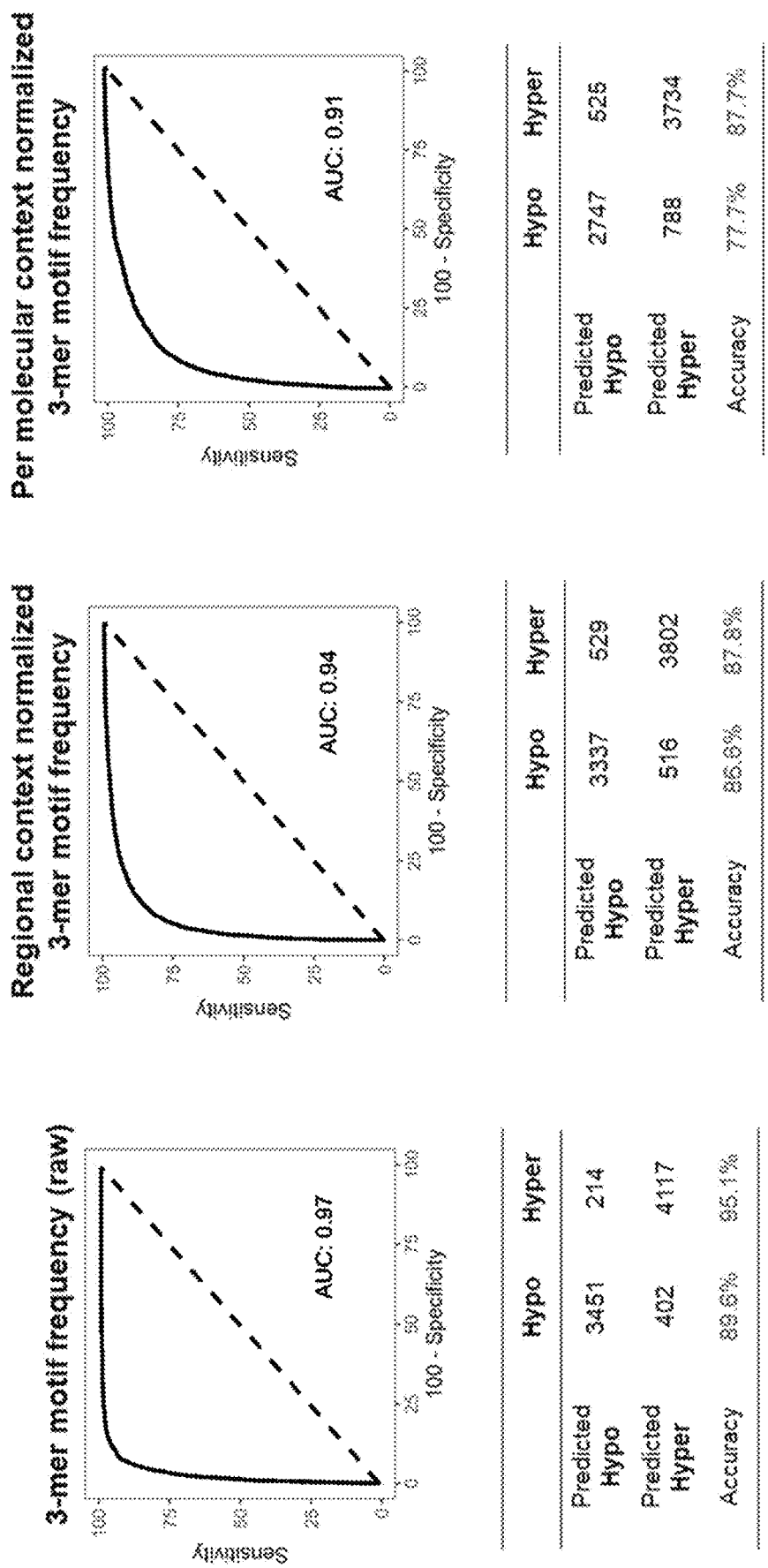
FIG. 38 shows results for 3-mer motifs for no normalization, regional normalization, and per molecule normalization according to embodiments of the present disclosure.

FIG. 38 shows results for 3-mer motifs for no normalization, regional normalization, and per molecule normalization according to embodiments of the present disclosure. The results using the raw 3-mer motif frequencies performed the best.

D. Which Ends Provide Most Differentiation

We investigated to see which ends provide the best differentiation for the prediction model.

Figure 39:
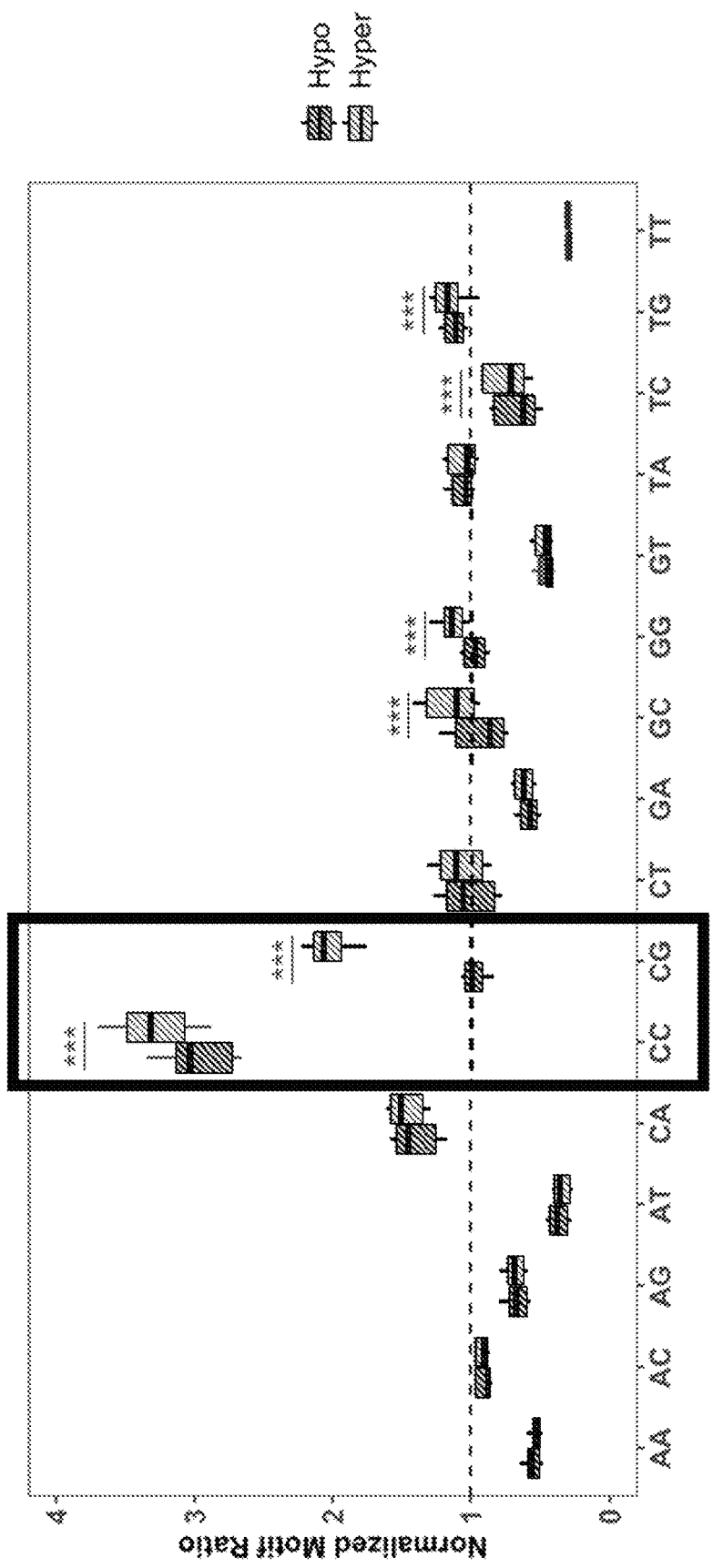
FIG. 39 shows differences in the normalized frequency (regional normalization) for different 2-mer end motifs according to embodiments of the present disclosure.

FIG. 39 shows differences in the normalized frequency (a regional normalization was used) for different 2-mer end motifs according to embodiments of the present disclosure. The Y axis shows the normalized motif frequency. If cutting was random, we would expect the motif frequency to be around one after normalization. We observe the two outliers with CC and the CG. Regardless of hypo-methylated or hyper-methylated, there are many CC ends. In hyper-methylated regions, the CC ends further increased.

For CG, in the hypo-methylated regions, there is no cutting preference because it is near the dash line at 1. But in hypermethylated region, it is preferred to cut at this CG. This is in line with other results herein. Also the CG end motif shows the greatest difference between the hypomethylated regions and the hypermethylated regions, which is consistent with the results above.

Given the difference between the normalized motif ratio (frequency) for CC and CG, such a ratio can be used to discriminate (classify) between a region being hypomethylated and being hypermethylated. Such classifications using calibration values can be performed as described above, e.g., for FIG. 29. Using regional normalization, the CG end motif provides the best separation.

Figure 40:
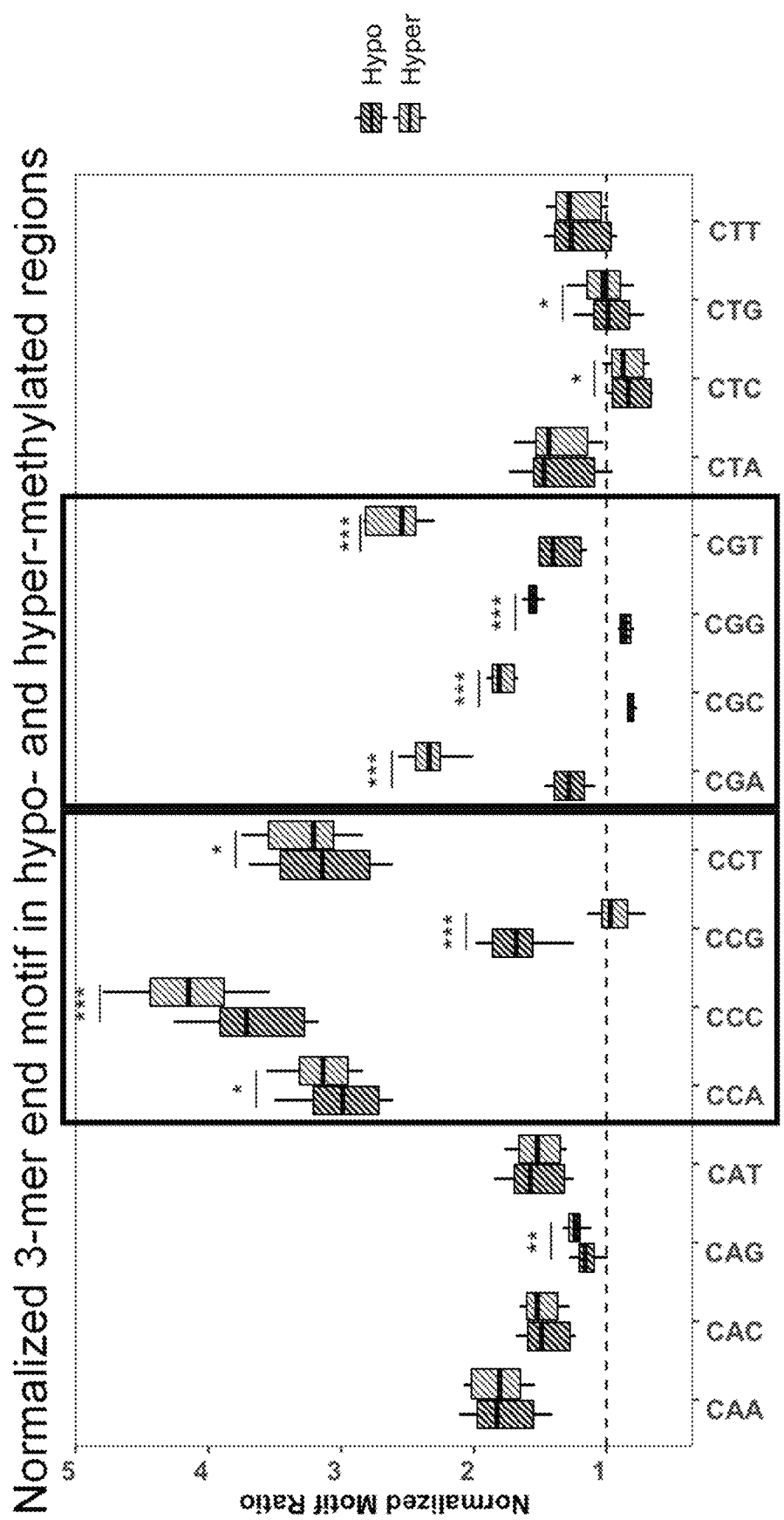
FIG. 40 shows differences in the normalized frequency (regional normalization) for different 3-mer end motifs according to embodiments of the present disclosure.

FIG. 40 shows differences in the normalized frequency (regional normalization) for different 3-mer end motifs according to embodiments of the present disclosure. The CGN end motif shows the greatest difference, which is consistent with the results above. Again, we look into the motifs starting with CC and CG regions. We can see the motifs CA and CT do not show very significant difference in the hypo-methylated region and the hyper-methylated region, but the CC and the CG motifs show some differences, with the CG motifs showing more differences than the CC motifs. Further, the differences are consistent with the hypermethylated regions having more amounts of the CN motifs.

E. Methods of Determining Methylation in a Region

Methods are provided for using cleavage information to determine methylation of a region in a genome. The methylation can be a property of the sample or a property of a particular region in the genome, where the location of the region can be defined relative to a reference genome. The cleavage information can be of various types, as described herein, e.g., sequence end motifs.

Figure 41:
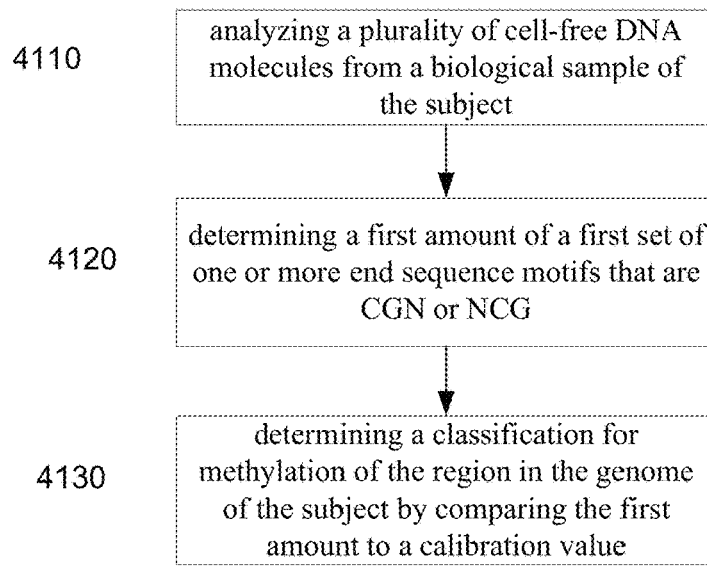
FIG. 41 is a flowchart illustrating a method for predicting methylation in a region according to embodiments of the present disclosure.

FIG. 41 is a flowchart illustrating a method 4100 for determining methylation in a region according to embodiments of the present disclosure. As with other methods described herein, method 4100 can be performed partially or entirely using a computer system. Blocks performing similar functionality as in other methods can be performed in a similar manner as described for those blocks in other flowcharts. The region may comprise disjoint subregions (i.e., not contiguous) that may be on a same chromosome or on different chromosomes.

At block 4110, a plurality of cell-free DNA molecules from a biological sample of the subject are analyzed. Block 4110 can be performed in a similar manner as block 2710 and vice versa. As with block 2710, analyzing a cell-free DNA molecule can include determining a location of the cell-free DNA molecule in a reference genome, e.g., when the region is smaller than the entire genome. The plurality of cell-free DNA molecules can be located in the region of the reference genome.

The location can be determined in various ways, as described herein, such as aligning sequence reads to the reference genome or using location-based probes. A location-based probe is one for which the sequence is largely or entirely based on a sequence present in a reference genome. Hence, the binding of a location-based probe can be used to indicate the genomic location of a bound piece of DNA. The bound piece of DNA can be a cell-free DNA molecule found in a bodily fluid, e.g., plasma, serum, saliva, urine, peritoneal fluid, cerebrospinal fluid, sweat, seminal fluid, semen, vaginal secretions, cervical fluids, etc.

The region can be the entire reference genome or a portion of the genome of the subject. The portion of the genome can be 10 Mb or less of a particular chromosome; other sizes of a region are mentioned herein. Thus, the plurality of cell-free DNA molecules can be from one or more particular regions of the reference genome. At least one of the one or more particular regions can correspond to a particular genotype or haplotype comprising one or more alleles. In this manner, methylation of a genotype, haplotype, and particular chromosome copy can be determined. If a subject has certain methylation levels at a genotype or a haplotype, such a property can indicate a pathology (e.g., via genomic imprinting, which is described in more detail elsewhere in this disclosure). For example, certain methylation levels (e.g., a particular methylation classification) can silence genes, which relates to a pathology, as may result from a disease (e.g., cancer, inflammation) or an abnormal condition/disorder of or linked to a physiological process (e.g., during cell differentiation or during development, or ageing). A copy number aberration can be such a pathology. Embodiments can also determine a normal level of a physiological process, e.g., monitoring of a stage of gestation or ageing of a person, or a type or level of genomic imprinting of a person.

The analysis can include determining an end sequence motif (also referred to as end motif) of at least one end of the cell-free DNA molecule. The end sequence motif can be determined from the outermost bases in a sequence read. If a sequence read only includes one end and not the entire DNA fragment/molecule (e.g., as one of paired reads covering both ends), the bases corresponding to the end of the DNA fragment are used and not the bases toward the middle of the fragment. An end of the cell-free DNA molecule can have a first position at the outermost position, a second position that is next to the first position, and a third position that is next to the second position.

At block 4120, a first amount of a first set of one or more end sequence motifs that have C at the first position and that have G at the second position is determined (e.g., an amount of CGN or anyone of more these motifs). The first set of one or more end sequence motifs can include one or more of CGA, CGC, CGG, and CGT, with CGN denoting all. In other embodiments, the first amount can be of a first set of one or more end sequence motifs that have C at the second position and G at the third position (e.g., NCG). In this example, the first set of one or more end sequence motifs can include one or more of ACG, CCG, GCG, and TCG, with NCG denoting all. Such example end motifs can be used in various ways as described herein to determine amounts and/or normalized parameters (e.g., frequencies) for use in making the classification. Additional normalization based on expected frequency per region or per fragment can be used.

Block 4120 can be performed in a similar manner as block 2720. For example, the first amount can be determined using sequencing or probe-based techniques, such as PCR. An amount of sequence reads having the particular end motif can be counted. As another example (e.g., as depicted in FIG. 4), probe-based techniques can be used. For example, a number of reactions positive for a particular probe can be used. As another example, an intensity signal (e.g., electrical or optical) from probes that are specific to a particular end motif can be used to determine the first amount.

At block 4130, a classification for methylation of the region in the genome of the subject is determined by comparing the first amount to a calibration value. The calibration value can be determined using cell-free DNA molecules that are from one or more calibration samples and that are located at regions (each including one or more CpG sites) having known classifications. The known classifications can be determined using a methylation-aware assay or from the results of others that used a methylation-aware assay.

Other amounts can be determined, e.g., for normalization. For example, when the first amount is determined using one or more CGN motifs, a second amount of a second set of one or more end sequence motifs that have C at the second position and G at the third position (e.g., NCG) can be determined. Determining the classification can then include normalizing the first amount with the second amount to obtain a normalized first amount that is compared to the calibration value. The second set of one or more end sequence motifs can include all of or one or more of ACG, CCG, GCG, and TCG.

Another example of an amount is an expected amount, as is described above. An expected amount can be determined of the first set of one or more end sequence motifs based on a reference sequence of the reference genome in the region. Then, determining the classification can include normalizing the first amount with the expected amount to obtain a normalized first amount (e.g., O/E ratio) that is compared to the calibration value.

As another example of normalization, a total amount of sequence motifs for the plurality of cell-free DNA molecules (e.g., in the region) can be determined. Then, determining the classification can includes normalizing the first amount with the total amount to obtain a normalized first amount (e.g., a motif ratio or relative frequency) that is compared to the calibration value.

As with other techniques described herein, a feature vector of multiple amounts can be provided to a machine learning model, e.g., as described in sections above. The different amounts can correspond to a selection of end motifs, e.g., those included in the first set and additional end motifs. Such end motifs included in the feature vector can be all of the k-mers for a particular k or just a subset. Accordingly, a respective amount of each 3-mer end sequence motif that has a C at the first position and that has G at the second position can be determined (i.e., four amounts for CGN). A feature vector including the respective amounts, which include the first amount, can be generated and then input into a machine learning model as part of determining the classification for methylation of the region in the genome of the subject. The machine learning model can be trained using cell-free DNA molecules that are from the one or more calibration samples. Additionally or alternatively, the feature vector can include respective amounts for each 3-mer end sequence motif that has a C at the second position and that has G at the third position (i.e., for NCG). As mentioned above, the feature vector can include respective amounts of all 3-mer end sequence motifs.

V. Predicting Methylation of Site in a Particular Fragment

Some embodiments can use the end motif patterns associated with a single plasma DNA molecule, combined with other features such as fragment size and sequence context, to predict its methylation status. The methylation status could be fully methylated, fully unmethylated or partially methylated. Various types of data can be used besides end motifs for determining a methylation level for the CpG sites on an individual fragment.

A. Inputs

Figure 42:
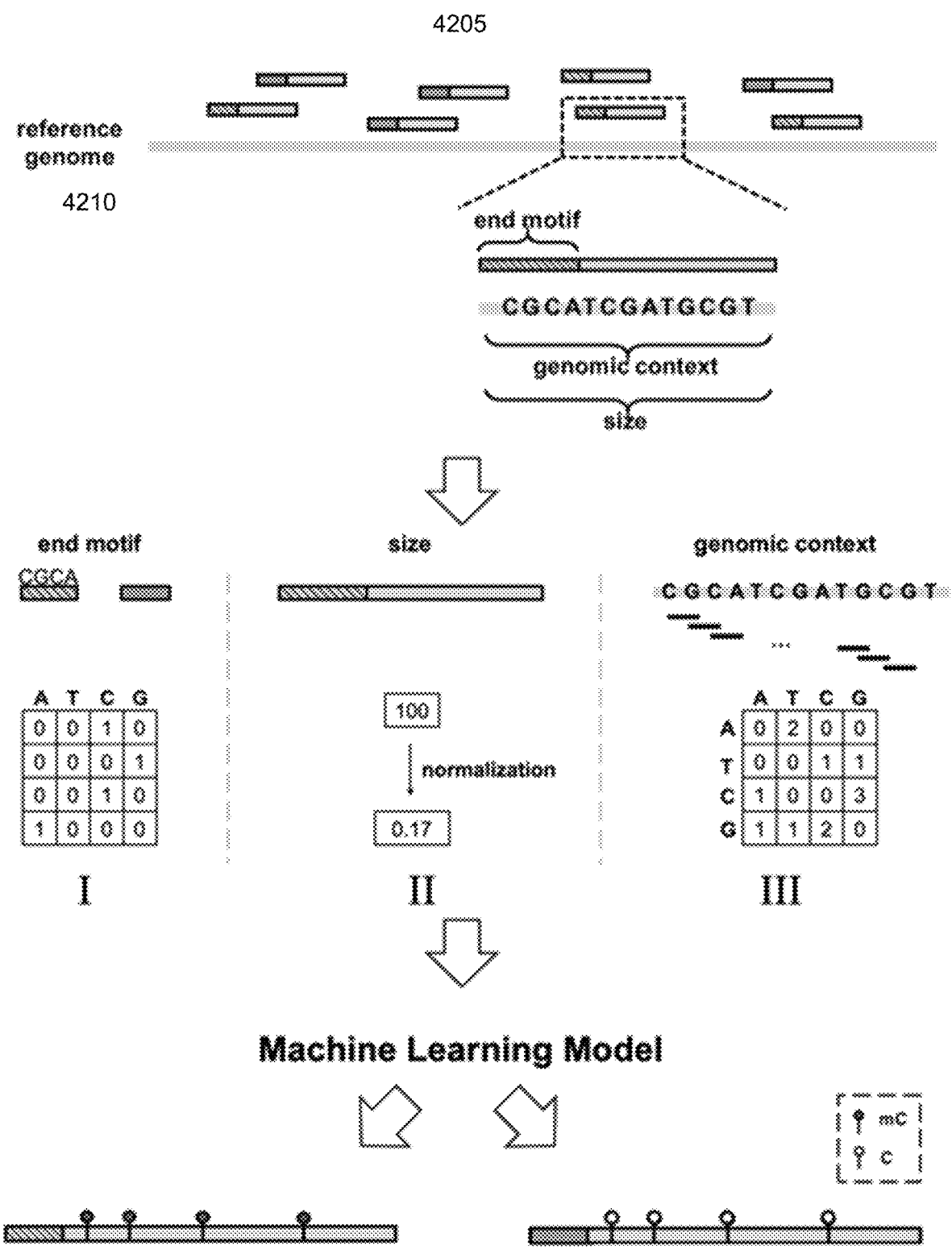
FIG. 42 shows an example workflow of a machine learning model for predicting methylation status at a single molecule level according to embodiments of the present disclosure. Figure discloses SEQ ID NOS 13 and 13, respectively, in order of appearance.

FIG. 42 shows an example workflow of a machine learning model for predicting methylation status at a single molecule level according to embodiments of the present disclosure. The reference genome 4210 is shown with fragments 4205 aligned. For each fragment, three types of information is shown: end-motifs, genomic (sequence) content, and the size. Such data can be formed into various data structures for creating a feature vector. One example for the feature vector is shown in FIG. 42.

On the left, the end motif is converted into a matrix that has one-hot encoding for each position. For example, the end-motif is a CGCA. The first base is a C, so the first row will be one for the C and zero for the other bases. The second base is the G, so the second row of G will be one. The third base is C; and the fourth base is A. Accordingly, we coded the end motif from the 5' end, a matrix on the basis of one-hot-encoding rule. A 4-dimensional vector was used for encoding a nucleotide. For example, [1, 0, 0, 0], [0, 1, 0, 0], [0, 0, 1, 0] and [0, 0, 0, 1] represent A, C, G, and T, respectively. Thus, for an end motif of 'CGCA', the matrix would be expressed as the format shown in FIG. 42 (denoted by the feature I). The end motif can be represented in other ways, e.g., using a value of 1 to 4 respectively assigned to each base type, e.g., A=1, C=2, G=3, and G=4.

In the middle, the use of size is shown. In this example, the size of the fragment size is determined based on the pair-end sequencing, and alignment of the sequence reads to a reference genome. When an entire molecule is sequenced, the alignment is not needed. A normalization can be done, e.g., by dividing by 600, as most cell-free DNA fragments are less than 600 bp. Accordingly, the fragment size can be determined by the outmost genomic coordinates of the aligned paired-end reads and normalized by a factor of 600 bp (denoted by the feature II).

On the right, the genomic context is a matrix that includes a dinucleotide pattern. The first base in the 2-mer is on the rows, and the second base is in the columns. For each particular 2-mer, a matrix element stores a count for the number of instances of that 2-mer. Thus, the sequence context can be encoded into a matrix comprising the counts of di-nucleotide types along a single plasma DNA molecule. With a 2-nt slide window to scan a single plasma DNA molecule, we determined di-nucleotide frequencies of a single plasma DNA molecule. A 2-dimensional (2-D) matrix was used to express di-nucleotide frequencies (denoted by the feature III). For example, if the frequency of "AT" di-nucleotide is 2, "2" would be filled into in the cell of raw "A" and column of "T". Other k-mer arrays (vectors, matrices, or higher order tensors) can be used. For trinucleotide pattern, there would be three dimensions to the array. The genomic (sequence) context can also be the entire sequence. Another example of genomic context is the GC percentage.

Two or more of these features can be combined (or just end motifs used alone) and input to a machine learning model for predicting whether this molecule is fully methylated or fully unmethylated, or partially methylated. The combined feature matrices containing the aforementioned features (I, II and III) were used for training a CNN model to determine whether one DNA fragment is fully methylated or fully unmethylated.

B. Results

Figure 43A:
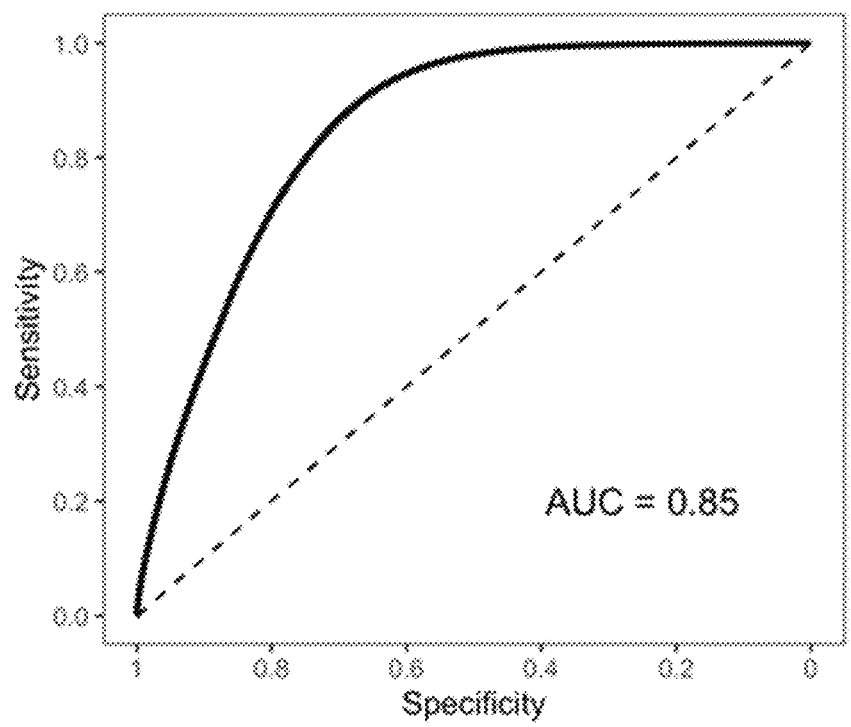
FIG. 43A shows the performance of methylation status analysis of single molecule using CNN on the basis of end motifs, sequence context, fragment sizes according to embodiments of the present disclosure.

FIG. 43A shows the performance of methylation status analysis of single molecule using CNN on the basis of end motifs, sequence context, fragment sizes according to embodiments of the present disclosure. One could obtain the model for differentiating the methylated and unmethylated molecules with an AUC of 0.85. The results suggested that the use of fragmentomic features with other characteristics derived from a single plasma DNA molecule possibly enabled the determination of the methylation status of that plasma DNA molecule.

Figure 43B:
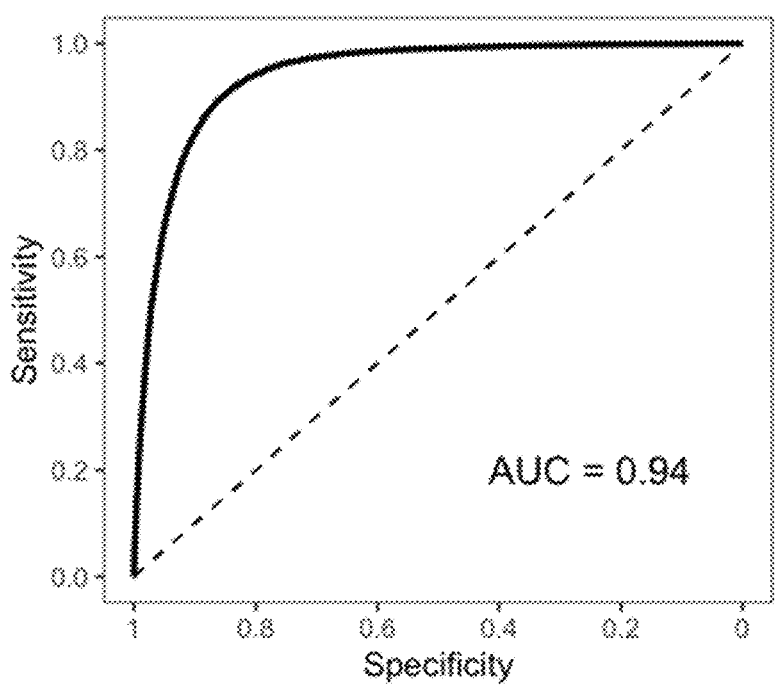
FIG. 43B shows the performance of methylation status analysis of single molecule using molecules with CGN and NCG end motifs based on a CNN model according to embodiments of the present disclosure.

FIG. 43B shows the performance of methylation status analysis of single molecule using molecules with CGN and NCG end motifs based on a CNN model according to embodiments of the present disclosure. Thus, the accuracy was determined a subset of the DNA fragments. Interestingly, if one focused on those molecules starting with CGN or NCG end motifs, the model performance could be significantly improved (i.e., the AUC of from 0.85 to 0.94; P value <0.0001, DeLong test). Hence, the selective analysis of subset of DNA molecules with certain motifs would allow for enhancing the classification power in deducing the methylation status of a single molecule.

The CGN and NCG motifs can act like a tag in the DNA fragment that enables distinguishing fully methylated and fully unmethylated DNA fragments on an individual, molecular level more accurately. Accordingly, on a per-fragment basis, embodiments can determine how methylated a particular fragment is.

C. Methods for Predicting Methylation of a Fragment Site

As described above, methods are also provided for using cleavage information to determine the methylation status at site(s) of a single fragment. The cleavage information can be of various types, as described herein, e.g., sequence end motifs.

Figure 44:
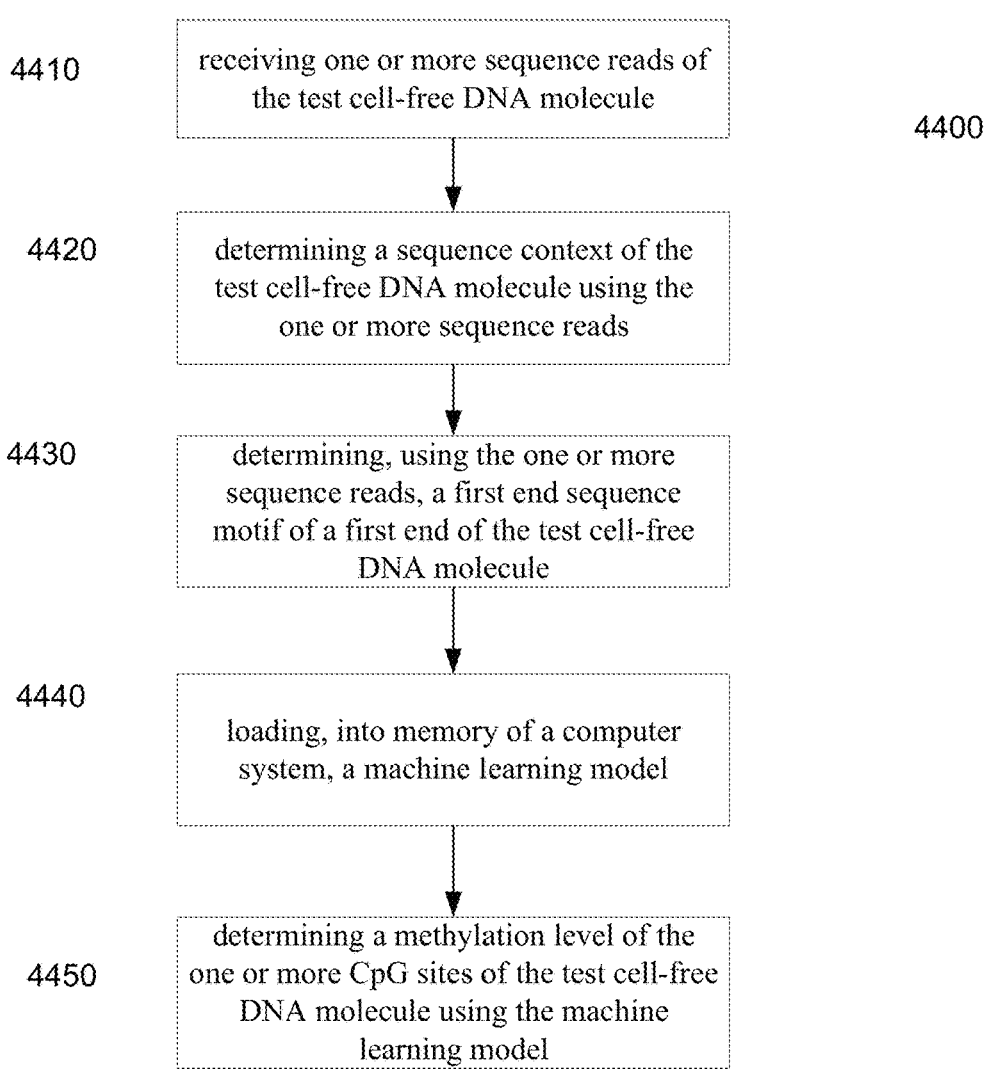
FIG. 44 is a flowchart illustrating a method for predicting methylation of a DNA fragment according to embodiments of the present disclosure.

FIG. 44 is a flowchart illustrating a method 4400 for predicting methylation of a DNA fragment according to embodiments of the present disclosure. As with other methods described herein, method 4400 can be performed partially or entirely using a computer system. Blocks performing similar functionality as in other methods can be performed in a similar manner as described for those blocks in other flowcharts.

At block 4410, one or more sequence reads of the test cell-free DNA molecule can be received. The test cell-free DNA molecule can be generated in various ways, e.g., using techniques described for block 2710 and 4110. The test cell-free DNA molecule can include one or more CpG sites.

At block 4420, a sequence context of the test cell-free DNA molecule is determined using the one or more sequence reads. Examples of the sequence context include combination of bases that appear sequentially (e.g., various k-mers, also referred to as K-mers). For instance, the sequence context can include a K-mer matrix specifying a number of instances of each K-mer in the test cell-free DNA molecule, wherein K is an integer. When K equals 2, the K-mer matrix is a di-nucleotide matrix specifying a number of instances of di-nucleotide pairs in the test cell-free DNA molecule. As another example, the sequence context can include sequence information from each nucleotide of the test cell-free DNA molecule (i.e., the entire sequence).

At block 4430, a first end sequence motif of a first end of the test cell-free DNA molecule is determined using the one or more sequence reads. The number of bases in the first end sequence motif can vary. For example, different k-mers can be used. If there is one sequence read for the entire molecule, the outermost k bases can be selected from either end of the sequence read. If two sequence reads are obtained from both ends, the bases corresponding to the ends of the DNA molecule can be identified based on position information obtained in a sequencing process. If probes are used, the signal corresponding to a particular probe provides the ordering from outermost toward the center of the DNA molecule. A second end sequence motif of a second end of the test cell-free DNA molecule can also be determined.

At block 4440, method 4400 includes loading, into memory of a computer system, a machine learning model that is trained using a training set of training cell-free DNA molecules having CpG sites whose methylation status is known. The training set can include sequence contexts and end sequence motifs of the training cell-free DNA molecules. As examples, the methylation levels of training cell-free DNA molecules can be determined using methylation-aware sequencing or by artificially causing all of the CpG sites to be methylated or unmethylated. For instance, whole genome amplification can make the newly synthesized DNA unmethylated, and CpG methyltransferase (M.SssI) can render an input DNA sample methylated. The training can involve various techniques and models, including ensemble models. For example, different subset of training samples can be used, and different subsets can be used for validation.

At block 4450, the machine learning model can determine a methylation level of the one or more CpG sites of the test cell-free DNA molecule. The sequence context of the test cell-free DNA molecule and the first end sequence motif (e.g., as part of a feature vector) are input to the machine learning model. Such a feature vector can use other features. For example, the second end sequence motif of the other end can also be input to the machine learning model. Another example feature is size of the test cell-free DNA molecule.

When the test cell-free DNA molecule includes a plurality of CpG sites, the methylation level can be a percentage of the plurality of CpG sites that are methylated. As another example, the methylation level can be whether a particular CpG site is methylated.

Various formats of the feature vector can be used. For example, the first end sequence motif can be one-hot encoded for inputting to the machine learning model. The format for the sequence context (or genomic context) can be a matrix of two or higher dimensions, e.g., based on the value of K used for the K-mers.

As mentioned above, the size can be input into the machine learning model as part of determining the methylation level of the one or more CpG sites of the test cell-free DNA molecule. The size can have various formats, e.g., a number of bases or a ratio relative to a reference size, e.g., 600 bp. The size can be determined in a variety of ways. For example, when one sequence read spans the test cell-free DNA molecule (e.g., as a result of single molecule sequencing), the size of the test cell-free DNA molecule can be determined by counting a number of bases in the one sequence read. As another example, when two sequence reads (paired-end) corresponding to both ends of the test cell-free DNA molecule are obtained, the size can be determined by aligning the two sequence reads to a reference genome.

Various types of machine learning models can be used, such as a convolutional neural network, recurrent neural network, transformer model (encoder-decoder model), random forest classification, and others described elsewhere in this disclosure. The machine learning model can also be a combination of models, thereby being an ensemble model.

VI. Detection of 5hmc Enriched or Depleted Regions

Much of the discussion above generally discussed about methylation and not any specific type of methylation, as it was generally applicable. Techniques can be used to detect a certain type of methylation. For example, hMe-Seal can be used to detect 5hmC methylation. We identify different fragmentation in regions that are 5hmC-enriched (higher proportion of methylation is from 5hmC than other regions) and 5hmC-depleted (lower proportion of methylation is from 5hmC than in enriched regions). In this manner, some embodiments can detect certain regions that have a higher or lower proportion of a certain type of methylation than other regions of the genome. Based on the cutting, some embodiments can determine whether a region is 5hmC enriched or depleted.

A. Relation Between End Motifs and 5Hmc-Enriched and -Depleted Regions 5-hydroxymethylcytosine (5hmC) is an important mammalian DNA epigenetic modification that has been linked to gene regulation and cancer pathogenesis. In bisulfite sequencing, both 5mC and 5hmC are read as cytosines and thus cannot be discriminated. We reasoned that the presence of 5hmC may alter the frequency of CG-containing motifs. To test this hypothesis, we obtained selective chemical labelling based 5hmC sequencing (hMe-Seal) data from 10 plasma DNA samples of healthy subjects (Song et al. Cell Res 2017; 27(10):1231-1242).

hMe-Seal is a method that uses β-glucosyltransferase (βGT) to selectively label 5hmC with biotin via azide-modified glucose for enriching 5hmC-containing DNA fragments for sequencing. Such a biotin can be captured by some beads, which capture 5hmC fragments and not f5mC. The higher sequencing depth around one CpG site represents a higher amount of 5hmC present in a sample. Those higher sequencing depth regions, forming a 'peak' signal across the genome (higher coverage), were defined as "5hmC-enrich regions". By using a peak calling method (e.g., MACS2), we identified 38,168 common 'peak' regions across 10 healthy subjects. We analyzed 4,631,823 CpG sites, which were determined to be commonly methylated across 8 healthy samples (in-house) by bisulfite sequencing. Among them, 25,102 CpGs were overlapped with 5hmC-enriched peak regions (referred to as group I; 5hmC-enriched regions) and 3,409,329 CpGs that were not present at any peak regions of 10 healthy subjects (referred to as group II; 5hmC-depleted regions).

We reasoned that those CpG sites in group I would have relatively more 5hmC modifications whereas those CpG sites in group II would relatively have less 5hmC modifications. Frequencies of CG-containing end motifs were obtained in these selected CpGs in the same 8 healthy plasma samples.

To compare the motif frequencies between group I and group II, we calculated the expected end motif frequencies of CG-containing motifs in these two groups from the reference genome that was used to normalize the observed end motif frequencies. The normalized value was calculated by the observed/expected ratio (O/E ratio). The expected frequency can be determined as described herein, e.g., by using a sliding window having a size k (corresponding to the k-mer end motif being used) to determine the frequency of each of the end motifs being analyzed. In other embodiments, just the observed frequency can be used. We then compared certain end motif frequencies between the two types of regions (5hmC-enriched and 5hmC-depleted).

Figure 45B:
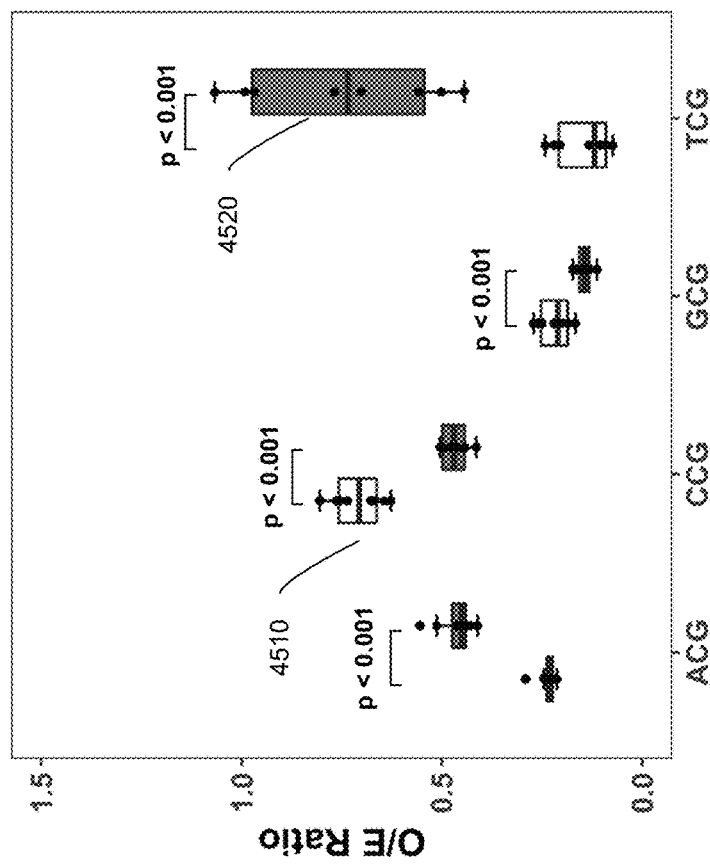
FIGS. 45A-45B are boxplots showing the O/E ratio of CGN and NCG motifs between 5hmC-enriched regions and 5hmC-depleted regions.
Figure 45A:
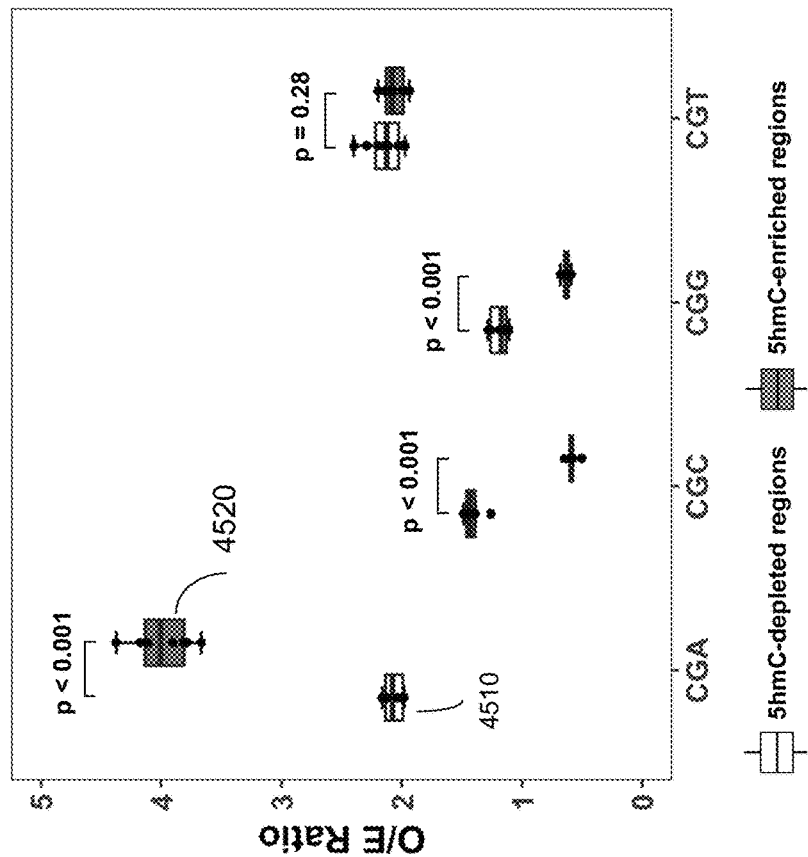

FIGS. 45A-45B are boxplots showing the O/E ratio of CGN (FIG. 45A) and NCG (FIG. 45B) motifs between 5hmC-enriched regions and 5hmC-depleted regions. As shown in FIGS. 45A-45B, compared with cfDNA molecules related to group II CpGs 4510 (depleted), the group I CpGs 4520 (enriched) showed significantly higher O/E ratios in CGA, ACG, and TCG motifs. For CGC, CGG, CCG, and GCG motifs, significantly lower O/E ratios were observed in 5hmC-enriched regions 4520 (i.e., group I CpG sites). These results indicated that the presence of 5hmC would affect the plasma DNA cleavage patterns.

Above, we showed that O/E ratios of CG-containing motifs were different between regions with and without 5hmC. The presence of 5hmC may alter the frequency of CG-containing motifs and O/E ratios of CG-containing motifs. The aberrations in CG-containing motifs can be used to predict the presence of 5hmC in a genomic region.

To illustrate the predictive capability, we used above mentioned identified common 'peak' regions (n=38,168). We then unified the length of peak regions to 200 bp (i.e., peak center+/−100 bp) and further selected peak regions containing at least 1 CpG site for each of the NCG context (i.e., ACG, CCG, GCG, TCG) (n=24,221). Those regions were referred to as regions with 5hmC in healthy control (also referred to as 5hmC-enriched).

For defining regions without 5hmC in healthy control (also referred to as 5hmC depleted), we divided the reference genome into 200-bp bins and identified bins that were not overlapped with regions with 5hmC and contained at least 1 CpG site for each of the NCG contexts (i.e., ACG, CCG, GCG, TCG) (n=992,991). As an example, we pooled WGBS reads of plasma DNA from 8 healthy control samples, and performed classification analysis for the regions with or without 5hmC. To this end, around 2,000 regions with 5hmC and 2,000 regions without 5hmC which had been covered by more than 20 CG-containing ends were used for the downstream analysis.

An SVM model was trained with the O/E ratios of CG-containing motifs (i.e., ACG, TCG, CCG, GCG, CGA, CGT, CGC, and CGG) using a dataset comprising 1,000 regions with and 1,000 regions without 5hmC, respectively. The trained model was used to analyze another independent dataset comprising 1,000 regions with and 1,000 regions without 5hmC, respectively.

Figure 46B:
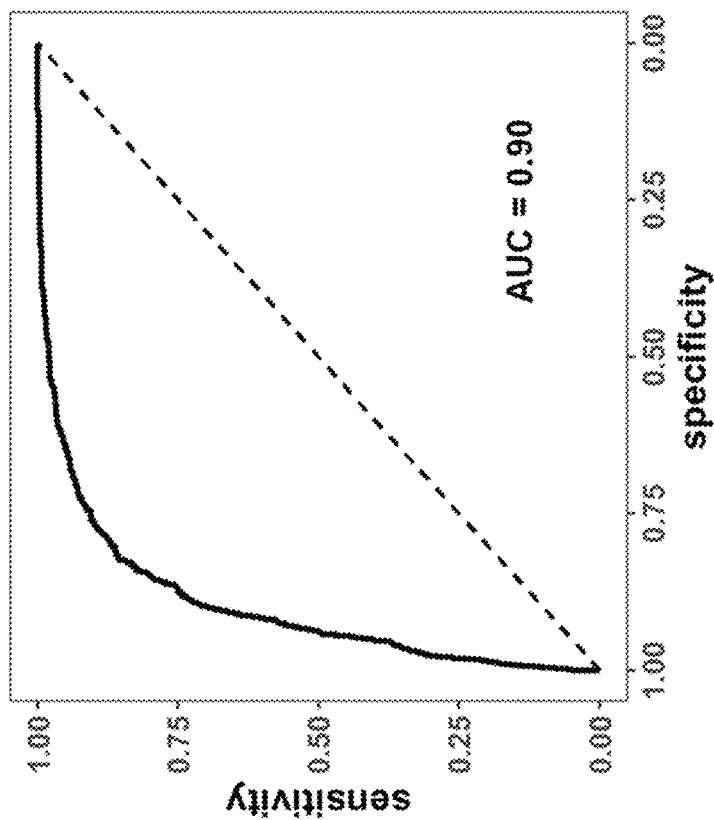
FIGS. 46A-46B show performance of 5hmC prediction on the basis of 5' 3-mer CG containing end motifs.
Figure 46A:
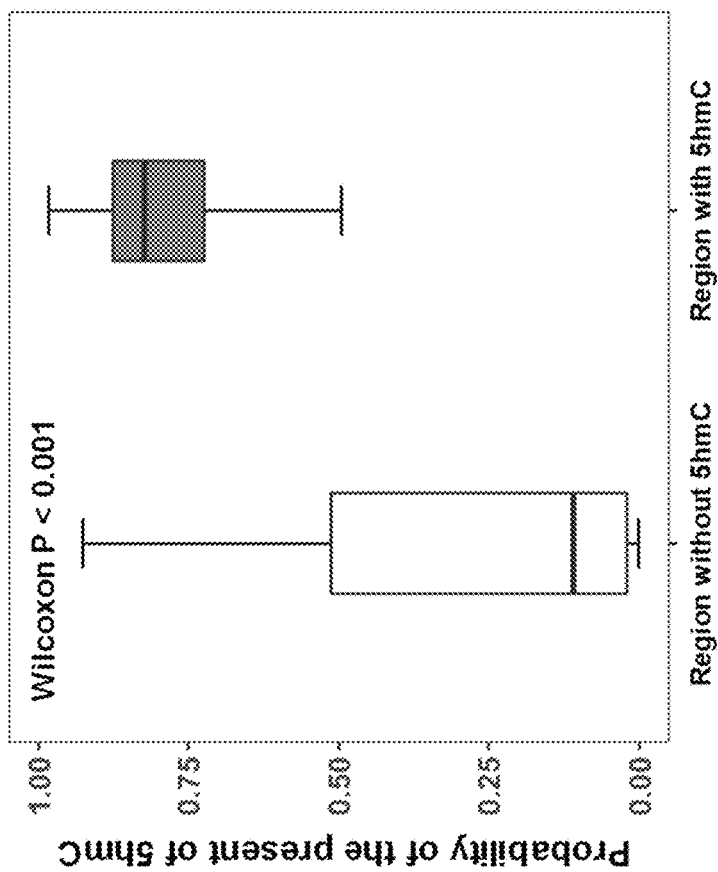

FIGS. 46A-46B show performance of 5hmC prediction on the basis of 5' 3-mer CG containing end motifs. FIG. 46A is a boxplot showing the probability of the presence of 5hmC between regions with and without 5hmC. FIG. 46B is an ROC analysis in differentiating between regions with and without 5hmC. As shown, regions with 5hmC showed significantly higher predicted probability than regions without 5hmC (P<0.001). The ROC analysis showed that the SVM model could reach an AUC of ~0.90 to distinguish regions with and without 5hmC, i.e., distinguish between regions that are 5hmC-enriched and regions that are 5hmC-depleted.

Besides O/E ratio individually or using a feature vector of the CG-containing motifs (e.g., SVM model shown above), other techniques described herein can be used. For example, a CGN/NCG ratio can be used for select end motifs, e.g., ones that have an opposite relationship. End motif frequencies can also be used, potentially as a feature vector of the CG-containing motifs (e.g., 1-8 values for the different 3-mer end motifs). The feature vector can be used in machine learning models, as described herein. Such amounts can be used directly without the normalization for the expected amount. Other normalization, e.g., using a total amount of end motifs of a particular group (e.g., CGN, NCG, or both) or of all end motifs of the desired length (e.g., 3-mer or 4-mer) may be used.

B. Method Using End Motifs to Detect 5hmc-Enriched and -Depleted Regions

Figure 47:
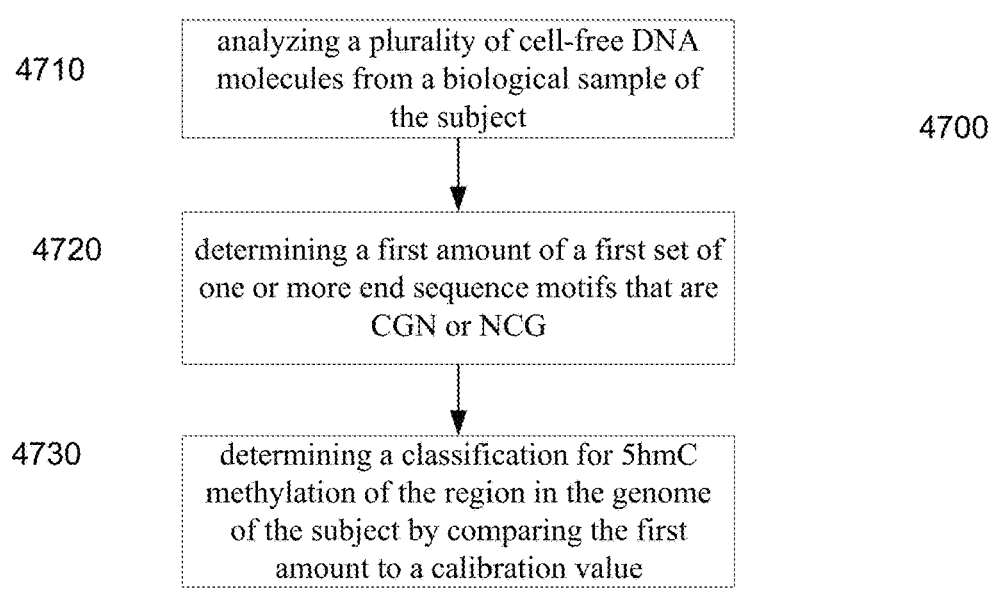
FIG. 47 is a flowchart illustrating a method for measuring 5hmC methylation of a region in a genome of a subject using cell-free DNA molecules.

FIG. 47 is a flowchart illustrating a method for measuring 5hmC methylation of a region in a genome of a subject using cell-free DNA molecules. As with other methods described herein, method 4700 can be performed partially or entirely using a computer system. Blocks performing similar functionality as in other methods can be performed in a similar manner as described for those blocks in other flowcharts.

At block 4710, a plurality of cell-free DNA molecules from a biological sample of the subject are analyzed. Block 4710 can be performed in a similar manner as block 2710 and block 4110. As with blocks 2710 and 4110, analyzing a cell-free DNA molecule can include determining a location of the cell-free DNA molecule in a reference genome, e.g., when the region is smaller than the entire genome. The plurality of cell-free DNA molecules can be located in the region of the reference genome.

The analysis can include determining an end sequence motif (also referred to as end motif) of at least one end of the cell-free DNA molecule, which may done in a similar manner as block 4110. The end sequence motif can be determined from the outermost bases in a sequence read. If a sequence read only includes one end and not the entire DNA fragment/molecule (e.g., as one of paired reads covering both ends), the bases corresponding to the end of the DNA fragment are used and not the bases toward the middle of the fragment. An end of the cell-free DNA molecule can have a first position at the outermost position, a second position that is next to the first position, and a third position that is next to the second position.

At block 4720, a first amount of a first set of one or more end sequence motifs that have C at the first position and that have G at the second position is determined (e.g., an amount of CGN or anyone of more these motifs). The first set of one or more end sequence motifs can include one or more of CGA, CGC, CGG, and CGT, with CGN denoting all. In other embodiments, the first amount can be of a first set of one or more end sequence motifs that have C at the second position and G at the third position (e.g., NCG). In this example, the first set of one or more end sequence motifs can include one or more of ACG, CCG, GCG, and TCG, with NCG denoting all. Such example end motifs can be used in various ways as described herein to determine amounts and/or normalized parameters (e.g., frequencies) for use in making the classification. Additional normalization based on expected frequency per region or per fragment can be used. Block 4720 can be performed in a similar manner as blocks 2720 and 4120.

At block 4730, a classification for 5hmC methylation of the region in the genome of the subject is determined by comparing the first amount to a calibration value. The calibration value can be determined using cell-free DNA molecules that are from one or more calibration samples and that are located at CpG sites having known classifications for a level of 5hmC methylation. The known classifications can be determined using an 5hmC-aware assay (e.g., as described above) or from the results of others that used a 5hmC-aware assay.

Other amounts can be determined, e.g., for normalization. For example, when the first amount is determined using one or more CGN motifs, a second amount of a second set of one or more end sequence motifs that have C at the second position and G at the third position (e.g., NCG) can be determined. Determining the classification can then include normalizing the first amount with the second amount to obtain a normalized first amount that is compared to the calibration value. The second set of one or more end sequence motifs can include all of or one or more of ACG, CCG, GCG, and TCG.

Another example of an amount is an expected amount, as is described above. An expected amount can be determined of the first set of one or more end sequence motifs based on a reference sequence of the reference genome in the region. Then, determining the classification can include normalizing the first amount with the expected amount to obtain a normalized first amount (e.g., O/E ratio) that is compared to the calibration value.

As another example of normalization, a total amount of sequence motifs for the plurality of cell-free DNA molecules (e.g., in the region) can be determined. Then, determining the classification can includes normalizing the first amount with the total amount to obtain a normalized first amount (e.g., a motif ratio or relative frequency) that is compared to the calibration value.

As with other techniques described herein, a feature vector of multiple amounts can be provided to a machine learning model, e.g., as described in sections above. The different amounts can correspond to a selection of end motifs, e.g., those included in the first set and additional end motifs. Such end motifs included in the feature vector can be all of the k-mers for a particular k or just a subset. Accordingly, a respective amount of each 3-mer end sequence motif that has a C at the first position and that has G at the second position can be determined (i.e., four amounts for CGN). A feature vector including the respective amounts, which include the first amount, can be generated and then input into a machine learning model as part of determining the classification for methylation of the region in the genome of the subject. The machine learning model can be trained using cell-free DNA molecules that are from the one or more calibration samples. Additionally or alternatively, the feature vector can include respective amounts for each 3-mer end sequence motif that has a C at the second position and that has G at the third position (i.e., for NCG). As mentioned above, the feature vector can include respective amounts of all 3-mer end sequence motifs.

VII. Fractional Concentration of Clinically-Relevant DNA

We also investigated fragmentation in different types of tissue. We analyzed the end motif groups CGN and NCG, as well as cleavage profiles, in regions/sites that have tissue-specific methylation pattern. The clinically-relevant DNA can be of any tissue type for which differentially methylated regions can be identified, e.g., regions that hypermethylated, hypomethylated, 5hmc-enriched, or 5hmc-depleted for the particular tissue from which the clinically-relevant DNA is derived. Example tissue types include fetal tissue, tumor tissue, or transplant tissue, or tissue from a particular organ, such as liver tissue. Tissue-specific alleles can used to detect tissue-specific DNA, e.g., to measure a calibration value for use in a calibration function, which can be used to provide the fractional concentration using a fragmentomic parameter. The DNA fragments from a particular region/site can be obtained via targeted techniques (also referred to as enrichment), which may be performed via amplification of certain regions or by capturing DNA from certain regions. Further details for enrichment can be found in other sections of this disclosure.

We performed paired-end bisulfite sequencing (75 bp×2 (i.e., paired-end sequencing), Illumina) in this disclosure. The genotypes regarding the maternal buffy coat and placenta/chorionic villus tissue samples were obtained using microarray-based genotyping technology (HumanOmni2.5 genotyping array Illumina), and informative SNPs were identified (i.e., where the mother was homozygous (denoted as AA genotype), and the fetus was heterozygous (denoted as AB genotype)). Fetal-specific DNA fragments were identified according to the DNA fragments carrying fetal-specific alleles at informative SNP sites. In this scenario, the B allele was fetal-specific, and the DNA fragments carrying the B allele were deduced to be originated from fetal tissues. The number of fetal-specific molecules (p) carrying the fetal-specific alleles (B) was determined. The number of molecules (q) carrying the shared alleles (A) was determined. The fetal DNA fraction across all cell-free DNA samples would be calculated by 2p/(p+q)*100%. The amount of fetal-specific alleles is different between samples (median: 198,248; range: 147,614-207,735).

A. Tissue-Specific Methylation for CGN and NCG

As we revealed that the number of DNA molecules with CGN and NCG ends were correlated with the methylation status of CpGs at or near the ends of cell-free DNA molecules, we further explored the possibility of using a relative amount of plasma DNA molecules terminated with CGN and/or NCG motif to reflect the methylation patterns. The relative amount can be measured in various ways. For example, the relative amount can be measured as a ratio (such as the CGN/NCG motif ratio, or NCG/CGN motif ratio, or CGN/(CGN+NCG), or NCG/(CGN+NCG)). Comparisons of CGN or NCG to other end motif(s) can also be used.

As another example, one could measure the percentage of cell-free DNA molecules ended with CGN over the total number of cell-free DNA molecules analyzed (e.g., sequenced) or the total number of cell-free DNA ends. Similarly, one could also measure the percentage of cell-free DNA molecules ended with NCG over the total number of cell-free DNA molecules analyzed (e.g., sequenced) or the total number of cell-free DNA ends. Further, such normalization or any other normalization mentioned herein can be performed by analyzing a same number of DNA molecules, producing a same number of reads, or using a same sized sample (e.g., specified number of ml). Thus, if the same number of DNA molecules are sequenced from one run to another, then the amount can be used directly, as there is effectively a normalization performed. Such various options for normalization can be used by any of the methods described herein.

Results below show that the relative amounts of plasma DNA molecules terminated with CGN or NCG motif at genomic regions exhibiting differential DNA methylation patterns across different tissue types can enable the determination of a probability of the tissue of origin of plasma DNA molecules and determination of a fractional concentration of cell-free DNA molecules of a particular type.

1. Motif Frequency for Fetal-Specific Alleles

We analyzed maternal plasma samples for regions that are hypermethylated and hypomethylated for the fetus. All 3-mer motifs were calculated for a selected region, and the motif frequency was determined as the amount of one type of motif (e.g., CGN or NCG)/the total amount of 3-mer motifs for the region.

Figures 48A, 48B:
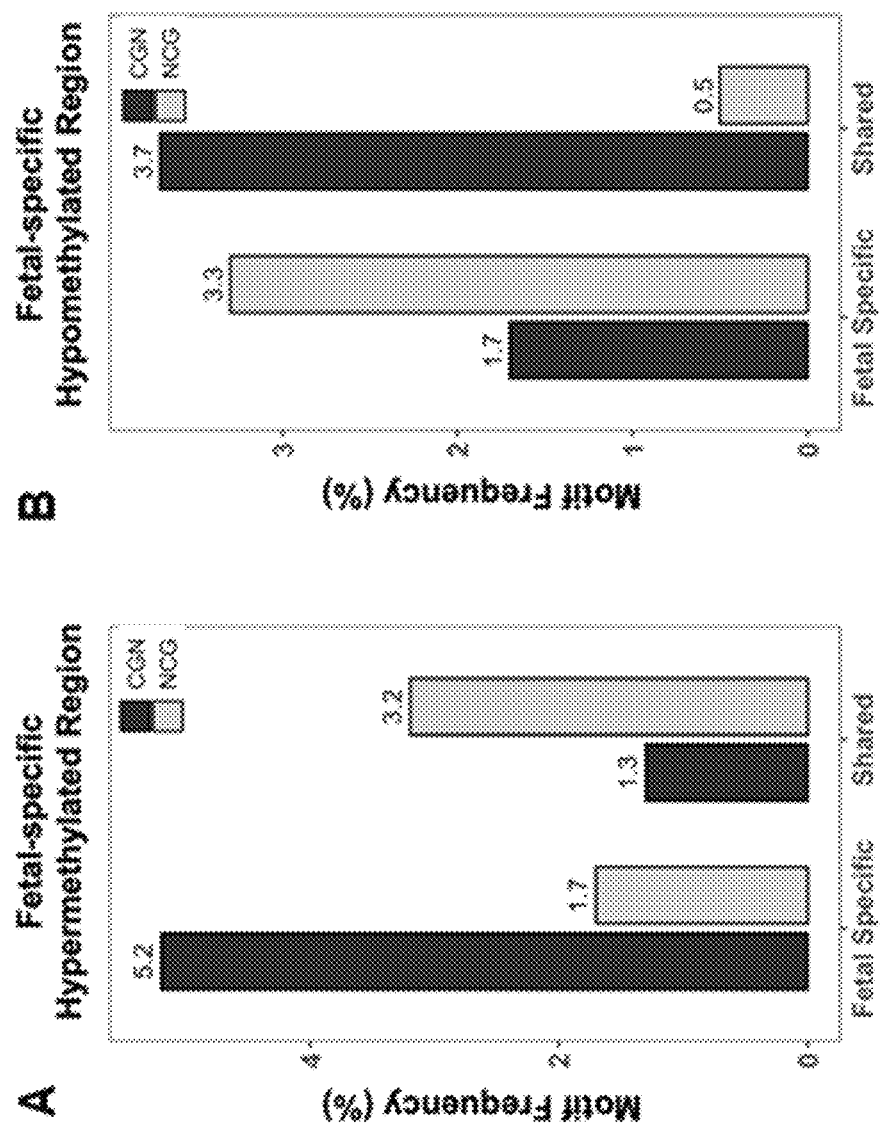
FIGS. 48A and 48B show motif frequencies for fetal-specific hypermethylated and hypomethylated regions according to embodiments of the present disclosure.

FIGS. 48A and 48B show motif frequencies for fetal-specific hypermethylated and hypomethylated regions according to embodiments of the present disclosure. The CGN and NCG end motif frequencies are distinct between DNA molecules carrying fetal-specific alleles and shared alleles, depending on the methylation status.

We analyzed fetal-specific and shared cfDNA from one $3^{rd}$-trimester pregnancy (sequencing depth: 270×). For a fetal-specific hypermethylated region (chr3:187,767,589-187,768,381, which has 9 CpG sites), the frequency of CGN end motifs for fetal-specific DNA molecules was 5.2%, higher than DNA molecules carrying alleles shared by the fetus and mother (1.3%). In contrast, the frequency of NCG end motifs for fetal-specific DNA molecules was 1.7%, lower than DNA molecules carrying alleles shared by the fetus and mother (3.2%). For the fetal-specific hypomethylated region (chr7:25,889,274-25,890,315, which has 9 CpG sites), we observed different patterns from the hypermethylated region. The fetal-specific DNA molecules showed a lower frequency of CGN end motifs but a higher frequency of NCG end motifs, compared with corresponding DNA molecules carrying alleles shared by the fetus and mother (CGN end motif: 1.7% vs 3.7%; NCG end motif: 3.3% vs 0.5%). These results further indicated that the use of CGN and NCG end motif frequencies could be informative for predicting methylation alterations across a number of genomic regions of interest.

This data shows that CGN and NCG are correlated to the amount of fetal DNA. Since the fetal DNA end with CGN at a different rate than the shared alleles, an amount of DNA molecules ending with CGN can reflect a fractional concentration of fetal DNA. The same is true for the DNA molecules ending with NCG. Further, since the behavior occurs for both hypermethylated and hypomethylation regions, both types of regions and both CGN and NCG can be used, thereby providing four types of measurements, or just one of the types of measurements can be performed.

2. Ratio of NCG and CGN

To test the ability to determine the fractional concentration of fetal DNA, fetal-specific sites were identified and tested. Placenta-specific hypermethylated (n=188,978) and hypomethylated (n=2,013,795) CpG sites were identified using bisulfite sequencing results of the buffy coat (sequencing depth: 75× haploid genome coverage) and the placenta tissues (sequencing depth: 94× haploid genome coverage). Placenta-specific hypermethylated sites were defined by those CpG sites with a methylation density of over 70% in the placenta tissues but below 30% in the buffy coat samples. Placenta-specific hypomethylated sites were defined by those CpG sites with a methylation density of below 30% in the placenta tissues but over 70% in the buffy coat samples. We determined the ratio of plasma DNA molecules terminated with CGN to NCG end motif in placenta-specific hypermethylated and hypomethylated CpG sites, respectively. We analyzed a total of 30 plasma DNA samples of pregnant women using massively parallel paired-end sequencing (median number of paired-end reads: 206 million; IQR: 142-232 million).

In addition, we identified fetal-specific alleles, specifically single nucleotide polymorphisms. We used the number of reads having the fetal-specific alleles to determine a SNP-based fetal fraction.

FIGS. 49A-49B show a correlation between the fetal DNA fraction and the CGN/NCG ratio based on plasma DNA molecules originating from placenta-specific hypermethylated CpG sites (FIG. 49A), and placenta-specific hypomethylated CpG sites (FIG. 49B) according to embodiments of the present disclosure. The measurements were performed for various pregnancies at different trimesters. The shape and color of the data point indicates whether the pregnancy was in the first, second, or third trimester. The amount of only CGN or only NCG (or any one end motif within these sets) may also be used.

The amount for CGN was determined using the amount of sequence reads that had CG at the end that covered the hypermethylated or hypomethylated site. The amount for NCG was determined using the amount of sequence reads that had NCG at the end, where the CG covered the hypermethylated or hypomethylated site As shown in FIGS. 49A and 49B, the CGN/NCG ratio from placenta-specific hypermethylated CpG sites and hypomethylated CpG sites were positively and negatively correlated with the fetal fraction deduced by the fetal-specific SNPs, respectively (Pearson's r: 0.90 and −0.86; P value <0.0001 for both correlations). The data indicates that the relative amounts of plasma DNA molecules ended with CGN and NCG (e.g., the CGN/NCG ratio) could be used for deducing a likelihood for the tissues of origin of plasma DNA molecules and determine a fractional concentration of cell-free DNA for clinically-relevant DNA, such as fetal DNA, tumor DNA, or transplant DNA.

The lines in FIGS. 49A-49B are examples of calibration functions. For any CGN/NCG ratio determined for a new sample, that value can be input to the linear function to provide an output on the X axis of the fetal fraction. Such a calibration function can be viewed as including calibration values of calibration data points, which also include the corresponding fractional concentration. The determination of a fractional concentration can include a comparison of a new CGN/NCG ratio (or other feature described herein) to a calibration value for which a corresponding fractional concentration is known. The known fraction concentrations can be determined via some other technique, such as a SNP analysis. Such a calibration function need only be determined once, so such a SNP-based analysis (which may not be applicable in all situations or take more time, assays, and effort to identify the SNPs) does not need to be performed for a new sample. Calibration functions can be more complex, such as machine learning techniques (e.g., support vector regression), which would still involve a comparison to a calibration value.

3. NCG or CGN Independently

In addition to using a ratio of CGN/NCG, CGN and NCG can be used independently. In one embodiment, a measurement window (e.g., 11 bp) centered on each placenta-specific hypermethylated or hypomethylated CpG site can be defined as placenta-specific hypermethylated and hypomethylated regions. The CGN and NCG motif frequency was calculated within the placenta-specific hypermethylated and hypomethylated regions. Each region has one CpG site. The motif frequency is determined by normalizing the amount of CGN or NCG with the total amount of end motifs from the region, e.g., (CGN or NCG)/total amount of ends in the region).

Figure 50A:
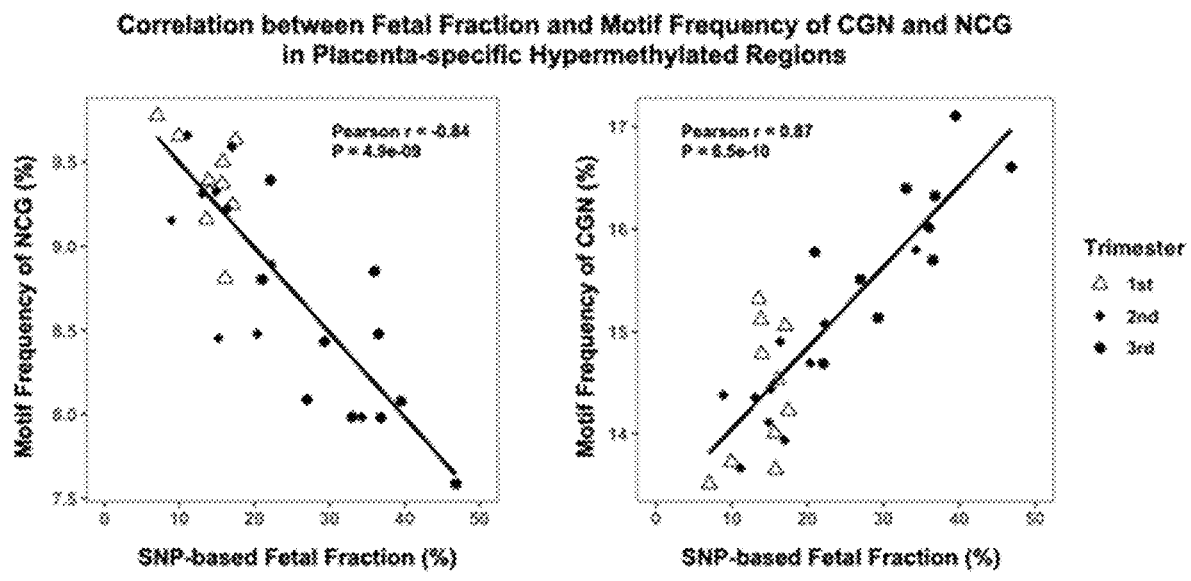
FIGS. 50A-50B show the correlation between the fetal DNA fraction and the frequency of NCG and CGN motifs based on plasma DNA molecules originating from placenta-specific hypermethylated CpG sites (50A), and placenta-specific hypomethylated CpG sites (50B) according to embodiments of the present disclosure.
Figure 50B:
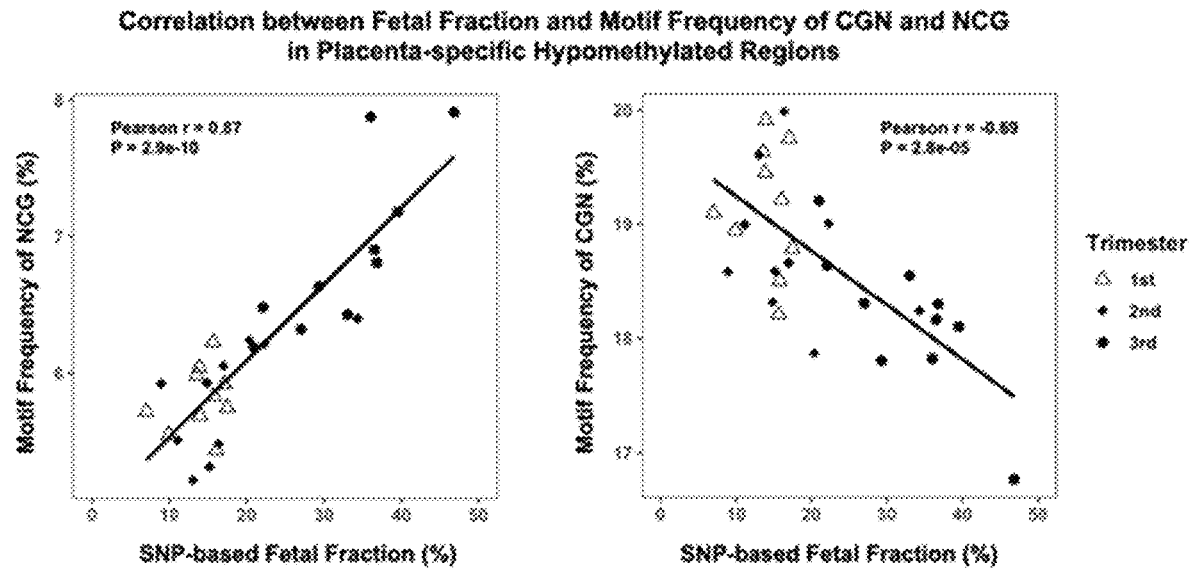

FIGS. 50A-50B show the correlation between the fetal DNA fraction and the frequency of NCG and CGN motifs based on plasma DNA molecules originating from placenta-specific hypermethylated CpG sites (FIG. 50A), and placenta-specific hypomethylated CpG sites (FIG. 50B) according to embodiments of the present disclosure. As shown in FIG. 50A, the frequency of NCG and CGN motifs derived from placenta-specific hypermethylated regions were negatively and positively correlated with the fetal fraction deduced by the fetal-specific SNPs, respectively (Pearson's r: −0.84 and 0.87; P value <0.0001 for both correlations). In contrast, the frequency of NCG and CGN motifs derived from placenta-specific hypomethylated regions were positively and negatively correlated with the fetal fraction deduced by the fetal-specific SNPs, respectively (FIG. 50B; Pearson's r: 0.87 and −0.69; P value <0.0001 for both correlations).

The CGN motif frequency was defined as the number of end motifs in the region having CGN. The NCG motif frequency was defined as the number of end motifs in the region having NCG. Such normalization can be performed in a variety of ways. For example, as described above, a total number of cell-free DNA molecules analyzed (e.g., sequenced) or the total number of cell-free DNA ends can be used instead of just limiting the normalization factor to just DNA within a measurement window around a CpG site.

Each one of these plots shows a calibration function that can be used according to embodiment of the present disclosure, e.g., as described herein. For example, a new value for the CGN motif frequency for a hypermethylated region can be compared to a calibration value (e.g., by inputting the value into the linear calibration functions shown in the plot on the right in FIG. 50A).

4. CGN/NCG for Hypo- and Hyper-Methylated Region in ML Model

In another embodiment, the CGN/NCG ratios derived from placenta-specific hypermethylated CpG sites and hypomethylated CpG sites, respectively, could be integrated together as two independent features for machine learning. In other implementations, the individual amounts, e.g., CGN or NCG may be used as independent features. Examples of such features are described above.

Such features can be input to a machine learning model, which can determine the fractional concentration of the clinically-relevant DNA. For instance, a support vector regression (SVR) model can be used, e.g., which can receive two (e.g., any variation of CGN/NCG ratio for hyper- and hypo-methylated CpG sites) to four (e.g., CGN and NCG amounts for hyper- and hypo-methylated CpG sites). In other embodiments, other algorithms could be used including but not limited to, linear/nonlinear regression, decision tree, Lasso regression, random forest, elastic network, Bayesian network, support vector machine, convolutional neural network, recurrent neural network, logistic regression, etc. As an example, one could use an SVR model to facilitate the determination of fetal DNA contribution in maternal plasma DNA of a pregnant woman.

Figure 51:
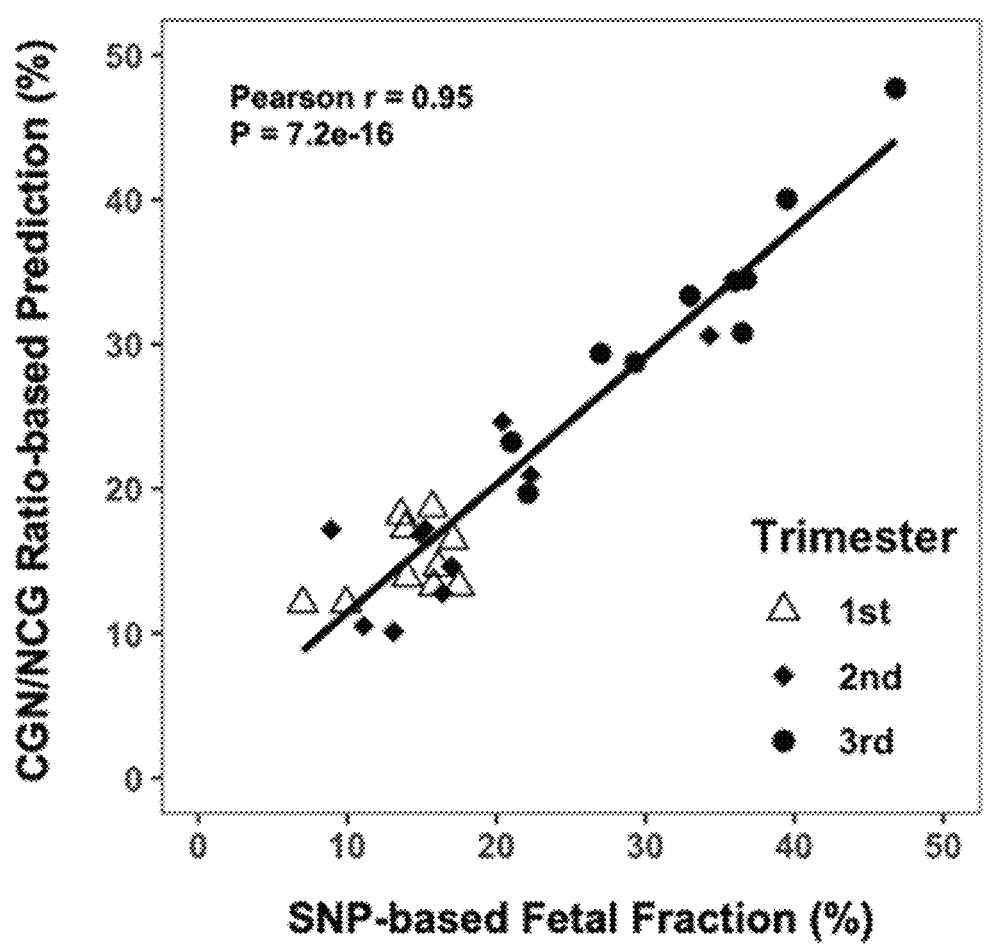
FIG. 51 shows the correlation of the fetal fraction deduced by SNP-based approach (x-axis) and using CGN/NCG ratios from placenta-specific hypermethylated and hypomethylated CpGs (y-axis) according to embodiments of the present disclosure.

FIG. 51 shows the correlation of the fetal fraction deduced by SNP-based approach (x-axis) and using CGN/NCG ratios from placenta-specific hypermethylated and hypomethylated CpG sites (y-axis) according to embodiments of the present disclosure. In this example, a SVR model was used.

As shown in FIG. 51, the fetal DNA contributions from pregnant samples estimated by the CGN/NCG ratio were correlated with the fetal fractions deduced by the SNP-based approach (Pearson's r: 0.95; P value <0.0001). This correlation was true for all three trimesters. The data suggested that the combined analysis of the CGN/NCG ratios from regions exhibiting tissue-specific hypomethylation and hypermethylation would enhance the determination of tissues of origin of plasma DNA molecules, for example the cfDNA contribution from placental tissues.

The calibration data points shown in FIG. 51 are examples of training data (e.g., calibration data points) used to determine the SVR calibration function. Such training data is from calibration samples, as is described herein for other examples. FIG. 51 shows the accuracy of the SVR calibration function.

5. Examples for Other Tissue Types

Other tissue types besides fetal/placental can be analyzed using loci having tissue-specific methylation status. For example, loci that are hypermethylated or hypomethylated in liver cells, blood cells, or colon cells can be used to determine a percentage (fractional concentration/contribution) of DNA fragments in a sample (e.g., plasma or serum) that are from each of the tissues. To illustrate the use of such measurements for different tissue types, the relative changes for different tissue types for different types of subjects (transplant and pregnant) are analyzed relative to healthy control.

As shown above (e.g., FIGS. 49A-49B), the CGN/NCG motif ratio from placenta-specific hypermethylated and hypomethylated CpGs was well correlated with the fetal fraction in maternal plasma DNA. In addition to determining the fractional concentration, the ending position of a given molecule at a tissue-specific locus (e.g., hypermethylated or hypomethylated at a given tissue) can be used to identify DNA fragments that are most likely from the particular tissue. The likelihood of a given DNA fragment being from the particular tissue is higher when the DNA fragment has an CGN motif (e.g., indicating likelihood of being methylated) at a hypermethylated locus for the particular tissue. In this manner, a sample can be enriched for DNA fragments from a particular tissue type using the end motif.

Figure 52:
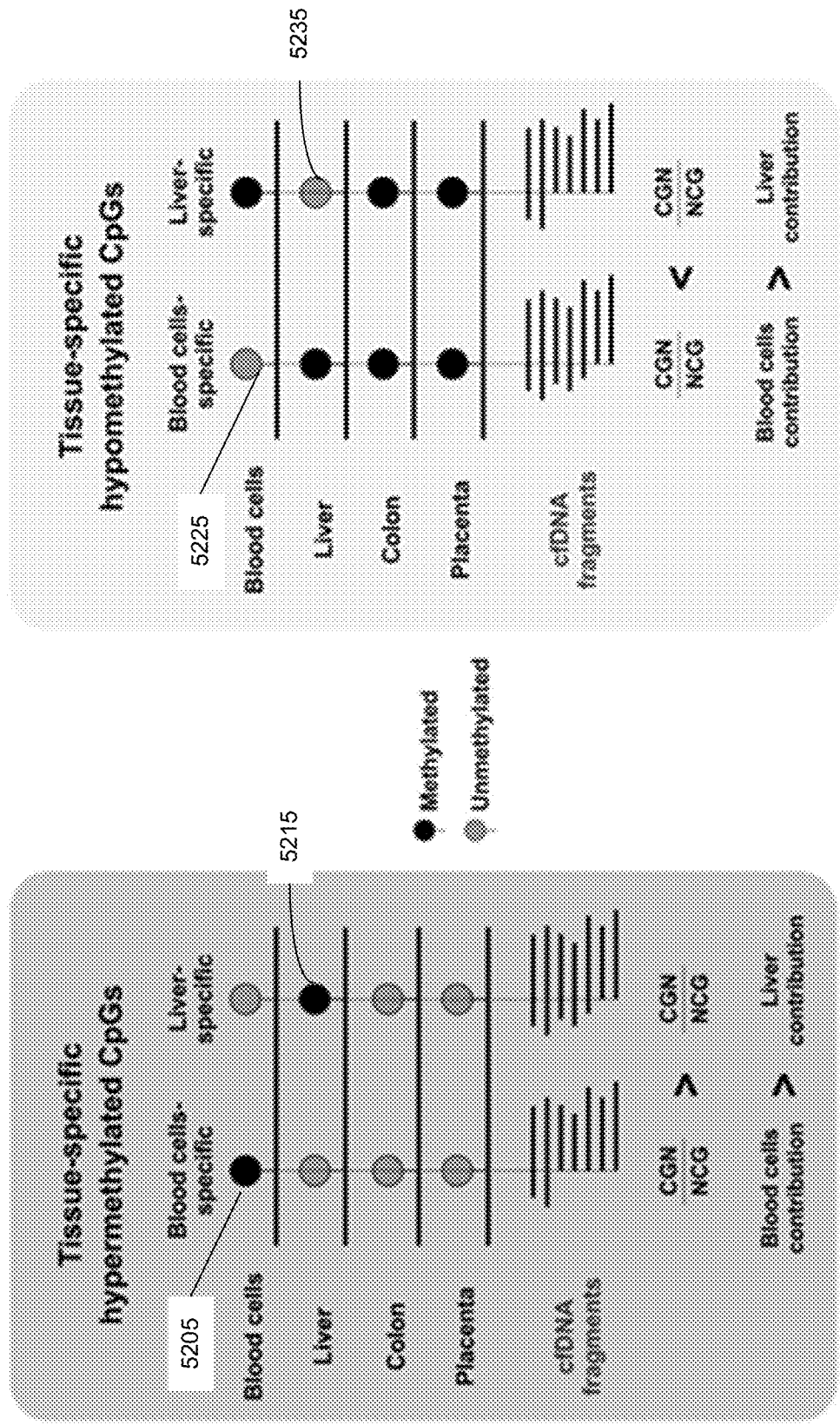
FIG. 52 shows a schematic for CGN/NCG motif ratio analysis based on tissue-specific methylated CpGs for blood and liver.

FIG. 52 shows a schematic for CGN/NCG motif ratio analysis based on tissue-specific methylated CpGs for blood and liver. FIG. 52 shows cfDNA fragments ending around a CpG site 5105 that is hypermethylated in blood cells, a CpG site 5115 that is hypermethylated in liver, a CpG site 5125 that is hypomethylated in blood cells, and a CpG site 5135 that is hypomethylated in liver. The schematic shows how the CGN/NCG motif ratio analysis can be done in a set of tissue-specific methylated CpGs across different tissue types.

Tissue-specific hypermethylated CpGs were defined as CpGs with a methylation density of over 70% in a target tissue (e.g., the liver) and below 30% across the remaining tissues being analyzed. Tissue-specific hypomethylated CpGs were defined as CpGs with a methylation density of below 30% in a target tissue and over 70% in the remaining tissues. The CGN/NCG motif ratio was calculated for each set of tissue-specific CpGs in a plasma DNA sample.

For tissue-specific hypermethylated CpGs, the target tissue contributed more DNA molecules cutting 5' to 'C' site in the CpG context into plasma DNA pool, thus leading to a higher CGN/NCG motif ratio. The other tissues on those CpG sites had the opposite preference. Hence, the CGN/NCG ratio of molecules derived from those tissue-specific hypermethylated CpG sites was positively proportional to the quantity of cfDNA contributed by the target tissue. In contrast, for tissue-specific hypomethylated CpGs, the target tissue contributes less DNA in plasma DNA molecules cutting 5' to 'C' site at the CpG context, leading to a lower CGN/NCG motif ratio. The CGN/NCG ratio of molecules derived from those tissue-specific hypomethylated CpG sites was negatively proportional to the quantity of cfDNA contributed by the target tissue.

Since the factional concentration of DNA from blood cells is higher in plasma than the fraction concentration of DNA from liver, the CGN/NCG ratio should be higher at the blood cell-specific hypermethylated locus than the CGN/NCG ratio at the liver-specific hypermethylated locus. This relationship is shown at the bottom of the panel for the hypermethylated CpGs. Conversely, the CGN/NCG ratio should be lower at the blood-specific hypomethylated locus than the CGN/NCG ratio at the liver-specific hypomethylated locus, which is shown at the bottom of the panel for the hypomethylated CpGs.

As an example, we identified 7,467, 3,756, 7,726, and 1,000 hypermethylated CpG sites specific to blood cells, liver, colon, and placenta, respectively, together with 40,788, 19,619, 93,510, and 631,734 hypornethylated CpG sites specific to the corresponding tissues based on the bisulfite sequencing results of the buffy coat, liver tissues, colon tissues, and placenta. We determined the ratio of plasma DNA molecules terminated with CGN to NCG end motif in those tissue-specific hypermethylated and hypomethylated CpG sites, respectively. We analyzed plasma DNA samples from one healthy control case (number of paired-end reads: 391 million), one liver transplant case (number of paired-end reads: 35 million), and one pregnancy woman (number of paired-end reads: 238 million) using massively parallel paired-end sequencing.

Figure 53B:
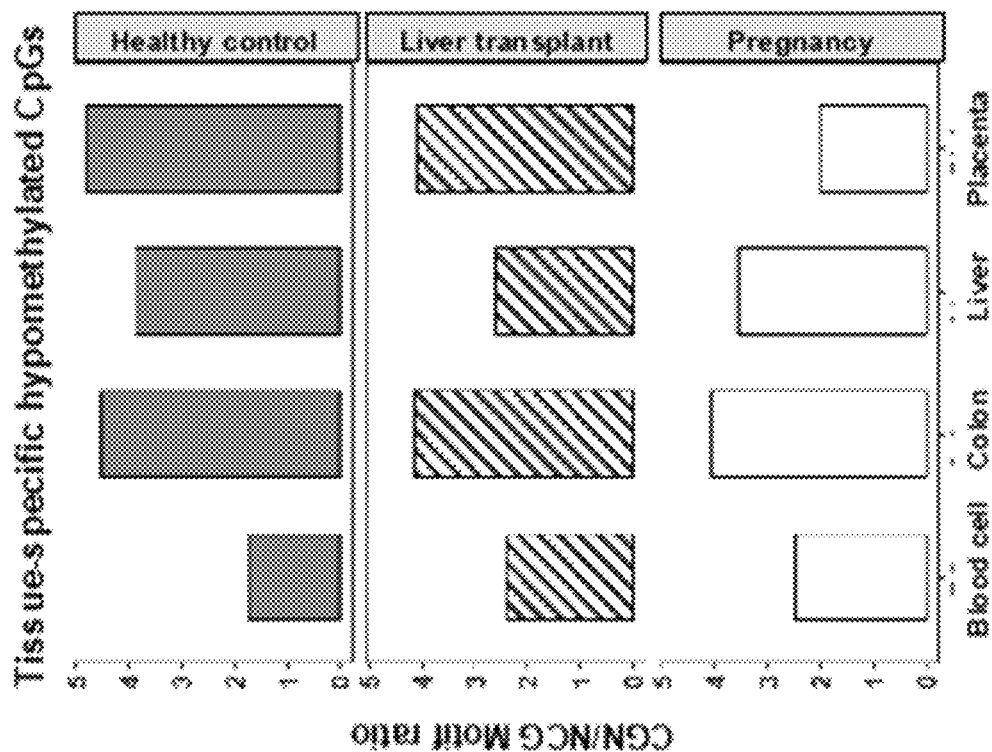
FIGS. 53A-53B show the CGN/NCG motif ratios from different tissue-specific hypermethylated (FIG. 53A) and hypomethylated (FIG. 53B) CpGs in plasma DNA of the healthy control, the liver transplant case, and the pregnancy case.
Figure 53A:
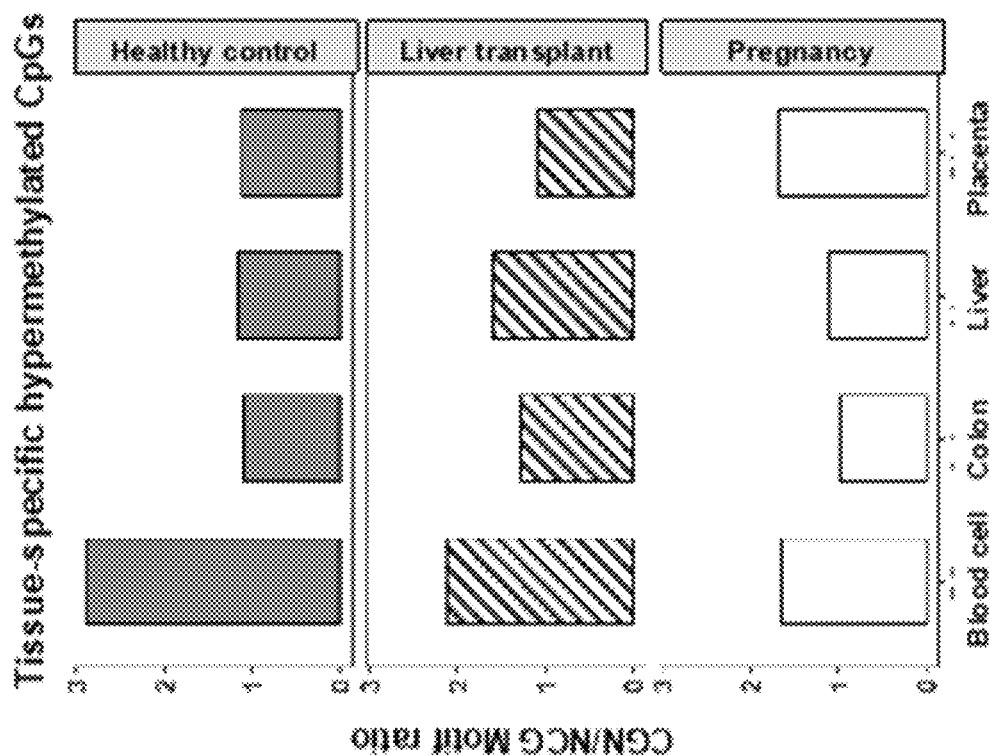

FIGS. 53A-53B show the CGN/NCG motif ratios from different tissue-specific hypermethylated (FIG. 53A) and hypomethylated (FIG. 53B) CpGs in plasma DNA of the healthy control, the liver transplant case, and the pregnancy case. For each tissue type (blood, colon, liver, and placenta), the motif ratio is provided for the three different subjects (healthy control, liver transplant, and pregnant woman). The relative values for the motif ratio show increases and decreases in the contributions for each of the tissue types for the different subjects.

As shown in FIG. 53A, in the healthy control case, the CGN/NCG motif ratio derived from the blood cell-specific hypermethylated CpG sites corresponded to the highest value, followed by the liver, with the least value from the placenta. This is a result of the liver transplant subject contributing more liver DNA, thereby reducing the contribution from blood cells. Similarly, the pregnant woman has cell-free fetal DNA so the blood contribution is reduced.

For tissue-specific hypomethylated CpG sites in FIG. 53B, CGN/NCG motif ratios appeared in reverse order. The higher CGN/NCG motif ratio at tissue-specific hypermethylated CpGs would reflect a higher methylation density of plasma DNA at those tissue-specific CpG sites of interest, indicating a higher contribution from that tissue. The lower CGN/NCG motif ratio at tissue-specific hypomethylated CpGs would reflect a lower methylation density of plasma DNA at those tissue-specific CpG sites of interest, indicating a higher contribution from that tissue.

These results were consistent with the concept that the blood cells were the major source contributing cell-free DNA to the plasma (Sun et al. Proc Natl Acad Sci USA. 2015; 112:E5503-5512). In the liver transplant case for which the liver cfDNA fraction was ~40% (SNP-based approach), the CGN/NCG motif ratio derived from the liver-specific hypermethylated, and hypomethylated CpG sites showed a substantial increase and decrease, respectively, compared to the plasma DNA of a healthy control. Liver contribution is around 10% in healthy control.

In the pregnancy case for which the fetal cfDNA fraction was ~39% (SNP-based approach), the CGN/NCG motif ratio derived from the placenta-specific hypermethylated and hypomethylated CpG sites showed a substantial increase and decrease, respectively, compared to the plasma DNA of a healthy control. The colon contribution stayed about the same across the different subjects.

The data suggested that the relative amount of plasma DNA molecules ended with CGN and NCG (e.g., the CGN/NCG ratio) could be used for deducing the tissues of origin of plasma DNA molecules from multiple tissues. Accordingly, a relative change (increase or decrease) in the contribution for different tissues can be determined using the motif ratio. For example, a baseline motif ratio for a healthy control can be used to determine whether a particular tissue contribution has changed significantly, e.g., by comparing the new motif ratio for a subject where the motif ratio is for a tissue-specific locus. A specific fractional contribution for any particular tissue type can be determined using a respective calibration function for a particular tissue type.

B. Tissue-Specific Methylation Pattern for Cleavage Profiles

In addition or alternatively to using end motifs (e.g., CGN and NGC), cleavage profiles can be used. The usage of the cleavage profiles can be similar as described above. One or more amounts (e.g., cleavage ratios/densities) can be determined. Such amounts can be used with one or more calibration values (e.g., as a calibration function) for which fractional concentrations are known and which form calibration data points, as described herein. Thus, a cleavage amount at a given position or a cleavage profile for two or more positions may be used.

1. Cleavage Profiles for Hyper- and Hypo-Methylated Sites

FIGS. 54A-54B show fetal-specific methylation is reflected in cleavage profiles of cfDNA fragmentation according to embodiments of the present disclosure. In this plot, black lines 5405 represent the cleavage profiles of fetal-specific DNA, and grey lines 5410 represent those of shared DNA. FIG. 54A shows cleavage profiles of fetal-specific and shared DNA molecules originating from placenta-specific hypermethylated CpG sites. The x-axis represents the positions relative to a CpG site of interest. The y-axis represents the mean cleavage ratio. FIG. 54B shows cleavage profiles of fetal-specific and shared DNA molecules originating from placenta-specific hypomethylated CpG sites.

We determined the cleavage profiles of fetal-specific and shared plasma DNA molecules from one pregnancy cfDNA sample, respectively, on the basis of the placenta specific hypermethylated (n=188,978) and hypomethylated (n=2,013,795) CpG sites. Placenta specific hypermethylated and hypomethylated CpG sites were identified using the bisulfite sequencing results of the buffy coat (sequencing depth: 75×) and the placenta tissues (sequencing depth: 94×). Placenta specific hypermethylated sites were defined by those CpG sites with a methylation density of over 70% in the placenta tissues but below 30% in the maternal buffy coat samples. Placenta specific hypomethylated sites were defined by those CpG sites with a methylation density of below 30% in the placenta tissues but over 70% in the maternal buffy coat samples.

For placenta specific hypermethylated CpG sites, fetal-specific fragments showed a higher cleavage ratio at the CpG sites than shared fragments (mainly of hematopoietic origin). In placenta specific hypomethylated CpG sites, fetal-specific fragments displayed a lower cleavage ratio at the CpG sites than shared fragments. These results indicated that tissue-specific cfDNA methylation differences could be reflected in cfDNA fragmentation patterns. Methylation patterns could be used for deducing DNA contribution from different tissues/organs to plasma DNA pool (Sun et al. Proc Natl Acad Sci USA. 2015; 112:E5503-5512). Therefore, we conjectured that the cleavage profiles would be useful for deducing DNA contribution from different tissues into the plasma DNA pool, such as placental DNA contribution in plasma DNA of a pregnant woman.

2. SVR Implementation

We use pregnancy samples as an example. We determined the cleavage profiles from placenta specific hypermethylated and hypomethylated CpG sites. Such cleavage profiles from 30 pregnancy samples (median paired-end sequencing reads: 206 million (IQR: 142-232 million)) were used for training a SVR model to predict the fetal DNA contribution based on the leave-one-out strategy. In other implementations, the SVR can use the amount (e.g., cleavage ratio) at position 0, which can be supplemented by the amount at other positions.

Figure 55:
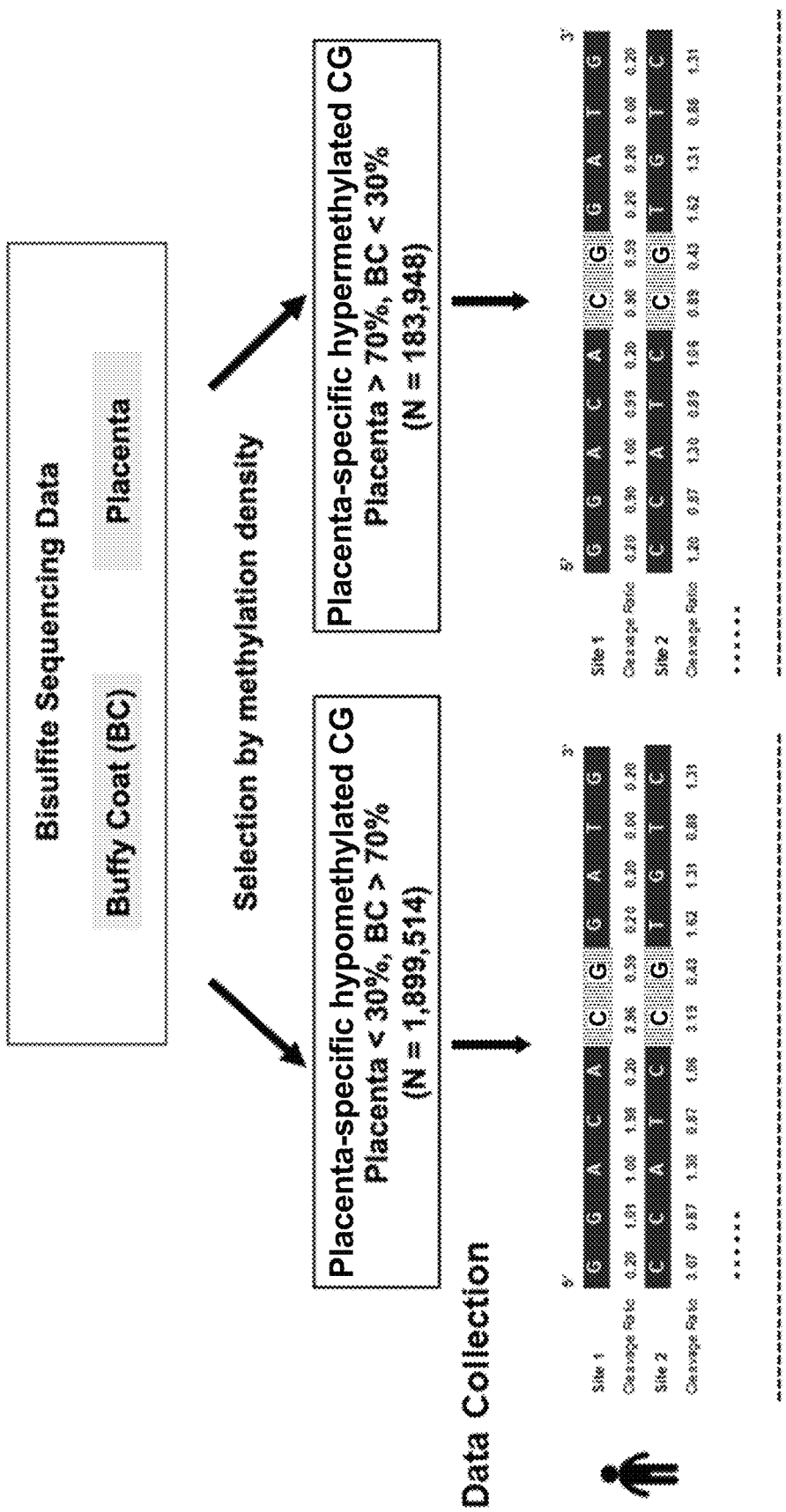
FIGS. 55 and 56 show marker selection, data collection, and training of an SVR model that determines the fetal fraction in a cell-free sample (e.g., plasma) according to embodiments of the present disclosure.
Figure 56:
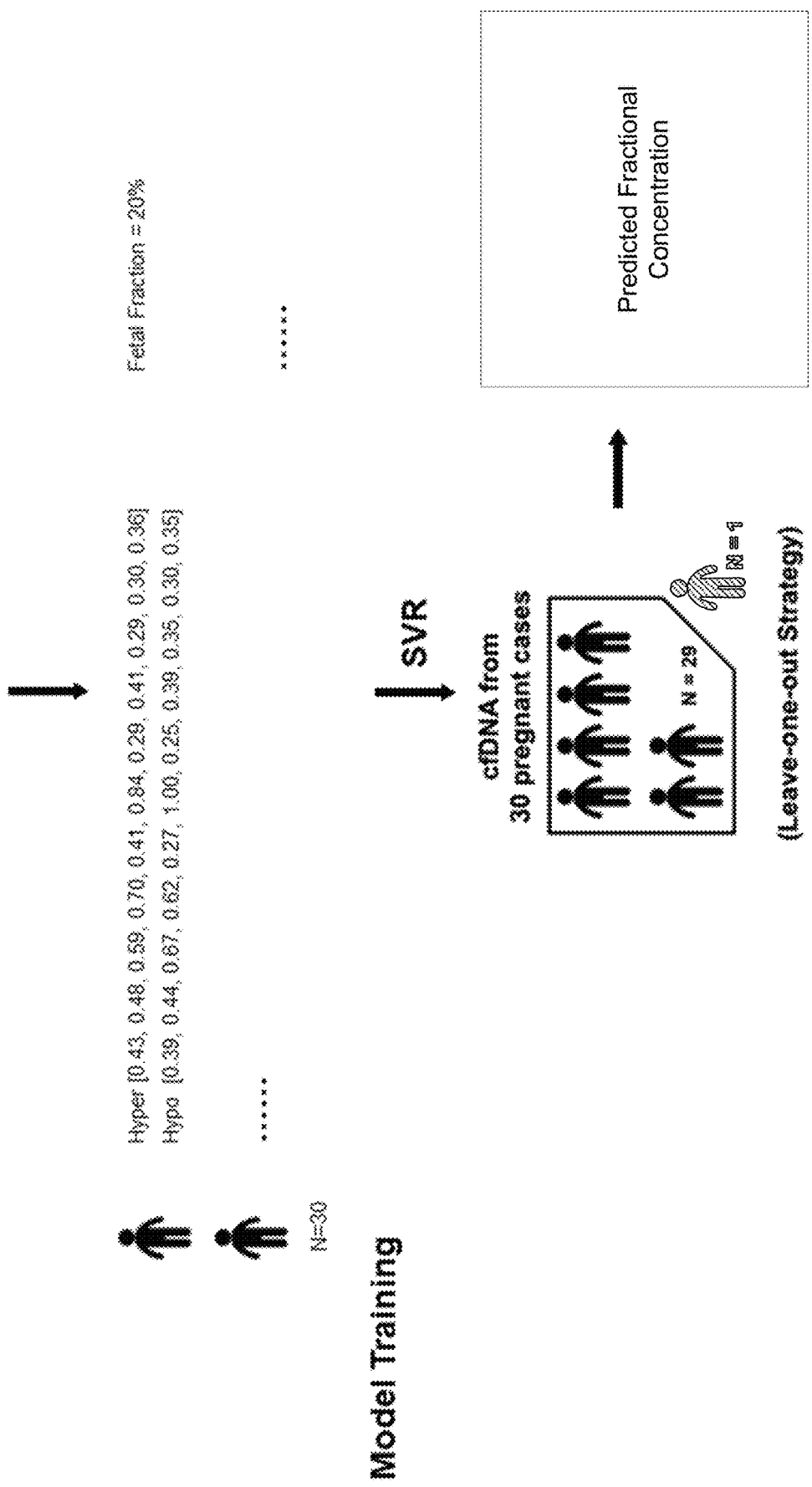

FIGS. 55 and 56 show marker selection, data collection, and training of an SVR model that determines the fetal fraction in a cell-free sample (e.g., plasma) according to embodiments of the present disclosure. We use bisulfite sequencing data from buffy coat and placenta. The marker criteria is the same as mentioned in the previous section.

For the data collection, we sequence individual samples and calculate the cleavage profile of each CpG site. For the hypermethylated CG, we calculate a merged cleavage profile that is the average cleavage ratio of each position. For one position, we will average all the numbers from individual sites and then make one number. The same is done for the hypomethylated sites.

For each patient, we have two vectors: one for the hypermethylated CG sites and another for the hypomethylated CG sites. Each vector contains 11 numbers that reflect the average cleavage ratio of each position. Other numbers of values may be used for different widths of the cleavage profile, as described herein, such as widths of 4, 5, 6, 7, 8, 9, and 10. For each training sample, the fetal fraction is determine using a fetal-specific allele.

The training of the SVR model was performed using the leave-one-out strategy, which trains the model with 29 samples, then predict the fetal fraction of one sample. Then, we train on a different 29 and test another one until all the samples of the thirty samples have been in the testing set and have a fetal fraction predicted. We compared the predicted fetal fraction with the SNP-based analysis.

Figure 57:
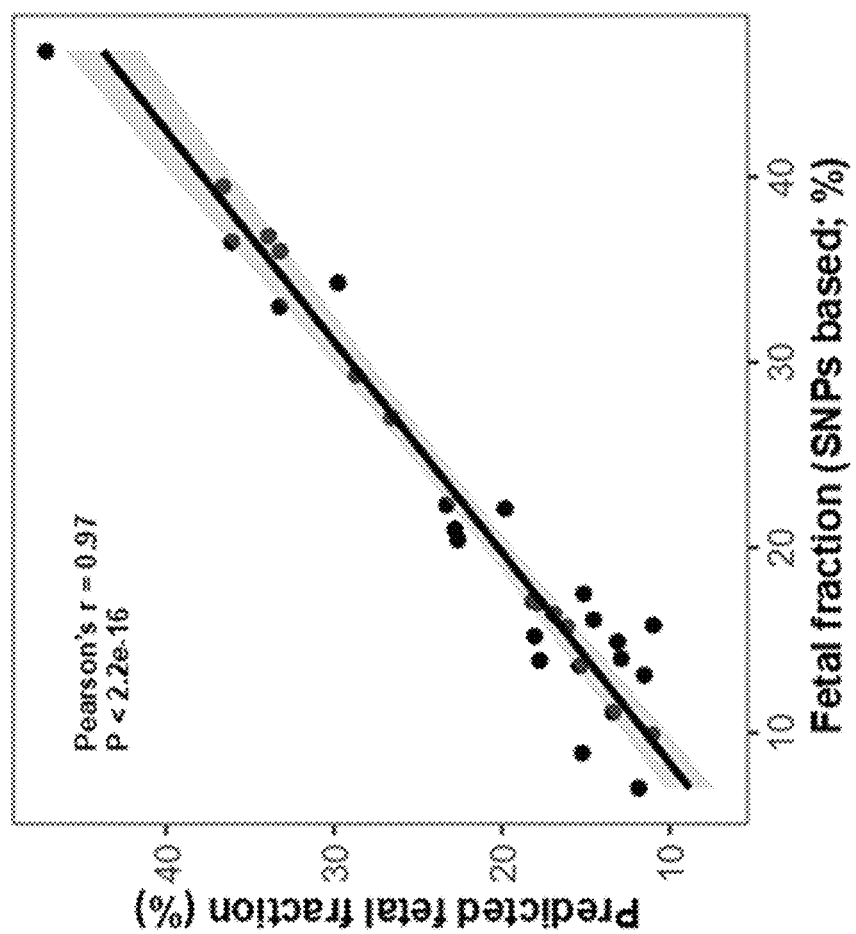
FIG. 57 shows the correlation between the fetal fractions deduced by proximal cleavage profiles and the SNP-based approach according to embodiments of the present disclosure.

FIG. 57 shows the correlation between the fetal fractions deduced by proximal cleavage profiles and the SNP-based approach according to embodiments of the present disclosure. The estimated fetal DNA contribution from pregnancy samples by the cleavage profiles was well correlated with the fetal fraction deduced by the fetal-specific SNPs (Pearson's r: 0.97; P value <0.0001). In various embodiments, the cleavage profile could be used to predict the DNA contribution of other tissues, including, but not limited to, the liver, brain, T cells, B cells, neutrophil, muscle, heart, placenta, ovary, breast, testis, etc.

The tissue fraction can be of clinically-relevant DNA, e.g., tumor DNA.

3. Cleavage Profiles for Individual Sites

The examples above combined measurements across CpG sites and then used the resulting cleavage profile. For example, a ratio of the amount of DNA molecules ending at the 0 position can be compared to the amount of DNA molecules ending at the −1 or 1 position (or a sum of both). Other positions can be used as well or instead, as described above. As another example, a cleavage profile could be input to a machine learning model.

However, in other embodiments, a separate amount can be determined for each CpG site and compared separately to a respective calibration value. Thus, if N CpG sites are analyzed, then N amounts can be determined, each amount corresponding to an amount of DNA fragments at a respective CpG site. Additionally, separate cleavage profiles can be determined for each CpG site (or some subset of sites), and these individual cleavage sites can be used, e.g., input to a machine learning model. Each cleavage profile could be input to a machine learning model to determine a fractional concentration for that particular CpG site. Such fractional concentrations could be averaged (including a weighted average based on the sequencing depth).

In another example, all of the cleavage profiles could be input at the same time to the machine learning model. In this manner, more features would be input to the machine learning model. Such a feature matrix can be the size of the number of CpG sites by the number of positions in the measurement window.

In a different example, separate cleavage ratios can be determined for each cleavage profile for different subsets of CpG sites, and the individual fractional concentrations can be averaged.

C. Determining Fractional Concentration of DNA from First Tissue Using Tissue-Specific Methylated Sites The fractional concentration of cell-free DNA molecules (cell-free DNA fragments) from a particular tissue type (e.g., clinically-relevant DNA) can be determined in various ways. For example, the amount of DNA fragments ending at the 0 or −1 position of one or more CpG sites in a new sample and calibration information (e.g., from calibration samples having known or measured fractional concentration by other means) can be used to determine the fractional concentration in the new sample.

Figure 58:
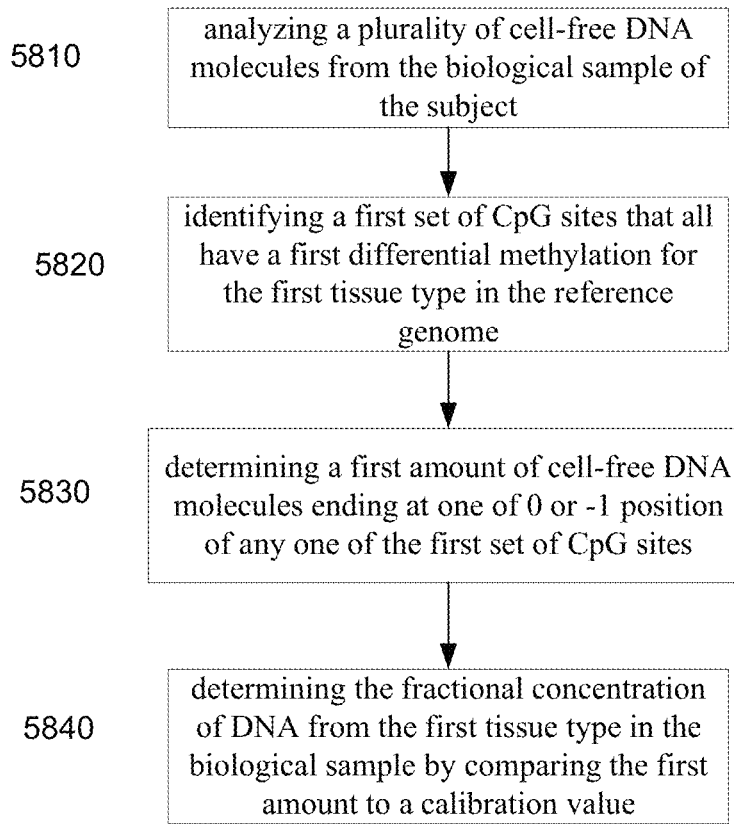
FIG. 58 is a flowchart illustrating a method for determining a factional concentration of a clinically-relevant DNA according to embodiments of the present disclosure.

FIG. 58 is a flowchart illustrating a method 5800 for determining a factional concentration of a clinically-relevant DNA according to embodiments of the present disclosure. The biological sample comprises cell-free DNA. As with other methods described herein, method 5800 can be performed partially or entirely using a computer system. Blocks performing similar functionality as in other methods can be performed in a similar manner as described for those blocks in other flowcharts.

At block 5810, method 5800 includes analyzing a plurality of cell-free DNA molecules from the biological sample of the subject. Analyzing a cell-free DNA molecule can include determining a genomic position in a reference genome corresponding to at least one end of the cell-free DNA molecule. Such analysis of each of the plurality of cell-free DNA molecules in block 5810 can be performed using any of the techniques described herein, e.g., as described with respect to other methods herein, such as in block 2710. In some implementations, the analysis of a cell-free DNA molecule can include determining an end sequence motif of at least one end of the cell-free DNA molecule, where an end of the cell-free DNA molecule has a first position at the outermost position, a second position that is next to the first position, and a third position that is next to the second position.

The analyzing can be done in various ways (e.g., as described herein) and can include physical steps, which may be controlled by a computer. As examples, analyzing can be performed by sequencing or PCR (e.g., droplet digital PCR) or mass spectrometry or electrophoresis.

At block 5820, method 5800 includes identifying a first set of CpG sites that all have a first differential methylation for the first tissue type in the reference genome. As examples, the first differential methylation can be that all of the first set of CpG sites are hypomethylated or that all of the first set of CpG sites are hypermethylated. Other examples are that all of the first set of CpG sites are 5hmC-enriched or that all of the first set of CpG sites are 5hmC-depleted. In some embodiments, both types of CpG sites may be used, e.g., when amounts at each are used as separate features for a machine learning model. In such an implementation, a second set of CpG sites of the other type (e.g., hypermethylated if the first set is hypomethylated) can be identified and a separate amount determined for the second set of sites.

The first set of CpG sites may include one or more CpG sites, e.g., one CpG site or a plurality of CpG sites.

At block 5830, method 5800 includes determining a first amount of cell-free DNA molecules ending at any one of the 0 or −1 position of any of the first set of CpG sites. Such an example corresponds to using the CGN motif for the 0 position. The first amount ending at the 0 or −1 position CpG sites can be further filtered, so that only a subset of the CGN motifs are used, e.g., CGA, CGT, CGC, or CGG, or some subset of these four end motifs. Such combinations can also be used for other techniques described herein in other sections. Other amounts can be determined, e.g., at another position around the CpG site, e.g., to determine a CGN/NCG ratio or a cleavage profile.

In another embodiment or as part of determining a different feature for a model, NCG end motifs may also be used, corresponding to the −1 position. For example, a first amount of a first set of one or more end sequence motifs that have C at the second position and G at the third position. The first set of end motifs can include one or more of the 3-mer motifs ACG, CCG, GCG, and TCG.

Accordingly, the first amount can be determined of a first set of one or more end sequence motifs. The first set of one or more sequence motifs can have C at the first position and G at the second position. As another example, the first set of one or more sequence motifs can have C at the second position and G at the third position.

The first amount can be normalized before being compared to the calibration value. The normalization can be done in various ways. For example, the normalization can use a number of cell-free DNA molecules ending within a region including a CpG site (e.g., a regional normalization a described above). As another example, the normalization can use a number of cell-free DNA molecules covering a CpG site (e.g., using sequencing depth, as described herein). As yet another example, the normalization can use an average or median depth of cell-free DNA molecules in a region including a CpG site.

When more than one CpG site is analyzed, instead of a single amount for each CpG site, respective amounts can be determined at each CpG site (e.g., as described in section B.3 above). Thus, determining the first amount can include determining respective amounts of cell-free DNA molecules ending at the 0 or −1 position of each of the first set of CpG sites. Then, determining the fractional concentration of DNA from the first tissue type can include comparing each of the respective amounts to a respective calibration value. Such respective amounts can be used in a feature vector for a model. Thus, comparing each of the respective amounts to the respective calibration value can be performed by inputting the respective first amounts as part of a feature vector into a machine learning model. An entire cleavage profile for each site can be used (See B.3 above). Accordingly, for each CpG site(s), a cleavage profile (e.g., for each position of at least two positions within a window around the CpG site) can be determined, e.g., by determining a respective amount of cell-free DNA molecules ending at the position. The respective amounts for the at least two positions and the CpG site can be included in the feature vector.

At block 5840, method 5800 includes determining the fractional concentration of DNA from the first tissue type in the biological sample by comparing the first amount to a calibration value. The calibration value can be determined from one or more calibration samples having known fractional concentrations of DNA from the first tissue type. The fractional concentration of DNA can have various resolution, e.g., above or below a certain percentage or within a range. Such range can have various resolutions, such as 5%, 10%, 15%, 20%, 25%, and 30% resolution or less. As an example, a 5% resolution can correspond to 35%-40%

In various embodiments, such techniques could be used to determine the DNA contributions of various tissues, including, but not limited to, the liver, brain, T cells, B cells, neutrophils, muscle, heart, placenta, ovary, breast, testis, tumor tissues (e.g. hepatocellular carcinoma, lung cancer, colon cancer, ovarian cancer), diseased tissues (e.g. tissues involved in inflammation (such as liver tissues involved in hepatitis, peritumoral tissues, and others) and tissues with increased cell death (such as ischemic or necrotic tissues or a tissue involved in traumatic injury), and tissues infected with one or more infectious agents (such as viruses or bacteria), etc.

As mentioned above, other amounts can be determined. For example, a second amount of cell-free DNA molecules ending at a first position within a window around any one the first set of CpG sites can be determined, such as the −1 position corresponding to NCG, if the first amount used the 0 position. Then, determining the fractional concentration can includes normalizing the first amount with the second amount to obtain a normalized first amount (e.g., CGN/NGC) that is compared to the calibration value. As examples, the first position can be at +1 or −1 from one of the one or more CpG sites. As another example, the window can be at least −2 to +2 from a CpG site, or at least −4 to +4 from a CpG site.

In some implementations, a cleavage profile can be determined in the window, e.g., as described above. The cleavage profile can be of at least two positions (e.g., the first position) in the window other than one of the CpG sites. For each of the at least two positions within the window, a respective amount (including the second amount) of cell-free DNA molecules ending at the position can be determined. As part of determining the fractional concentration, the first amount of cell-free DNA molecules ending at 0 or −1 position of the CpG site can be compared to the respective amount of cell-free DNA molecules ending at the position. For instance, a separate ratio of each of the respective amounts and the first amount can be determined.

In other implementations, the comparison of the respective amounts can be performed as part of a machine learning model (e.g., support vector regression). For example, a feature vector can include the respective amounts and the first amount. The feature vector can then be input into a machine learning model to determine the fractional concentration. The machine learning model can be trained using cell-free DNA molecules from the one or more calibration (training) samples having the known (e.g., measured) fractional concentrations of DNA from the first tissue type. The training can be performed using various techniques, as will be appreciated by the skilled person.

When a first set of one or more CpG sites are all hypomethylated for the first tissue type in the reference genome, a second set of one or more CpG sites that are all hypermethylated can be used (e.g., as described in FIGS. 45-47). A first feature vector can be generated for the first set, and a second feature vector can be generated for the second set. Both feature vectors can be input into the machine learning model as part of determining the fractional concentration. In any of these example techniques using a window, the at least two positions can include all positions within the window. As examples, the window can be at least +2 to −2 from a CpG site or at least +4 to −4 from a CpG site.

As described in section A above, multiple tissue types can be analyzed to determine fractional concentrations or changes thereof. In such an example, a second set of one or more CpG sites that are all hypomethylated or all hypermethylated for a second tissue type in the reference genome can be identified. A second amount of cell-free DNA molecules ending within a window around any one of the second set of CpG sites can be determined. Then, a change in a fractional concentration of DNA from the second tissue type in the biological sample can be determined by comparing the second amount to another calibration value (e.g., a baseline in a healthy control). Thus, the other calibration value can be determined from one or more other calibration samples.

D. Determining Fractional Concentration of Multiple Tissues

As mentioned above, some embodiments can perform a deconvolution to determine the fractional concentration of multiple tissues at a same time. Further, such a technique does not require identification of sites that are hypermethylated or hypomethylated in the particular tissue type. The cleavage profiles and/or the end motif profiles can be used to estimate the fractional concentrations for different tissue types.

A reference matrix A can include values at a set of sites, such as CpG sites and surrounding sites, e.g., when cleavage profiles are used. End motif values may also be used. Each column in the reference matrix can correspond to a different tissue type or to a different template sample (e.g., specified contributions for different tissues). The measurement of the values b (measurement vector) in the cell-free mixture (e.g., plasma, urine, etc.) can be used with A to determine the percentage contribution x of each tissue type of each template sample. This can be done by solving Ax=b.

The contribution vector x provides the percentage for each tissue type when the columns in A correspond to the different tissue types. In such embodiment, the reference values in the reference matrix from cells of the tissues can be prepared using various DNA nucleases (e.g., DNASE1L3, DNASE1, DFFB, etc.) to digest nuclei from those corresponding tissues. For example, the nuclei from the liver tissue can be subjected to DNASE1L3-based digestion. The sequencing data of digested DNA is analyzed to obtain reference values (e.g., of cleavage profiles and/or the end motif profiles) at various sites to obtain tissue-specific profiles of fragmentomics features to which the plasma fragmentomics features of cfDNA can be compared.

In another example, a reference can be generated through the analysis of tissue-specific cfDNA molecules. For example, one could use liver transplant cases, identify liver-specific DNA (e.g., using a tissue-specific allele) and use the liver-specific sequence reads to determine a tissue-specific profile. A similar technique can be used for other tissues.

When template samples are used, each template sample can correspond to a set of percentages that total 100%. For example, a liver transplant subject can be used as a template, with specified percentages for each of a set of tissues. Other templates might be for pathologies of each organ, e.g., so that there is a template for each tissue type whose contribution is to be determined. A healthy subject can also be used. To determine a percentage contribution for each tissue, the contribution of a template would be used in combination with the percentage of that tissue type for that template sample, which would be done for each template sample.

VIII. Pathology Detection

In addition to determining methylation and a fractional concentration of clinically-relevant DNA, disease detection (e.g., of cancer) was determined using cleavage profiles and end motif groups (CGN and NCG). For the end motifs, we performed a global analysis and amounts at specific CpG sites, e.g., ones that are hypermethylated in a particular tissue type and/or that are hypomethylated in a particular tissue type.

Cleavage profiles were also used at specific CpG sites, e.g., ones that are hypermethylated in a particular tissue type and/or that are hypomethylated in a particular tissue type, as well as CpG sites that do not have differential methylation among tissues but have different cleavage profiles for different levels of a pathology. Different types of pathologies (e.g., different types of cancers) can be determined using informative sites specific to different types of pathologies (e.g., different types of cancers). Surprisingly accurate results were obtained using the cleavage information (e.g., end motifs and cleavage profiles) around CpG sites relative to using other end motifs, e.g., the CCA or all 3-mer end motifs).

Viral and human DNA were used in different techniques. Example pathologies include cancer and autoimmune diseases (e.g., systemic lupus erythematosus (SLE)). The classification of the pathology can be the presence or absence of the pathology. In other examples, the classification can be of a severity of the pathology, e.g., as described herein, such as a size of one or more tumors or a surface area of one or more tumors. Such severity can be determined based on the extent of a parameter above a threshold/cutoff or relative to a calibration level from a subject that is known to have a particular severity (e.g., a stage of cancer).

A. Using CGN and/or NGC End Motifs

Cancers are typically hypomethylated when methylation is determined genome wide. This global hypomethylation is described in PCT publication WO2014/043763, which is incorporated by reference in its entirety for all purposes. FIG. 28 above shows that fragmentation at a CpG site reflects methylation. The following analysis shows that a pathology, such as cancer, can be determined using fragmentation, e.g., over a whole genome or over repeat sections of the genome. Such an analysis can also be performed for all or a large part of the genome, e.g., at least 10 Mb, 20 Mb, 50 Mb, 100 Mb, 500 Mb, 1 Gb or more. The part of the genome does not need to be contiguous, e.g., the 50 Mb could be split among five 10 Mb regions that are disjoint (i.e., not contiguous).

1. CGN/NCG Ratio

The genome-wide CGN/NCG ratios could be used to reflect genome-wide methylation levels and be used for disease detection. Global methylation density was analyzed for 6 healthy controls and 8 patients with hepatocellular carcinoma (HCC) with a median of 424 million paired-end bisulfite sequencing reads (IQR: 352-519 million).

Figure 59C:
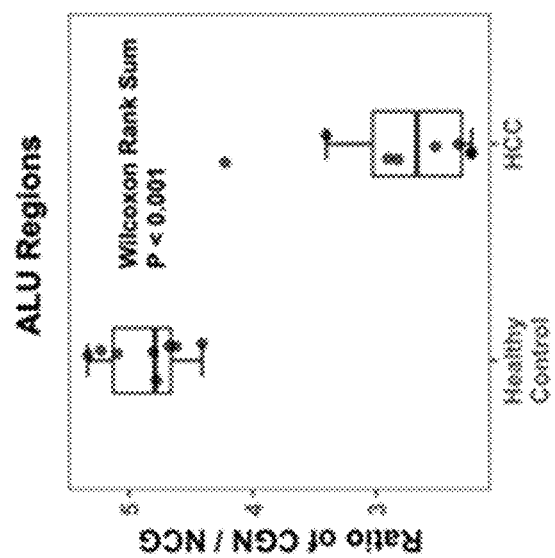
FIG. 59A-59C show boxplots illustrating the difference of genome-wide methylation density (FIG. 59A), genome-wide CGN/NCG ratio (FIG. 59B), and CGN/NCG ratio for Alu regions (FIG. 59C) between healthy controls and HCC cases according to embodiments of the present disclosure.
Figure 59B:
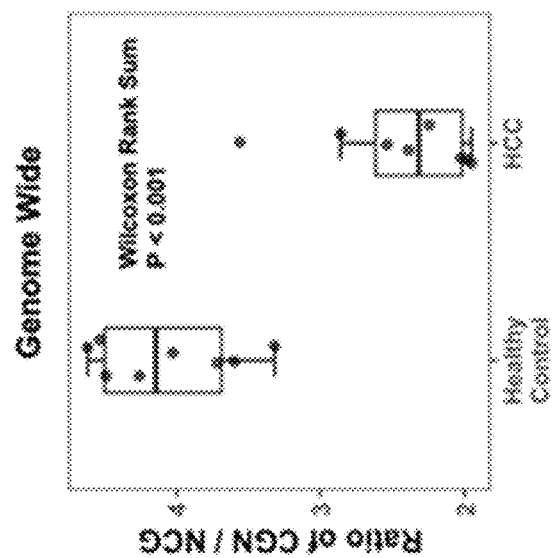
Figure 59A:
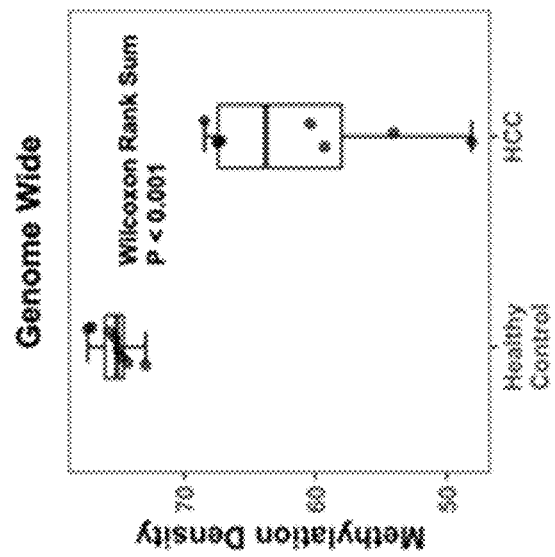
Figure 60A:
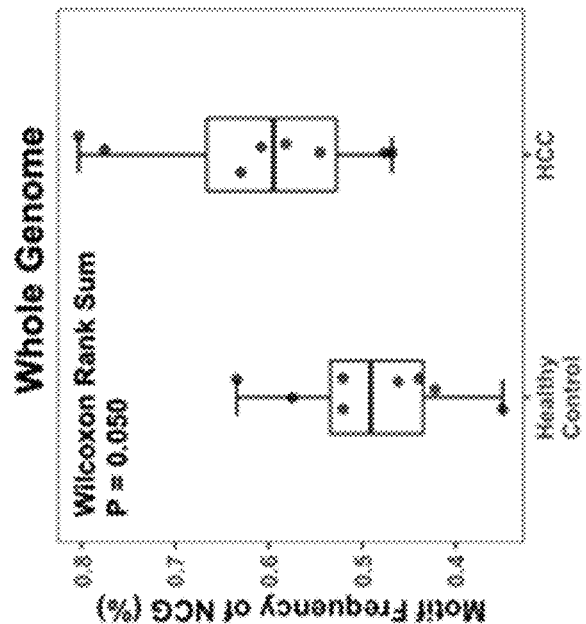
FIGS. 60A-60D show boxplots illustrating the difference of CGN and NCG motif frequency from whole genome and Alu regions between healthy controls and HCC cases according to embodiments of the present disclosure.
Figure 60B:
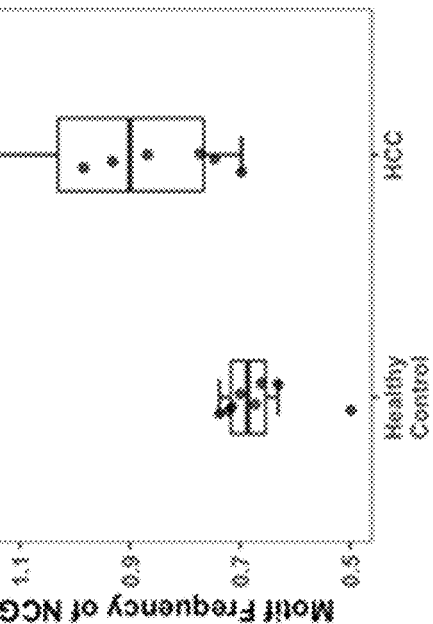
Figure 60C:
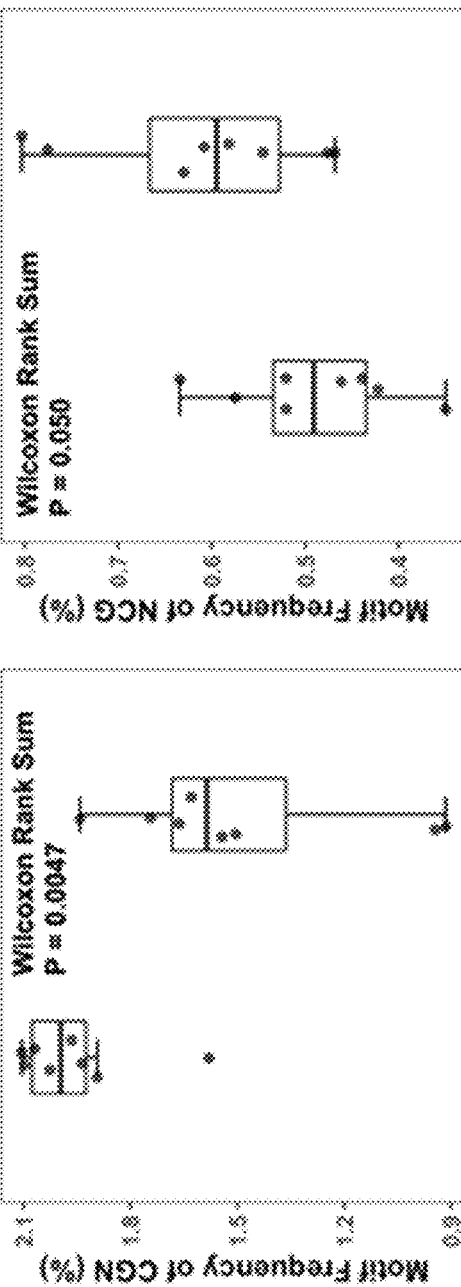
Figure 60D:
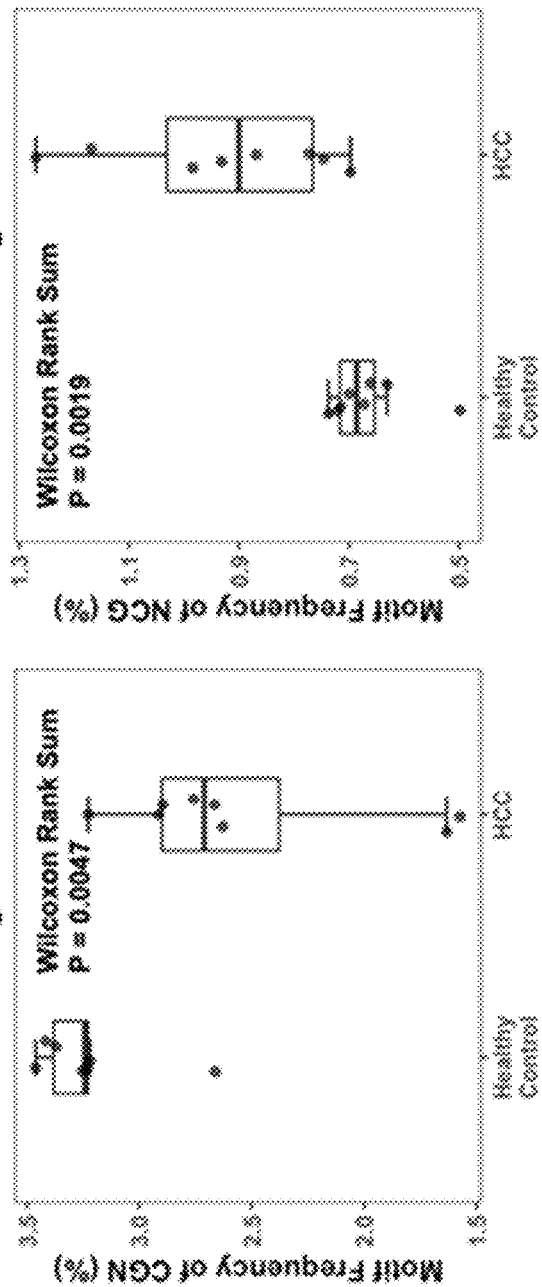

FIG. 59A-59C show boxplots illustrating the difference of genome-wide methylation density (FIG. 59A), genome-wide CGN/NCG ratio (FIG. 59B), and CGN/NCG ratio for Alu regions (FIG. 59C) between healthy controls and HCC cases according to embodiments of the present disclosure. As shown in FIG. 59A, HCC cases indicated significantly lower methylation levels compared with healthy controls (P value <0.001, Wilcoxon test). The genome-wide CGN/NCG ratio was analyzed for each patient and showed a significant reduction in the HCC group compared with the control group (FIG. 59B; P value <0.001, Wilcoxon Rank Sum test).

Besides genome-wide analysis, we hypothesized that the changes of CGN/NCG ratio across Alu regions or other repetitive elements could be useful for reflecting the corresponding alterations of methylation. Over 90% of methylated CpG sites in the human genome occur in DNA repetitive elements, such as Alu and LINE-1 (Zheng et al. Nucleic Acids Research. 2017; 45:8697-8711). The ALU region can effectively represent the whole genome. Other repeat regions can also be used. As an example, as shown in FIG. 59C, the CGN/NCG ratio from Alu regions showed a significant reduction in HCC cases compared with controls (P value <0.001, Wilcoxon Rank Sum test). These results indication that the use of genome-wide CGN/NCG ratio enabled the determination of the genome-wide global methylation as well as the detection of cancer.

Accordingly, the global and repeat-specific fragmentation patterns specific to CGN and NCG (e.g., as a ratio or individually) can provide accurate disease detection. The separation between healthy and HCC are surprising for the use of fragmentation values, which do not require the use of a methylation-aware assay.

2. CGN or NCG

The end motifs of CGN and NGC can also be used individually. The CGN and NCG motif frequency were calculated across the genome, as well as for the Alu regions.

FIGS. 60A-60D show boxplots illustrating the difference of CGN and NCG motif frequency from whole genome and Alu regions between healthy controls and HCC cases according to embodiments of the present disclosure. As shown in FIGS. 60A-60D, the CGN frequency from genome-wide and Alu regions showed a significant reduction in the HCC group compared with the control group (P value=0.0047, Wilcoxon Rank Sum test). Moreover, the NCG frequency from genome-wide and Alu regions is significantly increased in the HCC group compared with the control group (Genome-wide: P value=0.05; Alu regions: P value=0.0019, Wilcoxon Rank Sum test).

The separation is better using the ratio CGN/NCG (or variants thereof), but the individual amounts of these end motifs can also be used.

3. Multi-Cancer Analysis

The examples above were for HCC, but other cancers can also be detected. Because ALU has a better separation, we used ALU regions for the CGN/NCG ratios for the analysis of different cancer types. The decrease of CGN/NCG ratios in Alu regions can facilitate the detection of various cancers (i.e., pan-cancer detection). To this end, we analyzed 6 healthy controls and 8 patients with HCC, 10 patients with head and neck squamous cell carcinomas (HNSCC), 10 patients with colorectal cancer (CRC), 10 patients with lung cancer (LC), and 10 patients with NPC, with a median of 87 million paired-end sequencing reads (IQR: 73-127 million).

Figure 61:
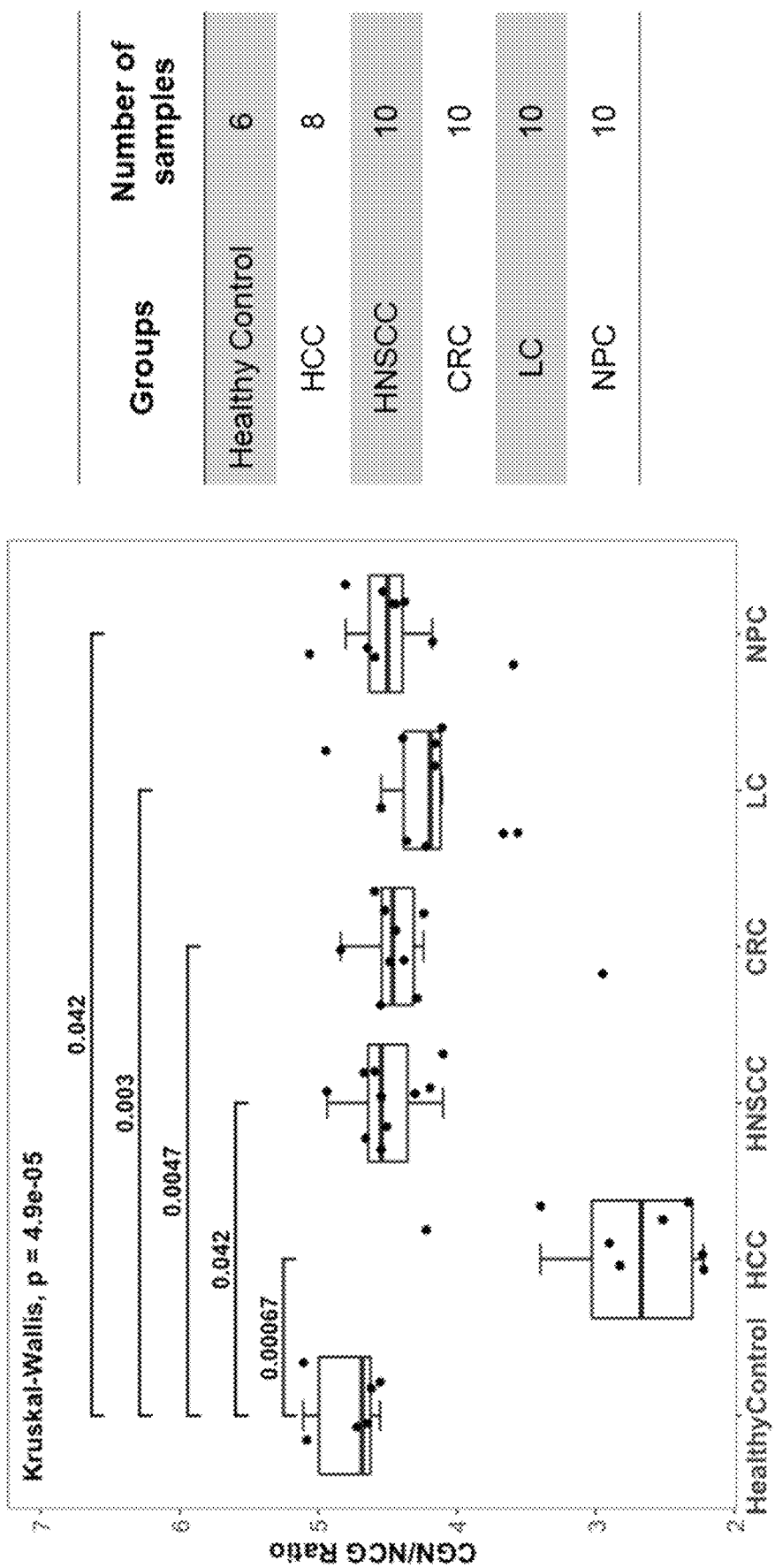
FIG. 61 shows the Alu region CGN/NCG ratio from healthy controls, HCC, HNSCC, CRC, LC, and NPC according to embodiments of the present disclosure.

FIG. 61 shows the Alu region CGN/NCG ratio from healthy controls, HCC, HNSCC, CRC, LC, and NPC according to embodiments of the present disclosure. P values between the two groups were calculated by using Wilcoxon Rank Sum test. As shown in FIG. 61, the CGN/NCG ratio from Alu regions from cancer subjects, including but not limited to, HCC, HNSCC, CRC, LC, and NPC, were significantly lower compared with control subjects (P value: HCC=0.00067; HNSCC=0.042; CRC=0.0047; LC=0.003; NPC=0.042, Wilcoxon Rank Sum test). Accordingly, the CGN/NCG ratio could serve as a biomarker for pan-cancer analysis. A better decrease in the separation value was seen for CRC, LC, and HCC.

4. PCR-Analysis

PCR may be used for any of the techniques described herein, e.g., as described above in section I. Such PCR analysis can be used for the global CGN/NCG ratio for the cancer diagnosis, as well as measuring methylation and fractional concentration of DNA from a particular tissue type. Accordingly, one can use digital or single molecule PCR assay to determinate CGN/NCG ratio by taking advantage of repetitive regions, such as Alu regions. In various examples, the digital PCR can be a droplet digital PCR assay, or one based on other types of partitioning (e.g., beads, or surfaces (e.g., on glass or in a flow cell) for carrying out reactions). In another embodiment, the digital PCR can be enabled with a microfluidics chip, e.g., from Fluidigm.

Figure 62:
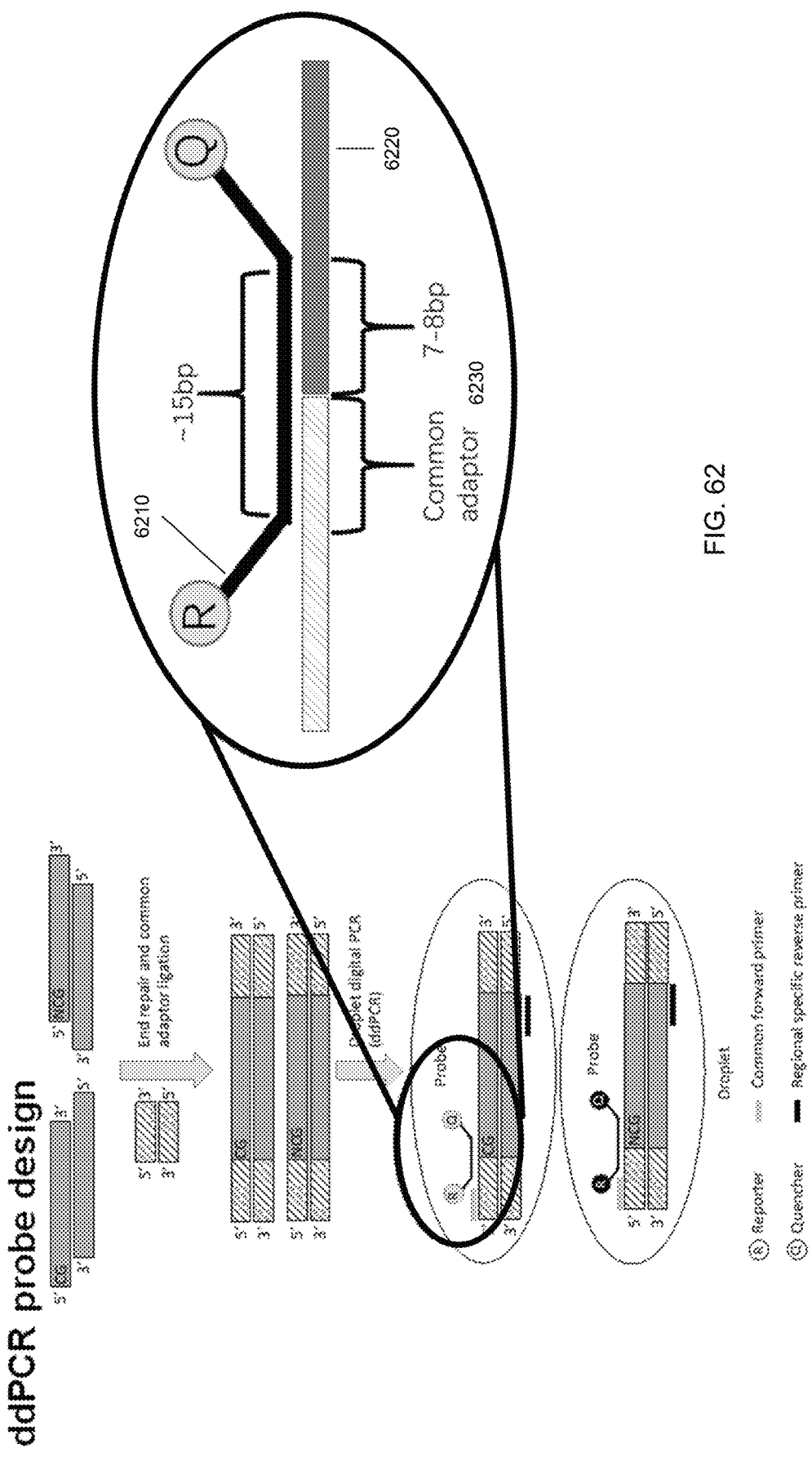
FIG. 62 shows an example technique using droplet PCR to determine NCG and CGN motifs in regions of interest and an example structure of the probe according to embodiments of the present disclosure.

FIG. 62 shows an example technique using droplet PCR to determine NCG and CGN motifs in regions of interest and an example structure of the probe according to embodiments of the present disclosure. For example, FIG. 62 shows a probe 6210 targeting a DNA template sequence 6220, which was ligated with a common adaptor 6230. The PCR can use a probe that covers the junction of common adaptor 6230 and the DNA template sequence 6220.

In the example shown, different probes are used for CGN and NCG. In this manner, we can distinguish NCG from CGN. As examples, for the junction part, the probe can have a size around 15 BP. The probe had one part with, for example, 7-8 bp in size hybridizing to a common adaptor region, while the other part of probe with, for example, a size of 7-8 bp was hybridized to the targeted Alu sequence. Other sizes for the hybridized portions can be used, as will be appreciated by the skilled person. We looked at the top CG probe and top NCG probes for the potential experiment design, i.e., the sequences that occurred the most for the 7-8 bp of the probe that are in the ALU region.

FIGS. 63A-63B show the top 10 CG probe and top 10 NCG probes for the potential experiment design according to embodiments of the present disclosure. We analyzed different combinations to see which probes provide the best results. The different combinations used one from CGN and one from NCG to determine the ratio.

Using the CG probe "CGCCTGT" and the NCG probe "TCGCTTGA" as examples, we performed in silico estimation of the potential performance of the ddPCR using the number of cfDNA fragments (as determined using sequencing results) ending with "CGCCTGT" and "TCGCTTGA" in the healthy controls and cancer patients. The CGN/NCG ratio in those targeted Alu regions that were supposed to be read by ddPCR assay would be reflected as the amount of "CGCCTGT" ended fragments divided by the amount of "TCGCTTGA" ended fragments in the sequencing results. The in silico estimation uses sequencing data to identify sequences, and then selects the corresponding sequences, as if they would be detected using the PCR probes.

Figure 64:
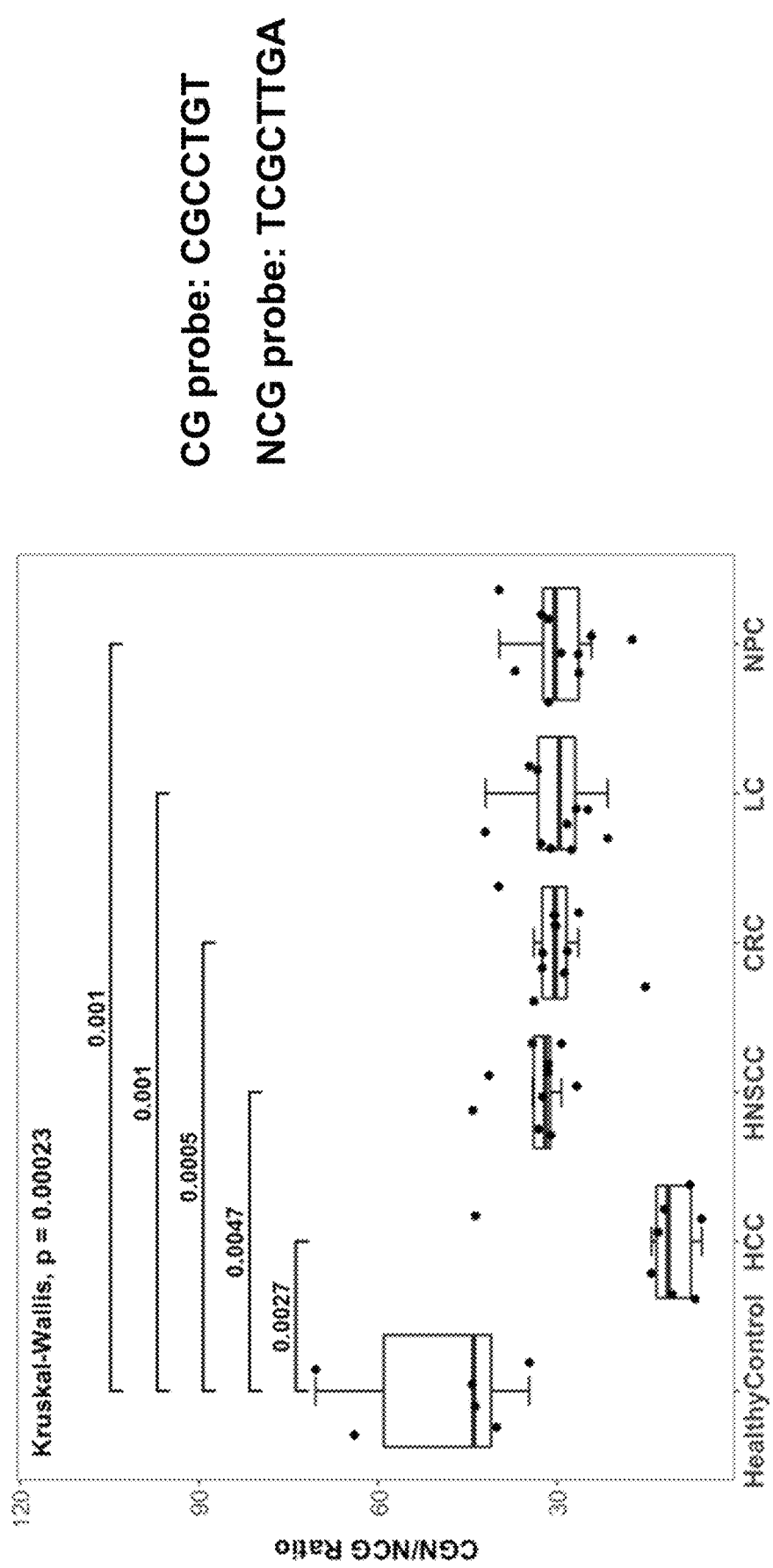
FIG. 64 shows an in silico analysis for the CGN/NCG ratio by ddPCR assay with probes containing Alu-related sequences "CGCCTGT" and "TCGCTTGA" across healthy controls, and subjects with HCC, HNSCC, CRC, LC, or NPC according to embodiments of the present disclosure.

FIG. 64 shows an in silico analysis for the CGN/NCG ratio by ddPCR assay with probes containing Alu-related sequences "CGCCTGT" and "TCGCTTGA" across healthy controls, and subjects with HCC, HNSCC, CRC, LC, or NPC according to embodiments of the present disclosure. P values between two groups were calculated by Wilcoxon Rank Sum test. As shown in FIG. 64, the CGN/NCG ratios from cancer subjects were significantly lower compared with control subjects (P value: HCC=0.0027; HNSCC=0.0047; CRC=0.0005; LC=0.001; NPC=0.001, Wilcoxon Rank Sum test). The separation was about as good for all of the cancers or better for some of the cancers than using the sequencing 3-mers for the CGN/NCG ratio, as shown above.

FIGS. 65A-65E show the ROC analysis in differentiating patients with HCC, HNSCC, CRC, LC, or NPC from healthy controls using CGN/NCG ratio by in-silico ddPCR assay according to embodiments of the present disclosure. The analysis used the same two sequences as used in FIG. 64. The CGN/NCG ratio deduced from the targeted Alu regions that could be assayed by ddPCR was able to differentiate HCC (AUC: 0.96), HNSCC (AUC: 0.92), CRC (AUC: 0.98), LC (AUC: 0.97), and NPC (AUC: 0.97) from healthy controls. The ROC are surprising for the use of these specific end motifs relative to using all 3-mer motifs for HCC, which provided 0.872 in previous work.

Probes with different sizes and/or multiplex could be used for cancer detection. Probes targeting the other regions of interest such as LINE-1 could be used for cancer detection and monitoring. In other examples, mass spectrometry (e.g., using a time-of-flight mass spectrometer) can be used for detection of reaction products containing DNA molecules.

A further example can use qPCR (real-time PCR) for detecting CGN and NCG frequency from specific regions.

Figure 66:
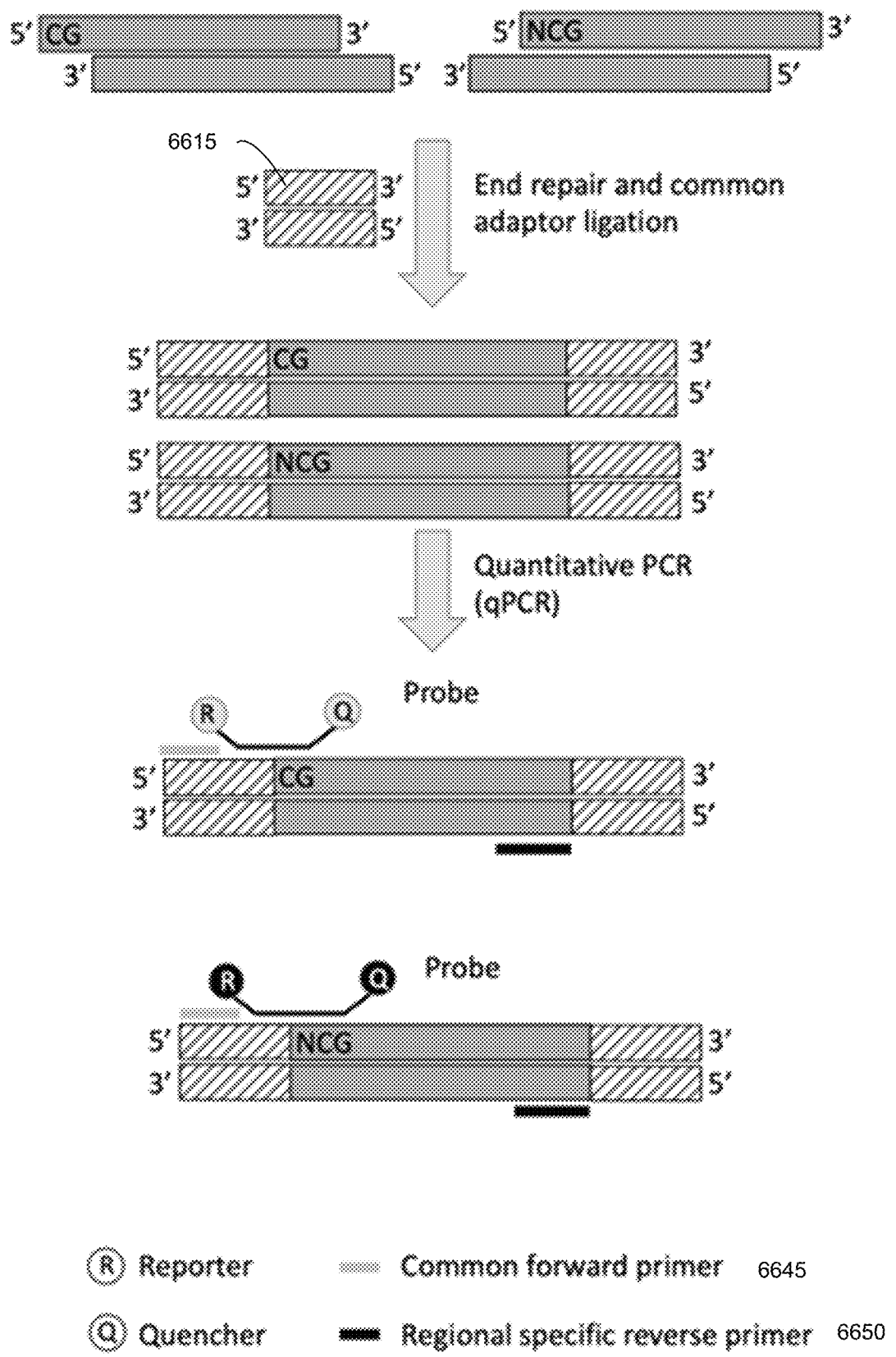
FIG. 66 shows an example method using qPCR to determine NCG and CGN motifs in regions of interest.

FIG. 66 shows an example method using qPCR to determine NCG and CGN motifs in regions of interest. The method is similar to that described in FIG. 4 such that the description for FIG. 4 can be applied to this technique. As shown, cell-free DNA molecules can be subjected to DNA end pair, A-tailing, and common adaptor ligation as optional steps. A pair of PCR primers can be designed in a way that one primer (e.g., common forward primer 6645) binds to the common adaptor region 6615 and the other primer (e.g., regional specific reverse primer 6650) binds to the specific region of interest. DNA molecules would be amplified by the pair of PCR primers and hydrolyze the fluorescent probe specific to a certain end motif (such as CGN or NCG end motif) to emit fluorescent signals, thus enabling the detection of the presence of a specific motif as well as the quantification of a specific motif.

FIGS. 67A-67C show an example for the designs of primers and probes. The amplified range (i.e., between the two primers) can be repeat regions including but not limited to LINEs (Long INterspersed Elements) and SINEs (Short INterspersed Elements). For illustration purposes, we designed a reverse primer (i.e., CCACTGCACTC-CAGCCTG (SEQ ID NO: 3)), which targeted the consensus sequence of Alu elements, a type of SINEs (FIG. 67A). Together with a forward primer that targeted the common adopter added, this pair of primers can be used to amplify Alu regions with end motif perseveved in the 5' end of the cfDNA. Two probe hybridizing sites (i.e., CGCCTGT and TCGCTTGA) were selected from the Alu consensus sequence of interest (i.e., 200 bp before the reverse primer) (FIG. 67A). Together with the 12-nt sequence from the common adaptor, CGN probe (i.e., CTCTTCC-GATCTCGCCTGT (SEQ ID NO: 4)) and NCG probe (i.e., CTCTTCCGATCT TCGCTTGA (SEQ ID NO: 5)) were designed (FIG. 67B).

To test the specificity of these probes, we determined possible hybridizing sites in the whole genome based on sequencing reads of cfDNA. As shown in FIG. 67C, most of the probe hybridizing sites were located within Alu regions with only ~0.3% being off-targeted. Thus, these two probes can provide good coverage and provide good results as explained below.

We tested such a PCR-based method in one mechanically-fragmented gDNA sample, one healthy control cfDNA sample, and one early-stage HCC cfDNA sample. For the qPCR testing, a relative fold change of CGN/NCG motif ratio was calculated based on the CT value determined from the qPCR assay.

Figure 68B:
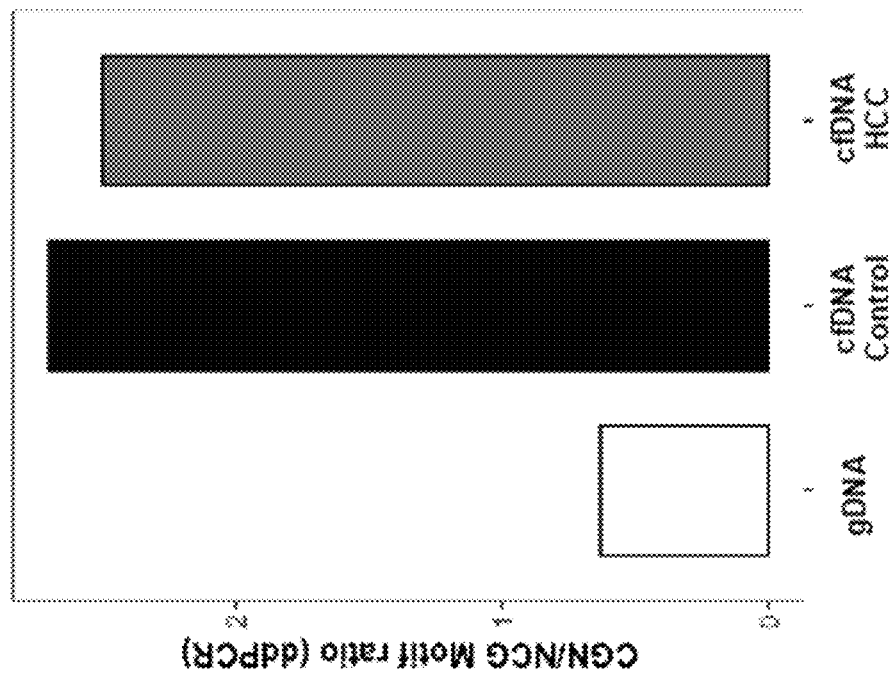
FIGS. 68A-68B show testing results from qPCR (A) and ddPCR (B). gDNA represents the mechanically fragmented gDNA sample and used as the control in qPCR assay.
Figure 68A:
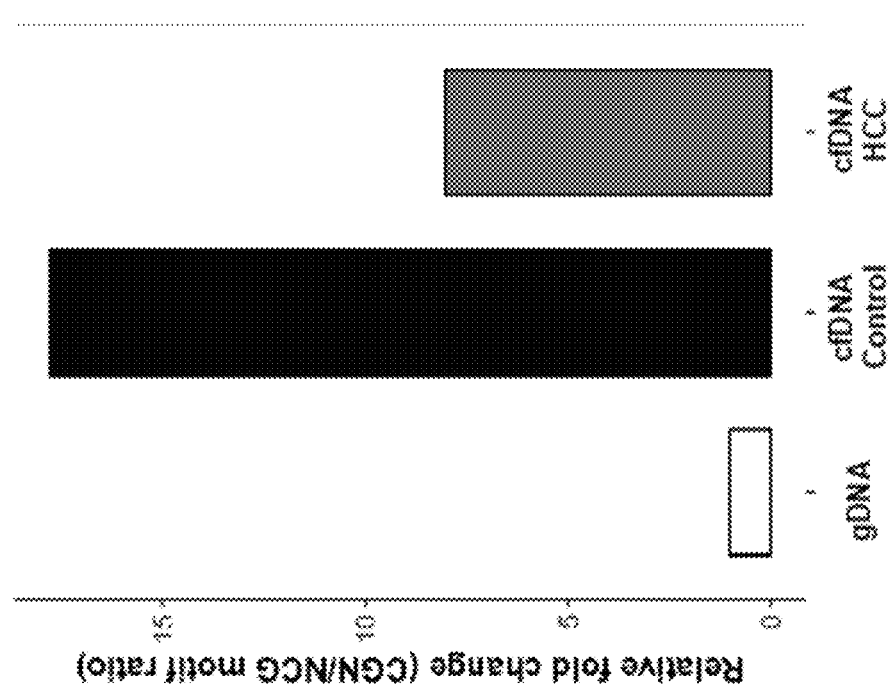

FIGS. 68A-68B show testing results from qPCR (68A) and ddPCR (68B). gDNA represents the mechanically fragmented gDNA sample and used as the control in the qPCR assay. Relative to the mechanically-fragmented gDNA sample, the fold change of CGN/NCG motif ratio was calculated based on the CT value determined from the CGN probe for the control (i.e., fragmented gDNA sample) ($CT_{CGN\ control}$) and the testing sample ($CT_{CGN\ testing}$), and from the NCG probe for the control ($CT_{NCG\ control}$) and the testing sample ($CT_{NCG\ testing}$) as follows:

Relative fold change of CGN/NCG motif ratio =

$$\frac{2^{-(CT_{CGN\,testing}-CT_{CGN\,control})}}{2^{-(CT_{NCG\,testing}-CT_{NCG\,control})}}$$

For the ddPCR testing, the CGN/NCG motif ratio was calculated as the amount of CGN probe positive droplets divided by the amount of NCG probe positive droplets.

As the gDNA sample was mechanically sheared to 200 bp, the end motifs present in the gDNA sample tended to be random (i.e., the CGN/NCG motif ratio was close to 1). In the healthy control cfDNA sample, as the Alu regions are usually hypermethylated, there were more CGN end motifs than NCG end motifs (i.e., CGN/NCG motif ratio >1). Indeed, in both testing results from the qPCR and ddPCR, the healthy control cfDNA sample showed a substantially higher CGN/NCG motif ratio than mechanically fragmented gDNA. Moreover, in both qPCR and ddPCR testing results, the CGN/NCG motif ratio from the HCC cfDNA sample was lower than that from healthy control cfDNA, which reflected the reduced methylation level in the HCC sample (i.e., hypomethylation).

The tumor-derived DNA was shorter than background DNA mainly of hematopoietic origin. The amplicon size corresponding to the CGN probe was longer than that corresponding to the NCG probe since the CGN probe is 86 nt away from the reverse primer while the NCG probe is only 45 nt. Thus, the amplicon corresponding to the NCG probe would be increased relative to the CGN probe in patients with cancer since there is a higher likelihood to have both the NCG probe and the reverse primer on the same fragment, i.e., as the distance is shorter. The result is an extra reduction of CGN/NCG motif ratio due to size properties. Hence, the CGN/NCG motif ratio targeting Alu regions can synergistically enhance the cancer signal related to the hypomethylation and size shortening regarding tumor-derived DNA molecules, which would lead to higher performance in cancer detection, monitoring, and prognosis.

5. End Motifs of Fragments of a Particular Size

In some embodiments, methylation-aware fragmentation analysis described in this disclosure can be performed using long-read sequencing technologies, including, but not limited to, nanopore sequencing (e.g., Oxford Nanopore Technologies) and single-molecule real-time sequencing (e.g., Pacific Biosciences). Using single molecule real-time sequencing (Pacific Biosciences), we sequenced plasma DNA samples from 15 healthy subjects (median reads: 970,633; IQR: 407,695-1,399,709). Putatively hypermethylated (4,631,823) and hypomethylated (307,831) CpGs in plasma were identified based on bisulfite sequencing of plasma DNA samples from 8 healthy subjects. Putatively hypermethylated CpGs were defined as CpGs with a methylation density of over 70% across all cases. Putatively hypomethylated CpGs were defined as CpGs with a methylation density below 30% across all cases. CGN/NCG motif ratios of putatively hypermethylated and hypomethylated CpGs in plasma were analyzed by pooling all single molecule real-time sequencing reads from these healthy subjects.

Figures 69A, 69B:
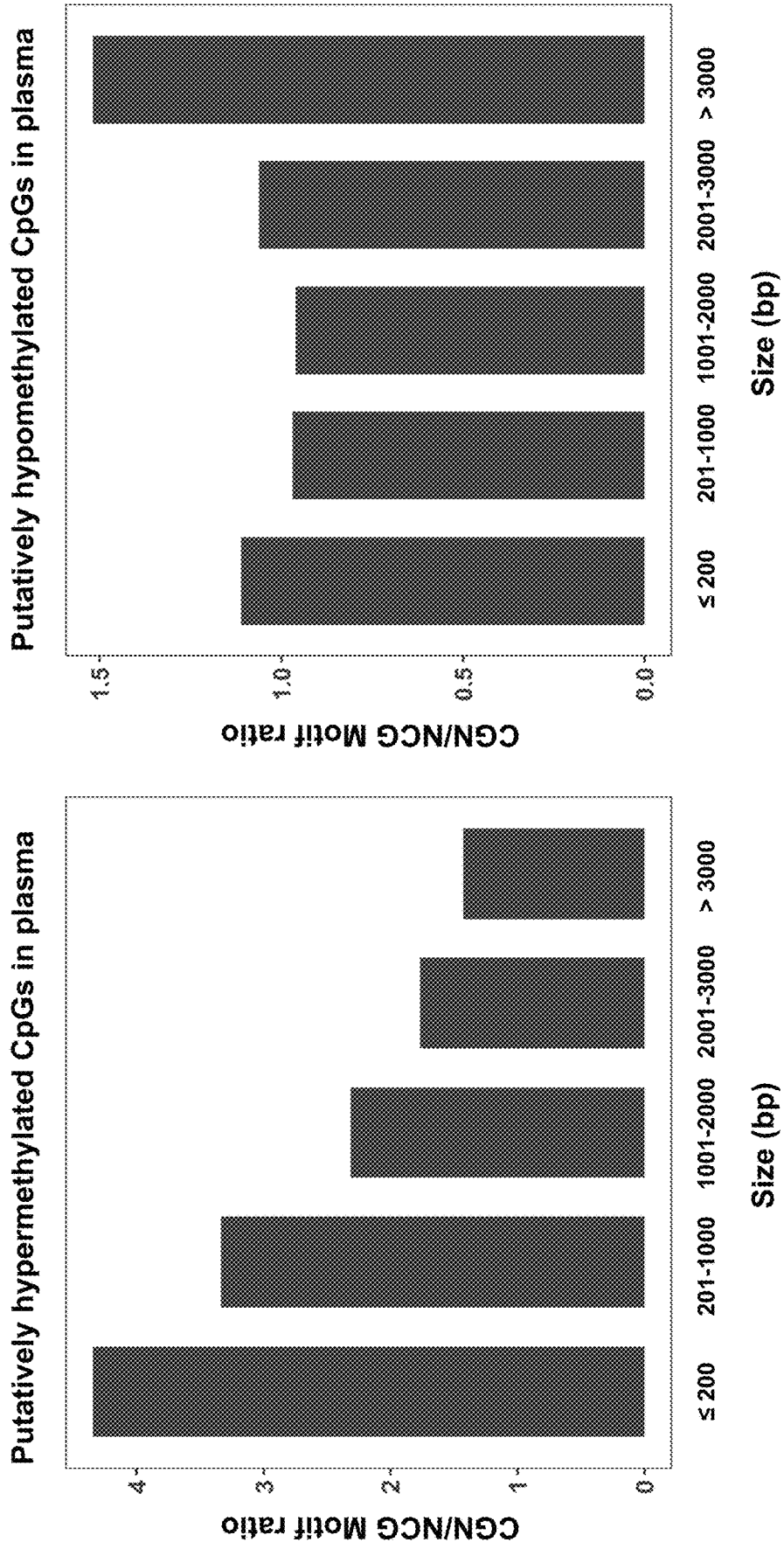
FIGS. 69A-69B show CGN/NCG motif ratio in putatively hypermethylated and hypomethylated CpGs across different size ranges for those single molecule real-time sequencing reads pooled from healthy subjects.

FIGS. 69A-69B show CGN/NCG motif ratio in putatively hypermethylated and hypomethylated CpGs across different size ranges for those single molecule real-time sequencing reads pooled from healthy subjects. As shown in FIG. 69A, the CGN/NCG motif ratio of putatively hypermethylated CpGs was decreased with the increase of cfDNA fragment size. As shown in FIG. 69B, the CGN/NCG motif ratio of putatively hypomethylated CpGs was decreased with the increase of cfDNA fragment size for the size range of <=1000 bp, while the value was increased with the increase of cfDNA fragment size for the size range of >1000 bp.

FIGS. 69A-69B indicate that, when the size range is different, the cutting preference is different. For long molecules, the CGN/NCG motif ratios of hypermethylated and hypomethylated CpG sites are closer in comparison than when the size is lower than 200. Thus, we investigated whether analyzing DNA fragments of a certain size range can provide an increase in accuracy.

To illustrative the usefulness of taking into account fragment sizes during methylation-aware fragmentation analysis, for illustration purples, we sequenced plasma DNA from 15 healthy subjects, 13 patients with chronic HBV infection (HBV carriers), and 45 patients with HCC using single molecule real-time sequencing (Pacific Biosciences). In one embodiment, the overall CGN/NCG motif ratio was calculated across healthy subjects, HBV, and HCC cases using short (<=200 bp) and long (>=1000 bp) plasma cfDNA molecules, separately. Other values for the short cutoff can be used besides 200 bp, such as 150 bp, 175 bp, 225 bp, and 250 bp. Other values for the long cutoff can be used besides 1000 bp, such as 6000 bp, 700 bp, 800 bp, 900 bp, 1,110 bp, 1,500 bp, and 2,000 bp.

FIGS. 70A-70C are boxplots showing the overall CGN/NCG motif ratios of short cfDNA fragments (<=200 bp; 70A) and long cfDNA fragments (>=1000 bp; 70B), and the difference in CGN/NCG motif ratio (70C) between short (<=200 bp) and long cfDNA fragments (>=1000 bp) across healthy subjects (Healthy), HBV carriers (HBV), and HCC cases. Due to the global hypomethylation of HCC, overall CGN/NCG motif ratios of HCC cases in short DNA fragments were significantly lower than that of healthy and HBV subjects (FIG. 70A). While for long DNA fragments, compared with healthy and HBV subjects, patients with HCC showed a higher overall CGN/NCG motif ratio (FIG. 70B).

In some embodiments, a first amount of short DNA fragments having CGN or NCG (or a ratio thereof) and a second amount of long DNA fragments having CGN or NCG (or a ratio thereof) can be used together. The use of a separation value (e.g., difference or ratio) between the two ratios can provide increased accuracy, e.g., because the change is in opposite directions for the short DNA fragments and the long DNA fragments. As another example, the first amount and the second amount can be used as inputs to a machine learning model (potentially four amounts of CGN and NCG for both short and long DNA fragments), such as a decision tree, SVM, regression, or a neural network.

Accordingly, motif ratios from cfDNA fragments with different lengths can be combined through, but not limited to, calculating the difference or the ratio between the CGN/NCG motif ratios of short and long cfDNA fragments. As shown in FIG. 70C, the difference in the CGN/NCG motif ratio between short and long cfDNA fragments was significantly lower in the HCC subjects compared with the non-HCC subjects.

Figure 71A:
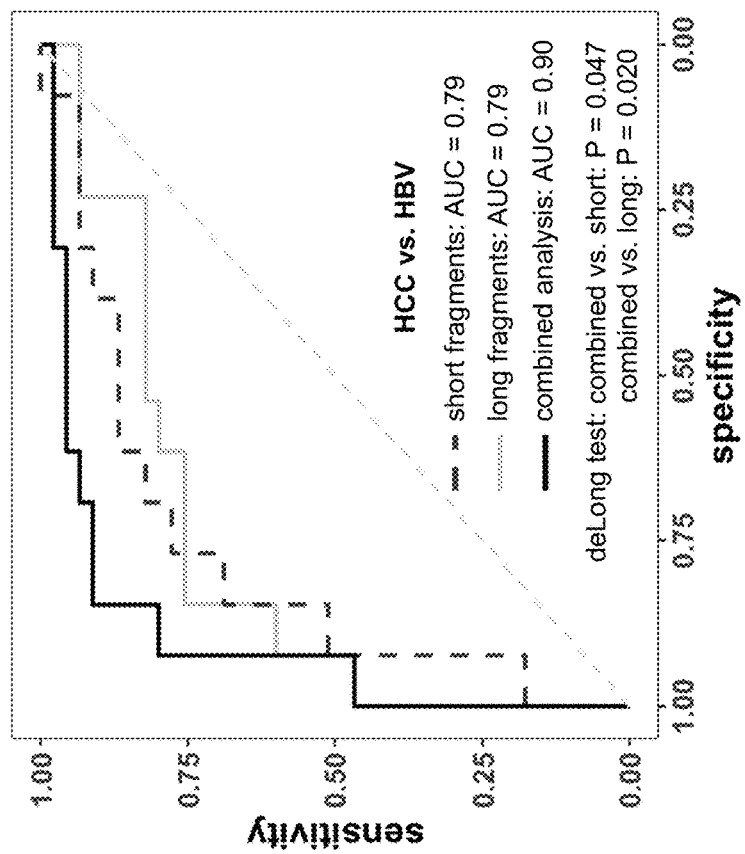
FIGS. 71A-71B show the performance of HCC detection on the basis of CGN/NCG motif ratio with size information.
Figure 71B:
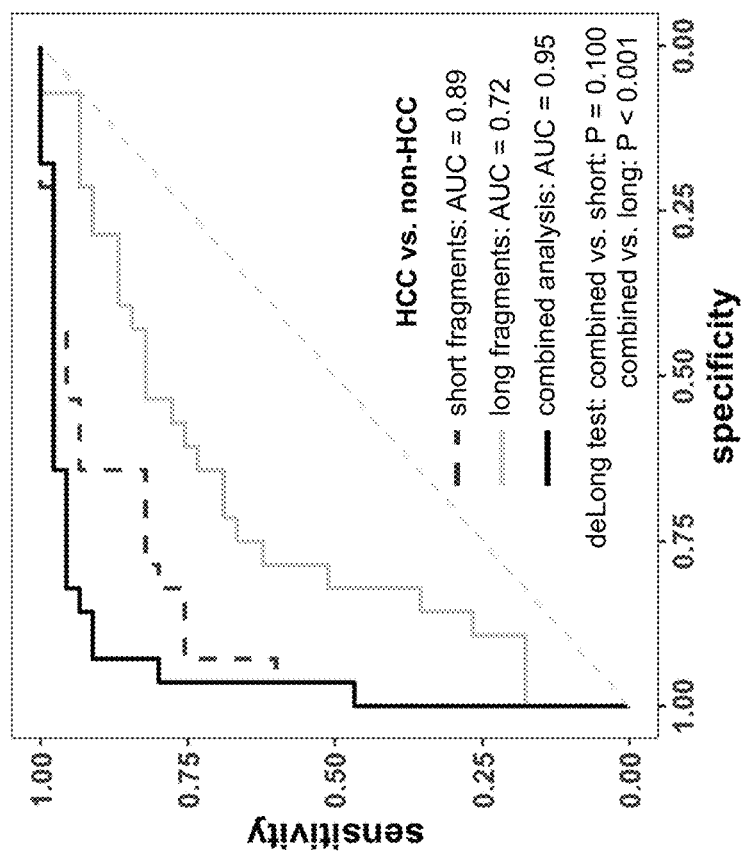

FIGS. 71A-71B show the performance of HCC detection on the basis of CGN/NCG motif ratio with size information. FIG. 71A shows the ROC analysis in differentiating between HCC and non-HCC (healthy and HBV subjects) using the overall CGN/NCG motif ratio of short cfDNA fragments (<=200 bp) and long cfDNA fragments (>=1000 bp), and the difference in CGN/NCG motif ratio between short (<=200 bp) and long cfDNA fragments (>=1000 bp) (combined analysis). FIG. 71B shows the ROC analysis in differentiating between HCC and HBV using the overall CGN/NCG motif ratio of short cfDNA fragments (<=200 bp) and long cfDNA fragments (>=1000 bp), and the difference in CGN/NCG motif ratio between short (<=200 bp) and long cfDNA fragments (>=1000 bp) (combined analysis).

The use of CGN/NCG motif ratio metric derived from short DNA led to an AUC of 0.89 for distinguishing the HCC cases from the non-HCC cases (healthy and HBV subjects; FIG. 71A), and an AUC 0.79 for HCC versus HBV carriers (FIG. 71B). The use of CGN/NCG motif ratio metric derived from long DNA could obtain an AUC of 0.72 for distinguishing HCC cases from non-HCC cases (healthy subjects and HBV carriers; FIG. 71A), and an AUC of 0.79 for HCC versus HBV subjects (FIG. 71B).

An AUC of 0.95 could be achieved for distinguishing the HCC cases from the non-HCC cases (healthy subjects and HBV carriers; FIG. 71A), with an AUC of 0.90 for HCC versus HBV subjects (FIG. 71B). Such performance was better than the corresponding AUC values using short or long cfDNA fragments alone. In another embodiment, short cfDNA fragments can be defined as cfDNA fragments with a length of lower than but not limited to 50 bp, 60 bp, 70 bp, 80 bp, 90 bp, 100 bp, 200 bp, 300 bp, 400 bp, 500 bp, 600 bp, 1000 bp, etc, and long cfDNA fragments can be defined as cfDNA fragments with a length of higher than but not limit to 300 bp, 400 bp, 500 bp, 600 bp, 700 bp, 800 bp, 900 bp, 1000 bp, 2000 bp, 3000 bp, 4000 bp, 5000 bp, etc. In yet another embodiment, cfDNA fragments with different sizes can be obtained from Illumina sequencing platforms, long-read sequencing technologies, or other platforms. Mass can also be used as a measure of size, instead of length.

6. Methods Using CGN and/or NCG End Motifs

The pathology can be determined in various ways. For example, the amount of DNA fragments ending at CpG sites (e.g., CGN end motifs, or subsets thereof) in a new sample. The amount can be determined using a group for DNA fragments within a particular size range. The classification can be determined using various models, such as a comparison of one amount to a threshold, cutoff, or reference value or a machine learning model. Such models can be trained using reference/calibration samples having known or measured classification (e.g., via using a different technique). As with training of other models, different accuracy goals can be selected, e.g., a desired tradeoff between sensitivity and specificity. Such training can be done for other techniques described herein.

Figure 72:
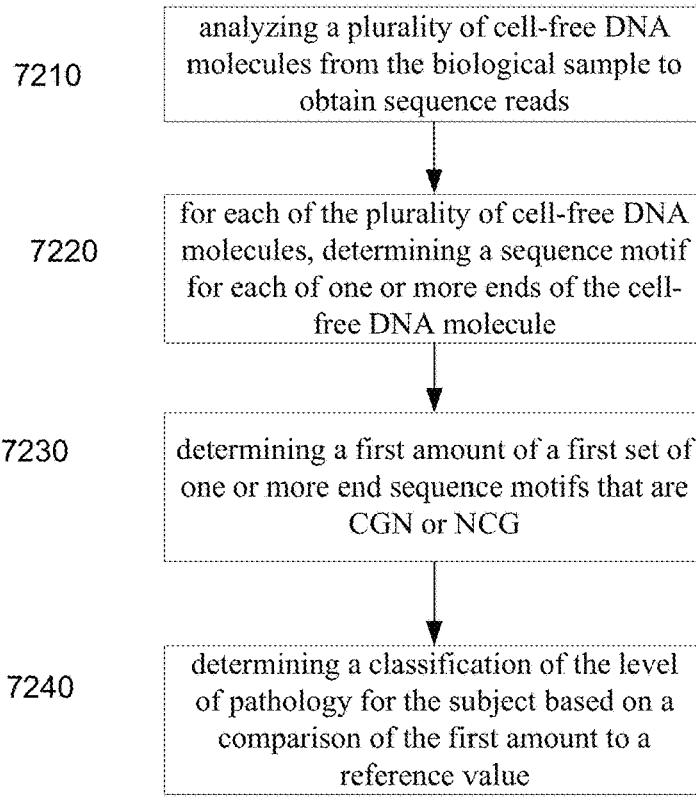
FIG. 72 is a flowchart illustrating a method for determining a level of a pathology according to embodiments of the present disclosure.

FIG. 72 is a flowchart illustrating a method 7200 for determining a level of a pathology according to embodiments of the present disclosure. The biological sample including cell-free DNA. As with other methods described herein, method 7200 can be performed partially or entirely using a computer system. Blocks performing similar functionality as in other methods can be performed in a similar manner as described for those blocks in other flowcharts.

At block 7210, method 7200 includes analyzing a plurality of cell-free DNA molecules from the biological sample to obtain sequence reads. The sequence reads can include ending sequences corresponding to ends of the plurality of cell-free DNA molecules. Block 7210 can be performed in a similar manner as block 2710 and other analysis steps described herein. In some implementations, analyzing a cell-free DNA molecule can include determining a location of the cell-free DNA molecule in a reference genome, e.g., when the analysis is of a region smaller than the entire genome. Such a region can be a chromosome. The plurality of cell-free DNA molecules can be located in the region of the reference genome. The location can be determined in various ways, as described herein, such as aligning sequence reads to the reference genome or using location-based probes.

At block 7220, method 7200 includes, for each of the plurality of cell-free DNA molecules, determining a sequence motif for each of one or more ends of the cell-free DNA molecule. Block 7220 can be implemented via any of the techniques described herein to determine an end motif, e.g., via sequencing or probe-based techniques, including PCR. Block 7220 can be implemented in a similar manner as block 4120. The end sequence motif can be determined from the outermost bases in a sequence read. If a sequence read only includes one end and not the entire DNA fragment/molecule (e.g., as one of paired reads covering both ends), the bases corresponding to the end of the DNA fragment are used and not the bases toward the middle of the fragment. An end of a cell-free DNA molecule can have a first position at the outermost position, a second position that is next to the first position, and a third position that is next to the second position.

At block 7230, method 7200 includes determining a first amount of a first set of one or more end sequence motifs that have C at the first position and that have G at the second position (e.g., an amount of CGN or any one of more these motifs). For example, the first set of one or more end sequence motifs can include one or more of CGA, CGC, CGG, and CGT, with CGN denoting any nucleotide at the third position. The first amount can be normalized in various ways.

In other embodiments, the first amount can be of a first set of one or more end sequence motifs that have C at the second position and G at the third position (e.g., NCG). In this example, the first set of one or more end sequence motifs can include one or more of ACG, CCG, GCG, and TCG, with NCG denoting all. Such example end motifs can be used in various ways as described herein to determine amounts and/or normalized parameters for use in making the classification. Block 7230 can be performed in a similar manner as block 2730 and similar steps described herein.

Other amounts can be determined and used, e.g., other end motifs, such as NCG to determine a CGN/NCG ratio. Thus, when the first amount uses CGN, a second amount of a second set of end sequence motifs that have C at the second position and G at the third position can be determined, corresponding to NCG or any subset thereof. The classification can then include normalizing the first amount with the second amount to obtain a normalized first amount that is compared to a reference value. As another example, a total amount of sequence motifs (e.g., in one or more particular regions) can be determined and used for normalization. The normalized first amount (e.g., a motif ratio or relative frequency) can again compared to the reference value.

As another example of normalization, a total amount of sequence motifs for the plurality of cell-free DNA molecules (e.g., in the region) can be determined. Then, determining the classification can includes normalizing the first amount with the total amount to obtain a normalized first amount (e.g., a motif ratio or relative frequency) that is compared to the reference value.

At block 7240, method 7200 includes determining a classification of the level of pathology for the subject based on a comparison of the first amount to a reference value. The reference value can be determined as part of training a model, e.g., using reference samples with known classifications. The comparison to the reference value can be performed in various ways, e.g., a direct comparison to the reference value, where values above or below indicate a different classification. As another example, the comparison can be performed via a machine learning model.

As mentioned above, the plurality of cell-free DNA molecules can be from one or more particular regions of a reference genome. The pathology can be in these one or more particular regions. For example, at least one of the one or more particular regions corresponds to a particular genotype or haplotype comprising one or more alleles. If a subject has certain amounts of fragmentation of certain end motifs (e.g., CGN and NCG) at a genotype or a haplotype, such a property can indicate a level of a pathology, resulting from a disease (e.g., cancer or inflammation) or an abnormal condition/disorder of or linked to a physiological process (e.g., via ageing, or a developmental process, or genomic imprinting, which is described in more detail elsewhere in this disclosure). A copy number aberration can be such a pathology. Embodiments can also determine a normal level of a physiological process, e.g., monitoring of a stage of gestation, ageing of a person, or a type or level of genomic imprinting of a person.

As with other techniques described herein, a feature vector of multiple amounts can be provided to a machine learning model, e.g., as described in sections above. The different amounts can correspond to a selection of end motifs, e.g., those included in the first set and additional end motifs. Such end motifs included in the feature vector can be all of the k-mers for a particular k or just a subset. Accordingly, a respective amount of each 3-mer end sequence motif that has a C at the first position and that has G at the second position can be determined (i.e., four amounts). A feature vector including the respective amounts, which include the first amount, can be generated and then input into a machine learning model as part of determining the classification of the level of pathology (e.g., an abnormal level of a physiological process) for the subject. Additionally or alternatively, the feature vector can include respective amounts for each 3-mer end sequence motif that has a C at the second position and that has G at the third position.

The analysis of the cell-free DNA molecules can include measuring a size of the cell-free DNA molecule. The first amount can then be determined for a first group of cell-free DNA molecules that are within a first size range, e.g., as described in section 5. As examples, the first size range can correspond to sizes that are less than a size cutoff or to sizes that are greater than a first size cutoff.

A second amount can be determined for a second group of cell-free DNA molecules that are within a second, different size range, e.g., corresponding to sizes that are less than a second size cutoff when the first range is greater than the first size cutoff. The second amount can be of one or more end motifs of CGN or NCG, as described above. The classification can then be determined using the first amount and the second amount. When CGN is used for long and short fragments, a third amount of NCG long DNA fragments and a fourth amount of NCG short DNA fragments can be used, e.g., as defined using the first size cutoff and the second size cutoff. As examples, the classification can use a ratio of the first amount and the second amount, can use a difference of the first amount and the second amount, or can use a machine learning model that receives the first amount and the second amount as separate inputs.

B. Tissue-Specific Hypo- or Hyper-Methylated Regions Sites

In addition to analyzing CGN and NCG generally (e.g., globally or over a large part of the genome), certain sites can be analyzed. For example, sites that are hypermethylated or hypomethylated for a particular tissue can be analyzed. Such an analysis can determine whether a particular type of cancer (e.g., tissue origin/source) is present. As examples, the size of the region can be at least 2 bp, 10 bp, 100 bp, 200 bp, 500 bp, 1 kb, 2 kb, 3 kb, 4 kb, 5 kb, 10 kb, 50 kb, 100 kb, 500 kb, 1 Mb, and so on. The DNA fragments from a particular region/site can be obtained via targeted techniques (also referred to as enrichment), which may be performed via amplification of certain regions or by capturing DNA from certain regions. Further details for enrichment can be found in other sections of this disclosure.

We analyzed samples from HCC patients. We identified differentially methylated regions between the liver and neutrophils (most common white blood cells), which represented a background of DNA of blood cells. The regions were each of 500 bp in length. In this way, we obtained liver-specific hyper-methylated regions and liver-specific hypo-methylated regions compared with neutrophils. The differentially methylated regions could include one or more CpG sites depending on the size of the regions.

For a liver hypermethylated region when enzyme (e.g., DNASE1L3) activity was comparable between disease and control group, the amount of CGN end motifs should increase, and the amount of NCG end motifs should decrease. Thus, the CGN/NCG ratio should increase. But if the enzyme activity was downregulated, then such a ratio might decrease. For liver hypomethylated regions, the amount of CGN should decrease, and the amount of NCG should increase. Thus, the CGN/NCG ratio should decrease.

When enzyme (e.g., DNASE1L3) activity was comparable between disease and control group, an HCC subject has a higher liver cell contribution to plasma than a healthy subject. From the liver hypermethylated regions, we expected a CGN increasing and NCG decreasing relative to a healthy subject. From a liver hypomethylated region, we expect CGN decreasing and NCG increasing. This will cause an increase of the CGN/NCG ratio in the hypermethylated regions, but decreasing of the CGN/NCG ratio in the hypomethylated regions.

Additionally, cleavage profiles or other methylation related cfDNA fragmentomic features from liver or HCC specific hypomethylated regions could be used for HCC detection. And methylation related cfDNA fragmentomic features from other tissue-specific hypomethylated or hypermethylated regions could be used for the detection of other cancers. For example, methylation related cfDNA fragmentomic features from colon-, breast-, or prostate-specific hypomethylated or hypermethylated regions could be used for colon cancer, breast cancer, or prostate cancer diagnosis, respectively. Such methylation related cfDNA fragmentomic features from specific regions could be deduced from targeted sequencing results. The targeted sequencing could be based on but not limited to probe-based hybridization, amplicon-based sequencing, immunoprecipitation followed by sequencing, etc.

1. CGN and/or NCG

End motif frequencies from tissue-specific hypomethylation or hypermethylation are used to detect and monitor diseases such as cancer. We analyzed 8 healthy controls, 17 patients with chronic hepatitis B (HBV), and 34 patients with hepatocellular carcinoma (HCC), with a median of 483 million paired-end sequencing reads (IQR: 395-549 million).

Figure 73A:
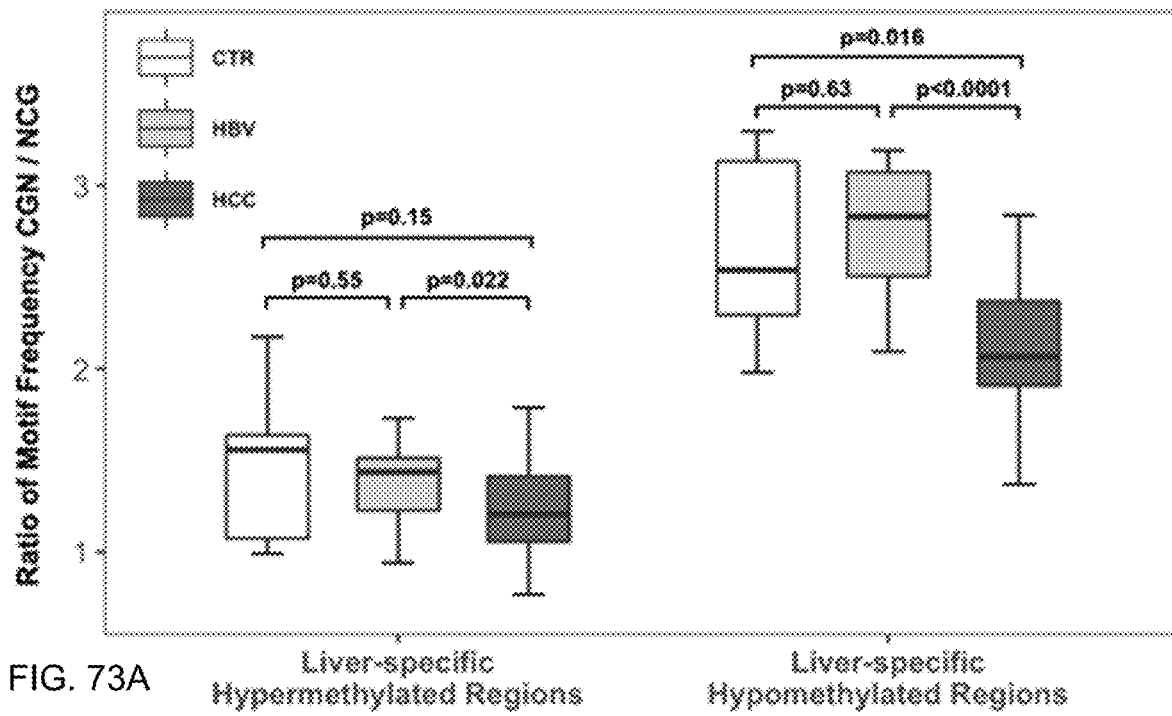
FIGS. 73A and 73B show the performance of HCC detection on the basis of the CGN/NCG motif ratio from liver-specific hypermethylated and hypomethylated regions according to embodiments of the present disclosure.
Figure 73B:
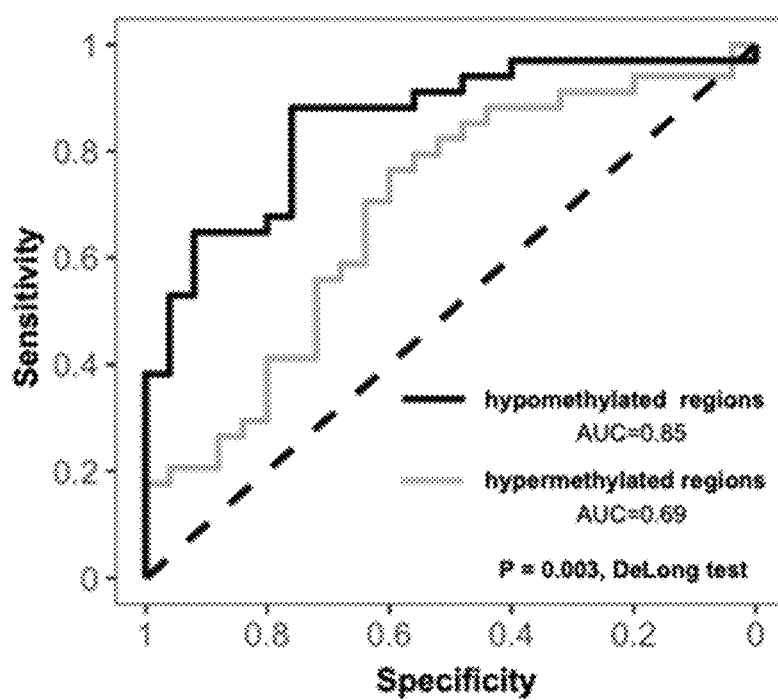

FIGS. 73A and 73B show the performance of HCC detection on the basis of the CGN/NCG motif ratio from liver-specific hypermethylated and hypomethylated regions according to embodiments of the present disclosure. FIG. 73A is a boxplot showing the CGN/NCG motif ratios from liver-specific hypermethylated and hypomethylated regions across healthy controls (CTR), patients with chronic hepatitis B (HBV), and patients with HCC (HCC). FIG. 73B is an ROC analysis in differentiating between patients with and without HCC using CGN/NCG motif ratios from liver-specific hypomethylated and hypermethylated regions, respectively.

Comparing HCC subjects with non-HCC subjects, a significantly higher CGN/NCG motif ratio (i.e., frequency of CGN motifs/frequency of NCG motifs) was observed across liver-specific hypomethylated regions (P value <0.001, Kruskal-Wallis test), whereas no significant difference was observed at liver-specific hypermethylated regions. The CGN/NCG motif ratio from liver-specific hypomethylated regions could serve as a biomarker for HCC, allowing for the detection of HCC patients with an AUC of 0.85 (P value=0.003, DeLong test).

These results indicate that the CGN/NCG motif ratios related to CpG sites with liver-specific hypomethylation show a better differentiating power of HCC patients from non-HCC individuals than liver-specific hypermethylation. Such enhancement in cancer detection was because the selective analysis of the CGN/NCG motif ratios from the hypomethylated regions could make the synergy of the characteristic cfDNA cleavage attributed by DNA methylation and the downregulated DNASE activity (e.g., both epigenetic aberrations and DNASE activity aberrations lead to the CGN/NCG motif ratios).

2. Using Vector of Respective 3-Mer or Higher Motifs

As the liver specific hypo-methylated regions may contain more information, we further use all the 3-mer motifs of this region to train an SVM model. Thus, the feature vector has 64 values of the amount of each of the 3-mers that occur in the hypo-methylated regions. Other machine learning models may be used, e.g., as described herein.

Figure 74A:
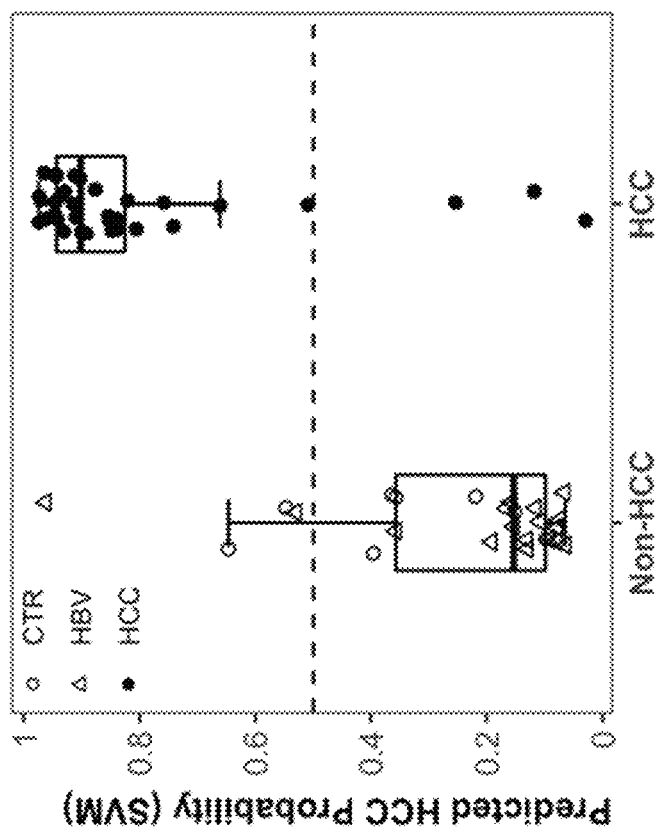
FIGS. 74A and 74B show performance of HCC diagnosis using SVM on the basis of 3-mer end motif frequencies from liver-specific hypomethylated regions according to embodiments of the present disclosure.
Figure 74B:
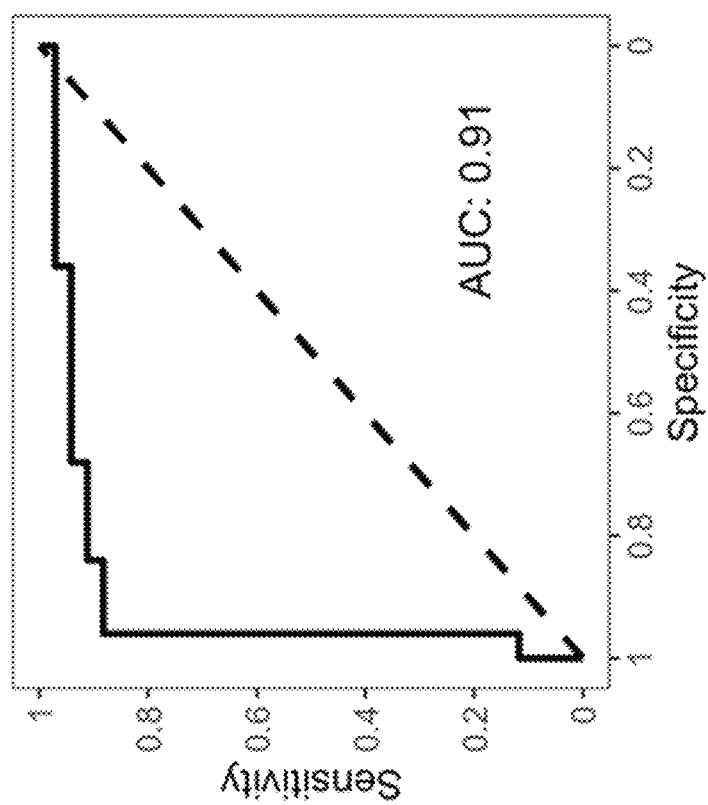

FIGS. 74A and 74B show performance of HCC diagnosis using SVM on the basis of 3-mer end motif frequencies from liver-specific hypomethylated regions according to embodiments of the present disclosure. FIG. 74A is boxplot showing the probability of determining to be HCC by 3-mer end motif frequencies for those plasma DNA molecules associated with liver-specific hypomethylated regions (CTR: healthy controls; HBV: patients with chronic hepatitis B; HCC: patients with HCC). FIG. 74B is an ROC analysis in differentiating patients with and without HCC using 3-mer end motif frequencies from liver-specific hypomethylated regions. The 3-mer end motif frequencies can be determined as an amount of a particular end motif divided by a total number of DNA fragments or total number of end motifs detect or used.

To further maximize the utility of end motifs from liver-specific hypomethylated regions, we constructed a SVM model using 5' 3-mer end motifs from liver-specific hypomethylated regions to perform HCC detection. The model performance could reach an AUC of around 0.91 to distinguish HCC or non-HCC.

Accordingly, the end motif frequencies from tissue-specific hypomethylation or hypermethylation can be used to detect and monitor diseases such as cancer. For example, from liver-specific hypomethylated regions, we constructed a SVM model using all 5' 3-mer end motifs to perform HCC detection. However, fewer than all 64 3-mer end motifs may be used. For example, only the eight motifs including CG may be used. These eight 3-mer motifs surprisingly provide increased accuracy compared to using all 64 end motifs. These eight motifs are specifically CGA, CGT, CGC, CGC, ACG, TCG, CCG, and GCG. Other subset of end motifs can also be used, e.g., subsets that do not include CG.

We further tested the possibility of HCC detection by using CG-containing 3-mer end motifs (a total of 8 types of end motif), instead of the use of all 64 types of 3-mer end motif. Based on the bisulfite sequencing results of the buffy coat and the HCC tissue, we identified 116,245 and 802,393 HCC-specific hypermethylated and hypomethylated CpGs, respectively.

In various implementations, any one or more of the CGN and/or NCG amounts which may be normalized, e.g., as frequencies, may be used. The frequencies may be determined in various ways. For example, the normalization may be performed as was done when all 64 end motifs were used. As another example, the normalization may be performed within a subset of the end motifs, e.g., by the number of end motifs within the subset. In one implementation, an NCG-related data vector, an CGN-related data vector, and a combined data vector (i.e., data vector for CG-containing end motifs) were used, which may be obtained from HCC-specific hypermethylated and hypomethylated CpGs for 55 non-HCC and 34 HCC cases, respectively.

In the NCG-related data vector, only NCG motif frequencies were used. For example, the frequency of ACG was calculated as the amount of ACG motifs/the total amount of NCG motifs. The sum of ACG, TCG, CCG, and GCG frequencies is 100%. Similar calculations were applied to the CGN-related data vector. For example, the frequency of CGA was calculated as the number of CGA motifs/the total amount of CGN motifs. The sum of CGA, CGT, CGC, and CGG frequencies is 100%. The combined data vector was calculated for all CGN and NCG motifs. For instance, the frequency of CGA was calculated as the number of CGA motifs/the total amount of CGN and NCG motifs. The sum of ACG, TCG, CCG, GCG, CGA, CGT, CGC, and CGG frequencies is 100%. These datasets were used to construct support vector machine (SVM) models, respectively.

Figure 75A:
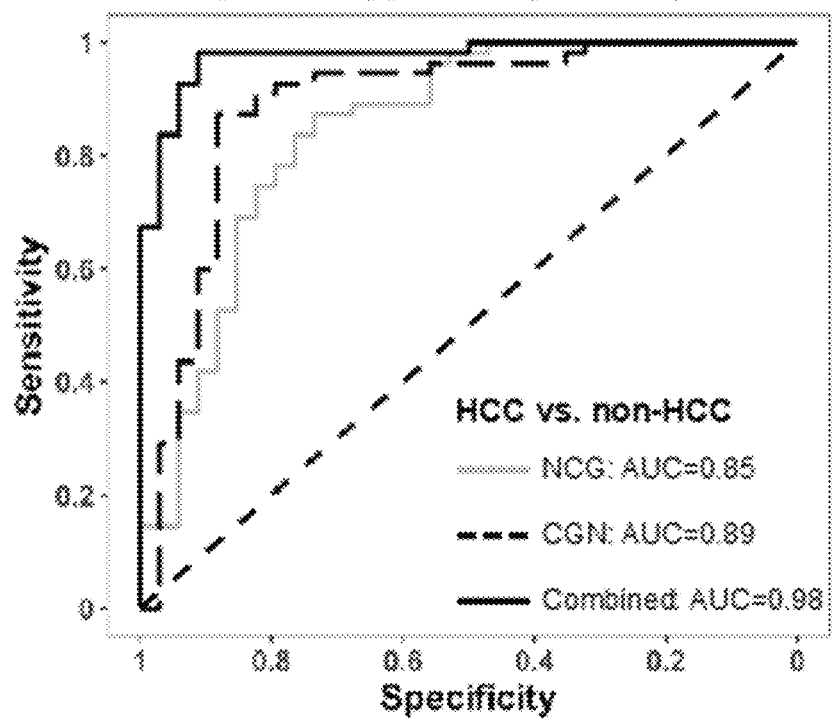
FIGS. 75A-75B show the performance of HCC detection based on CG-containing 3-mer end motifs from HCC-specific hypermethylated and hypomethylated CpGs.
Figure 75B:
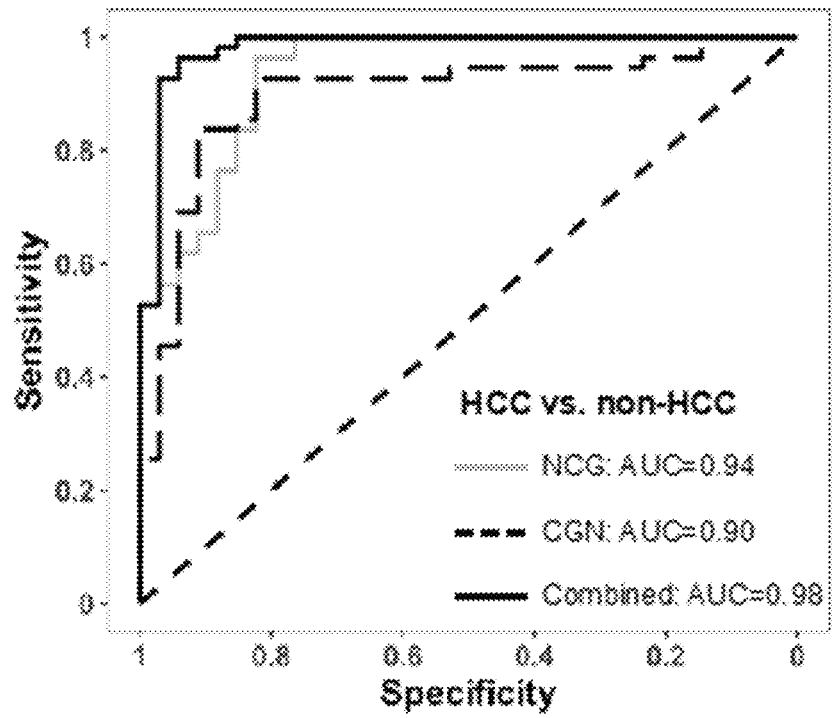

FIGS. 75A-75B show the performance of HCC detection based on CG-containing 3-mer end motifs from HCC-specific hypermethylated and hypomethylated CpGs. As shown in FIG. 75A, SVM models trained based on the NCG-related data vector, the CGN-related data vector, and the combined data vector from HCC-specific hypermethylated CpGs reached an AUC of 0.85, 0.89, and 0.98 to distinguish HCC patients from non-HCC cases, respectively. As shown in FIG. 75B, for HCC-specific hypomethylated CpGs, those models reached an AUC of 0.94, 0.90, and 0.98, respectively. The NCG-related data vector and the combined data vector performed better than the accuracy in FIG. 74B.

Some embodiments can combine the feature vectors from hypermethylated and hypomethylated sites for using in a training the machine learning model, e.g., an SVM.

Figure 76:
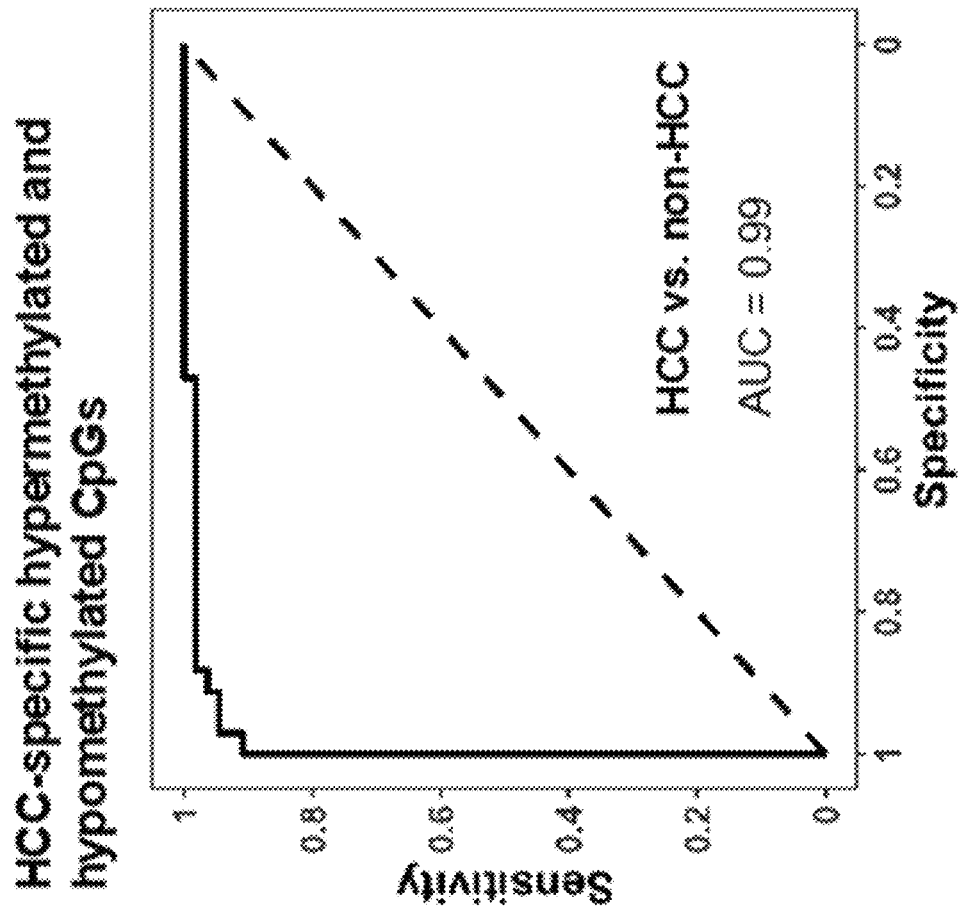
FIG. 76 shows the ROC analysis in differentiating patients with and without HCC using the combined data vector from HCC-specific hypermethylated and hypomethylated CpGs.

FIG. 76 show the ROC analysis in differentiating patients with and without HCC using the combined data vector from HCC-specific hypermethylated and hypomethylated CpGs. To further maximize the utility of end motifs from HCC-specific methylated CpGs, the combined vectors from HCC-specific hypermethylated and hypomethylated CpGs were integrated and used to train the SVM model which reached an AUC of 0.99 to distinguish HCC patients from non-HCC cases.

3. Using Cleavage Profiles

We also investigated whether cleavage profiles from tissue-specific hypermethylated and hypomethylated CpG sites could be used for detecting the subjects with pathological or physiological states. As explained above, cleavage profiles include two or more positions, e.g., with one being position 0, which includes end motifs of CGN.

a) Example Workflow

We used pregnancy as a model for illustration purposes. Pregnancy can be viewed as or is similar to pathological or physiological states in that another tissue type with different properties than the host is growing. For example, a fetus and a tumor are both globally hypermethylated along with certain sites that are hypermethylated, e.g., of tumor suppressor genes. Thus, if a subject can be correctly classified as pregnant with a fetus, where such tissue has specific methylation patterns, then embodiments can also be used to detect pathologies associated with other tissue types using hypo- or hyper-methylated CpG sites. Other analyses can a group of CpG sites (e.g., a CpG island). A region can be or include such one or more CpG sites.

FIG. 77 shows an example marker selection and data collection according to embodiments of the present disclosure. We identified placenta-specific hypermethylated sites that were defined by those CpG sites with a methylation density of over 70% in the placenta tissues but below 30% in the buffy coat samples. In other embodiments, these methylation density thresholds could be changed so as to achieve different diagnostic sensitivity and/or specificity, as described in various embodiments in this disclosure. Hypomethylation could be defined as, but not limited to, below 10%, below 20%, below 30%, below 40%, below 50%, etc. Hypermethylation could be defined as, but not limited to, over 40%, over 50%, over 60%, over 70%, over 80%, over 90%, etc. The threshold could be ranges, for example, but not limited to, 20%-30%, 30%-40%, 40%-50%, 60%-70%, 70%-80%, etc. Placenta-specific hypomethylated sites were defined by those CpG sites with a methylation density of below 30% in the placenta tissues but over 70% in the buffy coat samples.

For the data collection, we determined the cleavage profiles from placenta-specific hypermethylated and hypomethylated CpG sites. The cleavage profiles were determined using techniques described herein. Such cleavage profiles from 30 pregnancy samples (median paired-end sequencing reads: 206 million (IQR: 142-232 million)) and 9 non-pregnancy healthy female cases (median paired-end sequencing reads: 397 million (IQR: 350-424 million)) were determined. In this example implementation, the cleavage profiles can be generated by merging data for all of the sites of a particular type, e.g., merging the data for all the hypomethylated sites for one cleavage profile and all the hypermethylated sites for another cleavage profile.

Figure 78:
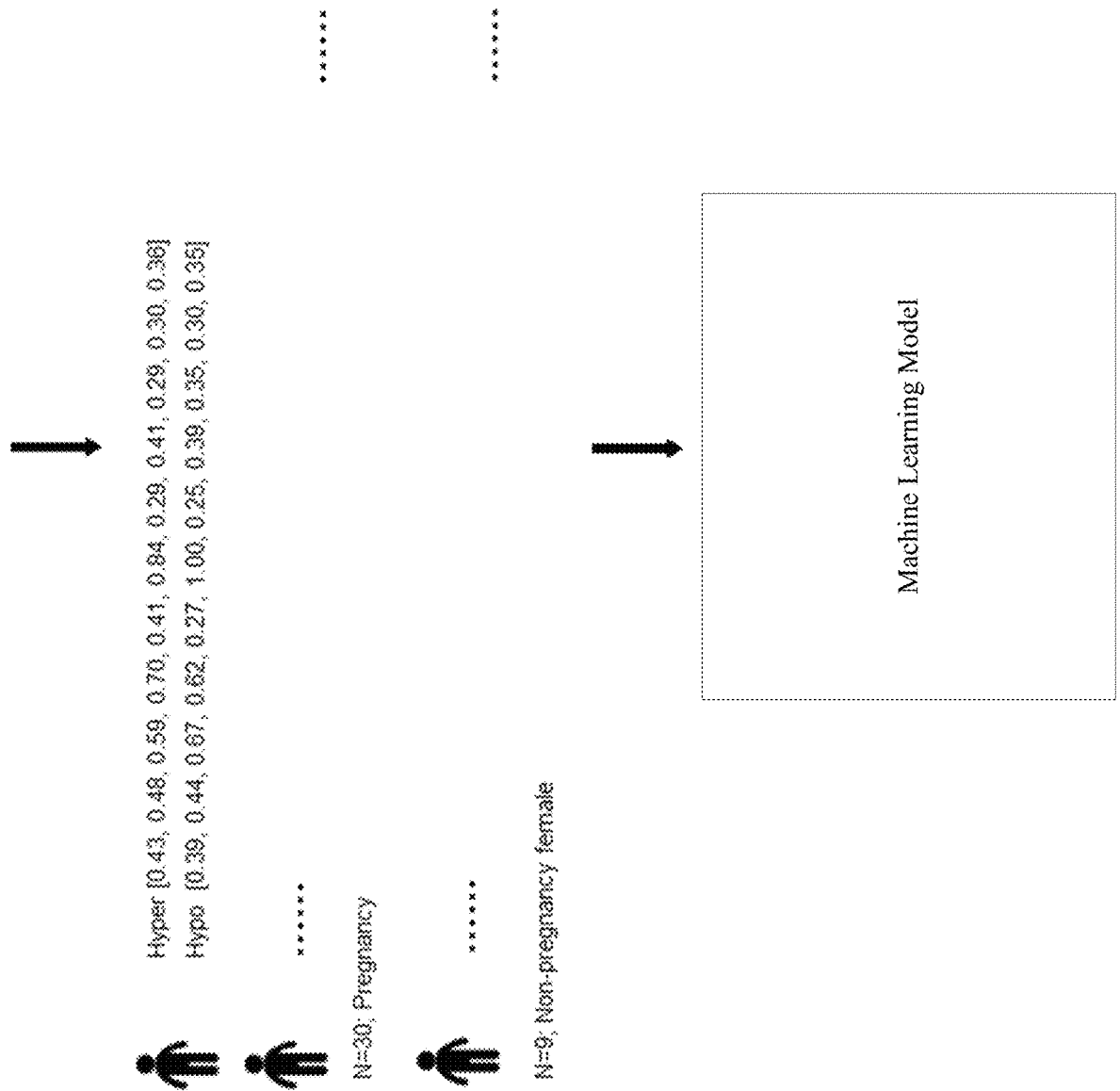
FIG. 78 shows workflow including generating cleavage profiles for various subjects for training a machine learning model according to embodiments of the present disclosure.

FIG. 78 shows workflow including generating cleavage profiles for various subjects for training a machine learning model according to embodiments of the present disclosure. In the example shown with a measurement window and using hypermethylated sites and hypomethylated sites, there are a total of 24 features. The machine learning model can then different subjects based on the features. Such results are provided below.

b) Clustering Results

In the results below, clustering was performed using principal component analysis (PCA). Other embodiments can used other types of machine learning, supervised or unsupervised, or combinations thereof, as are described elsewhere in this disclosure.

Figure 79B:
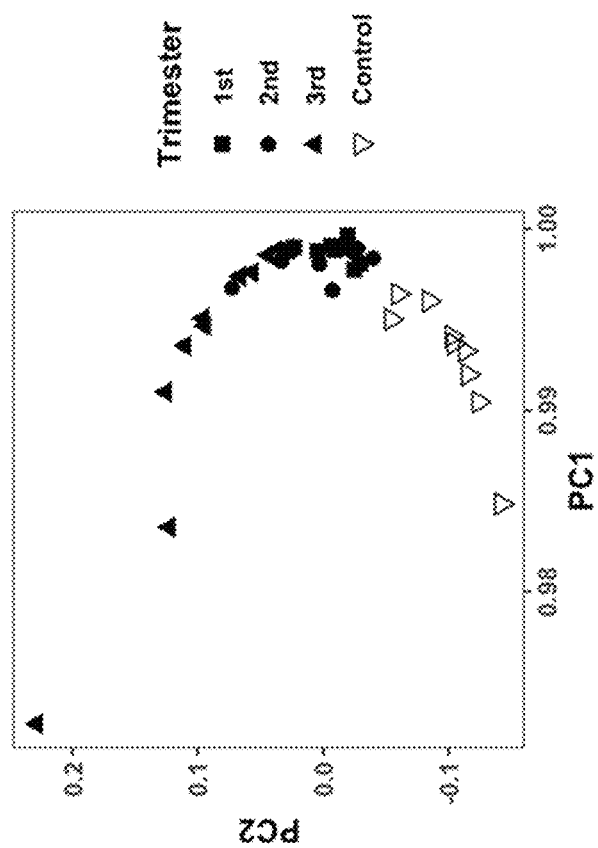
FIGS. 79A, 79B, and 80 show PCA analysis of pregnant and non-pregnant subjects by using cleavage profiles from placenta-specific hypermethylated sites (FIG. 79A), placenta-specific hypomethylated sites (FIG. 79B), or the combination of placenta-specific hypermethylated and hypomethylated sites (FIG. 80) according to embodiments of the present disclosure.
Figure 79A:
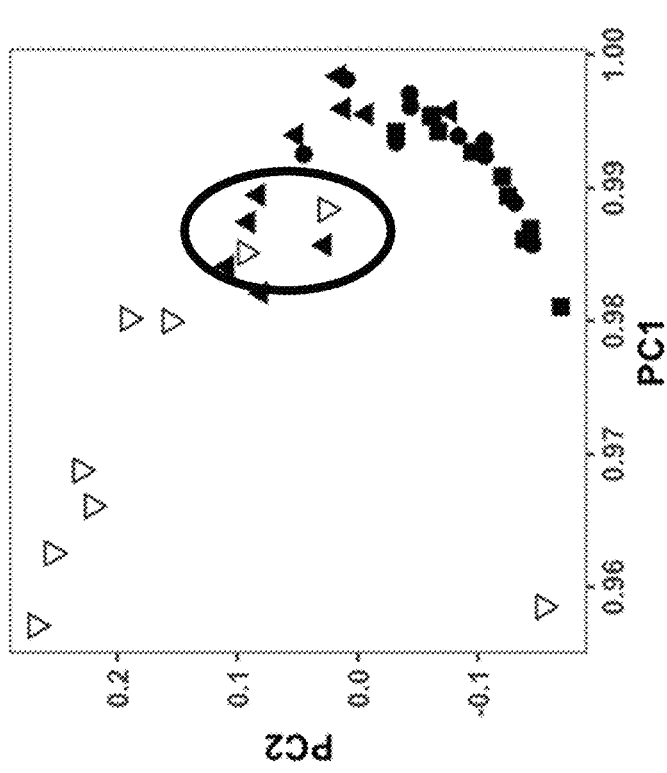
Figure 80:
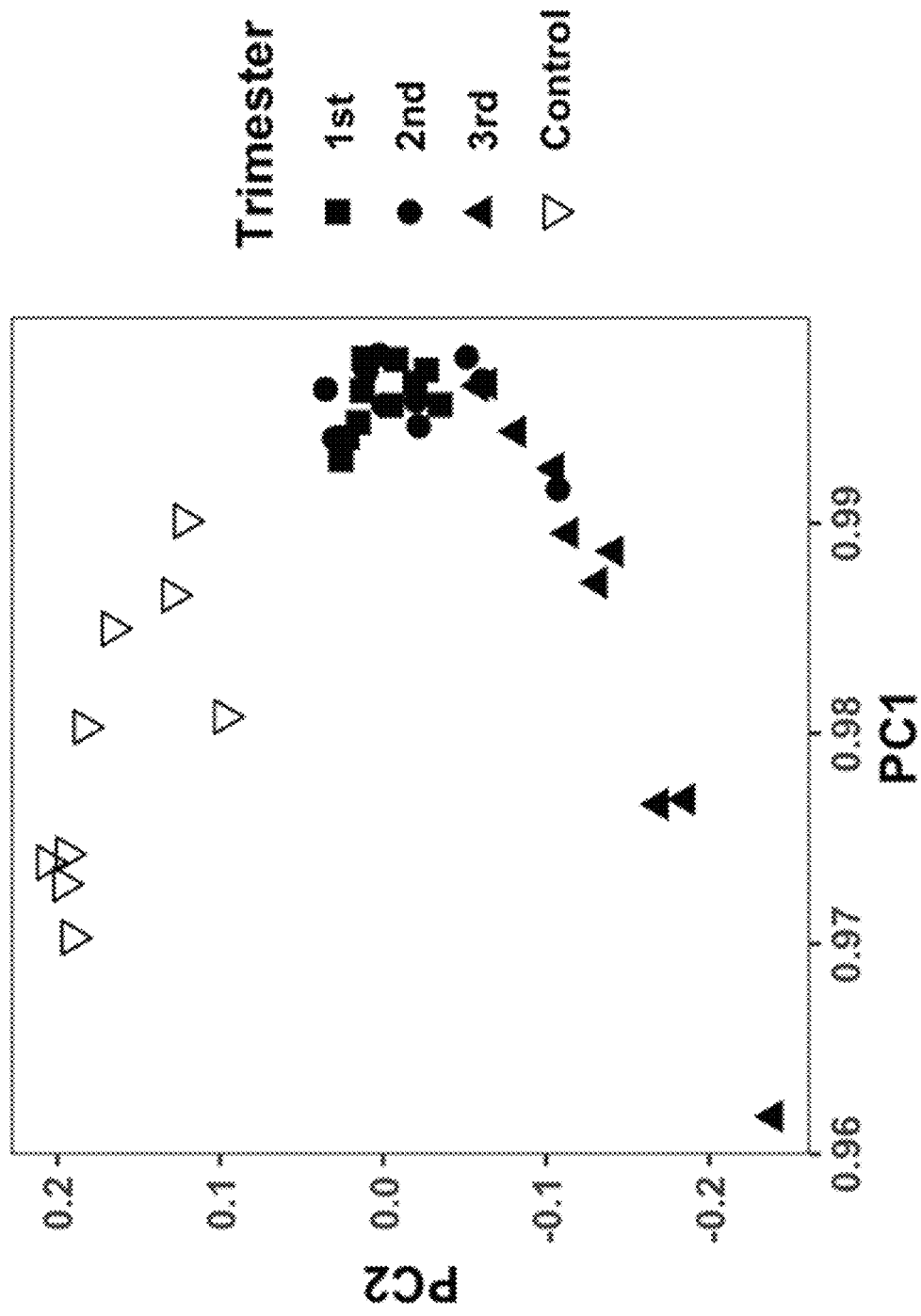

FIGS. 79A, 79B, and 80 show PCA analysis of pregnant and non-pregnant subjects by using cleavage profiles from placenta-specific hypermethylated sites (FIG. 79A), placenta-specific hypomethylated sites (FIG. 79B), or the combination of placenta-specific hypermethylated and hypomethylated sites (FIG. 80) according to embodiments of the present disclosure. The PCA analysis identifies a linear combination of the features that provides a best separation between the two types of subjects. A support vector machine can provide similar results. The PCA allows visualization along the two principal dimensions identified.

As shown in FIG. 79A, principal components (PCs) based on the cleavage profiles from placenta-specific hypermethylated sites (i.e., PC1 and PC2) could classify pregnant and non-pregnant subjects into two clusters, with only two non-pregnant subjects overlapping with pregnant subjects. Principal components based on the cleavage profiles derived from placenta-specific hypomethylated sites (i.e., PC1 and PC2) showed a better differentiation between pregnant and non-pregnant cases without any overlap between the two groups (FIG. 79B).

Moreover, PCs based on the cleavage profiles from both placenta-specific hypermethylated and hypomethylated sites (i.e., PC1 and PC2) displayed a complete separation between pregnant and non-pregnant cases (FIG. 80). The data suggested that the selective analysis of cleavage profiles derived from hypomethylated and/or hypermethylated CpG sites would improve the classification power for classifying different pathological and physiological states.

c) Example Use Cases

The cleavage profiles from tissue-specific hypomethylated or hypermethylated CpG sites would be useful for the detection of various cancers or other diseases. For example, the cleavage profiles from colon-, breast-, or prostate-specific hypomethylated or hypermethylated CpG sites could be used for colon cancer, breast cancer, or prostate cancer diagnosis, respectively. Thus, the cleavage profiles would be useful for prognostication and/or monitoring of a cancer patient.

For example, the proximal cleavage profiles from tissue-specific CpGs can be useful for deducing DNA contribution from different tissues into the plasma cfDNA pool, such as tumor DNA fraction in HCC patients, which could be used for HCC diagnosis. We determined the cleavage profiles from HCC-specific hypermethylated and hypomethylated CpG sites. Such cleavage profiles were used for training SVM models to perform HCC detection.

Figure 81:
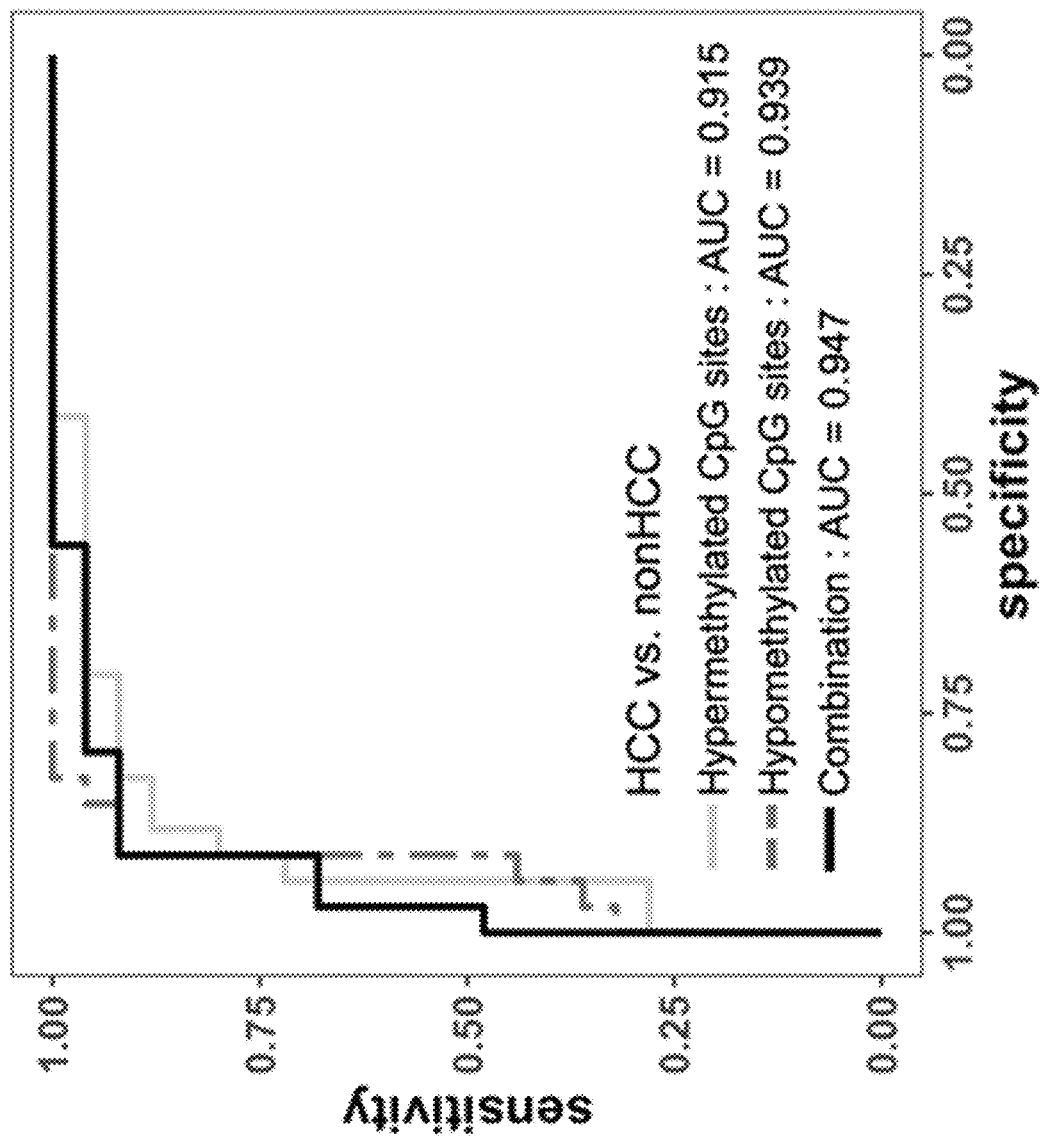
FIG. 81 shows the performance of HCC detection on the basis of the cleavage profiles.

FIG. 81 shows the performance of HCC detection on the basis of the cleavage profiles. The model performance could reach an AUC of 0.915, 0.939 and 0.947 to distinguish HCC patients from non-HCC controls when trained with cleavage profiles from HCC-specific hypermethylated or hypomethylated, or the combination of hypermethylated and hypomethylated CpGs.

d) Cleavage Profiles for Individual Regions Sites

The examples above combined measurements across regions (e.g., to determine CGN/NCG ratio) or CpG sites (e.g., to determine cleavage ratio). However, in other embodiments, a separate amount can be determined for each region or CpG site (e.g., CGN and/or NCG amounts) and compared separately to a respective reference value. Thus, if N regions or CpG sites are analyzed, then N amounts can be determined, each amount corresponding to an amount of DNA fragments at a respective region or CpG site. Such N amounts can be a feature vector that is input to a machine learning model. Additionally or instead, separate cleavage profiles can be determined for each CpG site (or some subset of sites), and these individual cleavage sites can be used, e.g., input to a machine learning model. Each cleavage profile could be input to a machine learning model to determine the level of a pathology.

In another example, all of the cleavage profiles could be input at the same time to the machine learning model. In this manner, more features would be input to the machine learning model. Such a feature matrix can be the size of the number of CpG sites by the number of positions in the measurement window. Thus, if N regions are used, with K positions in each cleavage profile, then the input feature vector can include a total of N*K values. In a different example, separate cleavage ratios can be determined for each cleavage profile for different subsets of CpG sites, and a majority vote can be used to determine the level of pathology.

4. Detection of Tissue of Origin for Cancer

As shown above, cleavage profiles or other methylation related cfDNA fragmentomic features from liver or HCC specific hypomethylated regions could be used for HCC detection. Thus, the tissue-specific regions/sites can be for a cancer tissue type, or just for the tissue itself. Methylation related cfDNA fragmentomic features from other tissue-specific hypomethylated or hypermethylated regions could be used for the detection of other cancers. For example, methylation related cfDNA fragmentomic features from colon-, breast-, or prostate-specific hypomethylated or hypermethylated regions could be used for colon cancer, breast cancer, lung cancer, bladder cancer, kidney cancer, or prostate cancer diagnosis, respectively, or differentially methylated regions specific to those cancers can be used. The cleavage profiles would be useful for classifying the subtypes of cancer such as adenocarcinoma versus squamous cell carcinoma. In yet another embodiment, methylation related cfDNA fragmentomic features from specific regions could be deduced from targeted sequencing results. The targeted sequencing could be based on but not limited to probe-based hybridization, amplicon-based sequencing, immunoprecipitation followed by sequencing, etc. Such enrichment can be performed for any technique described herein that used tissue-specific sites.

Accordingly, the analysis can be done for differentially methylated regions in various tissues. A classification can be determined for each technique, which determines whether a pathology (e.g., cancer) exists for each type of tissue. In this manner, a tissue of origin can be determined. If multiple tissue-specific techniques identify an existence of cancer, the tissue with the largest differential can be identified for further investigation, e.g., further imaging or biopsy.

In some embodiments, a machine learning model can use an input feature vector including fragmentomic features (e.g., end motifs or cleave profiles as described herein) for various tissue types. The tissue types can include cancer tissues and/or non-cancer tissues. The non-cancer tissues can include normal tissues and non-malignant tissues adjacent to a particular cancer tissue.

A superset of regions may be used. For example, one set of fragmentomic features can correspond to differentially-methylated regions for bladder cancer (or just bladder tissue), another set of features for prostate cancer (or just prostate), and another set for kidney cancer (or just the kidney). A particular model may be trained to identify a particular one of the cancers, with different model trained to detect a different one of the cancers. For example, one model can be trained to detect bladder cancer, even though fragmentomic features at prostate-specific methylated regions are also used in the model, i.e., in addition to bladder-specific methylated regions. The section on urine examples provides further details. Each model can provide a probability, and the type of cancer with the highest probability can be identified for further analysis, e.g., for treatment or for further screening tests (e.g., imaging), as are described herein.

The tissue-specific regions may be differentially-methylated with respect to all other tissue types also being used, or with respect to at least one other tissue type. For example, a type I hypermethylated marker can have a methylation of greater than a cutoff (e.g., 70%) in one tissue type, but then less than another cutoff (e.g., 30%) in other cancer tissues being tested or in a set of non-cancer tissues being used. Similar criteria can be used for hypomethylated markers. A type II hypermethylated marker can have a methylation of greater than a cutoff (e.g., 70%) in one tissue type, but then less than another cutoff (e.g., 30%) in at least one other cancer tissue being tested or in a set of non-cancer tissues being used. Similar criteria can be used for hypomethylated markers.

Instead of separate models, embodiments can use one multiclass model (e.g., a neural network such as one that has convolutional layers, a CNN), which provides probabilities for each of the cancer types whose tissue-specific methylated regions are used for generating the fragmentomic features. The section on urine examples provides further details.

In some implementations, the classification of cancer type can be performed after (or in conjunction with) a cancer vs non-cancer determination. Thus, the training samples might only be of a set of relevant cancer types (e.g., those whose DNA would show up significantly in urine), as it can be assumed that an initial model was used to detect cancer. Both models can use the same raw data, e.g., sequencing or PCR data about the end motifs of fragments.

Examples of classification of multiple cancer types with CG-containing 3-mer end motifs (plasma DNA) are provided below. We explored the possibility of using CG-containing 3-mer end motifs (a total of 8 types of end motifs) for the classification of multiple cancer types in plasma DNA. As an example, we performed clustering and classification analyses for a total of 45 plasma DNA samples (median reads: 457 million, IQR: 249-522 million), including 34 patients with hepatocellular carcinoma (HCC), 11 patients with colorectal cancer (CRC) samples. Such a CG-containing 3-mer end motif analysis can be performed using a set of tissue-informative methylation markers across different tissue types.

Figure 82:
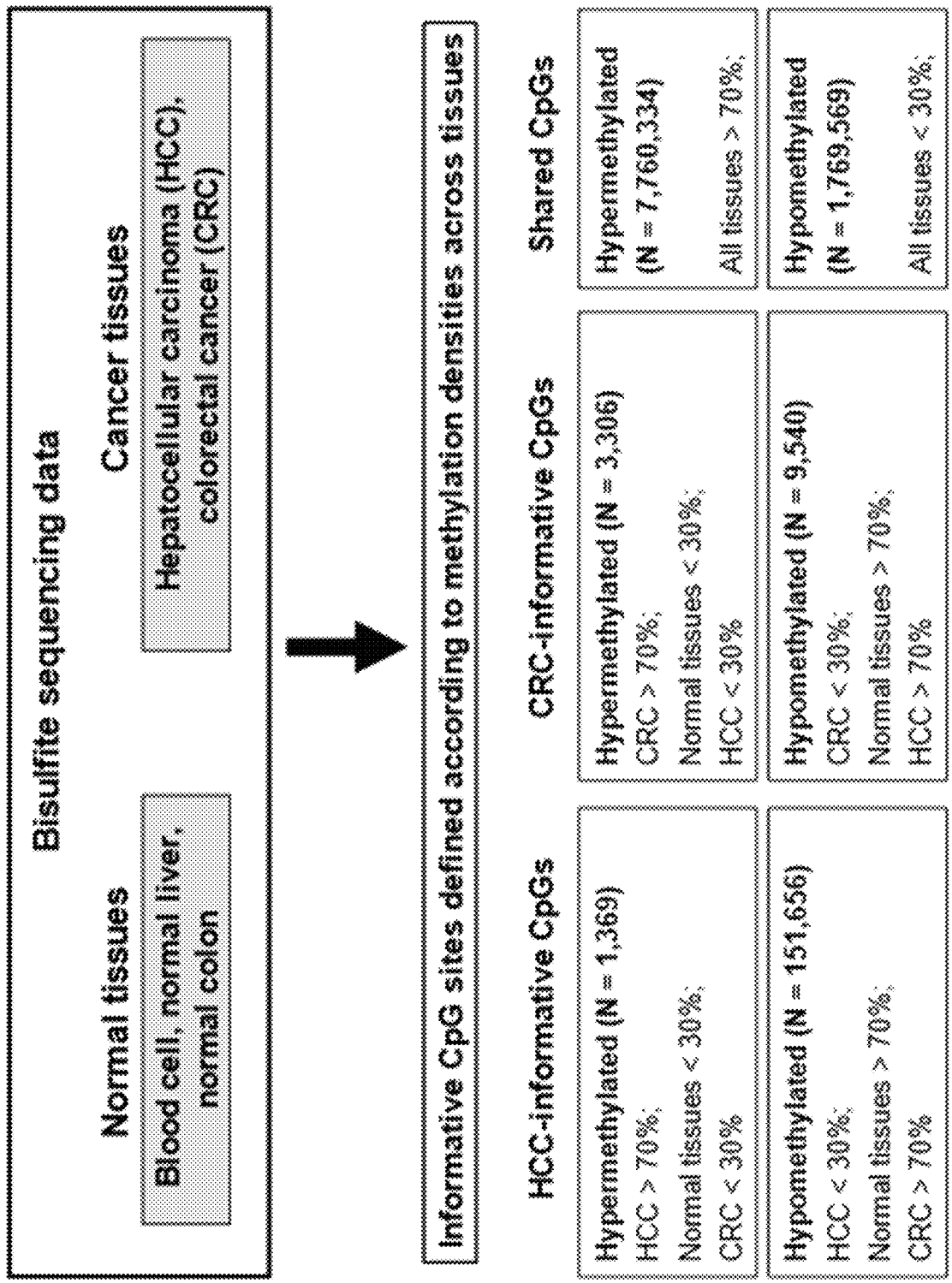
FIG. 82 shows a schematic for defining tissue-informative methylation markers.

FIG. 82 shows a schematic for defining tissue-informative methylation markers. For illustration purposes, we use the detection of an HCC as an example. HCC-informative hypermethylated markers were defined as CpGs for each of which the methylation density of a target cancer (e.g., HCC) is required to be above 70% whereas the methylation density for each of non-cancer tissues and CRC tissue is required to be below 30%, although other thresholds may be used. In this example, the non-cancer tissues include the blood cells, normal liver tissues, and normal colon tissues. The cancer tissue herein was the CRC cancer tissue. CRC-informative hypomethylated CpGs were defined as those CpG sites for each of which the methylation density of the target cancer tissue (e.g., HCC) is required to be below 30% whereas the methylation density for each of non-cancer tissues and CRC tissue is required to be above 70%. Similarly, one could define the CRC-informative informative hypermethylated markers, as well as hypomethylation markers.

In this example, frequencies of CG-containing 3-mer end motifs from tissue-informative hypermethylated and hypomethylated CpGs together with a set of commonly hypermethylated or hypomethylated CpGs across all tissues were considered as input features for clustering and classification analyses. The commonly hypermethylated and hypomethylated CpGs across all tissues were defined as a methylation density of over 70% or below 30% in normal blood cells, normal liver, normal colon, HCC, and CRC tissues, also referred to as the tissue-shared hypermethylated and hypomethylated CpG sites. There are a total of 48 features, including CG-containing end motif features from HCC cancer- and CRC cancer-informative hypermethylated and hypomethylated CpG sites, respectively [2 cancer types×(8 hypermethylated end motifs+8 hypomethylated end motifs)=32]; as well as CG-containing end motif features from tissue-shared hypermethylated and hypomethylated CpG sites (8+8=16).

Unsupervised clustering algorithms can be used, which may include but not limited to principal component analysis (PCA), t-distributed stochastic neighbor embedding (tSNE), uniform manifold approximation and projection (UMAP), etc.

FIG. 83A shows an unsupervised clustering analysis for patients with HCC and CRC on the basis of 5' 3-mer CG containing end motifs related to tissue-informative and tissue-shared CpG sites. A total of 48 5' 3-mer CG containing end motifs from HCC and CRC-informative hypermethylated and hypomethylated CpGs and tissue-shared hypermethylated and hypomethylated CpGs were used as input features. As shown, using these 48 end motif features, PCA analysis showed that patients with HCC and patients with CRC tended to be clustered into two groups. These results suggest that it is feasible to use CG-containing end motifs of cfDNA from cancer tissue-informative CpGs of different cancers to determine the cancer types in plasma DNA (i.e., location of a tumor).

We further attempted to a develop probabilistic classifier that can differentiate HCC from CRC, using the 48 input features mentioned above. In one embodiment, a support vector machine (SVM) was used to train the probabilistic classifier.

FIGS. 83B-83C show performance of HCC classifier on the basis of 5' 3-mer CG containing end motifs related to tissue-informative and tissue-shared CpG sites. FIG. 83B is a boxplot showing the probability of having HCC predicted by the classifier. FIG. 83C is a ROC analysis in differentiating between patients with HCC and with CRC using the classifier.

As shown, patients with HCC had higher probability scores compared with patients with CRC (median: 0.969 vs. 0.168). ROC analysis showed that the classifier could reach an AUC of ~0.97 to distinguish HCC from CRC patients. In various embodiments, the cancer types could be more than two, including, lung cancer, stomach cancer, esophageal cancer, etc. When more than 2 cancer types are considered, multiple binary classifiers can be used, and the cancer type that gives the highest probability score would be regarded as the most probable cancer type which the tested subject is suffering from. One can use one multiclass classification model (e.g., convolutional neural networks (CNN)) to analyze multiple cancer types without repeatedly performing multiple binary classifications using CG-containing end motifs related to tissue-informative and tissue-shared CpG sites. Other multiclass classification models can be used, including decision trees, random forests, deep neural networks, recurrent neural networks, etc.

5. Methods Using Tissue-Specific Differentially Methylated Regions/Sites

The level of pathology (e.g., cancer, inflammation, or an abnormal level of a physiological process) in a particular tissue type can be determined using one or more regions (which include or be defined by CpG sites) that are differentially methylated in the tissue type. The regions/sites of a same type (e.g., all hypermethylated or hypomethylated) can be analyzed together to generate a feature value (e.g., a CGN ratio) or a feature vector (e.g., different feature(s) for each region or site or of positions around a site).

Figure 84:
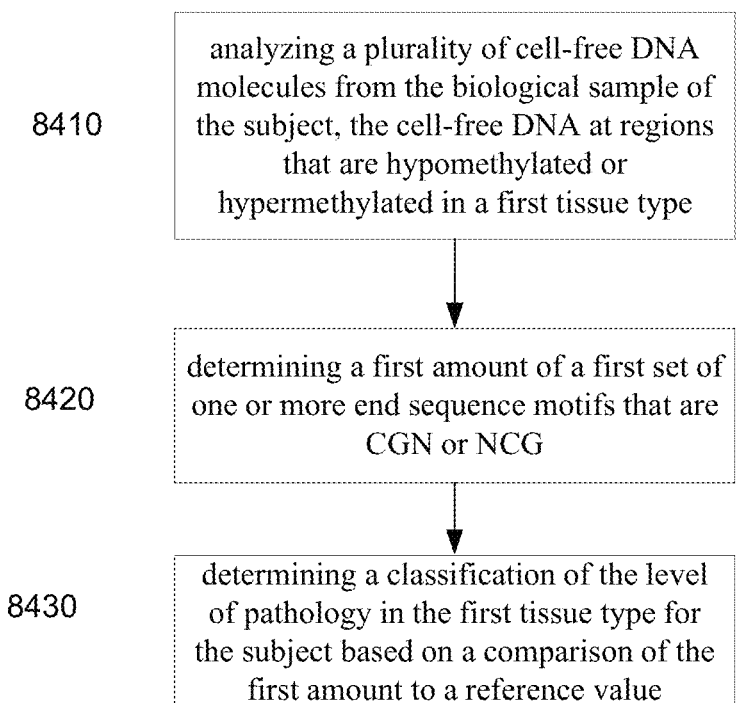
FIG. 84 is a flowchart of a method for determining a level of a pathology for a particular tissue using tissue-specific differentially methylated regions according to embodiments of the present disclosure.

FIG. 84 is a flowchart of a method 8400 for determining a level of a pathology for a particular tissue using tissue-specific differentially methylated regions according to embodiments of the present disclosure. The biological sample includes cell-free DNA. As with other methods described herein, method 8400 can be performed partially or entirely using a computer system. Blocks performing similar functionality as in other methods can be performed in a similar manner as described for those blocks in other flowcharts.

At block 8410, method 8400 includes (a) analyzing a plurality of cell-free DNA molecules from the biological sample of the subject. Block 8410 can be performed in a similar manner as block 2710. As with block 2710, analyzing a cell-free DNA molecule can include determining a location of the cell-free DNA molecule in a reference genome. The plurality of cell-free DNA molecules are located in a first set one or more regions of the reference genome. The location can be determined in various ways, as described herein, such as aligning sequence reads to the reference genome or using location-based probes. Each of the first set one or more regions is hypomethylated or each is hypermethylated in a first tissue type.

The analysis can include determining an end sequence motif (also referred to as end motif) of at least one end of the cell-free DNA molecule. The end sequence motif can be determined from the outermost bases in a sequence read. If a sequence read only includes one end and not the entire DNA fragment/molecule (e.g., as one of paired reads covering both ends), the bases corresponding to the end of the DNA fragment are used and not the bases towards the middle of the fragment. An end of the cell-free DNA molecule can have a first position at the outermost position, a second position that is next to the first position, and a third position that is next to the second position.

As with other methods described herein, analyzing the plurality of cell-free DNA molecules can includes measuring a size of the cell-free DNA molecule. The measurement can be performed in various ways, e.g., using physical separation (such as electrophoresis) and/or sequencing (such as whole molecule sequencing or alignment using paired-end reads).

At block 8420, method 8400 includes (b) determining a first amount of a first set of one or more end sequence motifs that have C at the first position and that have G at the second position. (e.g., an amount of CGN or anyone of more these motifs). In other embodiments, the first amount can be of a first set of one or more end sequence motifs that have C at the second position and G at the third position (e.g., NCG). Block 8420 can be performed in a similar manner as other techniques described herein that determine an amount of sequence motif(s), such as blocks 2720, 4120, or 7230. Given that such motifs include CGN and NCG, they can define CpG sites. When a plurality of regions are used, a total amount at the regions/sites can be determined or the respective amount at each region/site can be determined and used.

Other amounts can be determined and used, e.g., other end motifs, such as NCG to determine a CGN/NCG ratio. Thus, a second amount of a second set of end sequence motifs that have C at the second position and G at the third position can be determined, corresponding to NCG or any subset thereof. The classification can then include normalizing the first amount with the second amount to obtain a normalized first amount that is compared to a reference value. As another example, a total amount of sequence motifs (e.g., in one or more particular regions) can be determined and used for normalization. The normalized first amount (e.g., a motif ratio or relative frequency) can again compared to the reference value.

As another example of normalization, a total amount of sequence motifs for the plurality of cell-free DNA molecules (e.g., in the region) can be determined. Then, determining the classification can include normalizing the first amount with the total amount to obtain a normalized first amount (e.g., a motif ratio or relative frequency) that is compared to the reference value.

In some embodiments, the first amount can be determined for a first group of cell-free DNA molecules that are within a first size range. The first size range can correspond to sizes that are less than a size cutoff or that are greater than a second size cutoff.

At block 8430, method 8400 includes (c) determining a classification of the level of pathology in the first tissue type for the subject based on a comparison of the first amount to a reference value. Block 8430 can be performed in a similar manner as other techniques described herein that perform such a comparison to a reference/calibration value, such as blocks 4130, 5840, and 7240.

When the first set of sequence motif(s) define a first set of CpG site(s) within the first set of region(s), a cleavage profile can be determined. For each position of at least two positions within a window around a CpG site, a respective amount of cell-free DNA molecules ending at the position can be determined, thereby determining respective amounts. A feature vector including the respective amounts and the first amount can be input into a machine learning model to determine the classification of the level of pathology in the first tissue type for the subject, e.g., as described for section 4 above.

Both hypo- and hyper-methylated regions/sites can be used. The first set can be hypomethylated for the first tissue type and used to determine a first feature vector. A second feature vector can be generated using a second set of CpG site(s) that are hypermethylated. Both feature vectors can be input into the machine learning model.

Separate values can be determined for each region/site. Respective amounts of cell-free DNA molecules ending at each of the first set of CpG sites are determined, each of the respective amounts can be compared to a respective reference value, e.g., directly or by inputting the respective first amounts as part of a feature vector into a machine learning model. A cleavage profile can be determined for each site. Thus, for each of at least two positions within a window around each site, a respective amount can be determined. The respective amounts for the at least two positions, including the CpG site, can be included in the feature vector.

As with other techniques described herein, a feature vector of multiple amounts can be provided to a machine learning model, e.g., as described in sections above. The different amounts can correspond to a selection of end motifs, e.g., those included in the first set and additional end motifs. Such end motifs included in the feature vector can be all of the k-mers for a particular k or just a subset. Accordingly, a respective amount of each 3-mer end sequence motif that has a C at the first position and that has G at the second position can be determined (i.e., four amounts). A feature vector including the respective amounts, which include the first amount, can be generated and then input into a machine learning model as part of determining the classification of the level of pathology for the subject. Additionally or alternatively, the feature vector can include respective amounts for each 3-mer end sequence motif that has a C at the second position and that has G at the third position.

In some implementations, other tissues can be checked, thereby allowing a detection of the tissue causing the pathology, e.g., which type of cancer is present. Thus, blocks 8410-8430 can be repeated for one or more additional sets of one or more regions of the reference genome, where the one or more additional sets are all hypomethylated or all hypermethylated in one or more respective other tissue types.

As described in section 4 above, a tissue of origin can be determined. In such an implementation, the first tissue type can be a cancer tissue type. For example, when the biological sample is urine, the cancer tissued type can be selected from bladder cancer, kidney cancer, and prostate cancer. As another example, when the biological sample is plasma or serum, the cancer tissued type can be selected from liver cancer, colon cancer, lung cancer, and breast cancer.

The classification can indicate a level of a pathology, resulting from a disease (e.g., cancer or inflammation) or an abnormal condition/disorder of or linked to a physiological process (e.g., via ageing, or a developmental process, or genomic imprinting, which is described in more detail elsewhere in this disclosure). A copy number aberration can be such a pathology. Embodiments can also determine a normal level of a physiological process, e.g., monitoring of a stage of gestation, ageing of a person, or a type or level of genomic imprinting of a person.

As described for FIG. 82 and later examples for urine, the classification can use differentially-methylated regions for a plurality of tissue types, including the first tissue type. Other sets of cell-free DNA molecules from the biological sample can be analyzed, with each set of cell-free DNA molecules are located in a respective set of one or more regions of the reference genome. The other sets can be for tissue-specific methylation sites of other tissue types (e.g., other cancer types). Each of the respective set of one or more regions can be hypomethylated or hypermethylated in a respective tissue type of the plurality of tissue types.

Different region types can be used, e.g., type I, type II, and tissue shared, as described in section 4. A particular set of region(s), e.g., for a particular differential-methylation state and tissue type, can include multiple regions of multiple region types. A first region type (e.g., type I) can be differentially-methylated relative to other tissues. A second region type (type II) can be differentially-methylated relative to at least one other tissue but not all of the other tissues. A tissue-shared type can also be used, such that another particular set of region(s) are all hypomethylated or all hypermethylated in the cancer tissue type of a first tissue and a healthy first tissue, e.g., HCC tissue and healthy liver tissue.

In implementations differentiating among different types of pathology types (e.g., different cancer types), the classification can use a first machine learning model that is trained using all of the regions, including ones from different tissue types. Further, amounts of the sequence motif(s) for the same regions for other can be used to train one or more other machine learning models using training samples having the pathology in one or more other tissue types (e.g., for colon cancer if first tissue type is HCC). The classification of the level of pathology can use a multiclass machine learning model (e.g., a CNN) that provides a probability of each of the plurality of tissue types having the pathology. The plurality of tissue types can include cancer tissue types (e.g., bladder cancer and CRC) and non-cancer tissue types (e.g., bladder tissue and colon tissue).

C. Tissue-Specific 5hmC-Enriched and -Depleted Regions

As described above, 5-hydroxymethylcytosine (5hmC) is an important mammalian DNA epigenetic modification that has been linked to gene regulation and cancer pathogenesis. Different regions have different 5hmC methylation patterns. For example, some regions will be 5hmC-enriched or 5hmC-depleted in one tissue type (which may be a cancer tissue type), and other regions will be 5hmC-enriched or 5hmC-depleted in another tissue type. Such enrichment or depletion relates to the proportion of methylated molecules in a region that have 5hmC methylation relative to other types of methylation.

In one embodiment, HCC-specific 5hmC-enriched and 5hmC-depleted regions were identified by analyzing hMe-Seal data of plasma DNA samples from 10 healthy subjects and 11 HCC cases (Song et al. Cell Res 2017; 27(10):1231-1242). HCC-specific 5hmC-enriched regions were defined as regions across which the peak signals in sequencing coverage were present in HCC samples but were absent in healthy subjects. HCC-specific 5hmC-depleted regions were defined as regions across which the peak signals in sequencing coverage were present in healthy subjects but were absent in HCC samples.

We identified a total of 2,605 HCC-specific 5hmC-enriched regions and 32,918 HCC-specific 5hmC-depleted regions. Based on bisulfite sequencing data from HCC tissues and buffy coat, we identified 9,155,755 CpG sites which were determined to be commonly hypermethylated between two tissue types, e.g., methylation greater than a cutoff, such as 70%. There were 18,035 CpGs of the hypermethylated sites that were overlapped with HCC-specific 5hmC-enriched peak regions and 84,287 CpGs of the hypomethylated sites that were overlapped with HCC-specific 5hmC-depleted regions.

Based on 5' 3-mer CG containing end motifs from HCC-specific 5hmC-enriched and 5hmC-depleted CpGs, we performed an SVM analysis on a cohort including 38 healthy subjects, 17 HBV carriers, and 34 HCC. The SVM model based on the 3-mer CG-containing end motifs could reach an AUC of 0.96 for distinguishing the HCC from the non-HCC (healthy and HBV subjects) cases. The SVM model provides a probability for a subject to have HCC. The probability can be compared to a cutoff for a final determination of whether HCC exists.

Figure 85B:
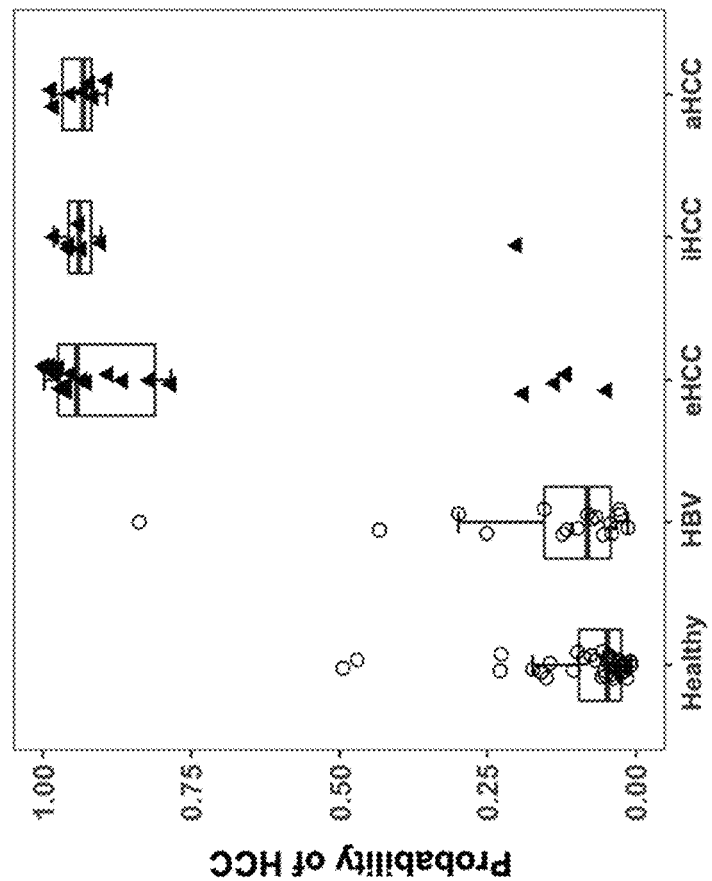
FIGS. 85A-85B show performance of HCC detection on the basis of 5' 3-mer CG containing end motifs from HCC-specific 5hmC-enriched and 5hmC-depleted CpGs.
Figure 85A:
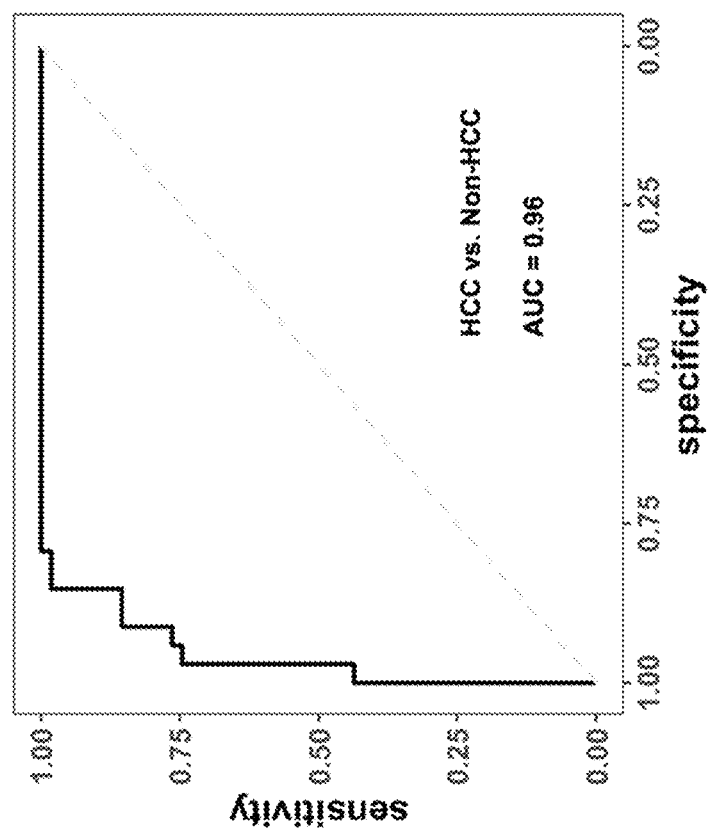

FIGS. 85A-85B show performance of HCC detection on the basis of 5' 3-mer CG containing end motifs from HCC-specific 5hmC-enriched and 5hmC-depleted CpGs. The SVM model can have a total of 16 features: the eight 3-mer end motifs that include CG in 5hmC-enriched regions and the eight 3-mer end motifs that include CG in 5hmC-depleted regions. In FIG. 85A, the probability of HCC is provided based on the separation of the 3-mer end O/E ratio relative to the training samples that had HCC or the training samples that were non-HCC. The horizontal axis of FIG. 85A corresponds to different subjects: healthy, HMB, early HCC (eHCC), intermediate HCC (iHCC), and advanced HCC (aHCC).

The majority of the eHCC subjects were identified as HCC with high probability. All except one of the iHCC subjects were identified as HCC with high probability. All of the aHCC subjects were identified as HCC with high probability. FIG. 85B shows an AUC of 0.96.

The data suggested that the CG-containing end motifs from regions with 5hmC could be also informative for cancer detection. In yet another embodiment, other tissue-specific or cancer-specific 5hmC regions may be used for other cancer diagnoses and classification. In some embodiments, the combined use of plasma DNA cleavage patterns related to 5mC and 5hmC can be implemented for enhanced cancer detection.

Besides O/E ratio individually or using a feature vector of the CG-containing motifs (e.g., SVM model shown above), other techniques described herein can be used. For example, a CGN/NCG ratio can be used for select end motifs, e.g., ones that have an opposite relationship. End motif frequencies can also be used, potentially as a feature vector of the CG-containing motifs (e.g., 1-8 values for the different 3-mer end motifs). The feature vector can be used in machine learning models, as described herein. Such amounts can be used directly without the normalization for the expected amount. Other normalization, e.g., using a total amount of end motifs of a particular group (e.g., CGN, NCG, or both) or of all end motifs of the desired length (e.g., 3-mer or 4-mer) may be used.

Accordingly, with respect to method 7200, the first amount can be determined for a first group of cell-free DNA molecules that are each located within one or more regions that are each 5hmC-enriched or each 5hmC-depleted for a particular tissue type. The pathology can be of the particular tissue type, e.g., of a particular cancer type. As an example, the particular tissue type can be the HCC cancer tissue. When the first group of cell-free DNA molecules are each located within one or more regions that are each 5hmC-enriched, the method can further comprise determining a second amount of the first set of one or more end sequence motifs of the plurality of cell-free DNA molecules that are each located within one or more regions that are each 5hmC-depleted for the particular tissue type. The classification can be determined using the first amount and the second amount, e.g., via a machine learning model analysis as is described above for SVM.

Similarly, with respect to method 7200, the first amount can be determined for a first group of cell-free DNA molecules that are each located within one or more regions that are each hypermethylated or hypomethylated for a particular tissue type. The pathology can be of the particular tissue type, e.g., of a particular cancer type.

D. Viral DNA

Besides DNA of the host (e.g., human, animal, mammal), DNA of viruses in the samples can be used to detect the pathology. Each of one or more viruses tested can be associated with one or more pathologies.

Various analysis of the host DNA can be used for the viral DNA. For example, one could use the CGN/NCG motif ratio of viral DNA molecules in the cell-free sample (e.g., plasma), or the individual CGN and NCG amounts can be used. As another example, certain CpG sites can be analyzed, e.g., hypermethylated, hypomethylated. As a further example, cleavage information (e.g., cleavage density or cleavage profiles) can be used, e.g., for CpG sites having similar (e.g., within a specified range) methylation levels between different classification of the pathology (e.g., present or not present) but having different cleavage properties. Similar methylation levels can include being hypermethylated or hypomethylated.

Such techniques can detect and monitor virus-related cancers such as but not limited to Burkitt's lymphoma, some types of Hodgkin's and non-Hodgkin's lymphoma, stomach cancer, nasopharyngeal carcinoma (NPC), hepatocellular carcinoma, cervical cancer, etc. Such cancer may be associated with viruses, including but not limited to, Epstein-Barr virus (EBV), hepatitis B virus (HBV), hepatitis C virus (HCV), human immunodeficiency virus (HIV), human herpesvirus 8 (HHV-8), human papillomavirus (HPV), etc.

We analyzed bisulfite sequencing data from 5 patients with infectious mononucleosis (IM, i.e., a non-malignant EBV-associated disease), 9 patients with EBV-associated lymphoma, and 62 patients with NPC, with a median of 18 million paired-end sequencing reads (IQR: 14-23 million). In some techniques, we can identify differentially methylated CpG sites in the viral genome between the non-cancer and the cancer subjects. From the methylation pattern of the cancer and non-cancer, we can identify the differentially CpG sites in the EBV genome between the two groups.

1. Lymphoma

Lymphoma-specific hypermethylated sites can be defined by those CpG sites with a methylation density of over 50% in EBV-associated lymphoma cases but below 50% in IM samples for plasma EBV DNA. Lymphoma-specific hypomethylated sites can be defined by those CpG sites with a methylation density of below 50% in EBV-associated lymphoma cases but over 50% in IM samples for EBV DNA. Other percentage thresholds (e.g., 30%, 35% 40%, 45%, 55%, 60%, 65% and 70%) can be used, and the same threshold does not need to be used for the lymphoma and the IM. For example, Lymphoma-specific hypomethylated sites can be defined by those CpG sites with a methylation density of below 45% in EBV-associated lymphoma cases but over 54% in IM samples for EBV DNA.

a) CGN/NCG Ratio

We analyzed the CGN/NCG ratios in those CpG sites for IM and EBV-associated lymphoma cases.

Figure 86B:
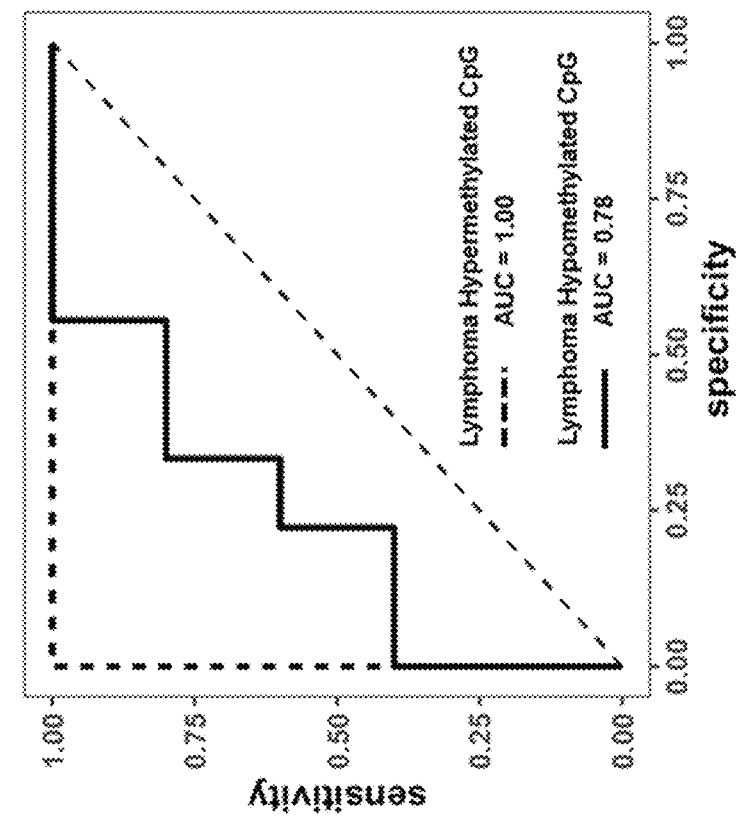
FIGS. 86A-86B show performance of EBV-associated lymphoma detection on the basis of the CGN/NCG ratio from lymphoma-specific hypermethylated and hypomethylated CpG sites of plasma EBV DNA according to embodiments of the present disclosure.
Figure 86A:
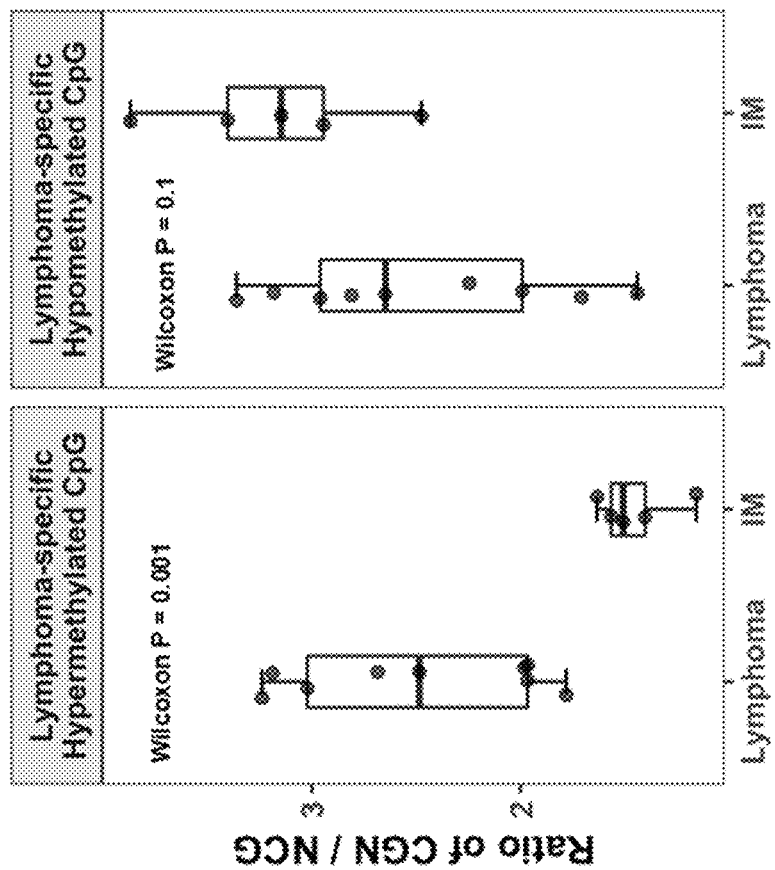

FIGS. 86A-86B show performance of EBV-associated lymphoma detection on the basis of the CGN/NCG ratio from lymphoma-specific hypermethylated and hypomethylated CpG sites of plasma EBV DNA according to embodiments of the present disclosure. FIG. 86A is a boxplot shows the CGN/NCG ratios from lymphoma-specific hypermethylated and hypomethylated sites across patients with infectious mononucleosis (IM) and patients with EBV-associated lymphoma (lymphoma). FIG. 86B shows an ROC analysis in differentiating between patients with IM and patients with EBV-associated lymphoma using CGN/NCG ratios based on lymphoma-specific hypomethylated and hypermethylated CpG sites, respectively.

Compared with IM subjects, a significantly higher CGN/NCG ratio (P value=0.001, Wilcoxon Rank Sum test) was observed across lymphoma-specific hypermethylated sites of EBV DNA, whereas no significant difference was observed across lymphoma-specific hypomethylated sites of EBV DNA in EBV-associated lymphoma cases (FIG. 86A). The CGN/NCG ratio from EBV DNA across lymphoma-specific hypermethylated sites could serve as a biomarker for EBV-associated lymphoma, allowing for distinguishing EBV-associated lymphoma patients from IM with an AUC of 1 (FIG. 86B).

As one can see, for the lymphoma specific hypermethylated CpG sites, we were able to separate all these IM cases from lymphoma cases or non-cancer from cancer patients. For the hypomethylated cases, the separation value is not as good. The hypermethylated analysis gives an AUC of one, and the hypomethylated analysis is 0.78.

b) CGN or NCG

We also analyzed CGN and NCG separately. The measurement window (e.g., 11 bp) centering on each of lymphoma-specific hypermethylated and hypomethylated CpG sites can be defined as lymphoma-specific hypermethylated and hypomethylated regions. The CGN and NCG motif frequency has been calculated within the lymphoma-specific hypermethylated and hypomethylated regions.

Figure 65A:
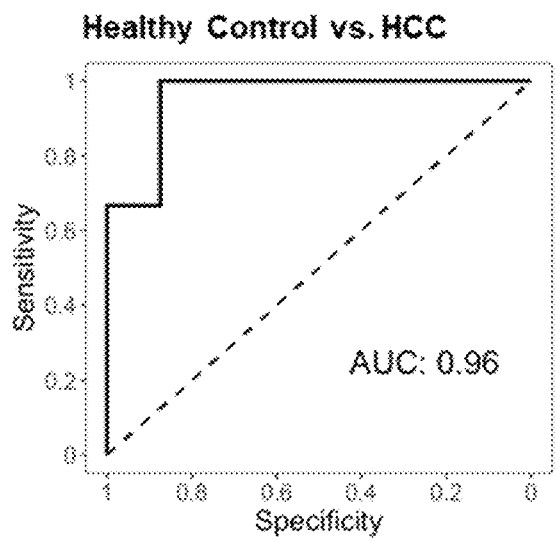
FIGS. 65A-65E show the ROC analysis in differentiating patients with HCC, HNSCC, CRC, LC, or NPC from healthy controls using CGN/NCG ratio by in-silico ddPCR assay according to embodiments of the present disclosure.
Figure 65B:
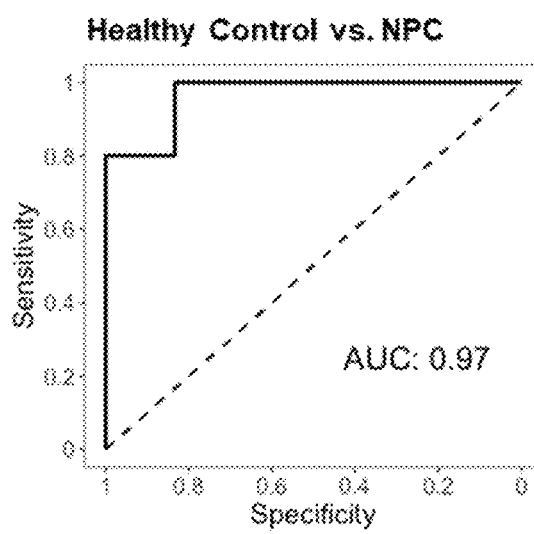
Figure 65C:
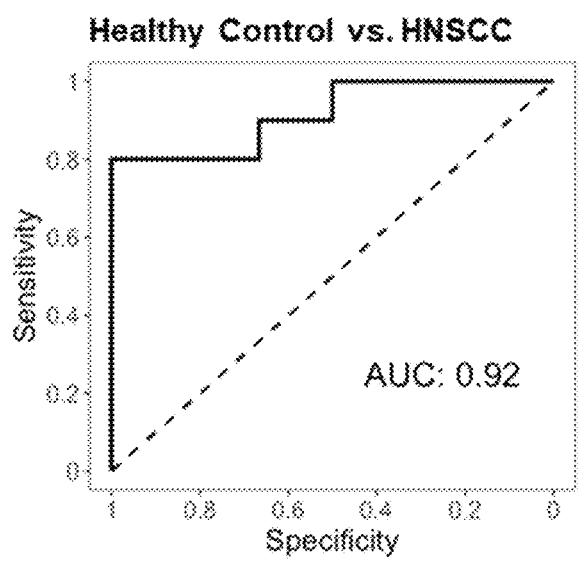
Figure 65D:
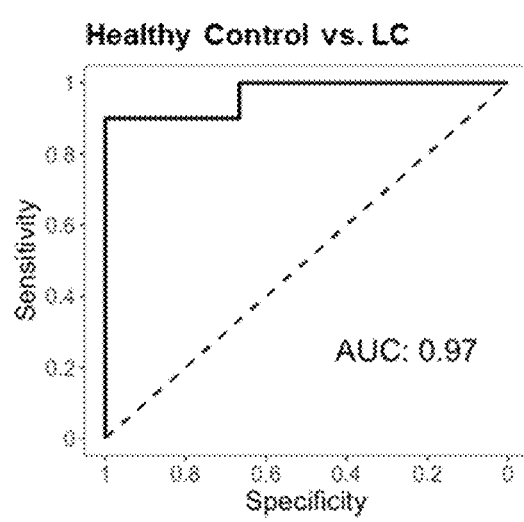
Figure 65E:
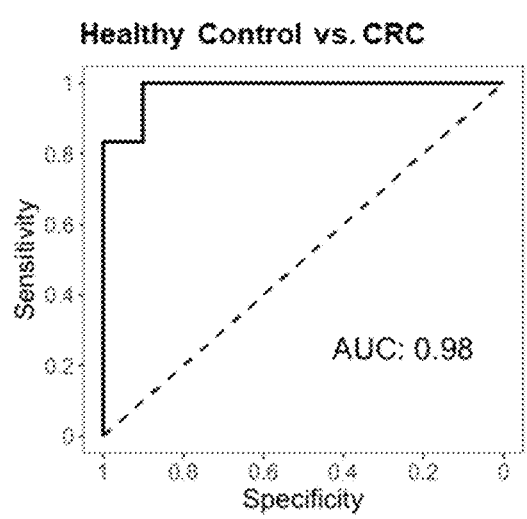
Figure 87B:
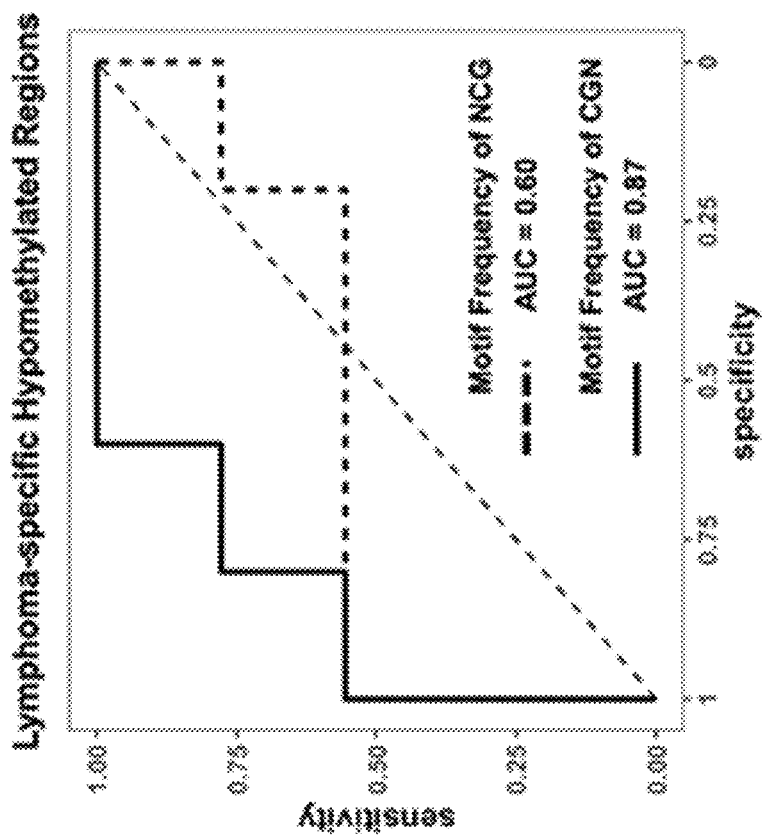
FIGS. 87A-87B show an ROC analysis in differentiating between patients with IM and patients with EBV-associated lymphoma using CGN and NCG motif frequency based on lymphoma-specific hypomethylated (A) and hypermethylated (B) regions according to embodiments of the present disclosure.
Figure 87A:
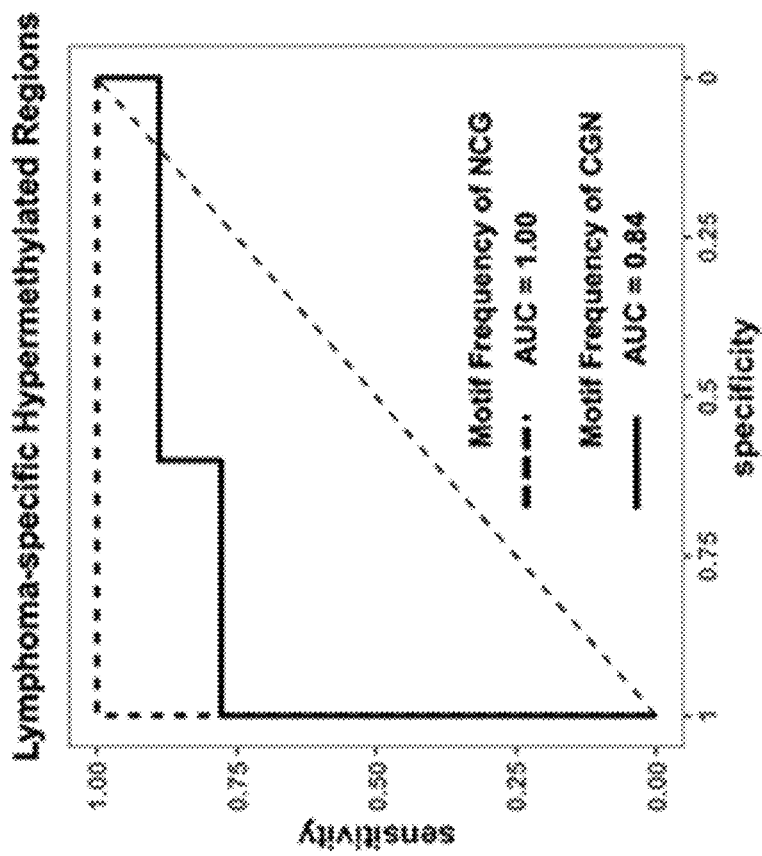

FIGS. 87A-65B show an ROC analysis in differentiating between patients with IM and patients with EBV-associated lymphoma using CGN and NCG motif frequency based on lymphoma-specific hypomethylated (A) and hypermethylated (B) regions according to embodiments of the present disclosure. As shown in FIG. 87A, for lymphoma-specific hypermethylated regions, the use of either CGN or NCG motif frequency showed a good diagnostic power for distinguishing EBV-associated lymphoma patients from IM (AUC: 1 for NCG; 0.84 for CGN). For lymphoma-specific hypomethylated regions, the use of CGN motif frequency showed a better diagnostic power for distinguishing EBV-associated lymphoma patients from IM (FIG. 87B; AUC: 0.87), compared with the use of NCG.

2. NPC

We also analyzed NPC. NPC-specific hypermethylated sites can be defined by those CpG sites with a methylation density of over 50% in NPC cases but below 50% in IM samples for EBV DNA. NPC-specific hypomethylated sites can be defined by those CpG sites with a methylation density of below 50% in NPC cases but over 50% in IM samples for EBV DNA. Other percentage thresholds (e.g., 30%, 35% 40%, 45%, 55%, 60%, 65% and 70%) can be used, and the same threshold does not need to be used for the NPC and the IM. For example, NPC-specific hypomethylated sites can be defined by those CpG sites with a methylation density of below 45% in EBV-associated NPC cases but over 54% in IM samples for EBV DNA.

a) CGN/NCG Ratio

We analyzed the CGN/NCG ratio in those CpG sites for IM and NPC cases.

Figure 88B:
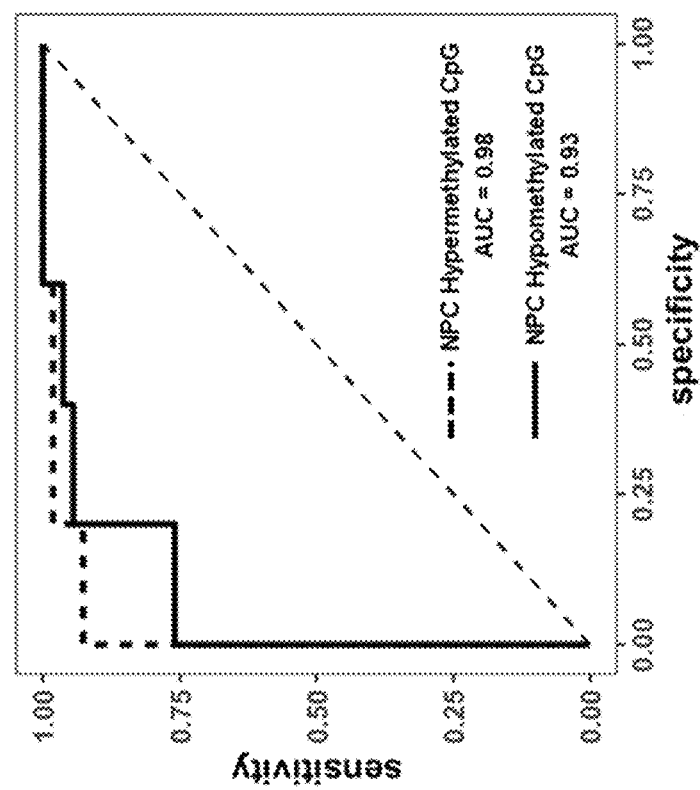
FIGS. 88A-88B show performance of NPC detection on the basis of the CGN/NCG ratio from NPC-specific hypermethylated and hypomethylated CpG sites in EBV DNA according to embodiments of the present disclosure.
Figure 88A:
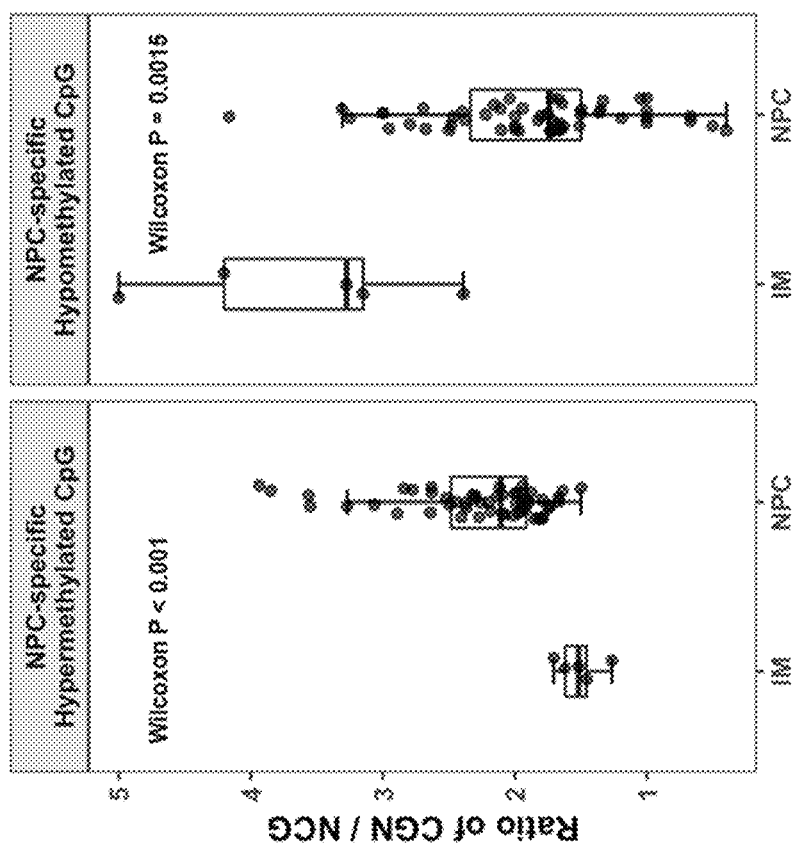

FIGS. 88A-88B show performance of NPC detection on the basis of the CGN/NCG ratio from NPC-specific hypermethylated and hypomethylated CpG sites in EBV DNA according to embodiments of the present disclosure. FIG. 88A is a boxplot shows the CGN/NCG ratios from NPC-specific hypermethylated and hypomethylated sites across patients with infectious mononucleosis (IM) and patients with nasopharyngeal carcinoma (NPC). FIG. 88B shows an ROC analysis of differentiation between patients with IM and patients with NPC using CGN/NCG ratios based on NPC-specific hypomethylated and hypermethylated CpG sites, respectively.

Compared with IM subjects, a significantly higher CGN/NCG ratio (P value <0.001, Wilcoxon Rank Sum test) was observed across NPC-specific hypermethylated sites of EBV DNA in NPC cases, and a significantly lower CGN/NCG ratio (P value=0.0015, Wilcoxon Rank Sum test) was observed across NPC-specific hypomethylated sites of EBV DNA in NPC cases (FIG. 88A). The CGN/NCG ratio from EBV DNA across NPC-specific hypermethylated sites and hypomethylated sites could serve as a biomarker for NPC, allowing for distinguishing NPC patients from IM patients with an AUC of 0.98 and 0.93, respectively (FIG. 88B).

b) CGN or NCG

We also analyzed CGN and NCG separately. The measurement window (e.g., 11 bp) centering on each of NPC-specific hypermethylated and hypomethylated CpG sites was defined as NPC-specific hypermethylated and hypomethylated regions. The CGN and NCG motif frequency was calculated within the NPC-specific hypermethylated and hypomethylated regions.

Figure 89B:
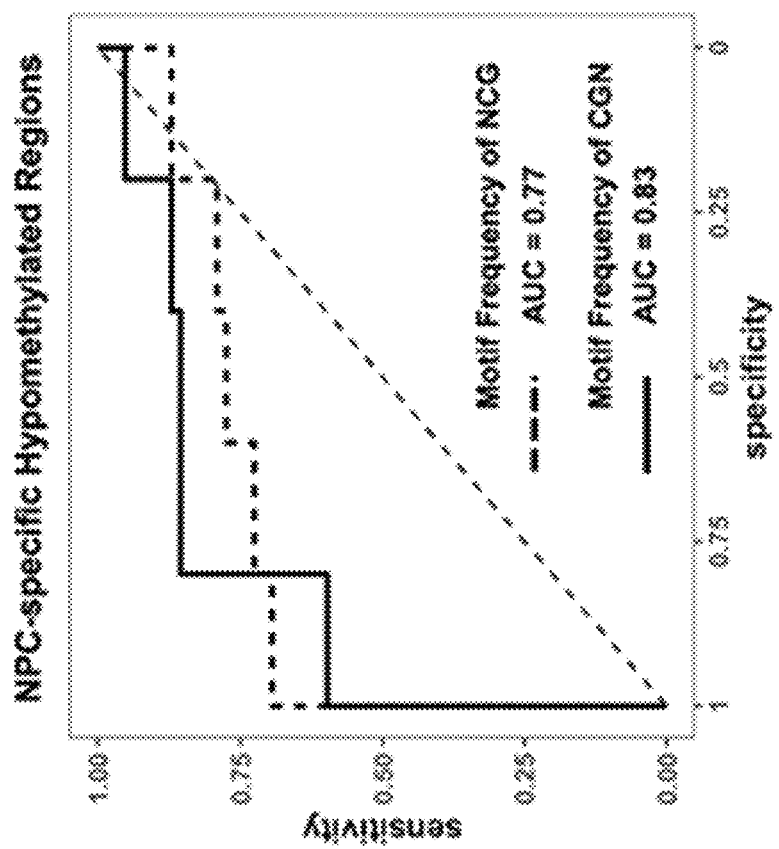
FIGS. 89A-89B show an ROC analysis in differentiating between patients with IM and patients with NPC using CGN and NCG motif frequency from NPC-specific hypomethylated (A) and hypermethylated (B) regions.
Figure 89A:
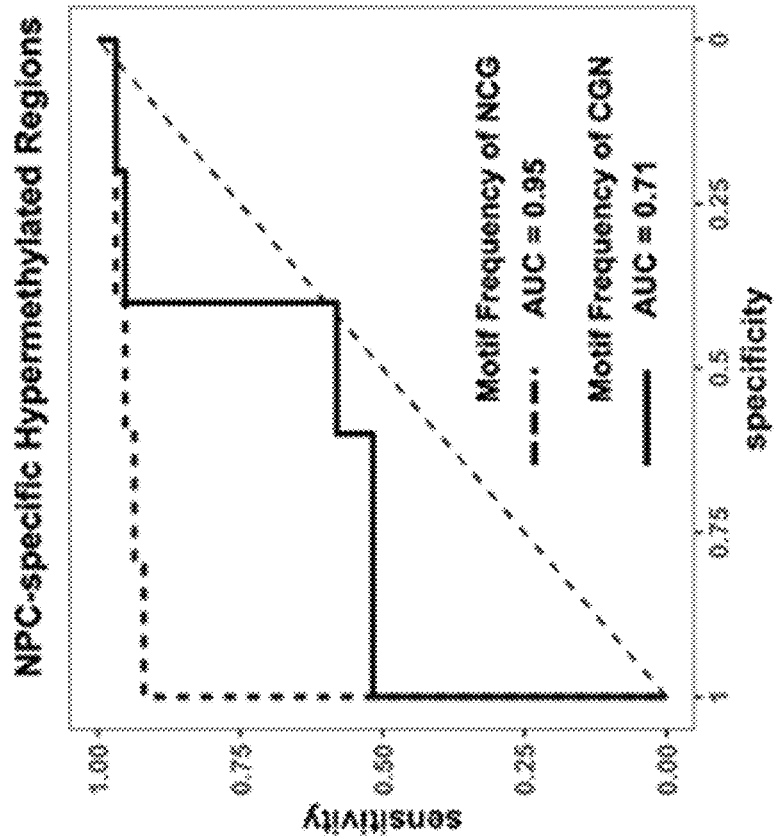

FIGS. 89A-89B show an ROC analysis in differentiating between patients with IM and patients with NPC using CGN and NCG motif frequency from NPC-specific hypomethylated (A) and hypermethylated (B) regions. As shown in FIG. 89A, for NPC-specific hypermethylated regions, the use of NCG motif frequency showed a better classification power for distinguishing EBV-associated lymphoma patients from IM than the use of CGN motif frequency (AUC: 0.95 for NCG and 0.71 for CGN, P Value=0.04, DeLong test). For NPC-specific hypomethylated regions, the use of NCG and CGN motif frequency showed similar classification power for distinguishing EBV-associated lymphoma patients from IM (FIG. 89B; AUC: 0.77 for NCG and 0.83 for CGN).

3. Non-Differentially Methylated CpG Sites (Cleavage Ratio)

We also analyzed cleavage information (e.g., cleavage ratio). As both DNA methylation and enzyme activity would affect the cleavage of plasma DNA molecules, in one example, one could selectively analyze the cleavage profile at non-differentially methylated CpG sites for disease detection, wherein the alteration in cleavage profiles might be mainly caused by enzyme activity. Such analysis would improve the sensitivity for disease detection particularly when the methylation and the enzyme activity functioning on cfDNA cleavages were characterized with antagonistic effects.

We analyzed the bisulfite sequencing data from 110 non-NPC cases with transiently positive EBV DNA, 50 non-NPC cases with persistently positive EBV DNA and 47 NPC cases, with a median of 22 million paired-end sequencing reads (IQR: 16-30 million).

a) Distribution of Cleavage Ratio and Selection of Sites

Figure 90B:
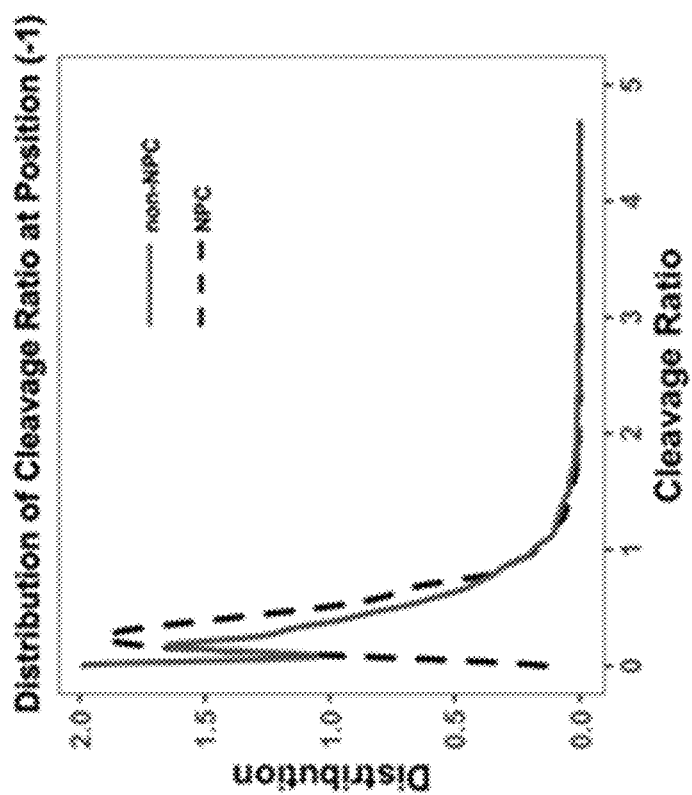
FIGS. 90A-90B show the distribution of cleavage ratio from NPC and non-NPC cases at −1 and 1 positions of each CpG site with a methylation density over 80% in both NPC and non-NPC cases.
Figure 90A:
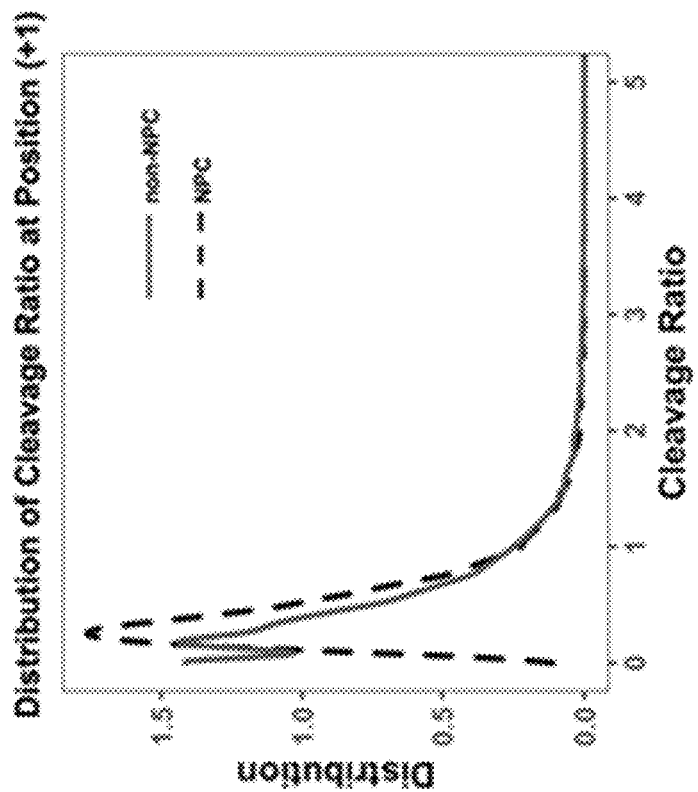

FIGS. 90A-90B show the distribution of cleavage ratio from NPC and non-NPC cases at −1 and 1 positions of each CpG site with a methylation density over 80% in both NPC and non-NPC cases. We determined the cleavage ratios at −1 and +1 positions of each CpG which was identified to be similarly methylated both in NPC and non-NPC cases (e.g., their methylation densities are both over 80%, are both below 20%, or are both between 40-60%). Other percentage ranges can be used, and the range can be smaller or larger than these examples. There was an increased probability to observe higher cleavage ratios derived from the positions −1 and +1 of a said CpG for NPC cases, compared with non-NPC subjects.

FIG. 91A shows the distribution for both −1 and 1 positions. The cleavage ratio was defined as the number of ends divided by sequencing depth at that position times 100. Such an increase of cleavage ratios at −1 and/or +1 positions could be useful for differentiating NPC cases from non-NPC cases. There was also a decrease in the cleavage ratio at position 0 in NPC, thereby showing that position 0 can also be used for differentiating NPC cases from non-NPC cases.

FIG. 91B shows the preference for cutting when an enzyme deficiency exists. If the subject has normal enzyme activity, the cutting will be preferred at the C. If the enzyme deficiency exists, then the cutting will be more uniform. If the C is the position zero, then in the position −1 (corresponding to NCG) and the +1 (corresponding to cut between C and G), there will be more cutting in the situation of enzyme deficiency compared to the normal enzyme. The deficiency can be matched to various cancers, e.g., NPC. With the methylation levels being matched, one can see the distribution is higher for the cleavage ratio at the −1 and the 1 compared to non-NPC.

We separated non-NPC and NPC cases into the training (e.g., 80% of samples) and testing (e.g., 20% of samples) datasets. In the training dataset, we identified CpG sites each of which displayed a methylation density over 80% in both non-NPC and NPC cases. A higher cleavage ratio at −1 or 1 position of a CpG was required in the NPC group than non-NPC. In total, we identified 10,483 informative positions showing a higher cleavage ratio in the NPC group, including 5,451 '−1' positions and 5,032 '+1' positions. In this example, any higher value was used. In other examples, the cleavage ratio can be required to be higher by a specified amount (e.g., a threshold or cutoff for the difference). The criteria of higher is a result of the distribution showing a higher cleavage at the −1 and 1 positions.

b) Difference Between NPC and Non-NPC

We determined the number of plasma EBV DNA fragments covering those informative positions (denoted as T) and the number of plasma EVB DNA fragments whose 5' ends were located at those informative positions (denoted as E). The "cleavage ratio of EBV DNA" for a sample was defined by E/T*100.

Figure 92A:
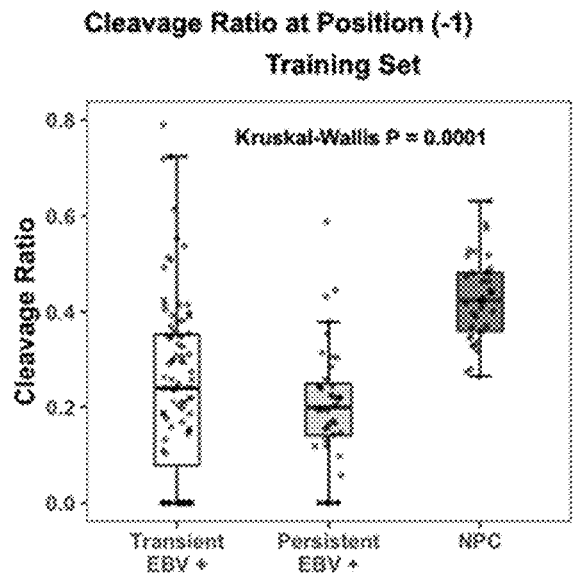
FIGS. 92A-92D show boxplots illustrated the difference of the cleavage ratios of EBV DNA between NPC and non-NPC cases in training and testing set at −1 and +1 informative positions
Figure 92B:
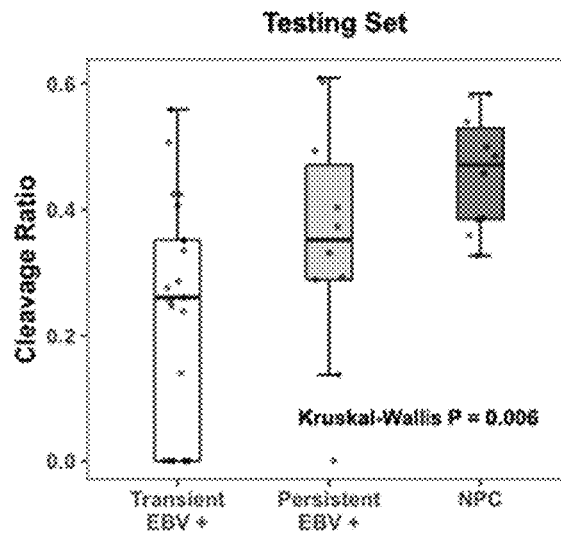
Figure 92C:
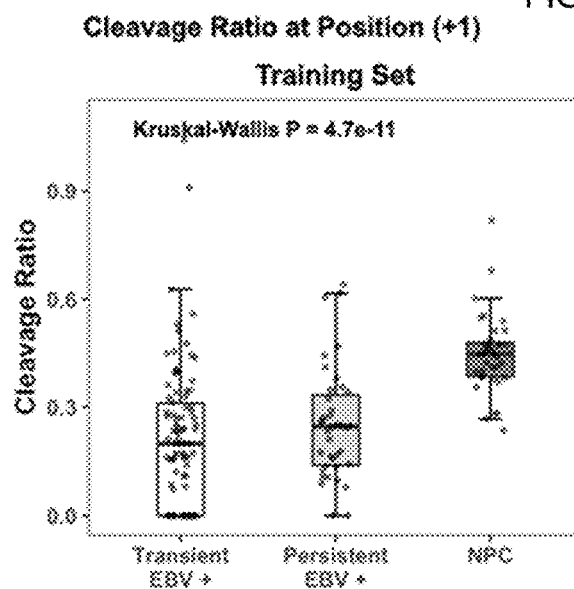
Figure 92D:
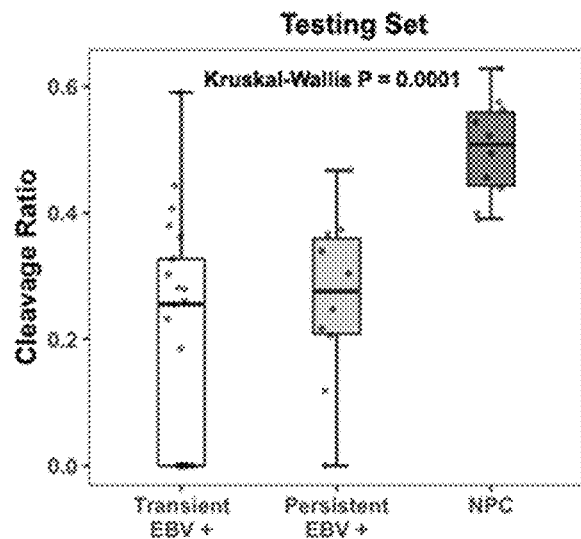

FIGS. 92A-92D show boxplots illustrated the difference of the cleavage ratios of EBV DNA between NPC and non-NPC cases in training and testing set at −1 and +1 informative positions. As shown in FIGS. 92A-92B, in both training and testing datasets, on basis of '−1' informative positions, we observed that the cleavage ratio of EBV DNA was higher in NPC cases compared with non-NPC cases (training dataset: P value=0.0001; testing dataset: P value=0.006, Kruskal-Wallis test). Moreover, in both training and testing datasets, on basis of '+1' informative positions, the cleavage ratio of EBV DNA was also higher in NPC cases compared with non-NPC cases (FIGS. 92C-92D, training dataset: P value <0.0001; testing dataset: P value=0.0001, Kruskal-Wallis test).

Figure 93B:
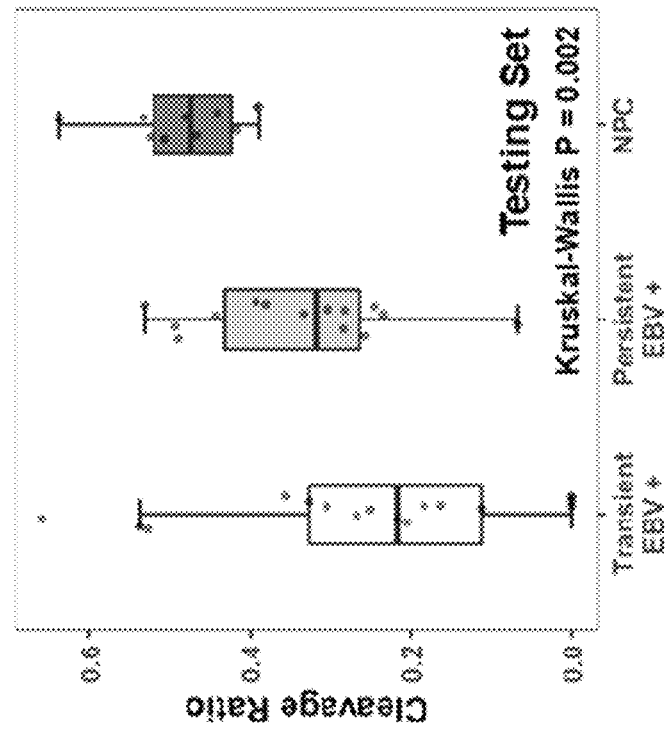
FIGS. 93A-93B show boxplots illustrating the difference of the cleavage ratios of EBV DNA at combined −1 and +1 informative positions between NPC and non-NPC cases in training (A) and testing (B) set.
Figure 93A:
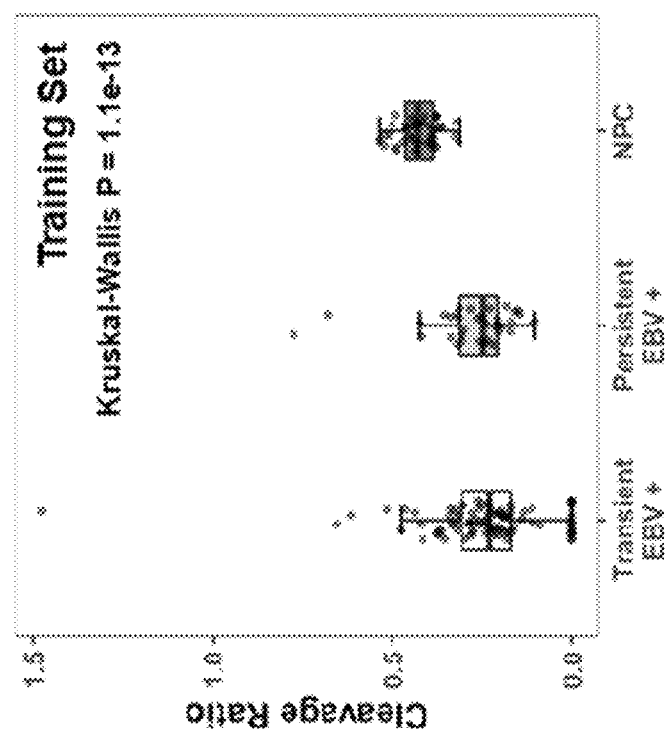

FIGS. 93A-93B show boxplots illustrating the difference of the cleavage ratios of EBV DNA at combined −1 and +1 informative positions between NPC and non-NPC cases in training (FIG. 93A) and testing (FIG. 93B) set. When combined the '−1' and '+1' informative positions, a higher cleavage ratio of EBV DNA could be observed in NPC cases (training dataset: P value <0.0001; testing dataset: P value=0.002, Kruskal-Wallis test). One can see that both training and testing sites showed a significant increase of the cleavage ratio at the −1 and +1 positions in NPC cases compared to the double and single positive also in testing cohort.

c) Cleavage Analysis, Along with Proportion and Size

In some embodiments, the cleavage analysis can be combined with an analysis of an amount of viral DNA fragments and/or combined with an analysis of a statistical value of a size distribution of the viral DNA fragments. Example statistical values include an average (mean), median, mode, or a ratio of amounts in two size ranges, which may or may not overlap. On the training side, if you combine the cleavage ratio of select CpG site with the proportion of EBV DNA, the sensitivity can be at around 100 percentage, with the specificity being around 94.6%.

Figure 94A:
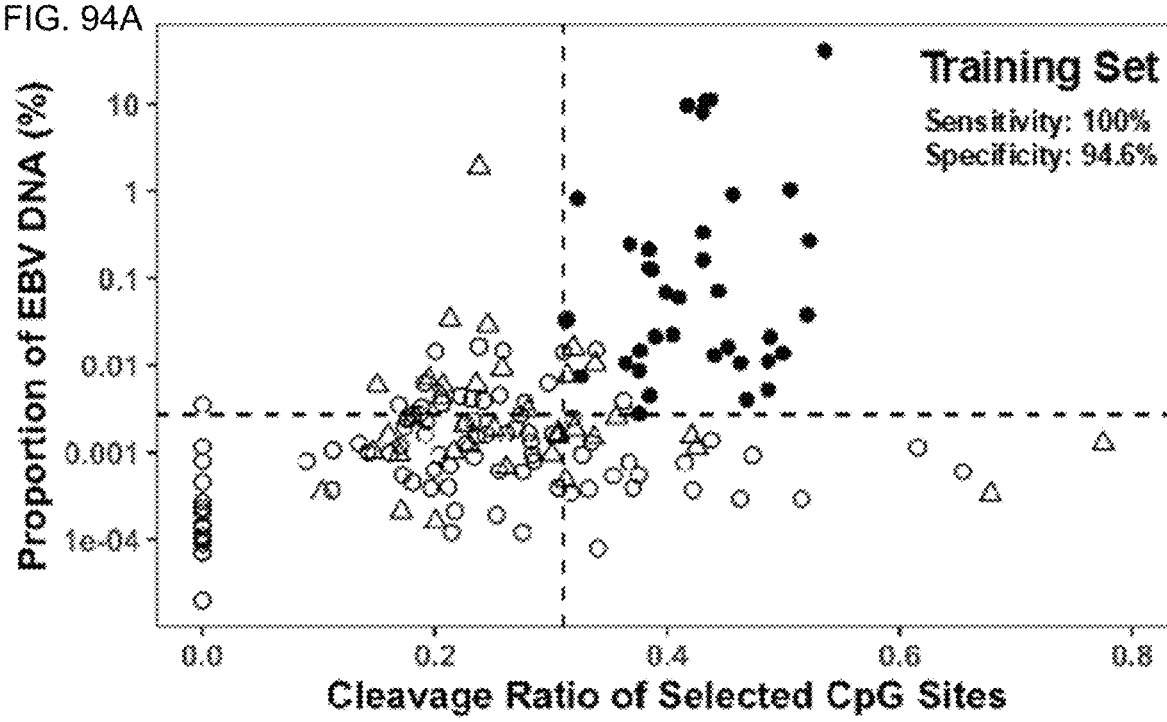
FIGS. 94A-94B show the diagnosis power of distinguish NPC cases from non-NPC cases by using the cleavage ratios of EBV DNA at the combined −1 and +1 informative positions and the EBV DNA proportion in training (A) and testing (B) set.
Figure 94B:
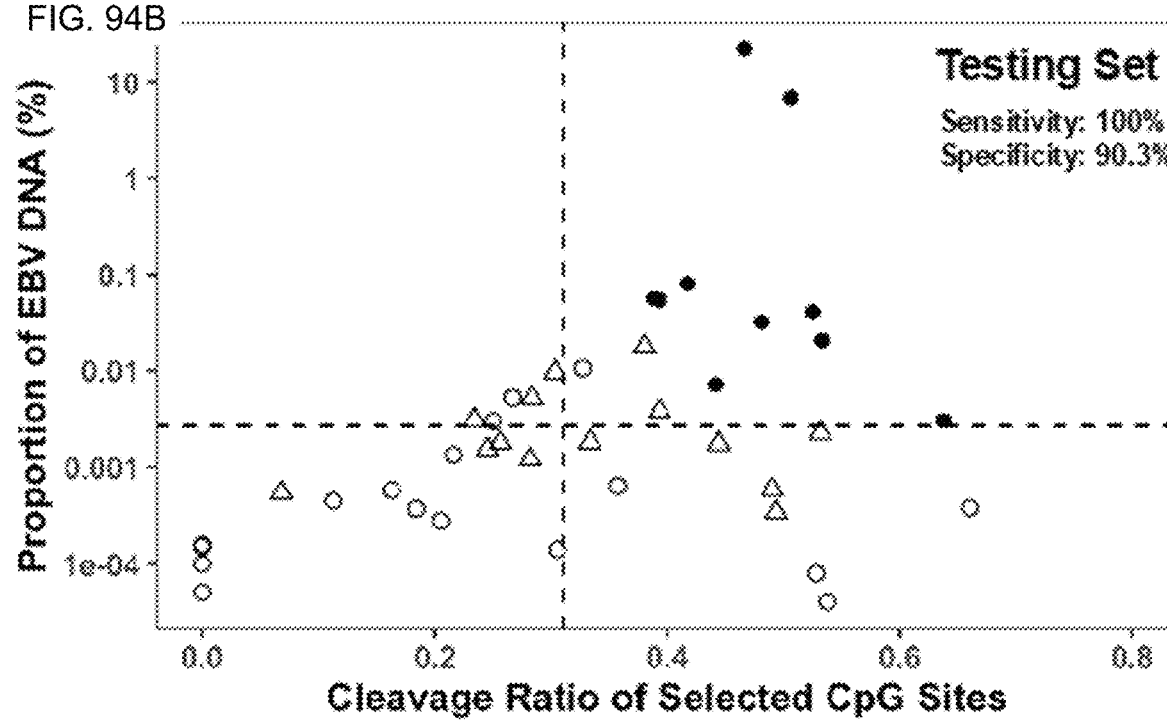

FIGS. 94A-94B show the diagnosis power of distinguish NPC cases from non-NPC cases by using the cleavage ratios of EBV DNA at the combined −1 and +1 informative positions and the EBV DNA proportion in training (A) and testing (B) set. (Cutoff: Cleavage ratio: 0.31; EBV DNA proportion: $2.7 \times 10^{-5}$). Example reference values for cleave and count (e.g., proportion) are shown in the dotted lines, e.g., as a count reference value and cleavage reference value, respectively. Thus, the corresponding parameters (proportion and cleavage) can be compared to the respective cutoff.

A size reference value can also be used to which a statistical value of a size distribution can be compared.

We carried out the combined analysis with the use of cleavage ratio and EBV DNA proportion for the differentiation between NPC cases and non-NPC cases, wherein the EBV DNA proportion was calculated as:

$$EBV \text{ DNA proportion} = \frac{EBV \text{ DNA reads}}{\text{the total number of sequenced DNA reads}} \times 100$$

If one adopted cutoffs (reference values) regarding EBV DNA proportion and the cleavage ratio to achieve a sensitivity of 100%, the cleavage ratio of EBV DNA from the combined '−1' and '+1' informative positions could reach a specificity of 94.6% in the training dataset and 90.3% in the testing dataset.

We further carried out the combined analysis with the use of EBV DNA proportion, size ratio, and cleavage ratio for the differentiation between NPC cases and non-NPC cases, wherein the size ratio of EBV DNA was calculated as:

$$EBV \text{ DNA Size Ratio} = \frac{\text{Proportion of } EBV \text{ DNA within } 80-110bp}{\text{Proportion of autosomal DNA within } 80-110bp}$$

If one adopted cutoffs regarding EBV DNA proportion, the cleavage ratio, and size ratio to achieve a sensitivity of 100%, the cleavage ratio of EBV DNA from the selected CpG sites could reach a specificity of 96.9% in the training dataset and 96.8% in the testing dataset.

FIG. 95 shows the diagnosis power of distinguishing NPC cases from non-NPC cases by using different metrics in training and testing dataset. "Count" represents the EBV DNA proportion. "Size" represents the EBV DNA size ratio. "Cleavage ratio" represents the cleavage at the combined −1 and +1 informative positions. (Cutoff: Cleavage ratio: 0.31; EBV DNA proportion: $2.7 \times 10^{-5}$; Size ratio: 5.0)

In FIG. 95, we combined the performance of different methods in EBV PCR positive cases. Without color is only single parameters and with color is the combined parameters. These results showed that the combined analysis of cleavage ratios of EBV DNA, EBV DNA proportion, and EBV DNA size ratio (sensitivity: 100%; specificity: 96.9% for training and 96.8% for testing) would be superior to the other approaches such as the methods based on the single metric such as cleavage ratio of EBV DNA (sensitivity: 100%; specificity: 73.6% for training and 61.3% for testing), EBV DNA proportion (sensitivity: 100%; specificity: 73.6% for training and 74.2% for testing), or EBV DNA size ratio (sensitivity: 100%; specificity: 34.9% for training and 38.7% for testing); and the combined analysis of cleavage ratio of EBV DNA, EBV DNA proportion, and EBV DNA size ratio (sensitivity: 100%; specificity: 96.9% for training and 96.8% for testing) would be superior to the other combinations based on two metrics such as the method based on EBV DNA proportion and EBV DNA size ratio (sensitivity: 100%; specificity: 80.6% for training and 87.1% for testing), and the method based on EBV DNA proportion and cleavage ratio of EBV DNA (sensitivity: 100%; specificity: 94.6% for training and 90.3% for testing).

For the combined analysis, each of the techniques used may be required to be positive for a positive classification of the pathology, thereby increasing the specificity. Since all have a sensitivity of 100%, there is no loss in sensitivity.

4. Use of CGN and/or NCG to Identify Sites

Some techniques identified sites as being differentially-methylated between NPC and non-NPC. Instead of using methylation to identify informative sites, some embodiments can skip the methylation analysis and identify sites that have a differential frequency for a CGN amount, a NCG amount, or a ratio of the two values, or any amount between −1 to 1 ending positions, as described above. Thus, instead of a workflow that selectively analyzed the cleavage profile at non-differentially methylated CpG sites for disease detection as described above, where the alteration in cleavage profiles might be mainly caused by enzyme activity, the CGN and/or NCG amounts can be used. The CGN/NCG motif ratio of viral DNA molecules in plasma or other samples can be used more than just to reflect methylation, which allowed for detecting and monitoring virus-related cancers such as nasopharyngeal carcinoma (NPC), infectious mononucleosis, lymphoma, etc.

Some embodiments can use the CGN/NCG motif ratio (or individual amounts) to identify informative CpGs that exhibit different methylation status between individuals without NPC (non-NPC) and with NPC. Those informative CpG sites could be further used to facilitate NPC detection.

Figure 96:
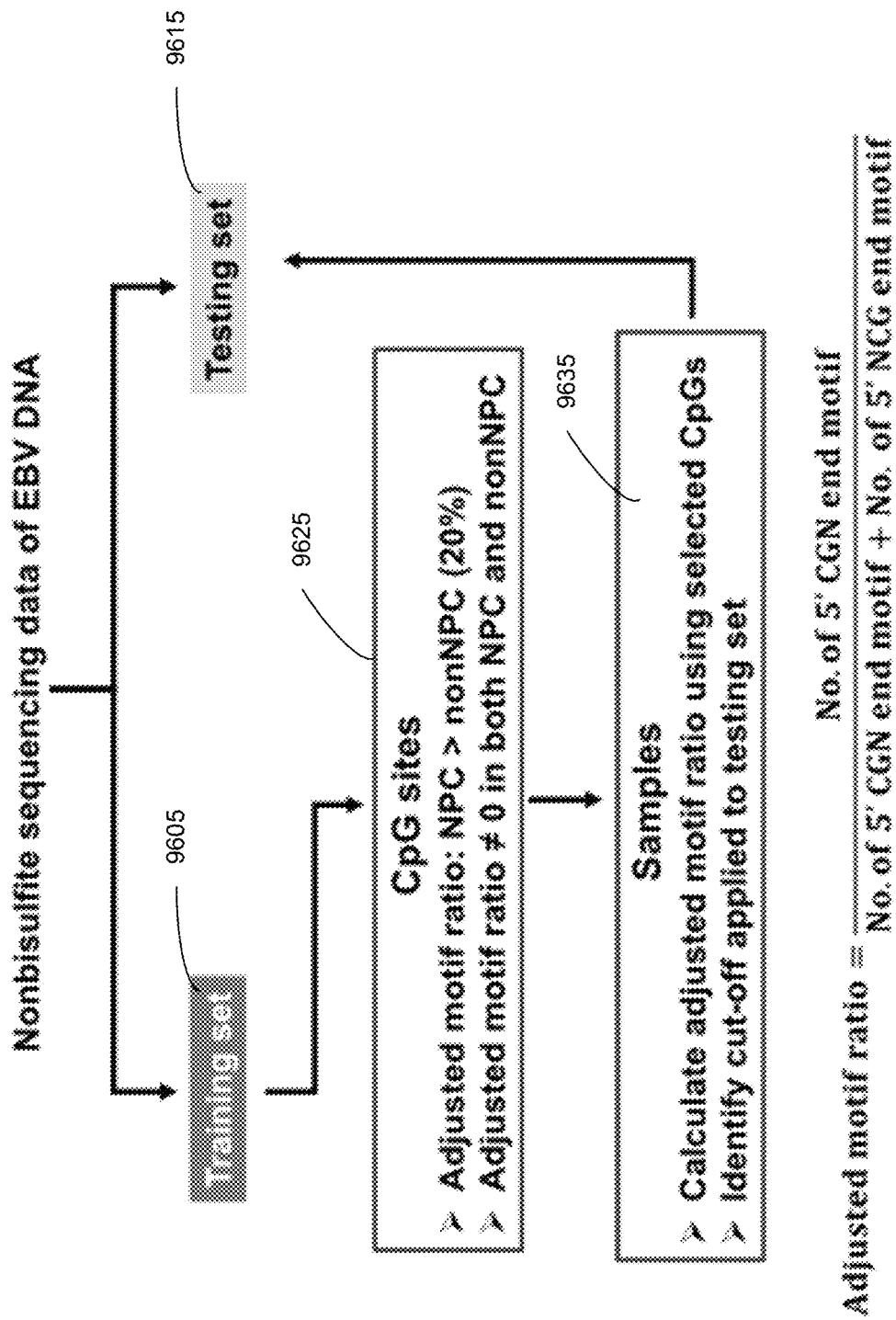
FIG. 96 shows a schematic for informative CpG selection based on the adjusted CGN/NCG motif ratio in the training set and NPC diagnosis in the testing set.

FIG. 96 shows a schematic for informative CpG selection based on the adjusted CGN/NCG motif ratio in the training set 9605 and NPC diagnosis in the testing set 9615. As shown, 272 and 65 EBV DNA positive non-NPC and NPC cases were divided into the training (non-NPC=230; NPC=31) and testing sets (non-NPC=42; NPC=34). The testing set includes subjects that were indistinguishable based on previous methods (i.e., EBV DNA proportion and size ratio).

In the training set 9605, at step 9625, we pooled together all sequenced reads of EBV DNA in plasma DNA from non-NPC individuals and NPC patients into dataset A and dataset B, respectively. Based on these two datasets, the adjusted CGN/NCG motif ratio was calculated for each CpG site. The adjusted CGN/NCG motif ratio is calculated as (the amount of 5' CGN motif)/(the amount of 5' CGN motif+the amount of 5' NCG motif). The adjusted ratio can account for situations when one of the amounts (CGN or NCG) is zero. Any of the motif ratios described herein can use this formulation.

1,425 CpG sites in the EBV genome were identified based on their adjusted CGN/NCG motif ratios fulfilling the criterion where the CGN/NCG motif ratios in dataset B (NPC) were at least 20% higher than dataset A (non-NPC) in the training set. Other percentages can be used besides 20% (e.g., 10%, 15%, or 25%), and sites can be identified where the ratio is lower by a specified percentage. Those sites identified in step 9625 were further confirmed with a higher methylation index in NPC cases than non-NPC individuals in a bisulfite sequencing dataset (non-NPC=160; NPC=47, FIG. 86A.).

Figures 97A, 97B:
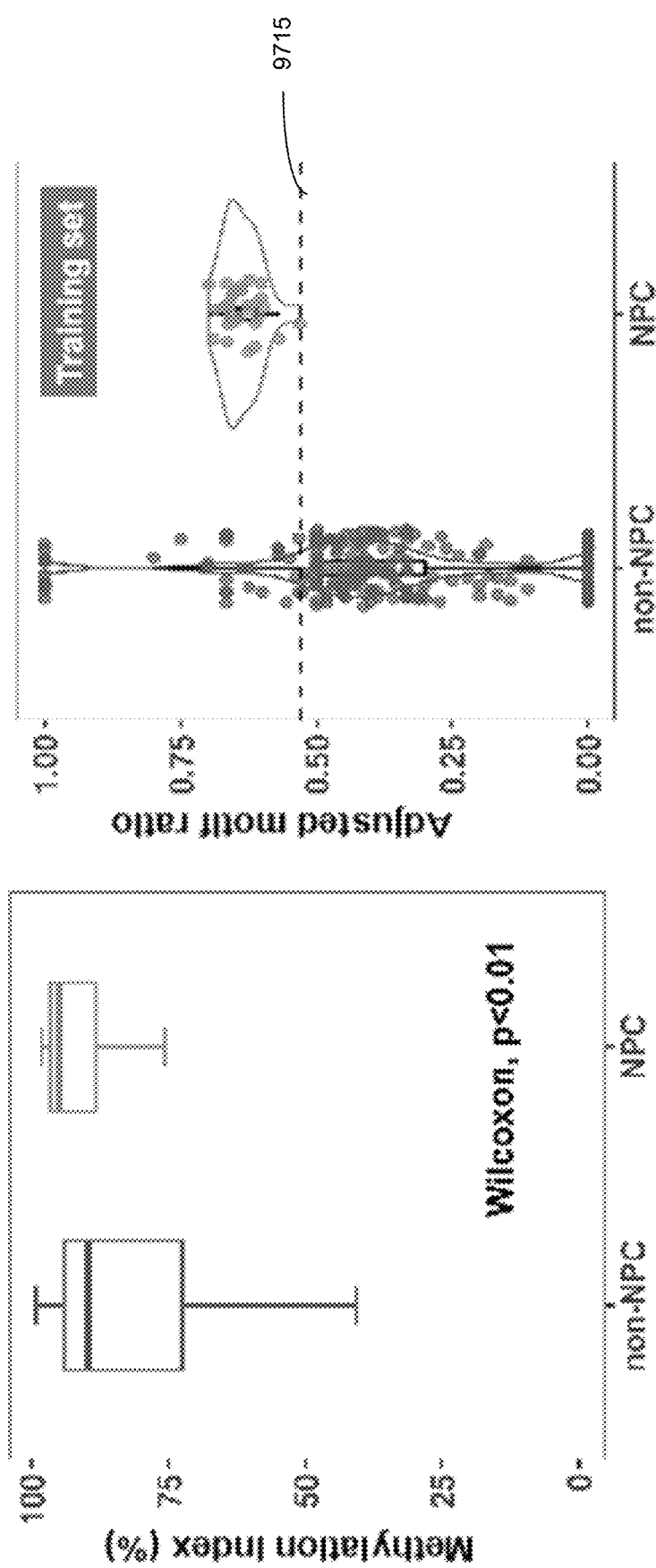
FIG. 97A shows the methylation index of informative CpGs measured by bisulfite sequencing between non-NPC and NPC cases.
FIG. 97B shows the adjusted CGN/NCG motif ratios of informative CpGs in the EBV genome between non-NPC and NPC individuals (training set).

FIG. 97A shows the methylation index of informative CpGs measured by bisulfite sequencing between non-NPC and NPC cases. As shown, the sites with the higher motif ratio in NPC than non-NPC had a higher methylation index as well. The CpG sites identified in this manner can account for other facts in addition to methylation for the different cutting, e.g., different enzyme activity.

At step 9635, samples were analyzed using the sites identified in step 9625. The adjusted CGN/NCG motif ratio from those selected CpGs was calculated for each individual in the training dataset, and a cutoff was determined by using the lowest value of the motif ratio for the NPC cases in this dataset (FIG. 97B).

FIG. 97B shows the adjusted CGN/NCG motif ratios of informative CpGs in the EBV genome between non-NPC and NPC individuals (training set). The dotted line 8615 shows the cutoff defined by the lowest value for the NPC cases. For the testing dataset comprising 42 non-NPC individuals and 34 NPC cases, which were indistinguishable based on the previous method (i.e., EBV DNA proportion and size ratio), the use of adjusted CGN/NCG motif ratio allowed additional 14 non-NPC cases to be excluded from the diagnostic conclusion of NPC, leading to an improved positive predictive value (i.e., 26.8%; FIG. 87B).

Figure 98A:
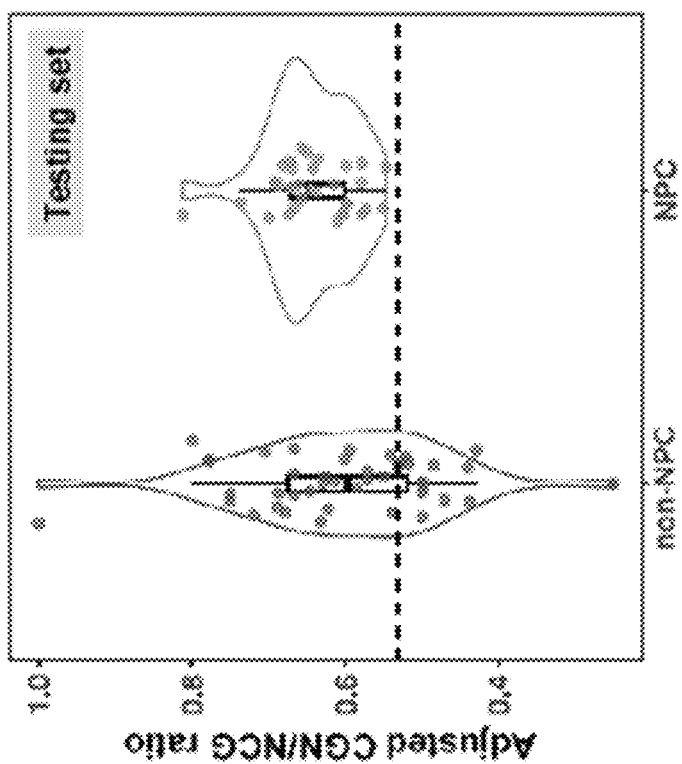
FIG. 98A shows the adjusted CGN/NCG motif ratios of informative CpGs in the EBV genome between non-NPC and NPC individuals (testing set).
Figure 98B:
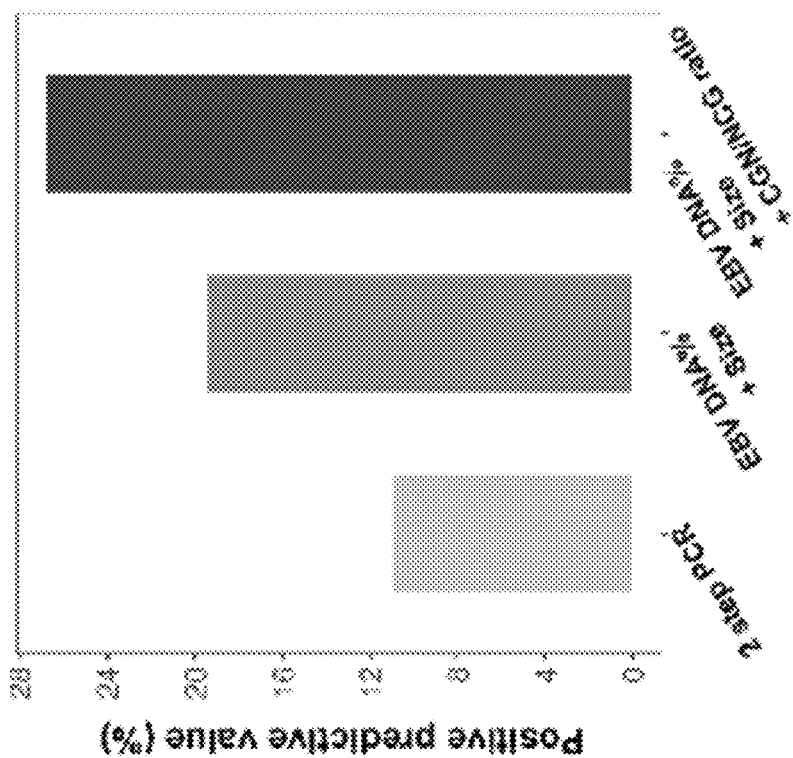
FIG. 98B shows positive predictive values archived by PCR-based assay, the approach based on EBV DNA proportion and size ratio, and the approach combined EBV DNA proportion, size ratio and cleavage motifs.

FIG. 98A shows the adjusted CGN/NCG motif ratios of informative CpGs in the EBV genome between non-NPC and NPC individuals (testing set). FIG. 98B shows positive predictive values archived by PCR-based assay, the approach based on EBV DNA proportion and size ratio, and the approach combined EBV DNA proportion, size ratio and cleavage motifs. The cutoff (dotted line) in FIG. 98A shows the additional 14 non-NPC cases that can be excluded from the test set. FIG. 98B shows the improvement in the positive predictive value over previous techniques of (1) using two steps of PCR to determine EBV DNA presence and (2) EBV DNA % in combination with size.

In another embodiment, CGN/NCG motif ratio or adjusted motif ratio of viral DNA molecules in plasma could be used to detect and monitor other virus-related cancers such as but not limited to Burkitt's lymphoma, some types of Hodgkin's and non-Hodgkin's lymphoma, stomach cancer, hepatocellular carcinoma, cervical cancer, etc. Such cancer may be associated with viruses, including but not limited to, Epstein-Barr virus (EBV), hepatitis B virus (HBV), hepatitis C virus (HCV), human immunodeficiency virus (HIV), human herpesvirus 8 (HHV-8), human papillomavirus (HPV), etc.

5. Methods for Using Cleavage of Viral DNA to Determine Pathology

The level of pathology can be determined using one or more regions (which include or be defined by CpG sites) that have similar methylation levels (e.g., within a specific range, such as above, 70%, between 60%-40%, and less than 30%). The regions/sites of a same type (e.g., all hypermethylated or hypomethylated) can be analyzed together to generate a feature value (e.g., a CGN ratio or cleavage ratio at another position around a CpG site) or a feature vector (e.g., different feature(s) for each region or site or positions around a site).

Figure 99:
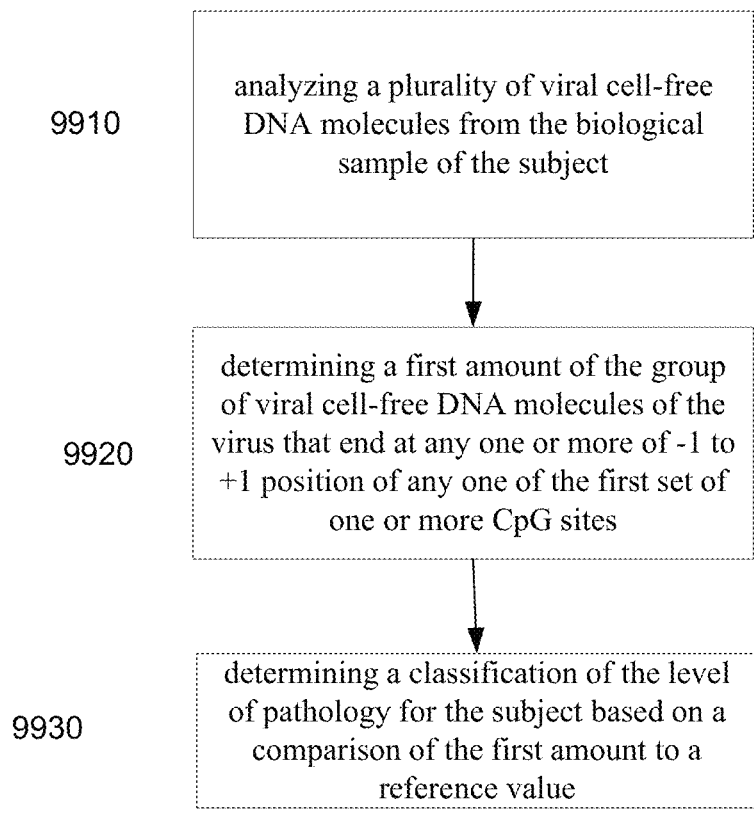
FIG. 99 is a flowchart illustrating a method to determine a level of pathology in a subject using a biological sample including cell-free DNA molecules from the subject and from a virus.

FIG. 99 is a flowchart illustrating a method 9900 to determine a level of pathology in a subject using a biological sample including cell-free DNA molecules from the subject and from a virus. The biological sample includes cell-free DNA. As with other methods described herein, method 9900 can be performed partially or entirely using a computer system. Blocks performing similar functionality as in other methods can be performed in a similar manner as described for those blocks in other flowcharts.

At block 9910, method 9900 includes analyzing a plurality of viral cell-free DNA molecules from the biological sample of the subject. Analysis of each of a group of the DNA molecules can include determining a location of the viral cell-free DNA molecule in a reference genome of the virus. The group of viral cell-free DNA molecules can be located in a first set of one or more CpG sites of the reference genome. Each of the first set of one or more CpG sites can have a methylation level within a specified range in subjects having the pathology, e.g., hypermethylated or hypomethylated. Block 9910 can be performed in a similar manner as block 2710. Each of the first set of one or more CpG sites can be differentially-methylated in subjects having the pathology relative to subjects not having the pathology, e.g., as described in section 1 and 2 above. But the methylation levels may be similar in subjects with and without the pathology, e.g., as described in section 3.

In another implementation for identifying the first set of sites, instead of methylation, differences of an amount at an ending position (e.g., CGN, NCG, a ratio, or any amount using −1 to 1 ending position) between healthy controls and subjects with the pathology can be used, e.g., as described above. Accordingly, each of the first set of one or more CpG sites can be identified using a first training set of samples from subjects having the pathology and a second training set of samples from subjects not having the pathology. The first amount at each of the first set of one or more CpG sites differs by at least a specified percentage between the first training set and the second training set.

The analysis can include determining an end sequence motif (also referred to as end motif) of at least one end of the viral cell-free DNA molecule. The end sequence motif can be determined from the outermost bases in a sequence read. If a sequence read only includes one end and not the entire DNA fragment/molecule (e.g., as one of paired reads covering both ends), the bases corresponding to the end of the DNA fragment are used and not the bases towards the middle of the fragment. An end of the cell-free DNA molecule can have a first position at the outermost position, a second position that is next to the first position, and a third position that is next to the second position.

The cell-free DNA from the host (e.g., a human) can also be analyzed as described in similar steps of other methods described herein, such as block 2710.

At block 9920, a first amount of the group of viral cell-free DNA molecules of the virus is determined that end at any one or more of −1 to +1 positions of any one of the first set of one or more CpG sites. The first amount can be determined using the end sequence motifs. As described above, the first amount may be the number of viral cell-free DNA molecules that end at the −1 position. The first amount may be the number of viral cell-free DNA molecules that end at the 0 position. The first amount may be the number of viral cell-free DNA molecules that end at the +1 position. Block 9920 may be performed in a similar manner as block 8420.

Accordingly, the first amount can be of a first set of one or more end sequence motifs that have C at the first position and that have G at the second position. The first set of one or more end sequence motifs can includes CGN, where N includes any nucleotide at the third position. As another example, the first amount can be of a first set of one or more end sequence motifs that have C at the second position and G at the third position. As yet another example, the first amount can be a sum of the viral cell-free DNA molecules that end at a −1 or +1 position of the first set of one or more CpG sites.

Other amounts can be determined, e.g., for normalization, as is described through the disclosure. For example, methods can include determining a second amount of a second set of end sequence motifs that have C at the second position and G at the third position. Determining the classification can include normalizing the first amount with the second amount to obtain a normalized first amount that is compared to the reference value. The second set of end sequence motifs can include NCG, where N includes any nucleotide at the first position.

A total amount of sequence motifs for the plurality of viral cell-free DNA molecules can be determined. Determining the classification can include normalizing the first amount with the total amount to obtain a normalized first amount that is compared to the reference value.

As other examples, the amounts in a window can be determined, e.g., to determine a cleavage profile.

At block 9930, a classification of the level of pathology for the subject is determined based on a comparison of the first amount to a reference value. Block 9930 may be performed in a similar manner as block 8430.

When a cleavage profile is determined, for each position of at least two positions within a window around any one the first set of one or more CpG sites, a respective amount of cell-free DNA molecules ending at the position can be determined, thereby determining respective amounts. A feature vector can include the respective amounts and the first amount. The feature vector can be input into a machine learning model as part of determining the classification of the level of pathology. The machine learning model is trained using cell-free DNA molecules from training samples having known classifications.

Each of the first set of one or more CpG sites can be hypomethylated or each can be hypermethylated in subjects having the pathology. If the first set is hypomethylated and the feature vector is a first feature vector, a second feature vector can be generated using a second set of one or more CpG sites that are all hypermethylated. The second feature vector and the first feature vector can be input into the machine learning model as part of determining the classification of the level of pathology.

Respective amounts of cell-free DNA molecules ending at each of the first set of CpG sites can be determined. Determining classification of the level of pathology can includes comparing each of the respective amounts to a respective reference value. Comparing each of the respective amounts to the respective reference value can be performed by inputting the respective first amounts as part of a feature vector into a machine learning model.

For each of the first set of one or more CpG sites and for each position of at least two positions within a window around the CpG site, a respective amount of cell-free DNA molecules ending at the position can be determined, thereby determining respective amounts. The feature vectors can include the respective amounts for the at least two positions and the respective amount for the CpG site.

Methods can include determining a respective amount of each 3-mer end sequence motif that has a C at the first position and that has G at the second position. A feature vector can include the respective amounts, which include the first amount. The feature vector can be input into a machine learning model as part of determining the classification of the level of pathology. Additionally or alternatively, the feature vector can include respective amounts for each 3-mer end sequence motif that has a C at the second position and that has G at the third position. The feature vector can include respective amounts of all 3-mer end sequence motifs.

Analyzing the plurality of viral cell-free DNA molecules can includes determining a size of each of the plurality of viral cell-free DNA molecules. A statistical value of a size distribution of the plurality of viral cell-free DNA molecules can be determined. Determining the classification of the level of pathology for the subject further can includes comparing the statistical value to a size reference value.

Method can further include determining an amount of the plurality of viral cell-free DNA molecules. Determining the classification of the level of pathology for the subject can further include comparing the amount to a count reference value.

IX. Allelic-Specific Fragmentation Analysis

Some embodiments can perform a fragmentation analysis for certain genotypes/haplotypes, which can correspond to different types of tissue. For example, a donor, a fetus, or a tumor can have a tumor-specific allele.

A. Genomic Imprinting

The results in this disclosure indicated that end motif frequencies from a genomic region of interest (i.e., regional end motif frequencies) could be used to predict its methylation density. Plasma DNA molecules originating from hypermethylated regions bore a higher frequency of 5'-CGN motif (where N can be A, T, C or G, i.e., the sum of CGA, CGT, CGC, and CGG end motifs) but a lower frequency of 5'-NCG motif (i.e., the sum of ACG, TCG, GCG, and CCG end motifs), when compared with those from hypomethylated regions (See FIG. 29).

We further reasoned that the use of relative frequencies of CGN and NCG motifs could be used to predict regional methylation alterations. For one $1^{st}$ trimester sample with a bisulfite sequencing depth of 13×, the regional 5'-CGN end motif frequency and 5'-NCG end motif frequency were determined for each genomic region of interest. In one example, we analyzed plasma DNA molecules from a region affected by genomic imprinting (i.e., the GNAS gene, located at chr20:57,415,043-57,415,176). Genomic imprinting is a process of silencing genes often involving the DNA methylation depending on its parent of origin.

FIGS. 100A and 100B show CGN and NCG end motif frequencies could be used for predicting genomic imprinting according to embodiments of the present disclosure. FIG. 100A shows allele-specific methylation at imprinted loci (the GNAS gene: chr20:57,415,043-57,415,176). The filled and unfilled circles represent the methylated and unmethylated CpG sites, respectively. Each row represents one sequenced DNA fragment. The vertical numbers indicate the genomic coordinates for CpG sites being analyzed (hg 19). The nucleotide alleles (A/G) correspond to the genomic location of SNP. Those molecules carrying the A alleles were methylated, and those carrying the G alleles were unmethylated. FIG. 100B shows a bar plot illustrating the CGN and NCG motif frequencies deduced from those molecules carrying A alleles and G alleles, respectively.

As shown in FIG. 100A, DNA fragments carrying alleles of "A" or "G" at a SNP site (rs1800900) are inherited from different parents. Those DNA fragments carrying G alleles were unmethylated, while those carrying A alleles were methylated. As shown in FIG. 100B, DNA fragments carrying A alleles (methylated) showed a higher frequency of CGN motifs (13.9% vs 3.7%) but a lower frequency of NCG motifs (20.8% vs 13.0%), compared with the corresponding DNA fragments carrying G alleles (unmethylated). These results suggested that the end motifs of CGN and NCG could be used for determining the status of genomic imprinting. In one embodiment, the approaches based on CGN and NCG end motifs could be used for detecting a number of diseases and disorders linked to genetic imprinting, including but not limited to Angelman syndrome, Prader-Willi syndrome, and Beckwith-Wiedemann syndrome.

If there is skewing in the end motif frequency between the two genotypes/haplotypes, then imprinting can be identified. If the end motif frequency is the same for the two alleles, then imprinting is not present. In this manner, bisulfite sequencing is not needed, as the sequencing information at the end of the fragments can provide information about the imprinting between the methylation levels and the alleles. In this manner, it can be determined which of the alleles is from the mother and which is from the father.

In one embodiment, cancer-specific methylation alteration could be predicted by analyzing the regional CGN and NCG end motifs. For example, differences in the end motifs can occur when copy number aberrations exist or when a tumor is differentially methylated between haplotypes.

B. Tonality

If there is an imbalance in the cleavage profile or CGN and/or NCG profiles between the two haplotypes, a tonality issue can be identified. One can determine a locus is heterozygous based on the reads aligning to that locus. For example, one allele can be A and the other can be T allele. For fragments with the A allele, it can be determined the percentage that end at a neighboring CpG site. The same can be done for the T allele. The ratio of the two differences can indicate a difference in fragmentation (e.g., due to methylation) between the two haplotypes In another case, women have two X chromosomes, but one of them for any one cell will be methylated and one is unmethylated. But if you summarize all the trillions of cells in the body, the methylation should be balanced.

The tonality imbalance in the cleavage profile or CGN and/or NCG profiles between the two haplotypes can be used to determine which haplotype is inherited from the mother. Assume maternal heterozygous sites (AB), where the two maternal haplotypes are Hap I and Hap II. If the maternal Hap I is transmitted into the fetus, then the maternal cfDNA linked to the Hap I would be over-represented compared to the Hap II, as some sites in which the foetus will be homozygous (AA) will skew the haplotype dosage linked to Hap I and Hap II. Thus, the over-represented Hap I will have more fetal-derived cfDNA than the Hap II. Hap I would show the hypomethylation nature. In this case, Hap I would have less CGN. Hence, CGN and NCG profiles could indicate which maternal haplotype would be inherited by the fetus, i.e., deducing the maternal inheritance of the feus. Accordingly, when the classification for methylation for the region is a first methylation level corresponding to a first haplotype of a female pregnant with a fetus, a second methylation level corresponding to a second haplotype of the female can be determined using a second amount of the first set of end sequence motif(s) for cell-free DNA molecules from the second haplotype. Then, an inherited haplotype of the fetus can be determined based on the first methylation level and the second methylation level.

Similarly, we can use CGN and/or NCG profiles to confirm whether the genetic aberrations (SNVs and copy number aberrations, CNAs) detected plasma DNA of patient are likely of tumoral origin. For example, if a mutation or CNA linked to less CGN is more likely to be related to cancer. In such a situation, the region can include a sequence variant or a copy number aberration determined from the plurality of cell-free DNA molecules, e.g., via a count of DNA fragments at a region or a size analysis, as described in U.S. Patent Publication Nos. 2013/0040824 and 2016/0201142. Whether the sequence variant or the copy number variation is from a tumor can be determined based on the classification for methylation of the region. For example, if the fragmentation indicates a methylation below a threshold, then the sequence variant or the copy number variation can be identified as originating from a tumor.

Such analyses can use any of the methylation classifications described above, including for an individual fragment, for a site, and for a region.

C. Sequencing Depth for Methylation Prediction

To estimate the sequencing depth required to determine whether a region is methylated or unmethylated, we used the GNAS imprinting locus as an example. The CGN and NCG end motif frequencies of methylated DNA fragments were found to 13.9% and 2.8%, respectively. Thus, the probability of having CGN end motifs among the end motifs containing CG dinucleotides in methylated DNA molecules was estimated to be 0.83, which is 13.9/(13.9+2.8).

For unmethylated DNA fragments in this example, the end motif frequencies of CGN and NCG were 3.7% and 13.0%, respectively. The probability of having CGN end motifs among the end motifs containing CG dinucleotides in unmethylated DNA was estimated to be 0.22.

Figure 101:
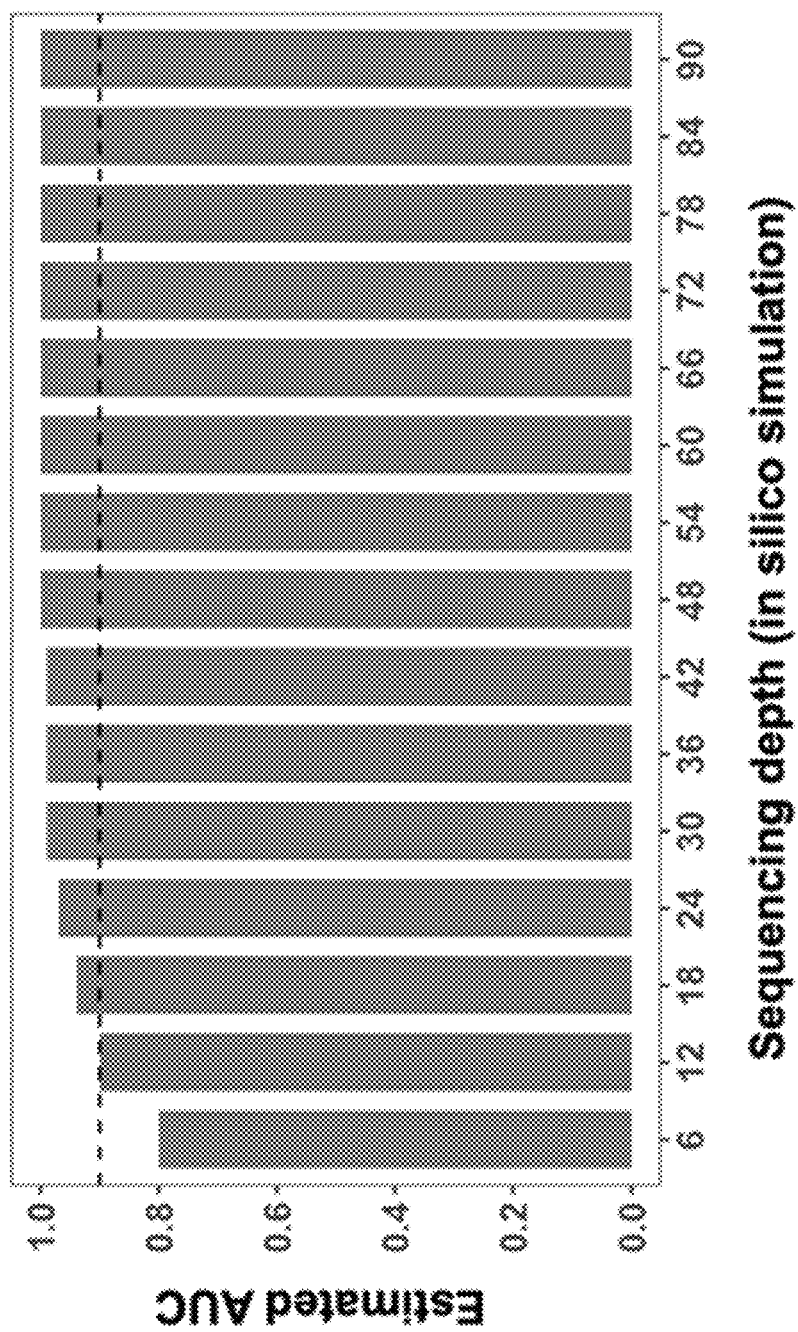
FIG. 101 shows performance in differentiating between methylated and unmethylated regions depending on the sequencing depths according to embodiments of the present disclosure.

FIG. 101 shows performance in differentiating between methylated and unmethylated regions depending on the sequencing depths according to embodiments of the present disclosure. We assumed that the CG-containing motifs (i.e., CGN and NCG end motifs) follow binomial distributions. The distributions of CGN end motifs in methylated regions and unmethylated regions could be written as Bin(n, 0.83) and Bin(n, 0.22), respectively, where "Bin" represented binomial distribution function and "n" represented total numbers of CG-containing motifs (ranging from 1 to 100). We performed simulation for 1,000 times for a given "n" and assessed the area under the receiver-operating characteristic curve (AUC) values for distinguishing between methylated and unmethylated regions based on CGN end motif frequency. The total numbers of CG-containing motifs (n) were used to deduce the corresponding sequencing depth. As shown in FIG. 101, with a sequencing depth of 18×, one could reach an AUC of >0.9. With a sequencing depth of 42×, one could reach an AUC of over 0.99.

X. Enrichment Techniques

Various techniques described above use DNA fragments at or covering certain regions/sites, e.g., hypermethylated, hypomethylated, 5hmC-enriched, or 5hmC-depleted in a particular tissue. The analysis of such regions/sites can include enrichment techniques, e.g., amplifying DNA from certain regions/sites (e.g., followed by sequencing) or capturing DNA from certain regions/sites (e.g., using probes).

A. Enrichments of Certain Regions Using CGN and NCG

Figure 102:
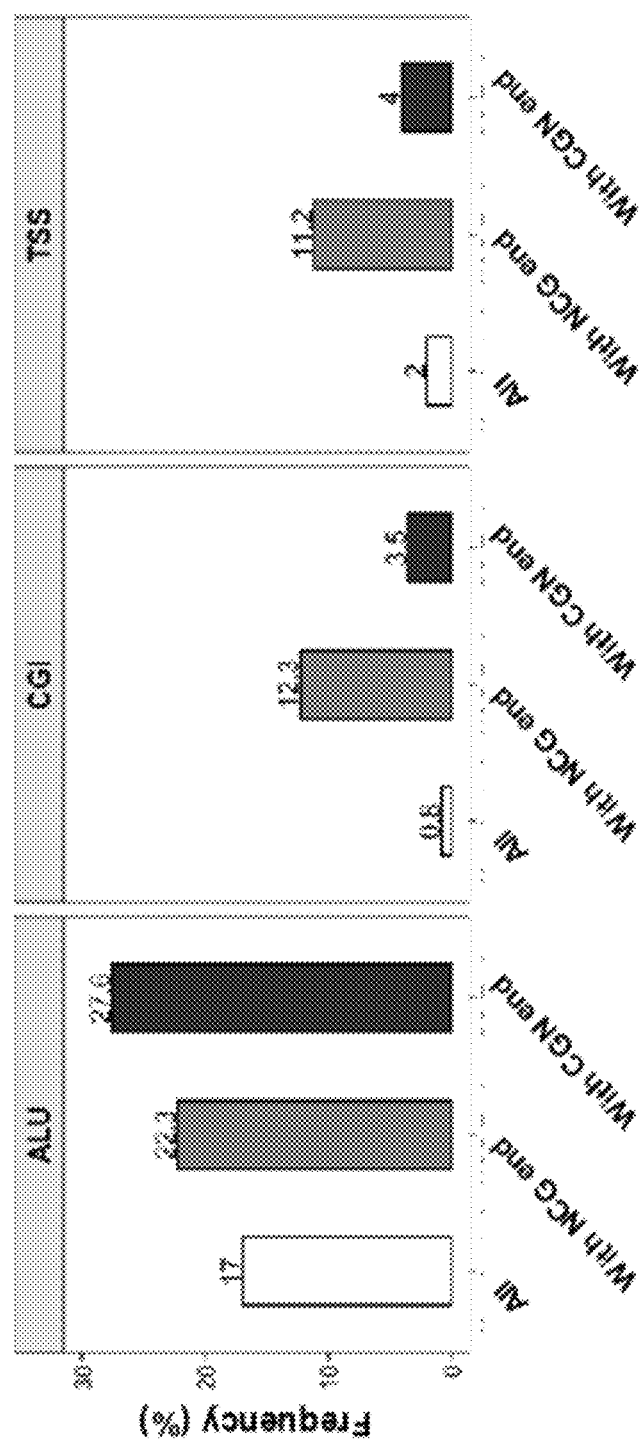
FIG. 102 shows the relative percentage of sequenced fragments aligned to certain genomic regions of interest could be enriched by selectively analyzing a subset of DNA molecules ending with a particular end motif.

FIG. 102 shows the relative percentage of sequenced fragments aligned to certain genomic regions of interest could be enriched by selectively analyzing a subset of DNA molecules ending with a particular end motif. (All: without selection; With NCG end: select DNA fragments with NCG end motif; With CGN end: select DNA fragments with CGN end motif).

As shown in FIG. 102, compared with all reads, the selective analysis of DNA molecules ending with NCG would relatively increase the number of reads mapping to CpG island (CGI) (12.3% vs 0.8%) and transcriptional start site (TSS) (11.2% vs 2%) regions, compared with a random sequencing approach. While the selective analysis of DNA molecules with CGN end motifs would relatively increase the amount of reads mapping to Alu regions (27.6% vs 17.0%).

B. Enrichment of CGN and NCG for Certain Regions

In various embodiments, CGN and NCG motif-containing DNA fragments from one or more regions of interest could be enriched during the library preparation. Such a technique can be used to efficiently analyze a region of interest.

Figure 103:
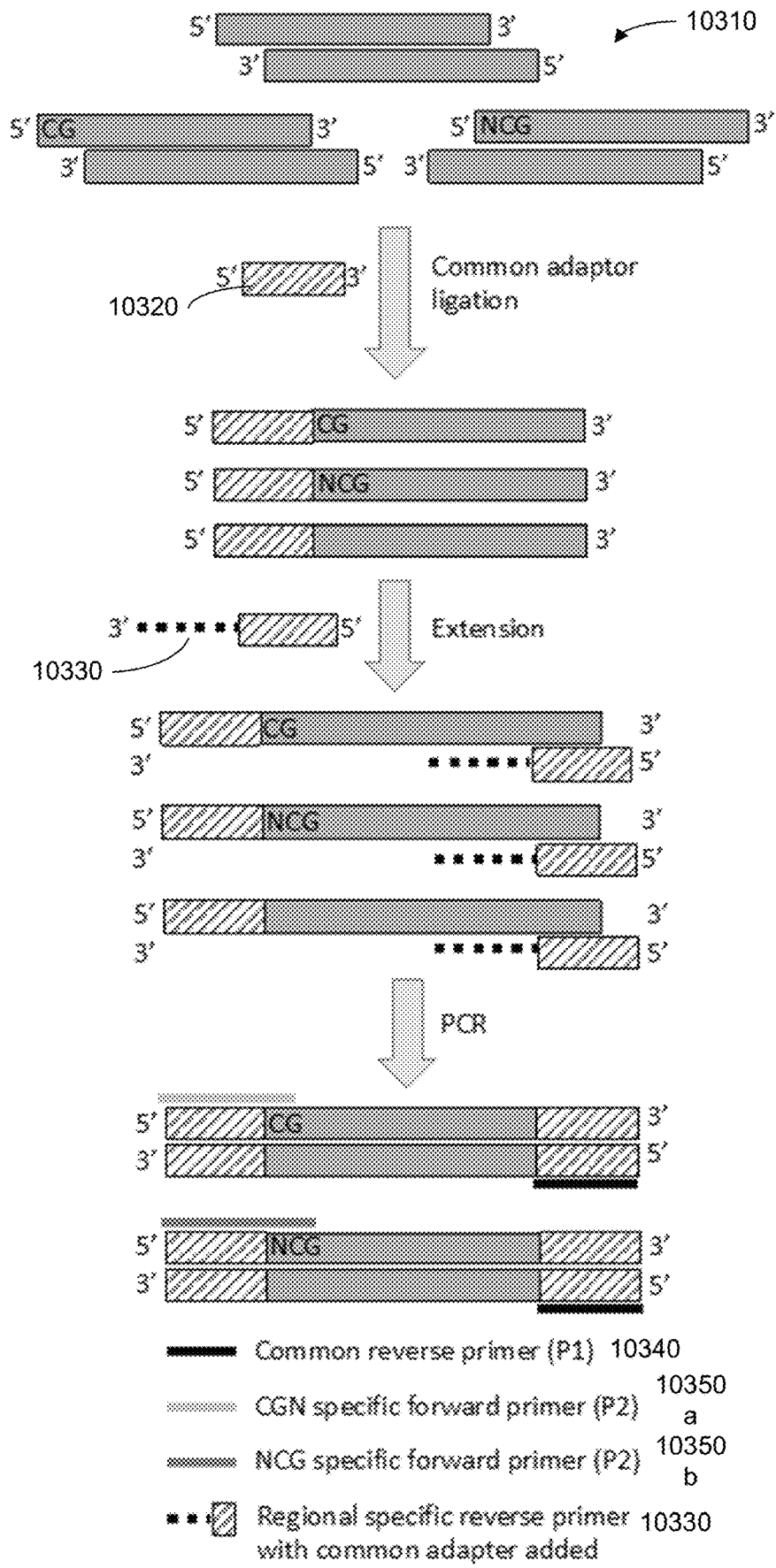
FIG. 103 is an example workflow for the sequencing library preparation by selectively amplifying DNA containing NCG or CGN end motifs from regions of interest according to embodiments of the present disclosure.

FIG. 103 is an example workflow for the sequencing library preparation by selectively amplifying DNA containing NCG or CGN end motifs from regions of interest according to embodiments of the present disclosure. Double strand cfDNA molecules 10310 can be denatured to single strand and subjected to common adaptor ligation at the 5'-end using a common adaptor 10320. A regional specific reverse primer 10330 can be used to extend the DNA strand opposite to a template strand from region of interest. The regional specific reverse primer 10330 could be linked to a common adaptor at the 5' end, thus ultimately introducing common adaptor 10320 to a DNA molecule through primer extension.

After certain DNA molecules corresponding to the region of interest are selected, DNA fragments having certain end motifs (e.g., CGN and NCG) can be amplified or detected. A pair of PCR primers can be designed in a way that one primer 10340 could bind to the common adaptor region (P1), and the other primer 10350a or 10350b could bind to the junctional region between the DNA and the common adaptor (P2). By controlling the last bases in the 3'-end of the P2 to be CG or NCG (i.e., ACG, CCG, TCG, GCG), we could preferentially amplify DNA fragments containing CG- or NCG-end motifs. Those libraries can be subsequently sequenced or detected using probes (e.g., the forward primer P2 can act as a probe). The sequenced fragments would be used to perform the analysis of CGN and NCG end motifs, for determining methylation alterations across regions of interest.

C. PCR-Free and Limited PCR Cycle for Sequencing Library Preparation

When performing enrichment, an enhanced methylation-aware fragmentation analysis can be performed through PCR-free library preparation or limited PCR preparation. PCR may also be performed as part of whole genome sequencing, and the analysis also applies to such a scenario.

In various embodiments, different PCR cycles can be used for library preparation of Illumina whole genome sequencing to improve methylation-aware fragmentation analysis. We sequenced libraries derived from one healthy cfDNA sample prepared with 4 PCR cycles (reads: 3,385,548), 8 PCR cycles (reads: 3,693,070), and without PCR (reads: 1,869,582).

Figure 104:
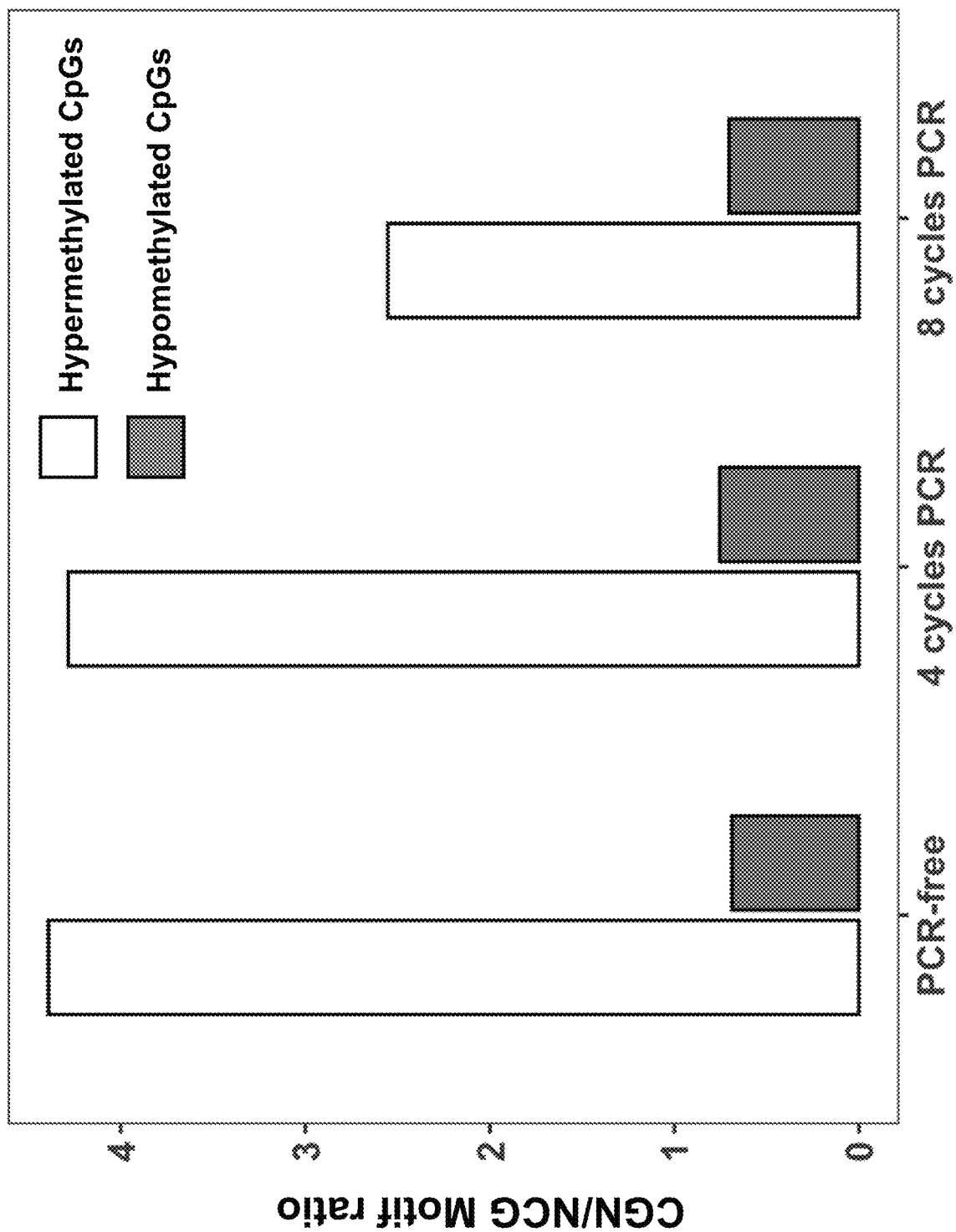
FIG. 104 shows the CGN/NCG motif ratios of putatively hypermethylated and hypomethylated CpGs in the sequencing libraries of plasma DNA prepared with 4 PCR cycles, 8 PCR cycles, and without PCR, respectively.

FIG. 104 shows the CGN/NCG motif ratios of putatively hypermethylated and hypomethylated CpGs in the sequencing libraries of plasma DNA prepared with 4 PCR cycles, 8 PCR cycles, and without PCR, respectively. As shown, the CGN/NCG motif ratio of putatively hypermethylated CpGs was higher in the library prepared without PCR (4.39) or with 4 PCR cycles (4.28), compared with that with 8 PCR cycles (2.55). There was no distinct difference in the CGN/NCG motif ratio for putatively hypomethylated CpGs between PCR and PCR-free libraries (PCR-free: 0.69; 4 PCR cycles: 0.75; 8 PCR cycles: 0.70; FIG. 104).

The difference in the CGN/NCG motif ratio between putatively hypermethylated and hypomethylated CpGs was 1.72-fold higher in the PCR-free library and 1.68-fold higher in the library prepared with 4 PCR cycles, in comparison with that prepared with 8 PCR cycles. When using PCR-free or four cycles PCR library, there can be better separation between hyper and hypomethylated CpG site in comparison with eight cycles of PCR library. These results indicated that lower PCR cycles used in the sequencing library preparation can improve methylation-aware fragmentation analysis. In some other embodiments, the number of PCR cycles can be but not limited to 1, 2, 3, 5, etc.

XI. Urinary Examples

Some examples are provided for urine samples.

A. Cleavage Profile and Motif Ratios

In addition to the CpG methylation analysis based on the use of cleavage profile of plasma cfDNA, the embodiments in this disclosure are also applicable to analyze CpG methylation analysis based on the cleavage profile of urinary cfDNA molecules. To investigate how urinary cfDNA fragmentation was correlated with DNA methylation, the cleavage profile of 18,280,640 hypermethylated CpG sites and 2,576,102 hypomethylated CpG sites were analyzed for 39 healthy control urinary cfDNA samples, with a median number of 75.8 million paired-end sequencing reads (interquartile range: 60.5-155 million). The cleavage ratio across genomic coordinates within a measurement window related to a CpG site was computed. As an example, the window herein was defined as 5 nucleotides (i.e., 5-nt) upstream and downstream of the C base in a CpG site (i.e., window size was 11 nt). For each sample, the cleavage profile from hypermethylated CpG sites or hypomethylated CpG sites were merged by calculating the mean cleavage ratio of each position within the 11-nt window.

Figure 105:
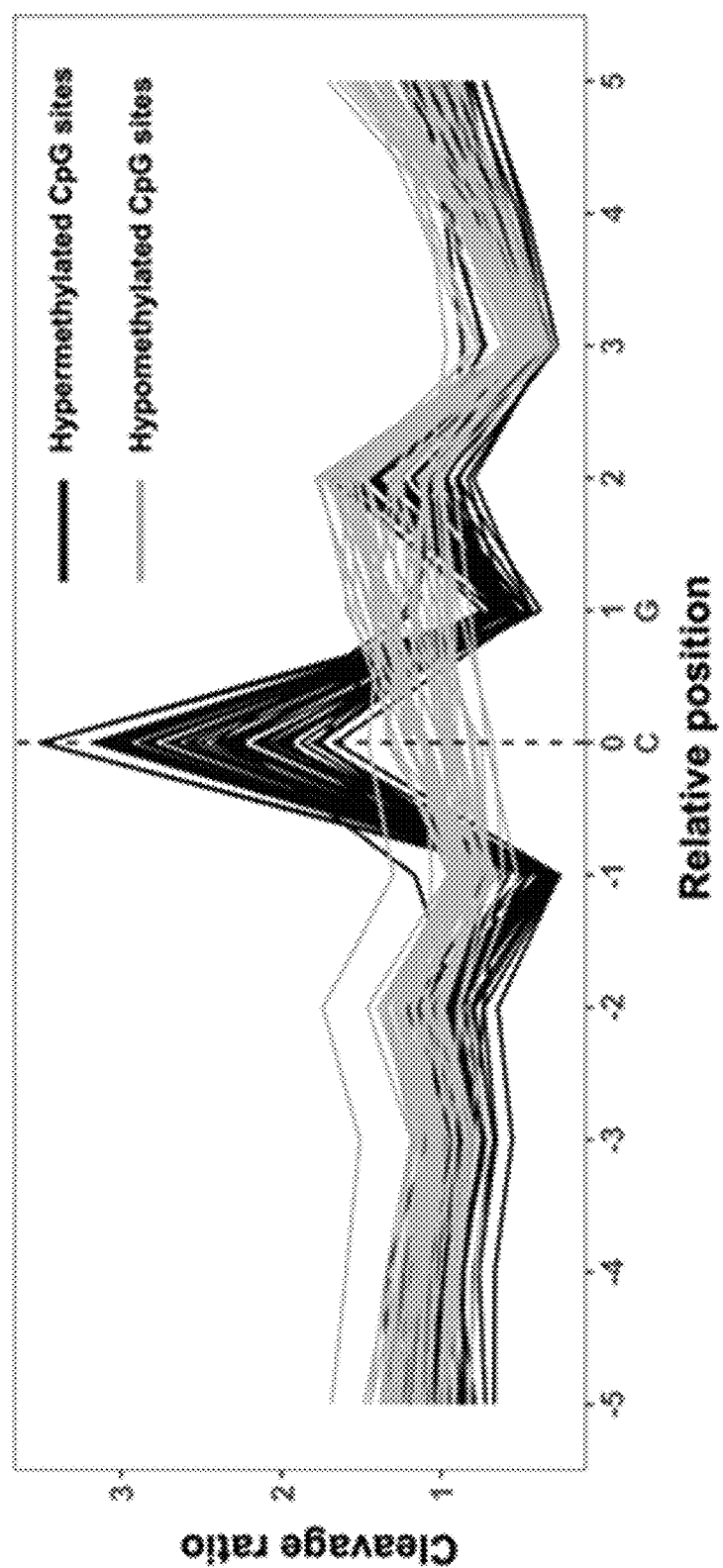
FIG. 105 shows a comparison of cleavage profiles between hypermethylated and hypomethylated CpG sites in urinary cfDNA samples of healthy controls.

FIG. 105 shows a comparison of cleavage profiles between hypermethylated and hypomethylated CpG sites in urinary cfDNA samples of healthy controls. The x-axis represents the nucleotide positions relative to a CpG site within a measurement window. The y-axis represents the mean cleavage ratio. FIG. 105 for urine is determined in a similar manner as cleavage profiles for plasma.

As shown in FIG. 105, the merged cleavage profiles of hypermethylated CpG sites showed a higher cutting preference at the position '0' (i.e., the cytosine nucleotide of the CpG site in question) (median cleavage ratio: 2.40; range: 1.66-3.51) than hypomethylated CpG sites (median cleavage ratio: 1.09; range: 0.67-1.46) (P value <0.001, Mann-Whitney U test). In contrast, at the position '−1' (i.e., one base before the cytosine nucleotide of the CpG site in question) and '1' (i.e., one base after the cytosine nucleotide of the CpG site in question), hypermethylated CpG sites showed a lower cutting preference (position '−1': median cleavage ratio: 0.37; range: 0.26-1.16; position '1': median cleavage ratio: 0.58; range: 0.38-1.22) than hypomethylated CpG sites (position '−1': median cleavage ratio: 0.83; range: 0.53-1.30; position '1': median cleavage ratio: 1.27; range: 0.82-1.60) (P value <0.001, Mann-Whitney U test).

The differential cleavage through methylation-aware fragmentation in urinary cfDNA at positions '0', '−1', and '1' relative to a CpG site would lead to the differential presentation of end motifs. Methylated CpG sites tended to have more endpoints at the position '0', enriching 5' CGN motifs, but less at the position '−1' and '1', depleting 5' NCG motifs and 5'C^GN motifs, respectively. 5' C^GN motifs refer to those motifs with a 'G' nucleotide at the 5' end of the cfDNA molecule and a 'C' nucleotide at one base before the 5' end (e.g., as determined by aligning to a reference genome). In contrast, the unmethylated CpG site attenuated such cutting preference. Thus, the number of DNA molecules with CGN, NCG, and C^GN ends correlate with the methylation status of CpGs at or near the ends of cell-free DNA molecules. The difference at '1' (C^GN motif) differs for urine relative to plasma, as not much difference was seen between methylated or unmethylated at the '1' position for plasma.

We further explored the possibility of using the relative amount of urinary cfDNA molecules terminated with CGN, NCG, or C^GN motif to reflect the methylation patterns. Individual amounts (as opposed to relative amounts) can also be used, e.g., with normalization by a total number of sequence reads or molecules analyzed; such normalization can be performed with any of the amounts described in this disclosure. As various examples, the relative amount could be measured by a ratio (such as the CGN/NCG motif ratio, CGN/(CGN+NCG), CGN/C^GN, or CGN/(NCG+C^GN), etc.).

FIGS. 106A-106D show boxplots illustrating the difference of methylation density (FIG. 106A), CGN/NCG ratio (FIG. 106B), CGN/C^G motif ratio (FIG. 106C), CGN/(NCG+C^G) motif ratio (FIG. 106D) across genome-wide regions, Alu regions and CpG islands in urinary cfDNA of healthy controls. Each dot represents a urinary cfDNA sample.

As shown in FIG. 106A, Alu regions showed higher methylation levels, while CpG islands showed lower methylation levels, compared to the overall methylation level of the whole genome in the human genome from 39 healthy control urinary cfDNA. We observed that the motif ratios (i.e., the CGN/NCG motif ratio, the CGN/C^G motif ratio, and the CGN/(CGN+C^G) motif ratio) across Alu regions, CpG islands, and the whole genome were concordant with the methylation levels determined by bisulfite sequencing (FIGS. 106B-106D). Thus, any of these three example values (as well as other example values involving CGN, NCG, and/or C^GN) can be used to determine methylation levels in a similar manner as described for plasma.

As other example values that can be used for urine, plasma, or other samples, one could measure the percentage of cell-free DNA molecules ended with CGN over the total number of cell-free DNA molecules analyzed (e.g., sequenced) or the total number of cell-free DNA ends. Similarly, one could also measure the percentage of cell-free DNA molecules ended with NCG or C^GN over the total number of cell-free DNA molecules analyzed (e.g., sequenced) or the total number of cell-free DNA ends.

As further examples, other methods can use statistical values of these example values to quantify the difference in cleavage profile between hypermethylated and hypomethylated CpGs for reflecting the methylation status of the CpG sites of interest, such as the moving average, variation in values within a window (e.g., variance or standard deviation (SD)), and entropy. For example, we can quantify the SD or variance to analyze the variability of the cleavage ratio in the measurement window. As shown in FIG. 105, one can see the variability in the cleavage ratio of hypermethylated profiles were larger than the hypomethylated profiles. Thus, the increase in the variation of values can indicate the increase of methylation level.

Moving average (also referred to as an average difference) is another metric to reflect the variability, e.g., by calculating the average absolute difference of all adjacent positions in the measurement window relative to the CpG site In another example, a moving average can be a measure accumulating the difference in the cleavage ratio between any two consecutive positions from the 5' to 3' or the 3' to 5'. For example, if a measurement window with 4 nt (e.g., from position −2 to position 1 with the C of the CpG site at position 0) is used, the moving average can be calculated based on the cleavage ratio (CR) of each position as follow:

$$\text{Moving average} = \frac{|CR_{(-2)} - CR_{(-1)}| + |CR_{(-1)} - CR_{(0)}| + |CR_{(0)} - CR_{(1)}|}{3}$$

Such statistical values are an example of using a first amount of cell-free DNA molecules ending at the CpG site and a second amount of cell-free DNA molecules ending at a first position within a window around the CpG site.

B. Tissue of Origin Analysis for Fractional Concentration

Besides determining methylation, the fractional concentration of clinically-relevant DNA can be determined in urine as described for plasma, and as is applicable to other samples that include cell-free DNA. The relative amounts of urinary cfDNA molecules terminated with CGN, NCG, or C^GN end motif at genomic regions exhibiting differential DNA methylation patterns across different tissue types can be used to determine the tissue of origin of urinary cfDNA molecules, e.g., a fractional concentration of DNA from a particular tissue type in urine.

We performed paired-end bisulfite sequencing (75 bp×2 (i.e., paired-end sequencing), Illumina) for urinary cfDNA from 26 kidney transplant patients (median number of paired-end reads: 154 million; IQR: 118-169 million). The genotypes regarding the donor and the recipient were obtained from the buffy coat using microarray-based genotyping technology (HumanOmni2.5 genotyping array Illumina), and informative SNPs were identified (i.e., where the recipient was homozygous (denoted as AA genotype), and the donor was heterozygous (denoted as AB genotype)). Donor-specific DNA fragments were identified according to the DNA fragments carrying donor-specific alleles at informative SNP sites. In this scenario, the B allele was donor-specific, and the DNA fragments carrying the B allele were deduced to be originated from donor tissues (i.e., kidney tissue). The number of donor-specific molecules (p) carrying the donor-specific alleles (B) was determined. The number of molecules (q) carrying the shared alleles (A) was determined. The donor DNA fraction across all cell-free DNA samples would be calculated by 2p/(p+q)*100%.

For illustration purposes, we determined the correlation between the CGN/NCG motif of the kidney-specific hypermethylated (n=8,827) and hypomethylated (n=14,692) CpG sites and the donor DNA fraction from urinary cfDNA of kidney transplant patients. Kidney-specific hypermethylated and hypomethylated CpG sites were identified using the bisulfite sequencing results of the buffy coat, kidney tissue, and urothelium. Kidney-specific hypermethylated sites were defined by those CpG sites with a methylation density of over 70% in the kidney tissue but below 30% in both the buffy coat and the urothelium. Kidney-specific hypomethylated sites were defined by those CpG sites with a methylation density of below 30% in the kidney tissue but over 70% in both the buffy coat and the urothelium.

Figure 107B:
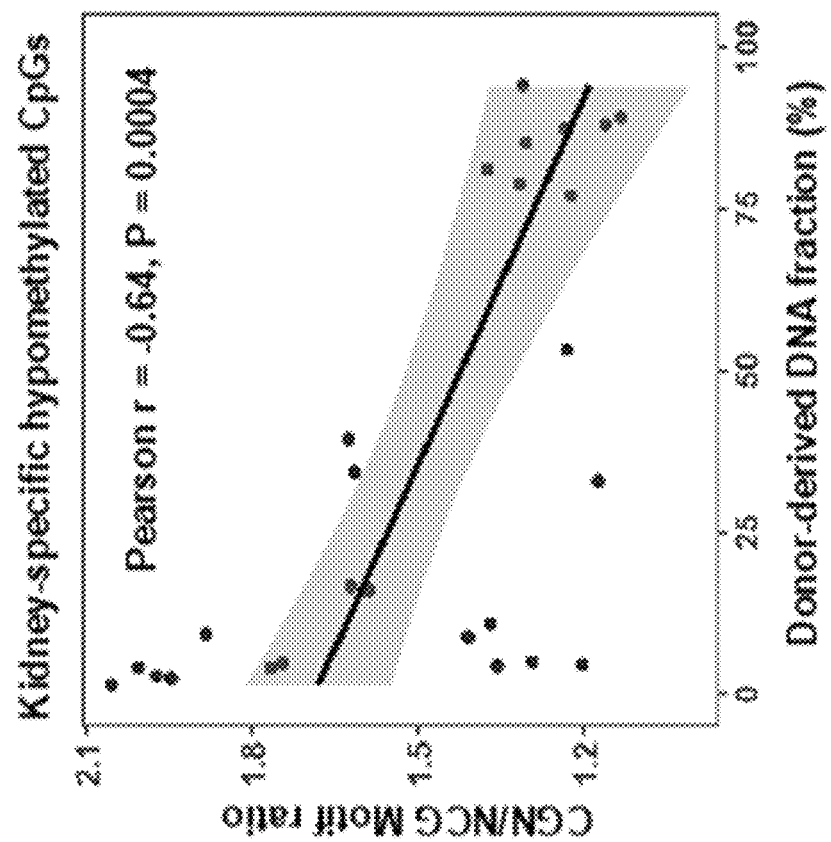
FIGS. 107A-107B show the correlation between the donor DNA fraction and the CGN/NCG ratio based on urinary cfDNA molecules originating from kidney-specific hypermethylated CpG sites (FIG. 107A), and kidney-specific hypomethylated CpG sites (FIG. 107B).
Figure 107A:
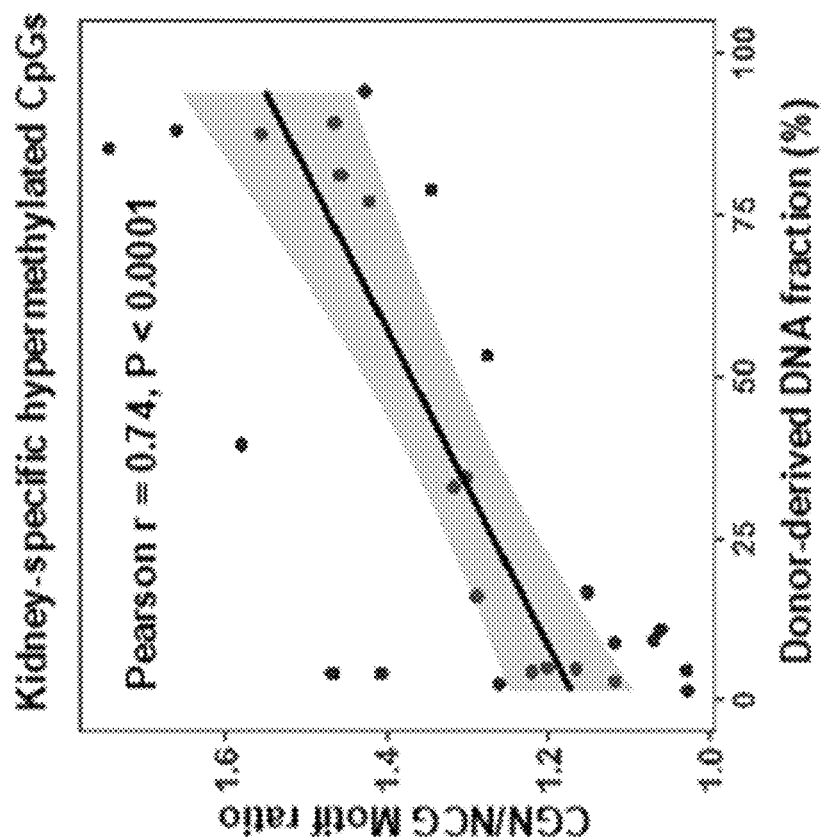

FIGS. 107A-107B show the correlation between the donor DNA fraction and the CGN/NCG ratio based on urinary cfDNA molecules originating from kidney-specific hypermethylated CpG sites (FIG. 107A), and kidney-specific hypomethylated CpG sites (FIG. 107B). As shown in FIGS. 107A-107B, the CGN/NCG ratio from kidney-specific hypermethylated CpG sites and hypomethylated CpG sites were positively and negatively correlated with the donor DNA fraction deduced by the donor-specific SNPs, respectively (Pearson's r: 0.74 and −0.64; P value <0.001 for both correlations). The data suggested that the relative amount of urinary cfDNA molecules ended with CGN and NCG (e.g., the CGN/NCG ratio) could be used for deducing the tissues of origin of urinary cfDNA molecules.

As the methylation-aware fragmentation in urinary cfDNA was closely related to the nuclease environment of the urine, various pre-analytic factors may influence the accuracy of the tissue of origin analysis through methylation-aware fragmentation, such as but not limited to the duration of cfDNA in the urine, the DNASE activity of the urine, and the PH value of the urine. To minimize the influence of those pre-analytic factors on the accuracy of tissue-of-origin analysis based on urinary cleavage profiles, cfDNA cleavage profiles from a set of reference CpG sites can be used to normalize those pre-analytic factors, which may affect the CGN/NCG ratio in tissue-specific regions for a sample.

The reference CpG sites include a first set of CpGs that were stably hypermethylated across various tissues (i.e., reference hypermethylated CpG sites, RefM) and a second set of CpGs that were stably hypomethylated across various tissues (i.e., reference hypomethylated CpG sites, RefU). In one embodiment, reference hypermethylated and hypomethylated CpG sites were determined based on the bisulfite sequencing results of the buffy coat, kidney tissues, and urothelium. Reference hypermethylated CpG sites were defined by those CpG sites with a methylation density of over 70% across all tissues, and reference hypomethylated sites were defined by those CpG sites with a methylation density of below 30% across all tissues.

Figures 108A, 108B:
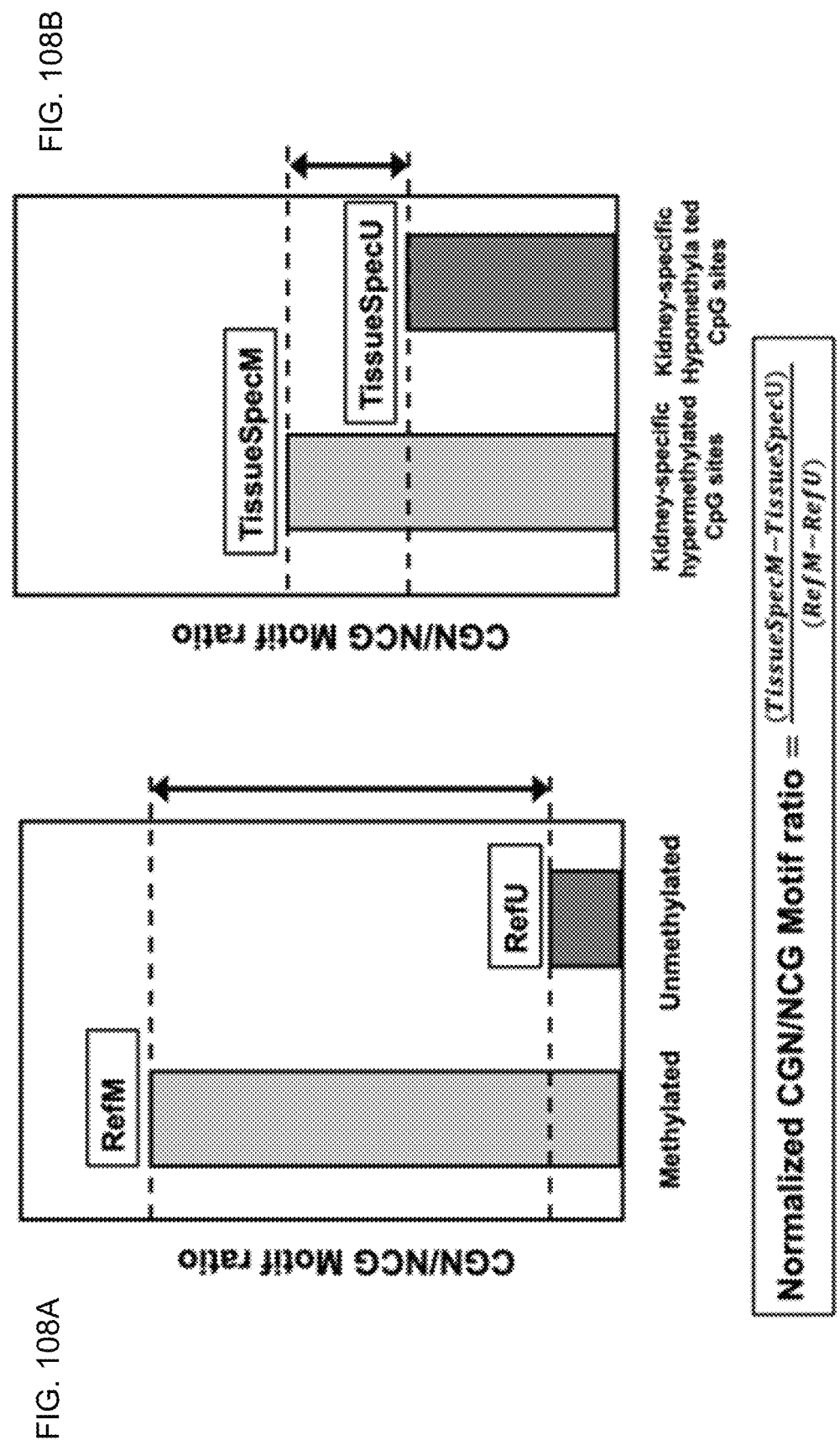
FIGS. 108A-108B shows a schematic for a CGN/NCG motif ratio normalization.

FIGS. 108A-108B shows a schematic for a CGN/NCG motif ratio normalization. As shown in FIG. 108A, the difference in CGN/NCG ratio between RefM and RefU was determined, denoted by RefM-RefU. Such a value can be used to normalize a tissue-specific value. For example, since the methylation difference is fixed (as hypermethylated and hypomethylated sites are used), the differences between RefM-RefU per patient will be a result of the other pre-analytic factors.

FIG. 108B shows the difference in CGN/NCG ratio from kidney-specific hypermethylated (TissueSpecM) and hypomethylated CpGs (TissueSpecU), denoted by TissueSpecM-TissueSpecU. This tissue-specific difference will depend on the amount of kidney DNA and the amount of pre-analytic factors. The pre-analytic factors can be filtered out by dividing by RefM-RefU, which has the same dependence on the pre-analytic factors.

The value of (TissueSpecM-TissueSpecU) can be normalized by (RefM-RefU) to reflect the kidney cfDNA fraction. FIG. 108 shows an example formula for the normalization. Other normalized values can just use the hypermethylated sites (e.g., just RefM) or just the hypomethylated sites (e.g., just RefU), or other combinations of the two. Further, the normalization can be a difference, such as TissueSpecM-RefM. Such a normalized value could minimize the pre-analytic factors mentioned above, as the numerator and denominator would be affected by those pre-analytic factors to a similar degree and thus would be cancelled out.

Figure 109:
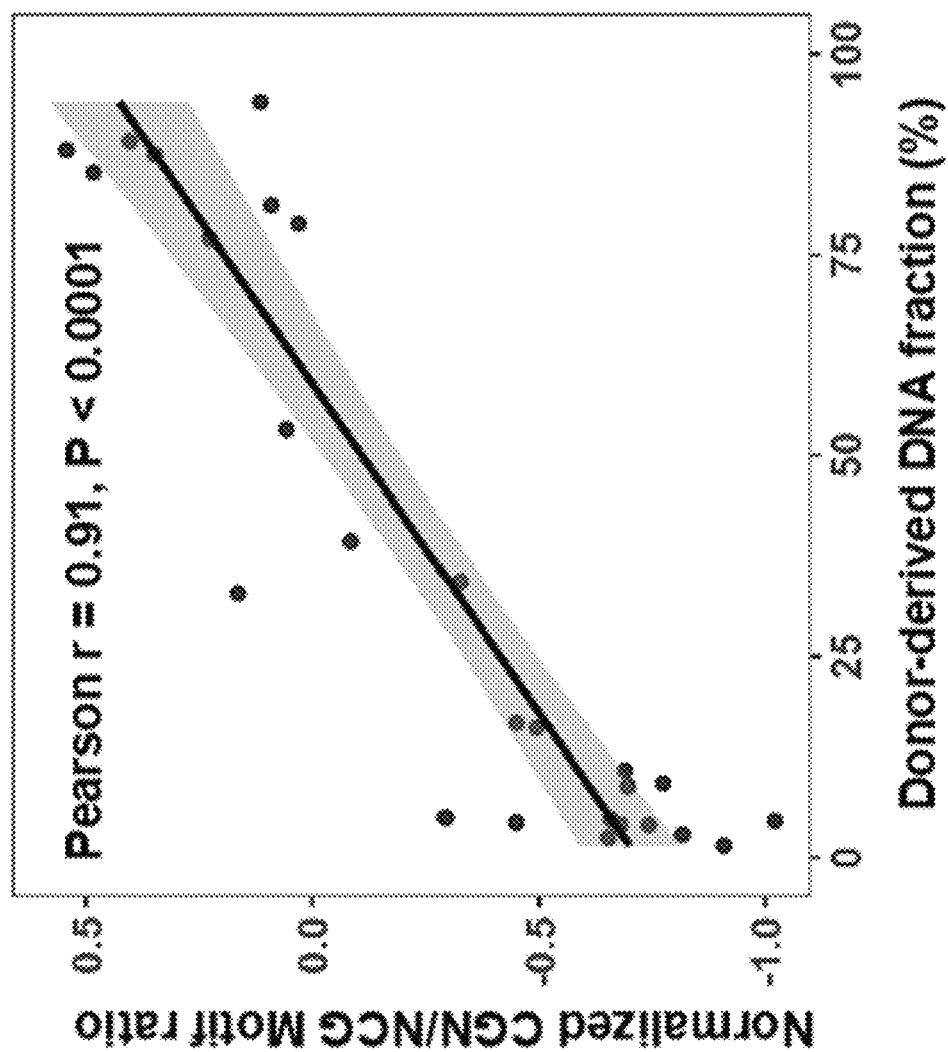
FIG. 109 shows the correlation between the donor DNA fraction and the normalized CGN/NCG motif ratio of urinary cfDNA from kidney transplant cases.

FIG. 109 shows the correlation between the donor DNA fraction and the normalized CGN/NCG ratio of urinary cfDNA from kidney transplant cases. For illustration purposes, we determined the CGN/NCG motif ratio of the reference hyper- (n=14,535,312) and hypomethylated (n=1,713,148) CpG sites). As shown in FIG. 109, the normalized CGN/NCG motif ratio calculated from kidney-specific hypermethylated and hypomethylated CpG sites showed a better correlation with the donor DNA fraction deduced by the donor-specific SNPs (Pearson's r: 0.91; P value <0.0001), compared with the CGN/NCG ratio before normalization (absolute Pearson's r<0.74; P value <0.001). The Pearson's r increased from 0.74 to 0.91. As other examples, the normalized CGN/NCG motif ratio could be calculated as but not limited to TissueSpecM/RefU, TissueSpecU/RefM, TissueSpecM/RefM, TissueSpecU/RefU, TissueSpecU/(RefM-RefU), or TissueSpecM/(RefM-RefU).

The CGN/NCG ratio (and other variants) can also be used to predict transrenal DNA contributions (another example of clinically-relevant DNA). For illustration purposes, we determined the CGN/NCG motif ratio of blood cell-specific hypermethylated (n=42,294) and hypomethylated (n=73,925) CpG sites and the reference hypermethylated (n=17,167,208) and hypomethylated (n=2,360,363) CpG sites for urinary cfDNA from 5 bone marrow transplant patients with the use of paired-end bisulfite sequencing (75 bp×2; Illumina). The median number of paired-end reads was 86.2 million (IQR: 69.7-87.5 million). Blood cell-specific hypermethylated and hypomethylated CpG sites were identified using the bisulfite sequencing results of the buffy coat, kidney tissue, and urothelium. Blood cell-specific hypermethylated sites were defined by those CpG sites with a methylation density of over 70% in the buffy coat but below 30% in both the kidney tissue and the urothelium. Blood cell-specific hypomethylated sites were defined by those CpG sites with a methylation density of below 30% in the buffy coat but over 70% in both the kidney tissue and the urothelium. Reference hypermethylated CpG sites were defined by those CpG sites with a methylation density of over 70% across all tissues, and reference hypomethylated sites were defined by those CpG sites with a methylation density of below 30% across all tissues.

Figure 110B:
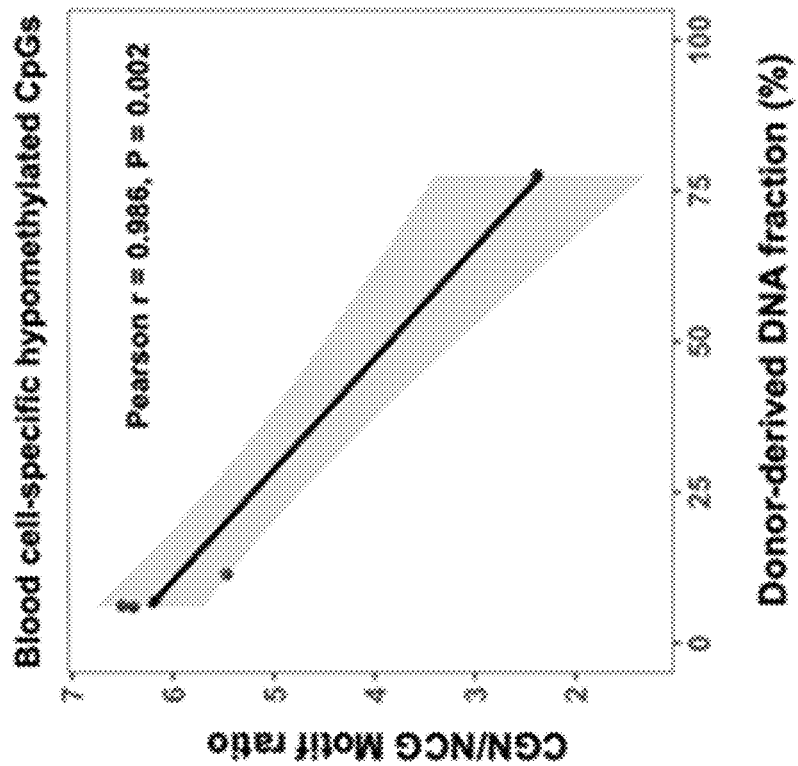
FIGS. 110A-110B show the correlation between the donor DNA fraction and the CGN/NCG motif ratio based on urinary cfDNA molecules originating from blood cell-specific hypermethylated CpG sites (FIG. 110A), and blood cell-specific hypomethylated CpG sites (FIG. 110B).
Figure 110A:
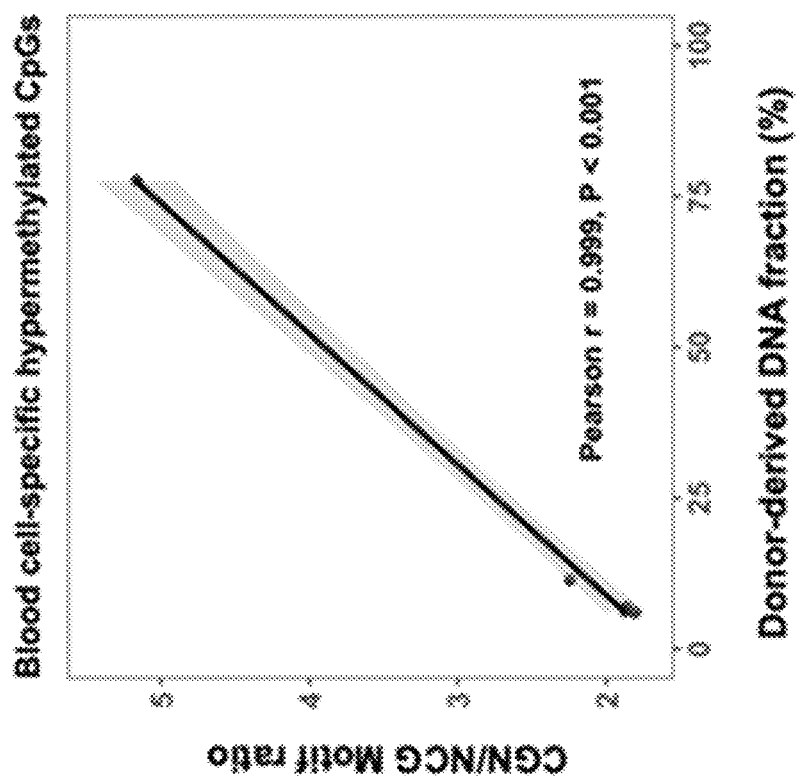

FIGS. 110A-110B show the correlation between the donor DNA fraction and the CGN/NCG ratio based on urinary cfDNA molecules originating from blood cell-specific hypermethylated CpG sites (FIG. 110A), and blood cell-specific hypomethylated CpG sites (FIG. 110B). As shown, the CGN/NCG ratio from those blood cell-specific hypermethylated CpG sites and hypomethylated CpG sites were positively (Pearson's r: 0.999; P value <0.001) and negatively (Pearson's r: −0.986; P value=0.002) correlated with the donor DNA fraction deduced by the donor-specific SNPs, respectively.

Figure 111:
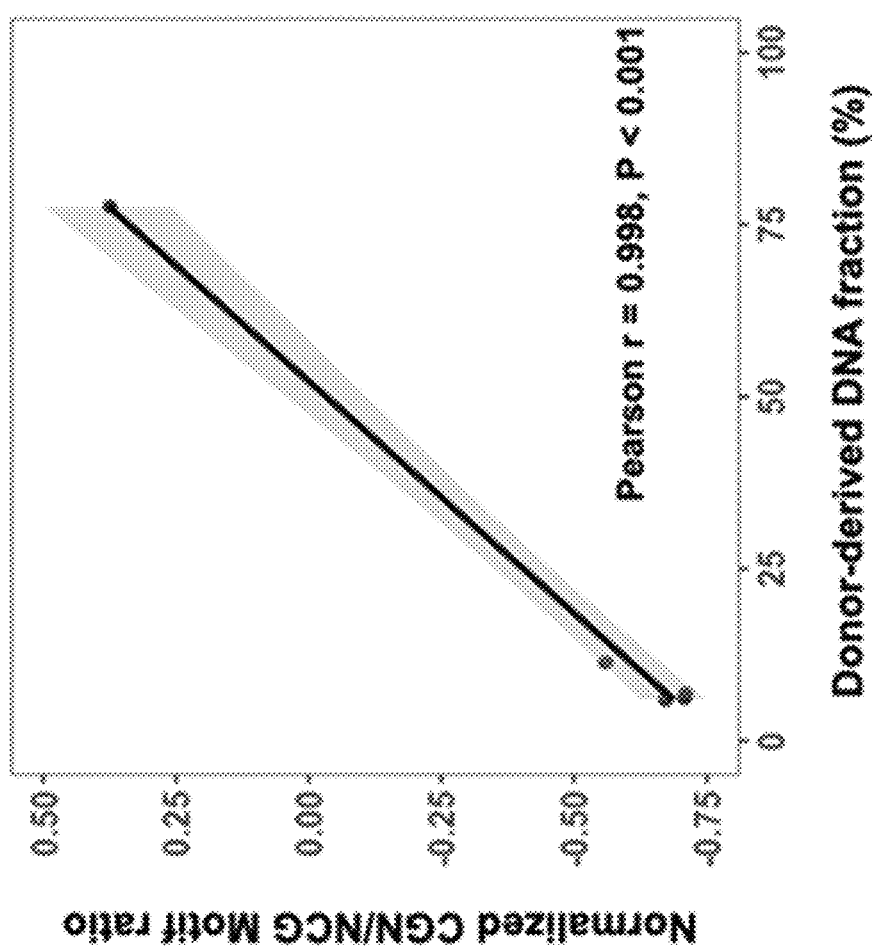
FIG. 111 shows the correlation between the donor DNA fraction and the normalized CGN/NCG motif ratio of urinary cfDNA from bone marrow transplant patients.

FIG. 111 shows the correlation between the donor DNA fraction and the normalized CGN/NCG ratio of urinary cfDNA from bone marrow transplant patients. The normalized CGN/NCG motif ratio calculated from blood cell-specific hypermethylated and hypomethylated CpG sites also showed a good correlation with the donor DNA fraction deduced by the donor-specific SNPs (Pearson's r: 0.998; P value <0.001). The data suggested that the relative amount of DNA molecules ended with CGN and NCG (e.g., the CGN/NCG ratio) could be used for deducing the transrenal DNA fraction of urinary cfDNA molecules.

In some embodiments, the CGN/NCG ratio could be used to predict the DNA contributions of other tissues, including, but not limited to, the bladder, liver, brain, T cells, B cells, neutrophils, muscle, heart, placenta, ovary, breast, testis, tumour tissues (e.g. bladder cancer and kidney cancer), diseased tissues (e.g. tissues involved in inflammation (such as bladder tissues involved in inflammation, and others) and tissues with increased cell death (such as ischemic or necrotic tissues or a tissue involved in traumatic injury), and tissues infected with infectious agents (such as a virus or a bacterium)), etc.

Accordingly, various embodiments can use a normalized amount to determine a fractional concentration of a first tissue type, e.g., transplant, fetal, tumor, or transrenal. For example, a second set of CpG sites can be identified that are all hypomethylated or all hypermethylated across a plurality of tissue types in the reference genome. A second amount of cell-free DNA molecules ending around any one the second set of CpG sites can be determined. And determining the fractional concentration can include normalizing the first amount with the second amount to obtain a normalized first amount that is compared to the calibration value.

C. Bladder Cancer Detection

Examples for plasma include pathology detection. As an example for pathology detection using urine, bladder cancer was investigated.

1. Motif Analysis

End motif frequencies from tissue-specific hypomethylation or hypermethylation could be used to detect and monitor diseases such as cancer. We sequenced urinary cfDNA from 39 healthy controls (median number of 75.8 million paired-end sequencing reads (IQR: 60.5-155.0 million)) and 46 patients with bladder cancer (median number of 42.0 million paired-end sequencing reads (IQR: 30.2-60.4 million)). For illustration purposes, the CGN/NCG motif ratio of the bladder cancer-specific hypermethylated (n=5,060) and hypomethylated (n=284,541) CpG from the urinary cfDNA were calculated. Bladder cancer-specific hypermethylated and hypomethylated CpG sites were identified using the bisulfite sequencing results of the buffy coat, kidney tissue, urothelium, and bladder cancer tissues. Bladder cancer-specific hypermethylated sites were defined by those CpG sites with a methylation density of over 70% in the bladder cancer tissues but below 30% in the buffy coat, urothelium, and kidney tissues. Bladder cancer-specific hypomethylated sites were defined by those CpG sites with a methylation density of below 30% in the bladder cancer tissues but over 70% in the buffy coat, urothelium, and kidney tissues. Such analysis is similar to section VII.B.

Figure 112B:
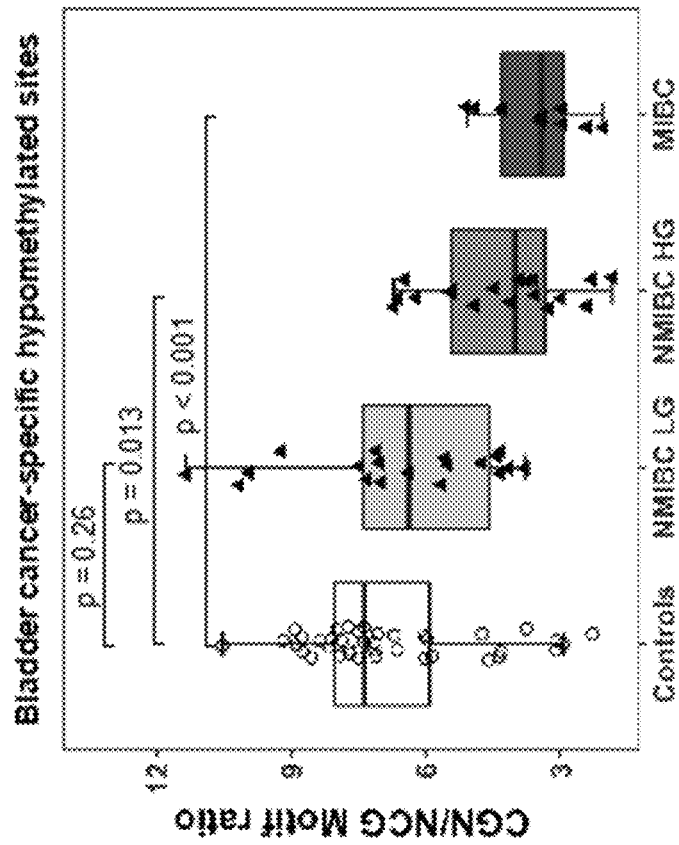
FIGS. 112A-112B are boxplots showing the CGN/NCG motif ratios from bladder cancer-specific hypermethylated and hypomethylated CpGs across healthy controls (controls), patients with low-grade non-muscle-invasive bladder cancer (NMIBC LG), high-grade non-muscle-invasive bladder cancer (NMIBC HG), and muscle-invasive bladder cancer (MIBC).
Figure 112A:
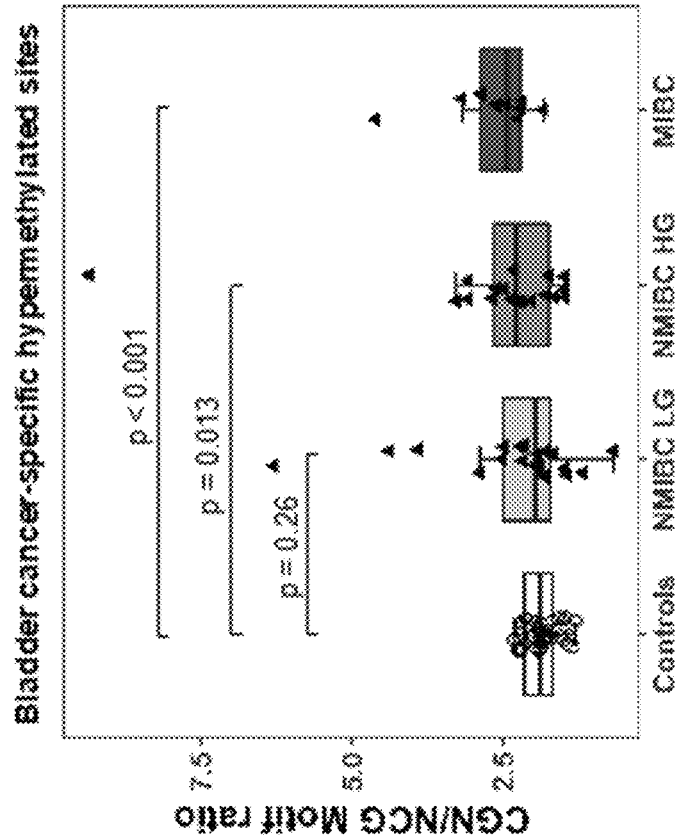

FIGS. 112A-112B are boxplots showing the CGN/NCG motif ratios from bladder cancer-specific hypermethylated and hypomethylated CpGs across healthy controls (controls), patients with low-grade non-muscle-invasive bladder cancer (NMIBC LG), high-grade non-muscle-invasive bladder cancer (NMIBC HG), and muscle-invasive bladder cancer (MIBC). Compared to healthy controls, a significantly higher CGN/NCG motif ratio was observed across bladder cancer-specific hypermethylated CpGs (P value=0.013 and <0.001, respectively; Kruskal-Wallis test), and a significantly lower CGN/NCG motif ratio was observed across bladder cancer-specific hypomethylated CpGs (P value=0.013 and <0.001, respectively; Kruskal-Wallis test) for those patients with high-grade non-muscle-invasive bladder cancer (NMIBC HG) and muscle-invasive bladder cancer (MIBC). However, in both bladder cancer-specific hypermethylated and hypomethylated CpGs, no significant difference was observed in CGN/NCG motif ratio between healthy controls and patients with low-grade non-muscle-invasive bladder cancer (NMIBC LG).

Normalization can be performed in a similar manner as in the previous description. Thus, a normalized CGN/NCG motif ratio from bladder cancer-specific hypermethylated and hypomethylated CpGs could be used for bladder cancer diagnosis.

For illustration purposes, we analyzed the CGN/NCG motif ratio of the reference hyper- (n=7,833,538) and hypomethylated (n=759,455) CpGs. Reference hypermethylated sites were defined by those CpG sites with a methylation density of over 70% in the bladder cancer tissues, buffy coat, urothelium, and kidney tissues. Reference hypomethylated sites were defined by those CpG sites with a methylation density of below 30% in the bladder cancer tissues, buffy coat, urothelium, and kidney tissues. The CGN/NCG motif ratio from bladder cancer-specific hypermethylated (TumorSpecM) and hypomethylated (TumorSpecU) CpGs could be normalized by the CGN/NCG motif ratio from reference hypermethylated (RefM) and hypomethylated (RefU) CpGs as follow:

$$\text{Normalized } CGN/NCG \text{ motif ratio} = \frac{\text{Tumor } SpecM - \text{Tumor } SpecU}{RefM - RefU}$$

Figure 113:
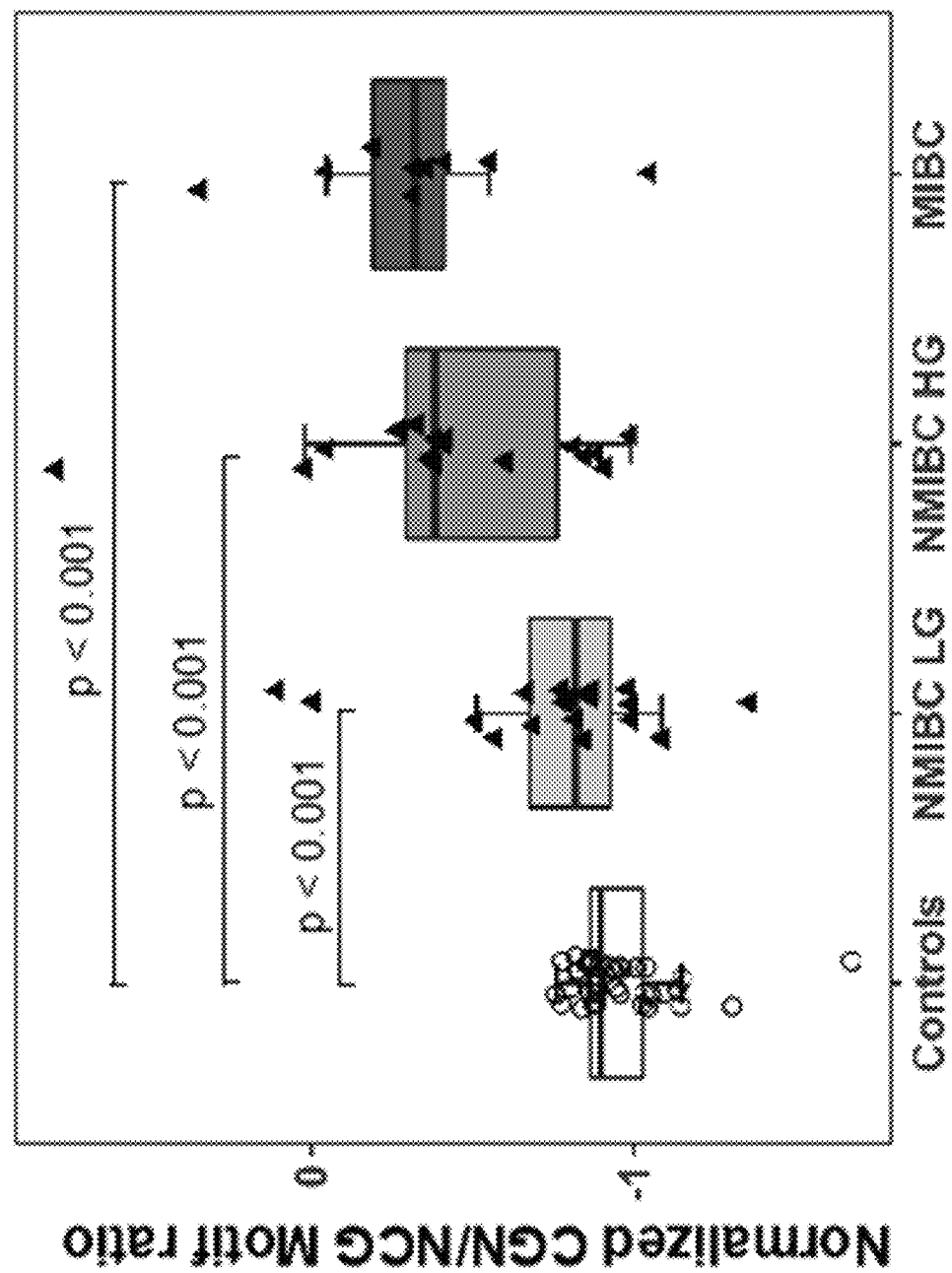
FIG. 113 is a boxplot showing the normalized CGN/NCG motif ratios from bladder cancer-specific hypermethylated and hypomethylated CpGs across healthy controls (controls), patients with low-grade non-muscle-invasive bladder cancer (NMIBC LG), high-grade non-muscle-invasive bladder cancer (NMIBC HG), and muscle-invasive bladder cancer (MIBC).

FIG. 113 is a boxplot showing the normalized CGN/NCG motif ratios from bladder cancer-specific hypermethylated and hypomethylated CpGs across healthy controls (controls), patients with low-grade non-muscle-invasive bladder cancer (NMIBC LG), high-grade non-muscle-invasive bladder cancer (NMIBC HG), and muscle-invasive bladder cancer (MIBC). As shown in FIG. 113, compared with healthy controls, a significantly higher normalized CGN/NCG motif ratio was observed across bladder cancer-specific hypermethylated and hypomethylated CpGs for patients with NMIBC LG, NMIBC HG, and MIBC (P value <0.001, Kruskal-Wallis test). Those results indicated that the normalization of tissue-specific CGN/NCG motif ratio with the use of proper reference methylation sties could improve the signal-to-noise level, leading to a better diagnosis power.

2. Cleavage Profile Analysis

The proximal cleavage profiles from tissue-specific CpGs can be useful for deducing DNA contribution from different tissues into the urinary cfDNA DNA pool, such as bladder cancer DNA contribution in bladder cancer patients, which could be used for bladder cancer diagnosis. Such an analysis can be similar to that performed in section VII.B.4. We determined the cleavage profiles from bladder cancer-specific hypermethylated and hypomethylated CpG sites. Such cleavage profiles were used for training a SVM model to perform bladder cancer detection.

Figure 114:
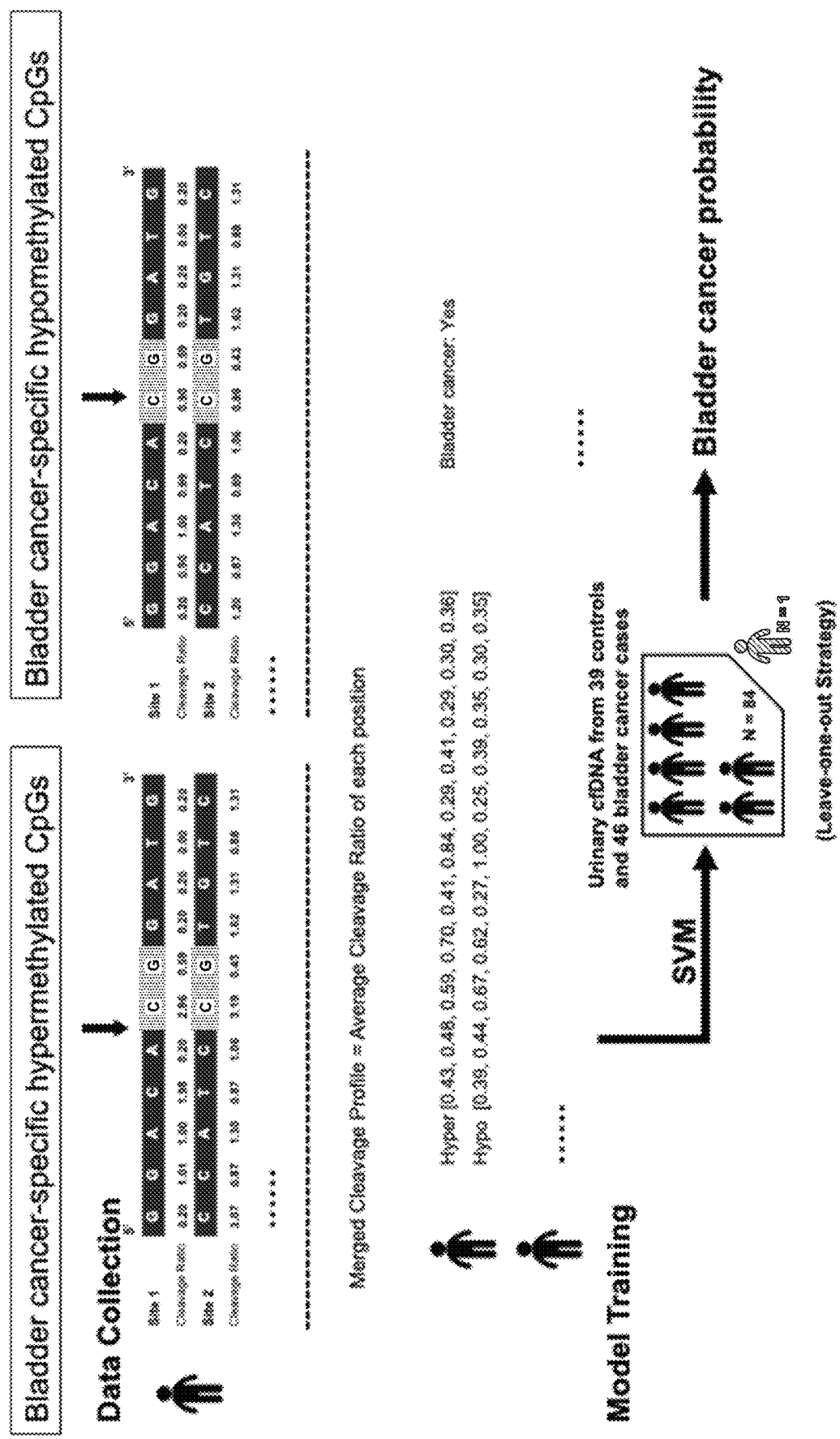
FIG. 114 is a schematic for SVM model training based on the cleavage profiles from bladder cancer-specific hypermethylated and hypomethylated CpG sites to perform bladder cancer detection. Figure discloses SEQ ID NOS 9, 11, 9, and 11, respectively, in order of appearance.

FIG. 114 is a schematic for SVM model training based on the cleavage profiles from bladder cancer-specific hypermethylated and hypomethylated CpG sites to perform bladder cancer detection. The model uses the cleavage profile to predict the probability of bladder cancer. As shown, 11 bases from the hypermethylated CpG site and the hypomethylated CpG site are used, but other number of bases can be used. The cleavage profiles (e.g., cleavage ratio at each position) at the hypermethylated sites can be merged (e.g., average at each position), and the same can be done for the hypomethylated sites. These two feature vectors can be used to train the SVM model, e.g., using a leave one out strategy.

Figure 115B:
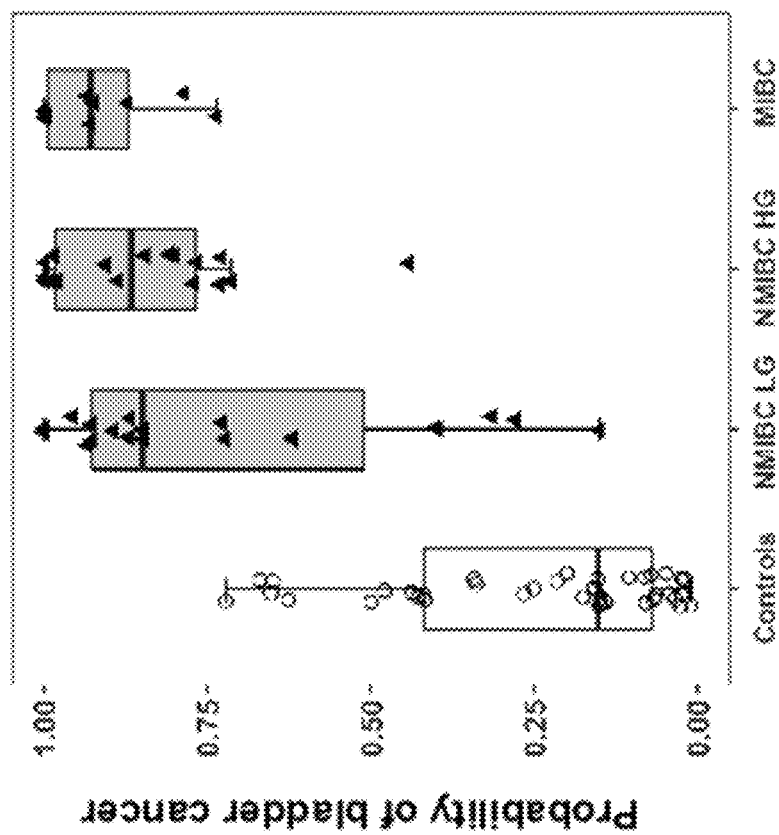
FIGS. 115A-115B show the performance of bladder cancer detection on the basis of the cleavage profiles.
Figure 115A:
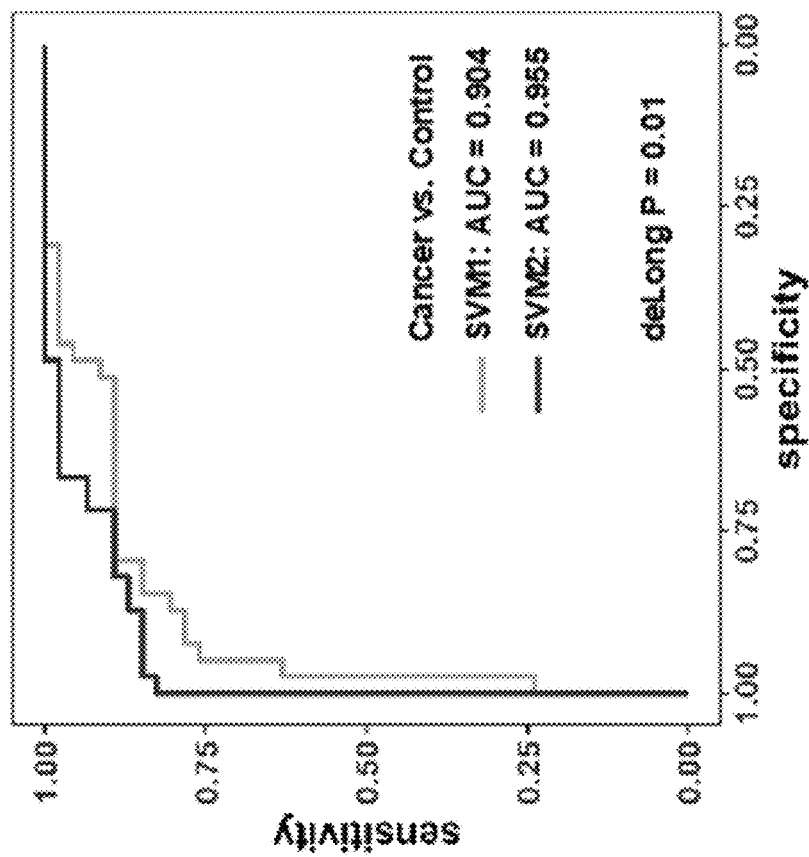

FIGS. 115A-115B shows the performance of bladder cancer detection on the basis of the cleavage profiles. FIG. 115A shows an ROC analysis in differentiating between patients with and without bladder cancer using the SVM model trained by the cleavage profiles from bladder cancer-specific hypermethylated and hypomethylated CpGs (SVM1). The model performance (SVM1) provides an AUC of 0.904.

To further maximize the utility of cleavage profiles, we constructed an SVM model using the cleavage profiles from bladder cancer-specific hypermethylated, bladder cancer-specific hypomethylated, reference hypermethylated, and reference hypomethylated CpGs to perform bladder cancer detection (SVM2). Thus, there are four feature vectors, e.g., each having a specified number of cleavage ratios, depending on the size of the window around the site. The reference sites are hypermethylated or hypomethylated across a plurality of tissues, e.g., as described above for the normalization. This refined model performance (SVM2) showed significant improvement up to an AUC of 0.955 compared with the SVM1 shown above (AUC: 0.904) (P=0.01, deLong test).

FIG. 115B is a boxplot showing the probability of bladder cancer predicted by SVM2 across healthy controls (controls), patients with low-grade non-muscle-invasive bladder cancer (NMIBC LG), high-grade non-muscle-invasive bladder cancer (NMIBC HG), and muscle-invasive bladder cancer (MIBC). As shown, when the subject has cancer, there is a higher probability compared to non-cancer, and the probability increases with the stage of cancer.

3. 3-Mer End Motif Analysis

In one embodiment, 5' 3-mer end motifs, 5' 3-mer CG-containing end motifs or other methylation-related cfDNA fragmentomic features from bladder cancer-specific hypermethylated and hypomethylated CpGs could be used for bladder cancer detection. We constructed an SVM model using 5' 3-mer CG containing end motifs from bladder cancer-specific hypermethylated and hypomethylated CpGs to perform bladder cancer detection.

Figure 116B:
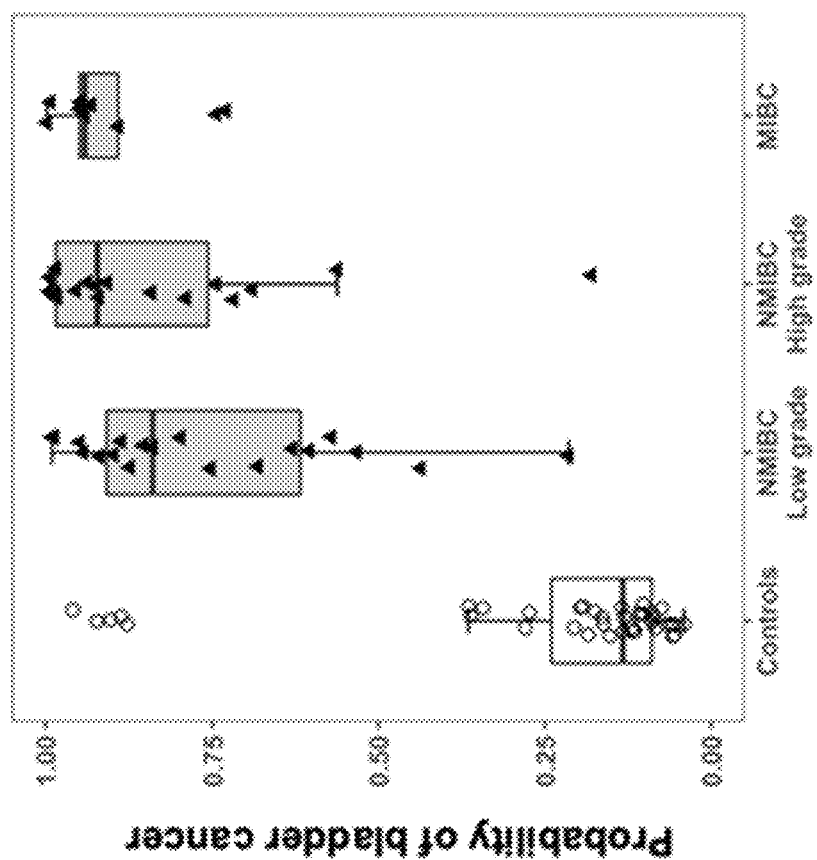
FIGS. 116A-116B show the performance of bladder cancer detection on the basis of 5' 3-mer CG containing end motifs.
Figure 116A:
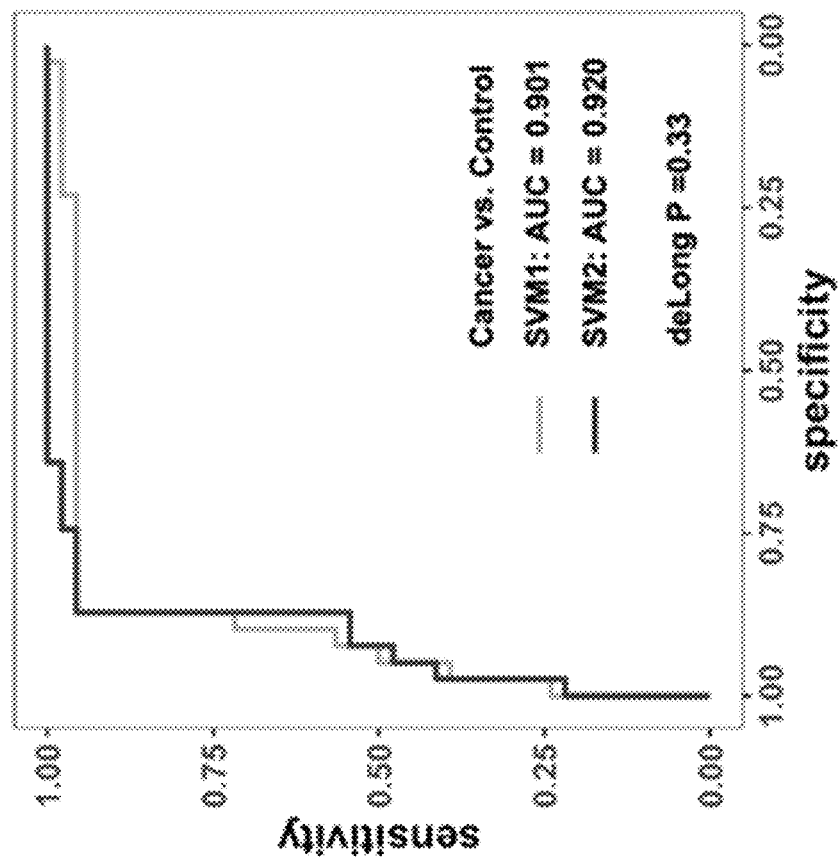

FIG. 116A is an ROC analysis in differentiating between patients with and without bladder cancer using the SVM model trained by the 5' 3-mer CG containing end motifs from bladder cancer-specific hypermethylated and hypomethylated CpGs (SVM1) or from bladder cancer-specific hypermethylated and hypomethylated CpGs and reference hypermethylated and hypomethylated CpGs (SVM2). The reference CpGs are defined above. The model performance (SVM1) could reach an AUC of 0.901. This refined model performance (SVM2) showed improvement up to an AUC of 0.920 compared with the SVM1 shown above (AUC: 0.901).

FIG. 116B is a boxplot shows the probability of bladder cancer predicted by SVM2 across healthy controls (controls), patients with low-grade non-muscle-invasive bladder cancer (NMIBC LG), high-grade non-muscle-invasive bladder cancer (NMIBC HG), and muscle-invasive bladder cancer (MIBC). As shown, when the subject has cancer, there is a higher probability compared to non-cancer, and the probability increases with the stage of cancer.

4. Analysis by Bins

Some embodiment can perform a per bin (region of the genome) analysis, e.g., with respect to method 7200. DNA fragments from each bin can be analyzed to determine an end motif frequency around a CpG site (e.g., CGN, NCG, C^GN, or ratios thereof, including normalized values). If a bin has an aberrant CG end motif frequency, then a bin can be labelled as aberrant. A number of aberrant bins can be used to detect a level of pathology, e.g., cancer.

For example, the CGN/NCG motif ratio could be used to reflect hypomethylation levels of urinary cfDNA, which could be applied to bladder cancer detection. For each bin, we can compare the CGN/NCG motif ratio (or other CG end frequency) to a reference (cutoff) value, e.g., determined from a healthy individual. Thus, each bin can have a different reference value, which may be a lower boundary based on a standard deviation (e.g., different of 3 STD from an average). If the motif ratio is low enough, we can infer the bin is hypomethylated. A determination can also be made for hypermethylation. The number of aberrant bins can be compared to a threshold, which can discriminate between subjects with different levels of cancer, e.g., those with cancer and those without cancer.

If normalization is performed, the reference hypermethylated sites (n=7,833,538) can be defined by those CpG sites with a methylation density of over 70% in the bladder cancer tissues, buffy coat, urothelium, and kidney tissues. Reference hypomethylated sites (n=759,455) can be defined by those CpG sites with a methylation density of below 30% in the bladder cancer tissues, buffy coat, urothelium, and kidney tissues. The CGN/NCG motif ratio from each bin (BinR) can be normalized by the CGN/NCG motif ratio from reference hypermethylated (RefM) and hypomethylated (RefU) CpGs as follows:

$$\text{Normalized } CGN/NCG \text{ motif ratio} = \frac{\text{Bin} R - RefU}{RefM - RefU}$$

The values for RefM and RefU are patient-specific.

Figure 117:
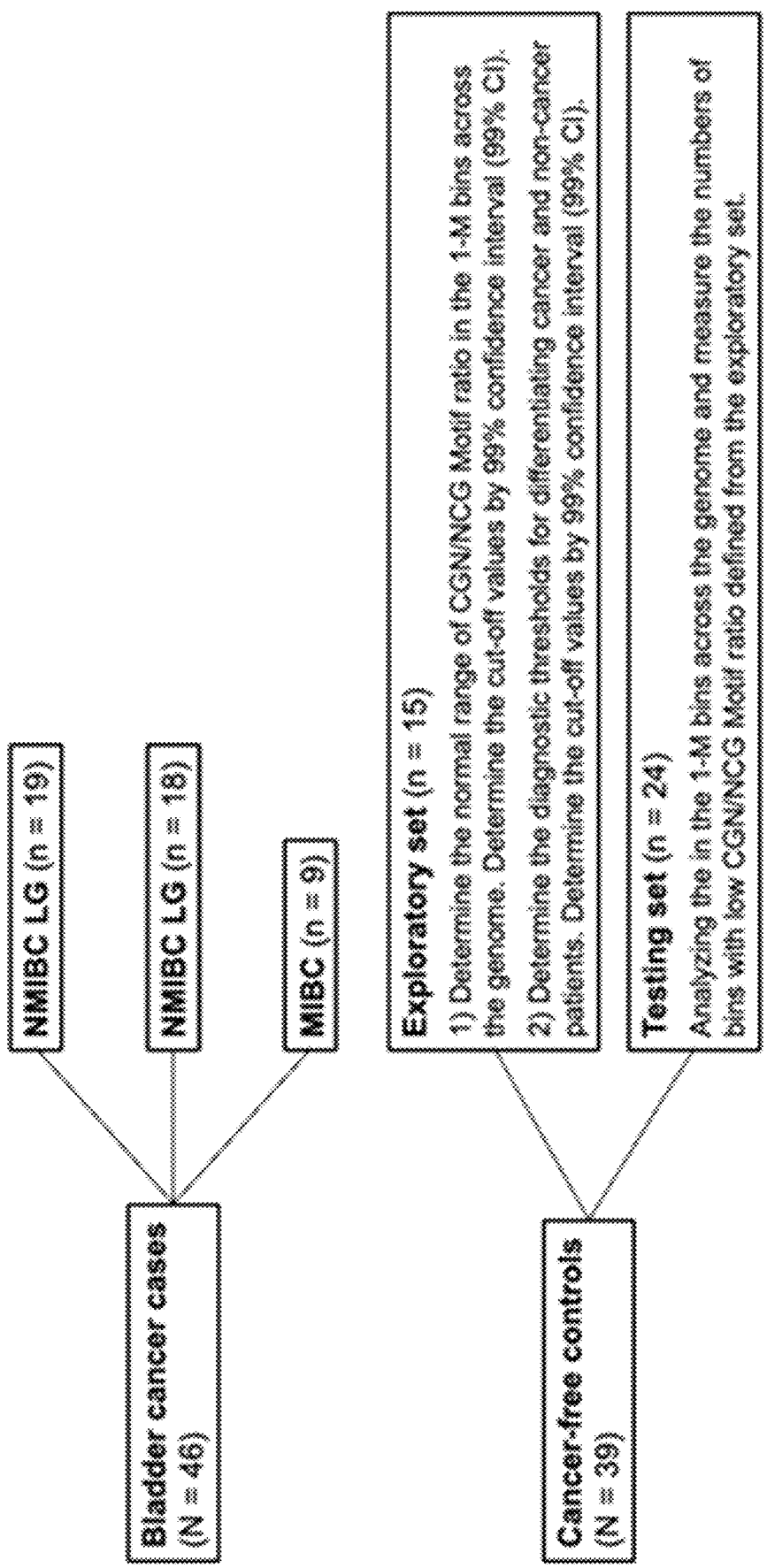
FIG. 117 is a schematic diagram of the bladder cancer cases and cancer-free controls.

FIG. 117 is a schematic diagram of the bladder cancer cases and cancer-free controls. The cancer-free controls are separated into an exploratory set and a testing set. In one example, 15 cancer-free controls in the exploratory set were used to establish the baseline normalized CGN/NCG motif ratio across the whole genome by 1-Mb bins. Bins may be of other size, e.g., 100 kb, 500 kb, 2 MB, 3 Mb, and so on.

Two items are determined for the exploratory set. For (1), the cutoff value to determine whether a bin is aberrant was determined by the 99% confidence interval, but other criteria can be used. In one example, a bin was determined to be a significantly low normalized CGN/NCG ratio bin when it with a normalized CGN/NCG motif ratio below 2.56 SD of the mean of the normalized CGN/NCG motif ratio in the exploratory set. In some other embodiments, the number of SD below the mean could be 0.5, 1, 2, 3, 4, 5, 10, etc.

For (2), the diagnostic threshold for the number of aberrant bins to differentiate between cancer and non-cancer. The number of bins showing significantly low CGN/NCG motif ratio (referred to as motif aberration) were calculated for each case for the exploratory set. The diagnostic threshold for classifying whether or not a patient has a cancer were determined by using the mean value of motif aberration values plus 2.56 SD based on the exploratory set. In some other embodiments, the number of SD above the mean could be 0.5, 1, 2, 3, 4, 5, 10, etc.

The bladder cancer cases and the testing set are then analyzed for performance using the per-bin cutoffs from (1) and the threshold from (2). The analysis was applied to all remaining cases that were not present in exploratory dataset (i.e., testing set), including 24 cancer-free controls and 46 patients with bladder cancer.

Figure 118B:
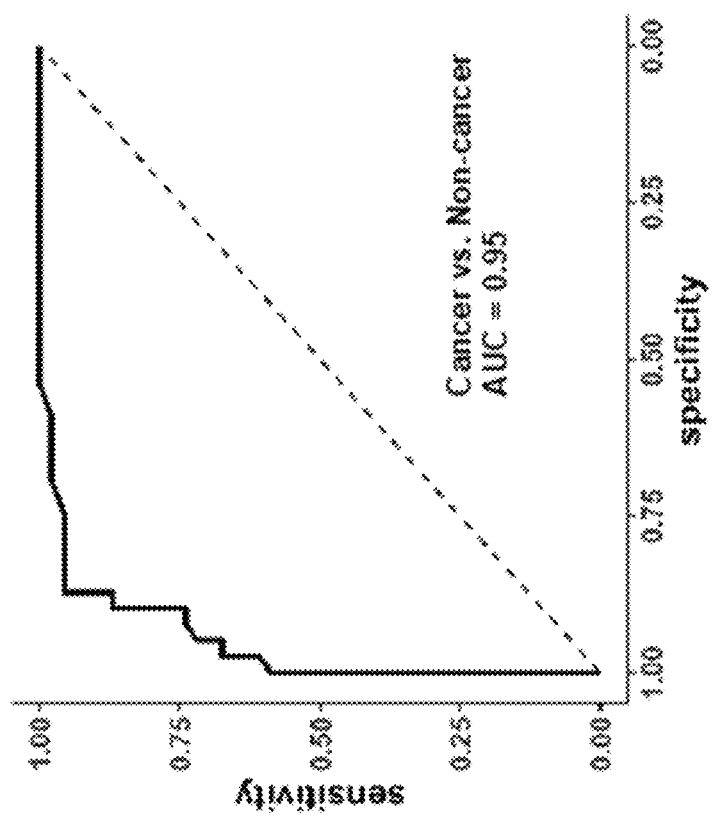
FIGS. 118A-118B show bladder cancer diagnosis with the number of bins with significantly low normalized CGN/NCG motif ratio (i.e., motif aberration).
Figure 118A:
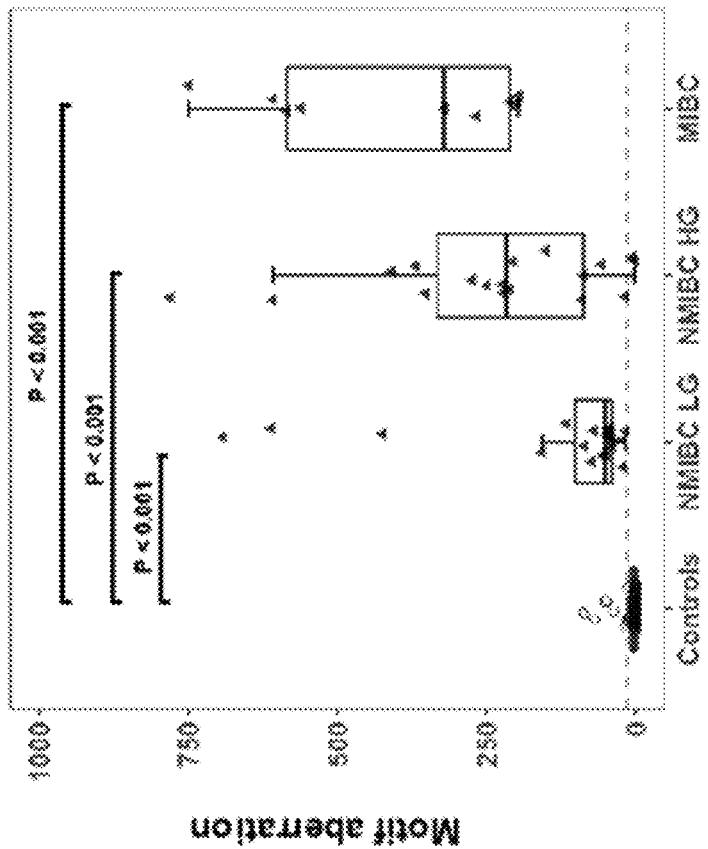

FIGS. 118A-118B show bladder cancer diagnosis with the number of bins with significantly low normalized CGN/NCG motif ratio (i.e., motif aberration). FIG. 118A is a boxplot shows the amount of significantly low normalized CGN/NCG motif ratio bins (i.e., hypomethylated) in healthy controls (controls), patients with low-grade non-muscle-invasive bladder cancer (NMIBC LG), high-grade non-muscle-invasive bladder cancer (NMIBC HG), and muscle-invasive bladder cancer (MIBC). The bladder cancer cases have more aberrant bins. The dashed line represents the cutoff determined in the exploratory set. FIG. 118B is an ROC analysis in differentiating between patients with and without bladder cancer using motif aberration.

As shown in FIG. 118A, patients with bladder cancer showed a larger proportion of 1-Mb bins with motif aberrations (P value <0.001, Kruskal-Wallis test). The use of motif aberrations could reach an AUC of 0.95 to distinguish cancer patients from non-cancer controls (FIG. 118B). A sensitivity of 95.7% and a specificity of 87.2% was achieved.

Motif aberration could be used for the detection of residual disease. For illustration purposes, we determined the amount of motif aberration in paired preoperative and postoperative urinary cfDNA samples of 4 bladder cancer patients (median number of paired-end sequencing reads: 68.1 million; IQR: 62.2-76.5 million).

Figure 119:
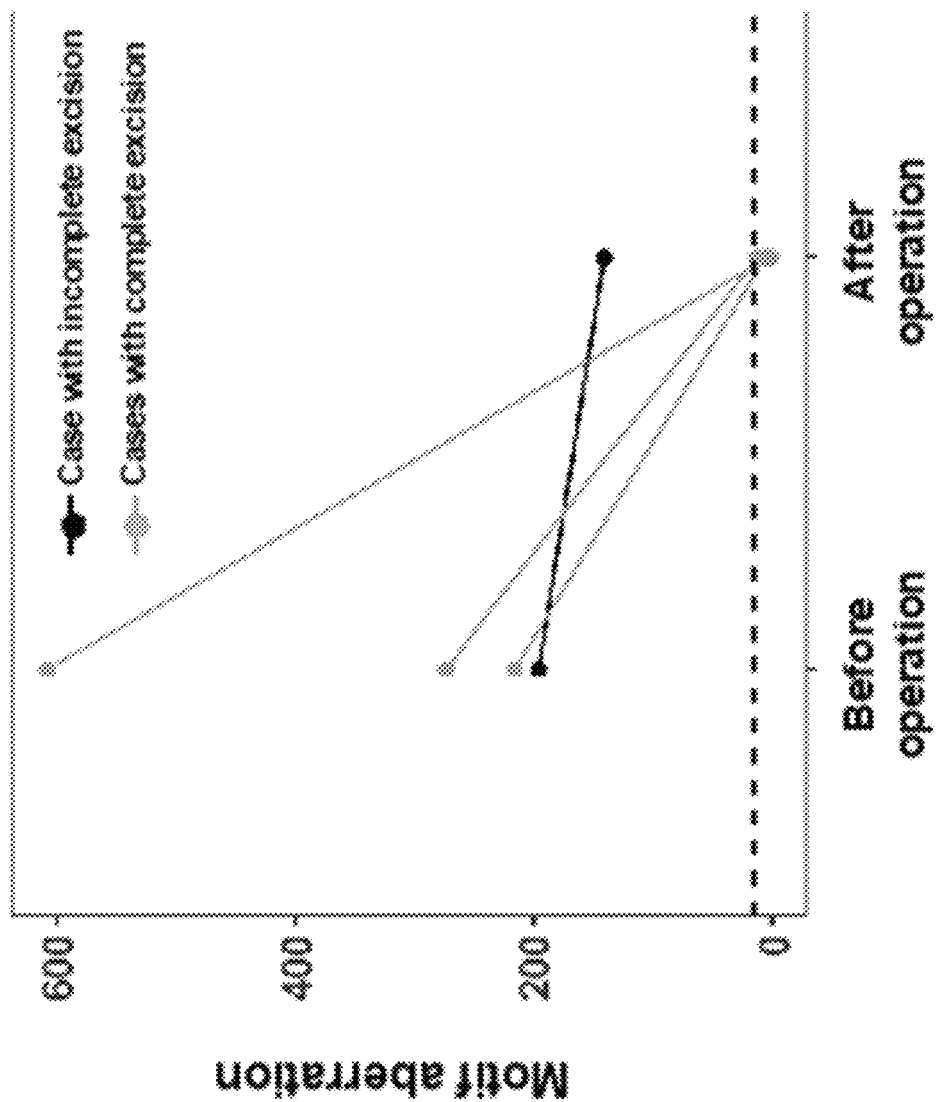
FIG. 119 shows residual disease diagnosis with the use of the amount of bins showing significantly low normalized CGN/NCG motif ratio (motif aberration) in the urinary cfDNA from bladder cancer patients.

FIG. 119 shows residual disease diagnosis with the use of the amount of bins showing significantly low normalized CGN/NCG motif ratio (i.e., motif aberration) in the urinary cfDNA from bladder cancer patients. As shown, before surgical operation all 4 cases showed a large number of bins with significantly low normalized CGN/NCG motif ratio. After surgical operation, motif aberration was drastically reduced to be below the diagnostic cut-off value in 3 cases with complete excision. The complete excision of such 3 cases had been confirmed based on histopathological analysis. The case showing a persistently high amount of aberrant bins had been confirmed to be a margin-positive residual disease. These results suggested that the use of CGN/NCG motifs could not only provide a tool for cancer detection but also allow for the monitoring of cancer treatment, with prognostic values.

Methylation-related urinary cfDNA fragmentomic features from other tissue-specific hypermethylated or hypomethylated CpGs could be used for the detection of other cancers. For example, methylation-related urinary cfDNA fragmentomic features from kidney cancer- and prostate cancer-specific hypermethylated or hypomethylated CpGs could be used for kidney cancer and prostate cancer detection, respectively. Since transrenal DNA can be detected (e.g., as shown above for determining the fractional concentration), other cancers whose cfDNA is in blood and then into urine can be detected. The methylation-aware fragmentation in urinary cfDNA can be used for classifying the subtypes of cancer such as adenocarcinoma versus squamous cell carcinoma. Such methylation related cfDNA fragmentomic features from specific regions could be deduced from targeted sequencing results. The targeted sequencing could be based on but not limited to probe-based hybridization, amplicon-based sequencing, immunoprecipitation followed by sequencing, etc.

Such techniques can be used to determine a classification of a level of pathology in a subject, e.g., in combination with respect to method 7200 of FIG. 72. A plurality of cell-free DNA molecules can from a first region of a plurality of regions of a reference genome, and other pluralities can be from others of the plurality of regions (bins). That is each bin can be analyzed as described above. The comparison of the first amount (CGN or NCG) to a reference value (also referred to as a cutoff above) can indicate whether the first amount for the first region is aberrant. This aberrant determination can be made for each of the plurality of regions. The number of aberrant regions can be compared to a threshold to determine the classification of the level of pathology. In some implementations, for each of the plurality of regions, a respective amount of end sequence motifs that have C at the first position and that have G at the second position can be compared to a region-specific reference value, e.g., as described above.

D. Differentiating Among Different Cancers Using Feature Vector of Different DMRs In some embodiments of this disclosure, we have demonstrated that the analysis of the relative amounts of CGN or NCG end motif of plasma DNA at certain genomic regions (e.g., having a tissue-informative methylation pattern) enabled the determination of the tissue of origin of plasma DNA molecules, e.g., as described in section VIII.B.4. As examples, a tissue-informative methylation pattern can include hypermethylation, hypomethylation, 5hmC-enriched, or 5hmC-depleted regions. Hypermethylated regions can include partially hypermethylated regions, e.g., where the region is differentially-methylated with respect to at least one other tissue type but not necessarily all other tissues types. Hypomethylated regions can also include partially hypomethylated regions. We explored the possibility of using one or more CG-containing 3-mer end motifs (e.g., a total of 8 types of end motif) for the classification of multiple cancer types using such regions.

The tissue types used to determine a tissue of origin of a cancer or other pathology can include one or more of various cancer tissues and/or non-cancer tissues. Examples below perform classification of multiple cancer types with CG-containing 3-mer end motifs. Some or all of the 3-mers can be used. Other embodiments can use other k-mers, which may represent different ending locations relative to a CpG site.

1. Clustering Using DMRs of Different Cancer Types

In one embodiment, CG-containing 3-mer end motif analysis can be performed using a set of tissue-informative methylation markers across different tissue types, including cancer tissues and non-cancer tissues. The non-cancer tissues can include normal tissues and non-malignant tissues adjacent to a particular cancer tissue.

Figure 120:
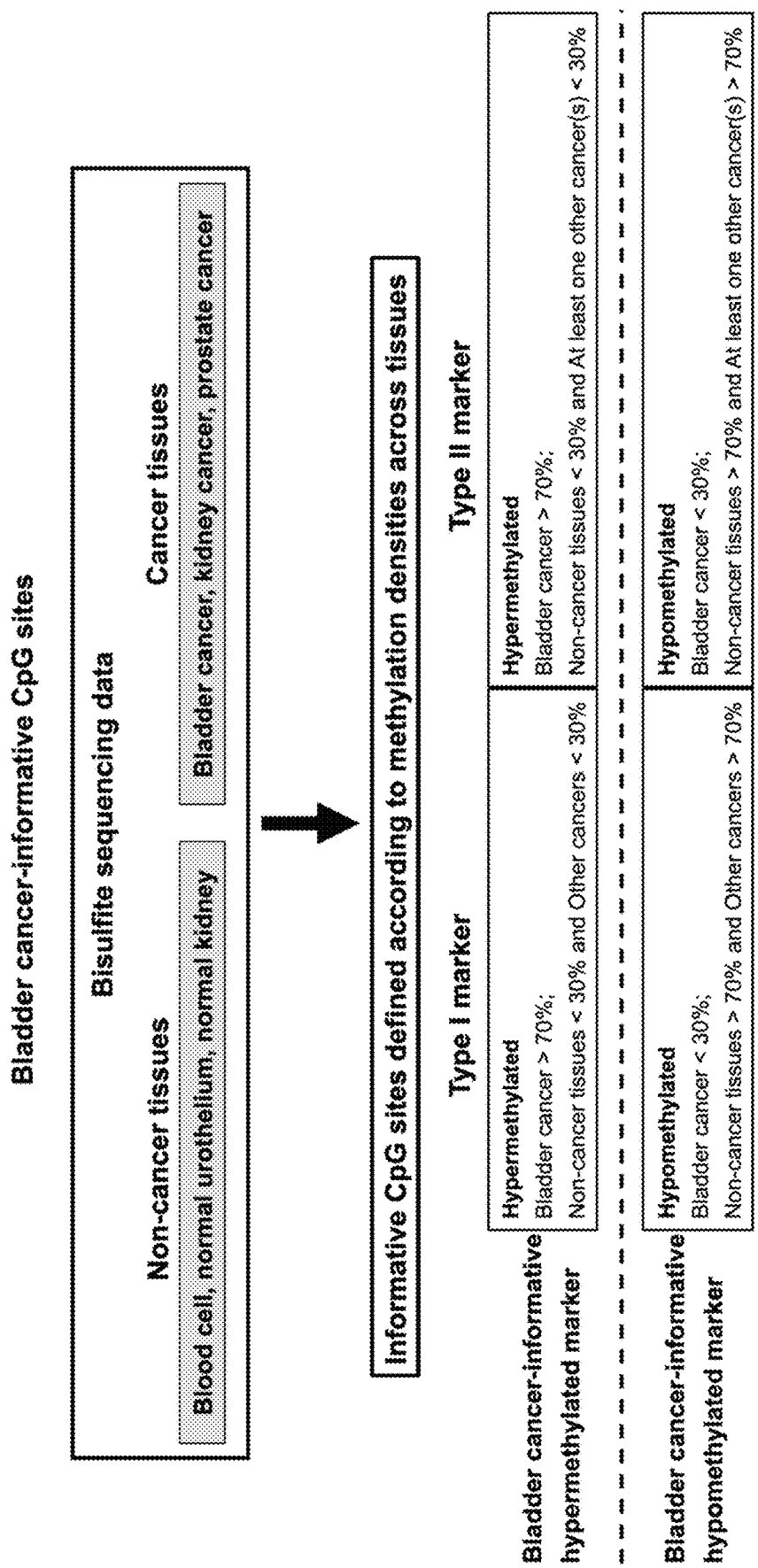
FIG. 120 shows a schematic for defining tissue-informative methylation markers using bladder cancer as an example.

FIG. 120 shows a schematic for defining tissue-informative methylation markers using bladder cancer as an example. Bisulfite sequencing data is used from non-cancer and cancer tissues. The non-cancer tissue include blood cells, normal urothelium, and normal kidney. The cancer tissues include three types of cancer tissues: bladder cancer, kidney cancer, and prostate cancer. Two types of regions have a tissue-informative methylation pattern. One is a Type I marker that is more specific, and the other is a Type II marker that is less specific. Both types have hypermethylated and hypomethylated markers. Either or both types can be used, and various types of tissue-informative methylation patterns can be used.

One can define two types of tissue-informative methylation markers, namely, type I and type II methylation markers, depending on the methylation patterns across different tissues. For illustration purposes, we use the detection of a bladder cancer as an example.

Type I hypermethylated markers were defined as CpGs for each of which the methylation density of a target cancer (e.g., the bladder cancer) is required to be above 70% whereas the methylation density for each of non-cancer tissues and two other cancer tissues is required to be below 30%. In this example, the non-cancer tissues include the normal urothelium, blood cells, and the normal kidney tissues adjacent to the kidney cancer. The two cancer tissues include kidney cancer and prostate cancer tissues.

Type I hypomethylated CpGs were defined as those CpG sites for each of which the methylation density of the target cancer tissue (e.g., the bladder cancer) is required to be below 30% whereas the methylation density for each of non-cancer tissues and two other cancer tissues (i.e., kidney cancer and prostate cancer tissues) is required to be above 70%.

Type II hypermethylated markers were defined as CpGs for each of which the methylation density is required to be over 70% in the target cancer tissue (e.g., the bladder cancer) while each corresponding CpG methylation density is required to be below 30% across the non-cancer tissues and at least one of other types of cancer (i.e., kidney cancer or prostate cancer).

Type II hypomethylated CpGs were defined as those CpGs each showing a methylation density of below 30% in the target cancer tissue but over 70% in the non-cancer tissues and at least one of the other types of cancer. Type I and Type II hypermethylated markers were combined and referred to as tissue-informative hypermethylation markers (e.g., bladder cancer-informative hypermethylation markers). Type I and Type II hypomethylated markers were combined and referred to as tissue-informative hypomethylation markers (e.g., bladder cancer-informative hypomethylation markers). Similarly, one could define the kidney cancer-informative and prostate cancer-informative hypermethylated markers, as well as hypomethylation markers.

Figure 121:
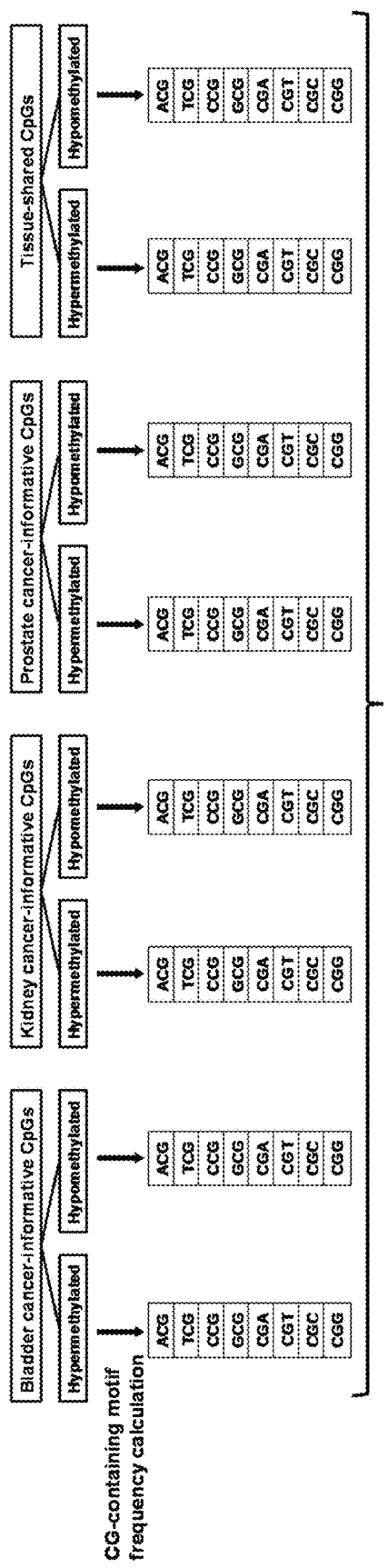
FIG. 121 shows a schematic for multiple cancer clustering with CG-containing end motifs.

FIG. 121 shows a schematic for multiple cancer clustering with CG-containing end motifs. A total of 64 motif features, including CG-containing end motif (i.e., ACG, TCG, CCG, GCG, CGA, CGT, CGC, CGG) frequency from bladder cancer-, kidney cancer-, prostate cancer-informative, and tissue-shared hypermethylated and hypomethylated CpG sites were calculated for each patient. Only CG-containing end motifs were calculated. In this example, the sum of frequency of ACG, TCG, CCG, GCG, CGA, CGT, CGC, and CGG is 100%, but other types of normalization to determine the frequency can be used. These 64 motif features can be used for unsupervised clustering of different subjects, e.g., the different patient IDs shown.

When the sample is plasma or serum, such tissue-shared sites can be of various tissues present in the sample, such as different blood cells, as well as other organs of the body (e.g., liver, colon, breast, lung, and pancreas).

As shown in FIG. 121, there are a total of 64 features for use in a feature vector, including CG-containing end motif features from bladder cancer-, kidney cancer- and prostate cancer-informative hypermethylated and hypomethylated CpG sites, respectively [3 cancer types×(8 hypermethylated end motifs+8 hypomethylated end motifs)=48]; as well as CG-containing end motif features from tissue-shared hypermethylated and hypomethylated CpG sites (8+8=16).

Thus, for each patient, there will be a vector of 64 features for determining which cancer type is present. For example, patient one has 64 features and is indicated as having bladder cancer. Patient two also has 64 features and is labeled as bladder cancer. The patients were clustered to see if these markers can separate the different cancer types without any training.

As an example, we performed clustering and classification analyses for a total of 72 urinary cfDNA samples, including 46 bladder cancer, 16 kidney cancer, and 10 prostate cancer samples. In one embodiment, frequencies of CG-containing 3-mer end motifs from tissue-informative hypermethylated and hypomethylated CpGs together with a set of commonly hypermethylated or hypomethylated CpGs across all tissues were considered as input features for clustering and classification analyses. The commonly hypermethylated and hypomethylated CpGs across all tissues were defined as a methylation density of over 70% or below 30% in normal urothelium, blood cell, normal kidney, bladder cancer, kidney cancer and prostate cancer tissues, also referred to as the tissue-shared hypermethylated and hypomethylated CpG sites. Various unsupervised clustering algorithms can be used, which may include but not limited to principal component analysis (PCA), t-distributed stochastic neighbor embedding (tSNE), uniform manifold approximation and projection (UMAP), etc.

Figure 122:
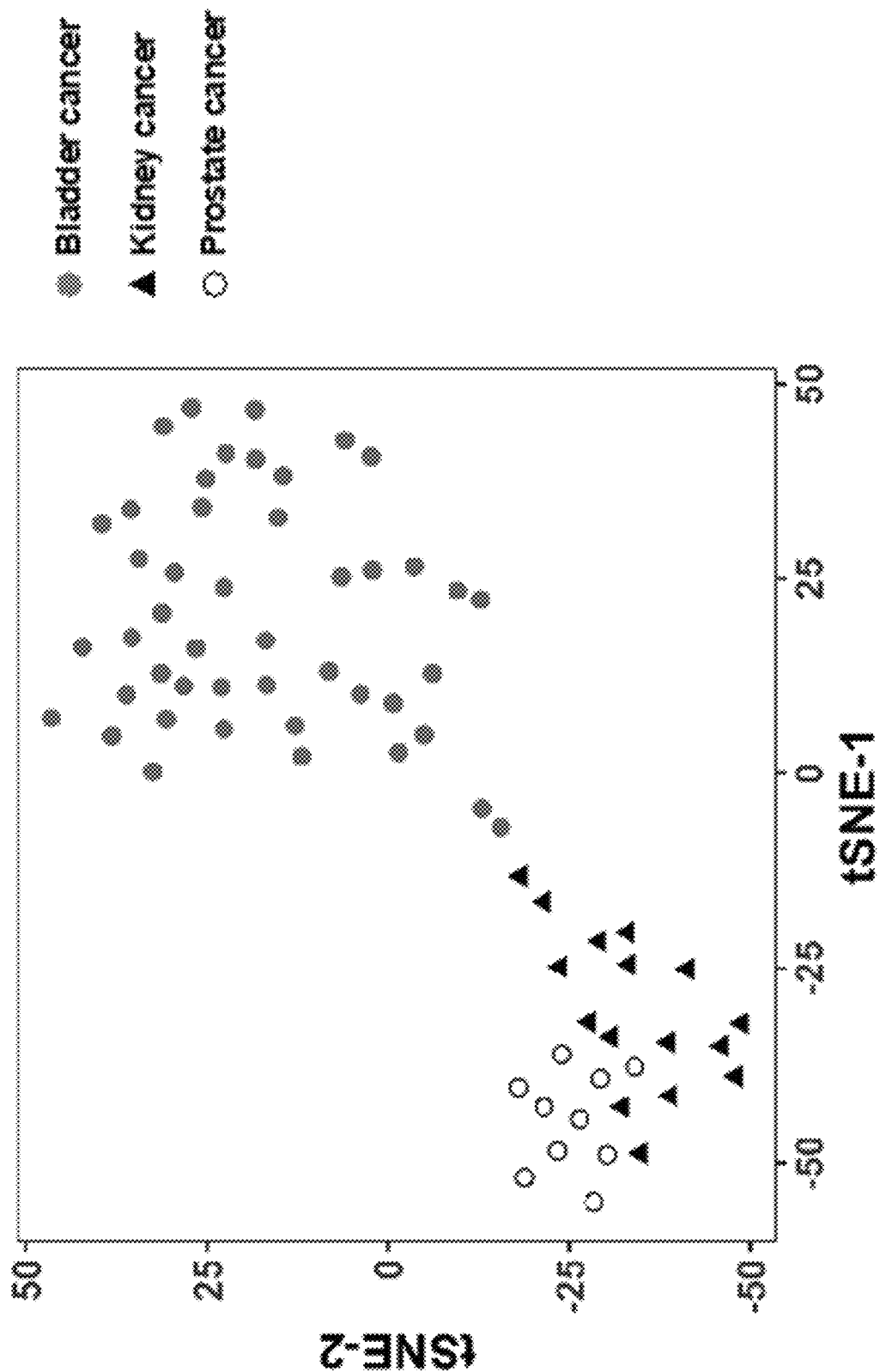
FIG. 122 shows unsupervised clustering analysis for patients with bladder, kidney and prostate cancers on the basis of 5' 3-mer CG containing end motifs related to tissue-informative and tissue-shared CpG sites.

FIG. 122 shows unsupervised clustering analysis for patients with bladder, kidney and prostate cancers on the basis of 5' 3-mer CG containing end motifs related to tissue-informative and tissue-shared CpG sites. A total of 64 5' 3-mer CG containing end motifs from bladder, kidney, and prostate cancer-informative hypermethylated and hypomethylated CpGs and tissue-shared hypermethylated and hypomethylated CpGs were used as input features.

As shown, using 64 end motif features deduced from tissue-informative and tissue-shared CpG sites, tSNE analysis showed that patients with bladder cancer tended to cluster together, while patients with kidney cancers and patients with prostate cancer were clustered into another two groups. These results suggest that it is feasible to use CG-containing end motifs of cfDNA from cancer tissue-informative CpGs of different cancers to determine the cancer types (i.e. cancer locations).

2. Classification of Cancer Type Using Multiple Binary Classifications

We further attempted to develop probabilistic classifiers that can differentiate cancer types, using 64 input features mentioned above. In one embodiment, a support vector machine (SVM) was used to train probabilistic classifiers, but other machine learning models can be used, e.g., as described herein. The training was performed among different types of cancer related to urine. Other types of cancer can be used when plasma is the sample. Also, such models can differentiate when cancer is present or not. In the present example, cancer detection is performed as an initial assay, e.g., using any of the techniques described herein or via other techniques.

Figure 123:
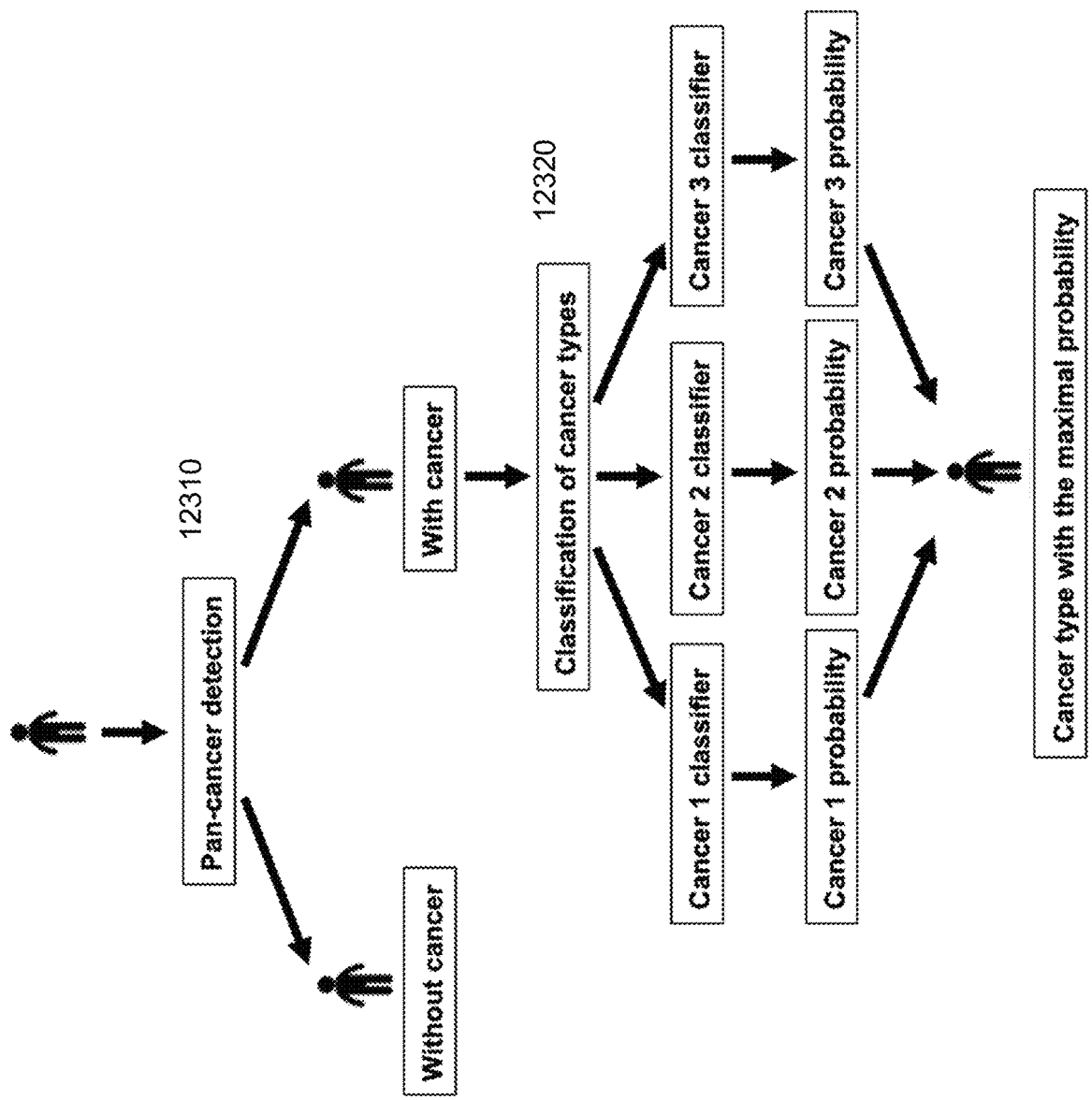

FIG. 123 shows a schematic for classification of multiple cancer types with multiple binary classifications. As shown, one can classify a subject based on the cancer status, i.e., whether a subject has cancer or not. If the test subject is classified as having cancer, the subject will be further subjected to the classification of cancer types. As SVM is usually used for binary classification, multiple binary classifications can be used to determine the cancer type for a patient detected to have cancer when more than two cancer types are being considered. For illustration purposes, three cancer types, including bladder, kidney and prostate cancers, are considered as possible cancers in this example.

In step 12310, the classifier would consider if a person has a bladder cancer (Group A cancer) or non-bladder cancers (including both kidney cancer and prostate cancer; denoted as Group B cancers). In step 12320, samples of subjects identified as having cancer are analyzed using each of three classifier that perform a binary classification for a particular cancer. Each classifier provides a probability the subject as the particular cancer for which that classifier was trained. For example, cancer 1 classifier can provide a probability the subject has bladder cancer, and cancer 2 classifier can provide a probability the subject has kidney cancer.

Each of the 64 motif features mentioned above, including CG-containing end motif (i.e., ACG, TCG, CCG, GCG, CGA, CGT, CGC, CGG) frequency from bladder cancer-, kidney cancer-, prostate cancer-informative, and tissue-shared hypermethylated and hypomethylated CpG sites were calculated for each patient. Three SVM classification models (i.e., bladder cancer classifier, kidney cancer classifier, and prostate cancer classifier) were trained and tested with a leave-one-out strategy based on these 64 motif features.

A first SVM classifier (referred to as bladder cancer classifier) was constructed by analyzing the end motif features from bladder cancer-, kidney-cancer, prostate-cancer informative and tissue-shared CpG sites (i.e., 64 features) between Group A and Group B.

A second SVM classifier (referred to as kidney cancer classifier) was then constructed by analyzing the same set of end motif features which were used in the first SVM classifier but with the use of different patient groups, namely patients with kidney cancers (Group A) versus patients with bladder or prostate cancers (Group B). Thus, the classification analysis would be repeated by changing another type of cancer (for example kidney cancer) to be the Group A cancer, and the non-kidney cancers (i.e., bladder cancer and prostate cancer) to be the Group B cancer.

A third SVM classifier (referred to as prostate cancer classifier) was constructed by analyzing the same end motif features as used in the previous two SVM classifiers, but comparing different patient groups, namely, patients with prostate cancer (group A) versus patients with other cancers (group B).

Figure 124B:
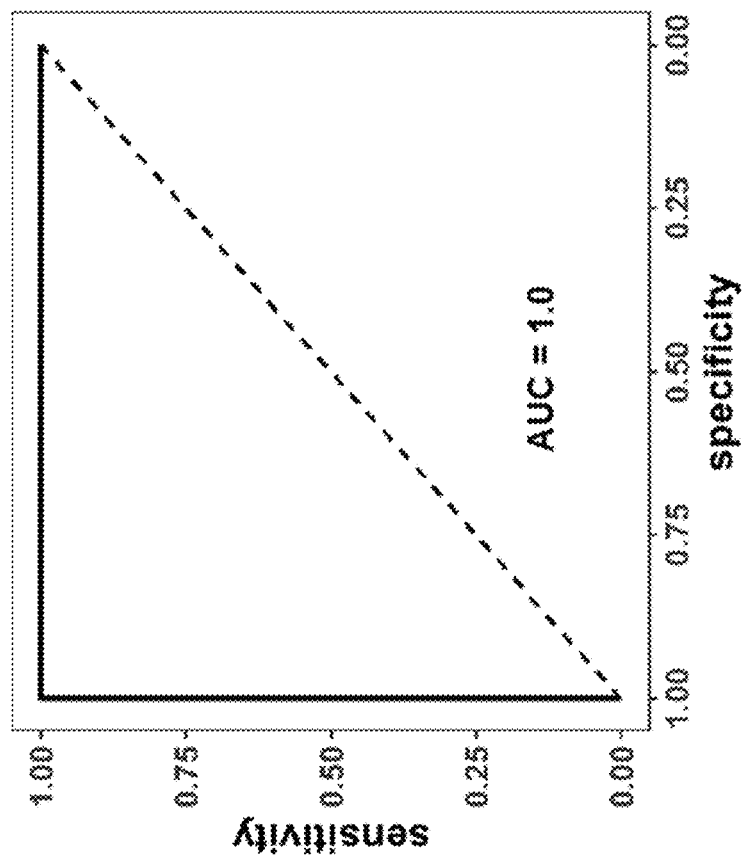
Figure 124A:
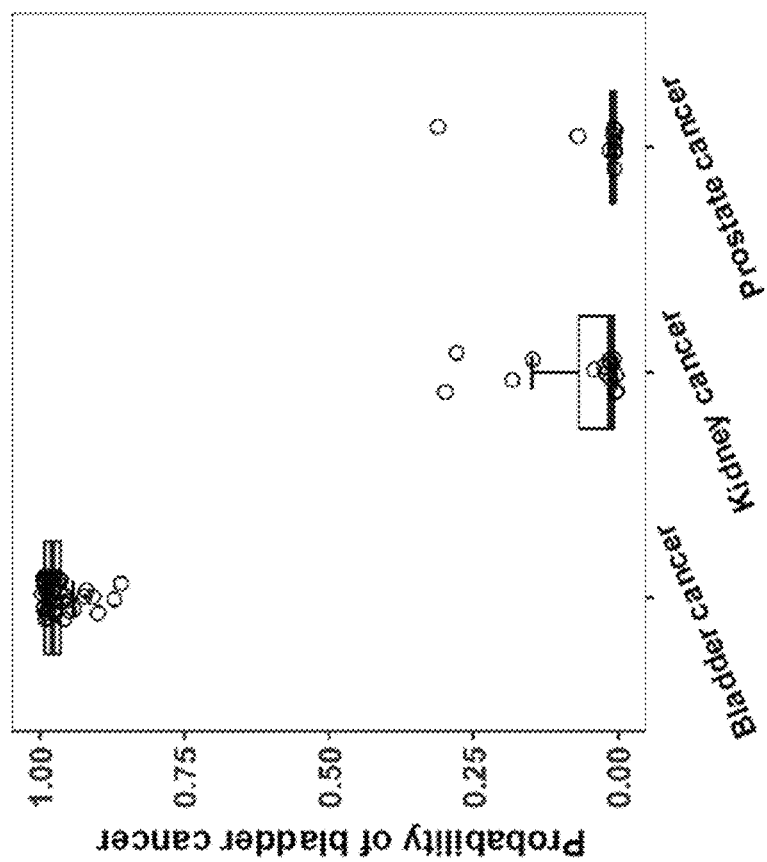

FIGS. 124A-124B show performance of bladder cancer classifier on the basis of 5' 3-mer CG containing end motifs related to tissue-informative and tissue-shared CpG sites. FIG. 124A is a boxplot shows the probability of having bladder cancer predicted by the bladder cancer classifier. FIG. 124B shows an ROC analysis differentiating between patients with bladder cancer and with other cancer types using bladder cancer classifier.

As shown, using the bladder cancer classifier, patients with bladder cancer had higher probability scores compared with patients with kidney and prostate cancers (median: 0.979 vs. 0.012; range: 0.860-0.997 vs. 0.005-0.036). ROC analysis showed that the AUC for the bladder cancer classifier was determined to be 1.00 for distinguishing bladder cancer patients from other cancers.

Figure 125A:
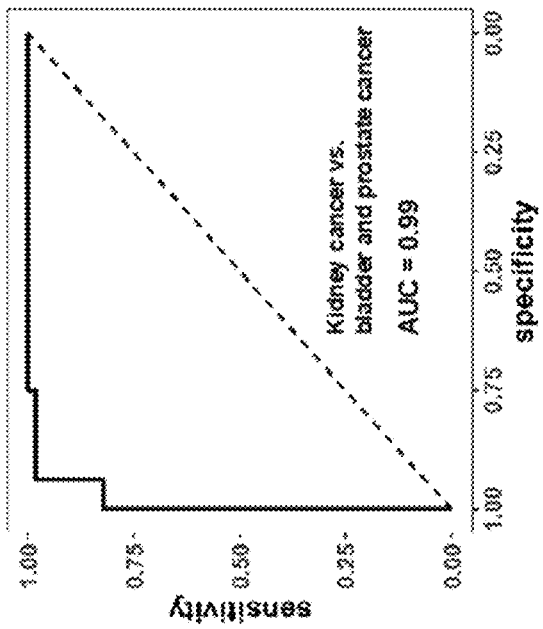
Figure 125B:
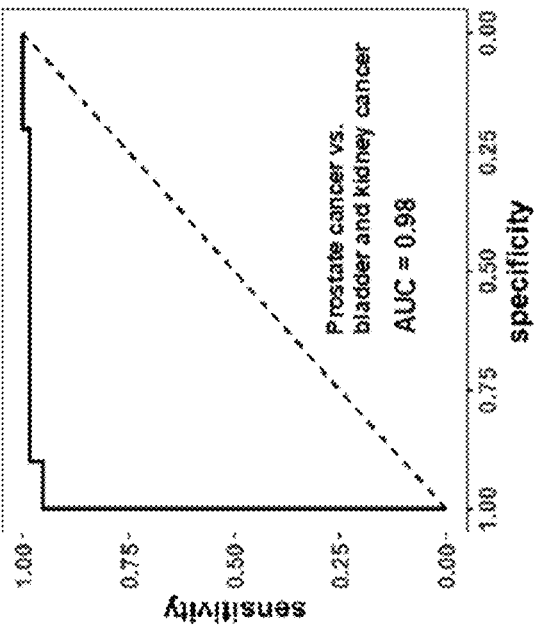
Figure 125C:
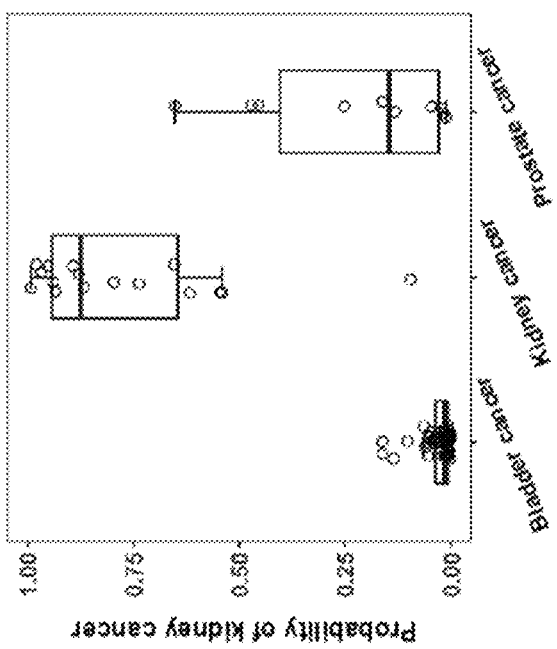
Figure 125D:
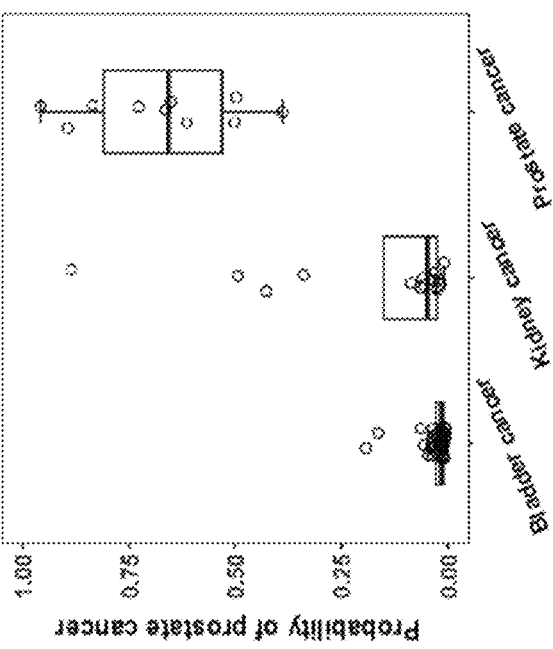

FIGS. 125A-125D shows performance of kidney cancer and prostate cancer classifiers on the basis of 5' 3-mer CG containing end motifs related to tissue-informative CpG sites together with tissue-shared CpG sites. FIG. 125A is a boxplot showing the probability of having kidney cancer predicted by kidney cancer classifier. FIG. 125B shows an ROC analysis differentiating between patients with kidney cancer and with other cancer types using kidney cancer classifier. FIG. 125C is a boxplot showing the probability of having prostate cancer predicted by prostate cancer classifier. FIG. 125D shows ROC analysis in differentiating between patients with prostate cancer and with other cancer types using prostate cancer classifier. As shown, the kidney cancer classifier and prostate cancer classifier achieved an AUC of 0.99 and 0.98 to identify kidney type and prostate cancer type, respectively.

After determining the probability score using the different cancer-type-specific classification models, the cancer type that gives the highest probability score can be regarded as the most probable cancer type that the tested subject is suffering. As an illustrative example, a sample is classified using the 3 classifiers, i.e., bladder cancer classifier, kidney cancer classifier, prostate cancer classifier. The probability scores for the sample using these 3 classifiers are 0.91, 0.12 and 0.08, respectively. As the sample has the highest probability score in the bladder cancer classifier, bladder cancer is considered to be the most probable cancer type which the patient is suffering from based on the results of this analysis. As shown in Table 3, the multiple binary classifications based analysis showed an overall accuracy of 97.2% (70/72), with an accuracy of 100% (46/46), 93.8% (15/16), and 90% (9/10) for bladder, kidney, and prostate cancers, respectively.

TABLE 3

Performance of bladder, kidney and prostate cancer classification on the basis of 5' 3-mer CG containing end motifs related to tissue-informative and tissue-shared CpG sites according to the maximal probabilistic score of multiple binary classifiers.

| Cancer type | Predicted as bladder cancer | Predicted as kidney cancer | Predicted as prostate cancer |
|---|---|---|---|
| Bladder cancer (N = 46) | 46 (100%) | 0 | 0 |
| Kidney cancer (N = 16) | 0 | 15 (93.8%) | 1 |
| Prostate cancer (N = 10) | 0 | 1 | 9 (90%) |

3. Classification of Cancer Type Using Multiple Binary Classifications

Some embodiments can use a multiclass classification model (e.g., convolutional neural networks (CNN)) to analyze multiple cancer types without repeatedly performing multiple binary classifications using CG-containing end motifs related to tissue-informative and tissue-shared CpG sites. In a multiclass classification model, there is one model that provides multiple probabilities, e.g., three probabilities for each three difference cancers in the example above. As an example, the same input features can be the 64 CG-containing end motifs in the example above.

FIGS. 126A-126B shows a schematic illustration for multiple cancer classification using a CNN model on the basis of CG-containing motifs. Frequencies of CG-containing 3-mer end motifs from tissue-informative hypermethylated and hypomethylated CpGs together with a set of tissue-shared hypermethylated or hypomethylated CpGs were analyzed. There are a total of 64 features, including CG-containing end motif features from bladder cancer-, kidney cancer- and prostate cancer-informative hypermethylated and hypomethylated CpG sites, respectively [3 cancer types×(8 hypermethylated end motifs+8 hypomethylated end motifs)=48]; as well as CG-containing end motif features from tissue-shared hypermethylated and hypomethylated CpG sites (8+8=16).

These 64 features were used to construct the input matrix 12620 where the column represents the type of CG-containing motifs (i.e., ACG, TCG, CCG, GCG, CGA, CGT, CGC, CGG) and the row represents the motif frequency be calculated. For instance, the "ACG" motif frequency from bladder cancer-informative hypermethylated CpGs (13.21) was filled in the corresponding cell between a column of "Bladder cancer-informative hypermethylation" and a row of "ACG". There were three output probabilities from CNN for which the sum was 1. The label with the highest probability can indicate the cancer type from which a test subject may suffer.

We performed a leave-one-out strategy for training a CNN model and testing the performance. There were three output probabilities from CNN for which the sum was 1. The label with the highest probability can indicate the cancer type from which a test subject may suffer. For example, if three output probabilities were 0.1, 0.2, and 0.7 for bladder, kidney and prostate cancers, respectively, prostate cancer is considered the most probable cancer type based on this analysis. If the three output probabilities were 0.8, 0.1, and 0.1 for the three types of cancers respectively, bladder cancer is considered as the most probable cancer type. if three output probabilities were 0.1, 0.6, and 0.3 for the three types of cancers respectively, kidney cancer is considered as the most probable cancer type.

Table 4 showed an overall accuracy of ~91.7% (66/72) with an accuracy of 100% (46/46), 81.3% (13/16), and 70% (7/10) for bladder, kidney, and prostate cancers, respectively. In another embodiment, multiple cancer classification analyses can be done in cfDNA from other body fluids, such as plasma, cerebrospinal fluid, saliva, pleural fluid, etc. In some embodiments, the cancer types could be more than three, including liver cancer, colorectum cancer, lung cancer, etc. In other embodiments, other multiclass classification models can be used, including decision trees, random forests, deep neural networks, recurrent neural networks, etc.

TABLE 4

Performance of bladder, kidney and prostate cancer classification on the basis of 5' 3-mer CG containing end motifs related to tissue-informative and tissue-shared CpG sites according to the maximal probabilistic score of CNN model.

| Cancer type | Predicted as bladder cancer | Predicted as kidney cancer | Predicted as prostate cancer |
|---|---|---|---|
| Bladder cancer (N = 46) | 46 (100%) | 0 | 0 |
| Kidney cancer (N = 16) | 0 | 13 (81.3%) | 3 |
| Prostate cancer (N = 10) | 0 | 3 | 7 (70.0%) |

With more samples for the training set, the models can improve. When more cancer types are used, more input features will be used, which might benefit the multiclass model more than the individual binary classifiers.

Accordingly, when the classification can uses differentially-methylated regions for a plurality of tissue types, including the first tissue type, other sets of cell-free DNA molecules from the biological sample can be analyzed. Each set of cell-free DNA molecules are located in a respective set of one or more regions of the reference genome, with each of the respective set of one or more regions being hypomethylated or hypermethylated in a respective tissue type of the plurality of tissue types. As shown in FIG. 126A, the feature vector can form a matrix with each row corresponding to one of the respective sets of one or more regions of the reference genome. A column can correspond to the respective amount of each sequence motif of the first set, and the machine learning model can be a convolutional neural network.

XII. Treatments

A. Further Screening Modalities

Based on any classification, e.g., regarding a pathology or fractional concentration of clinically-relevant DNA, the subject can be referred for additional screening modalities, e.g. using chest X ray, ultrasound, computed tomography, magnetic resonance imaging, or positron emission tomography. Such screening may be performed for cancer.

B. Treatment Selection

Embodiments of the present disclosure can accurately predict disease relapse, thereby facilitating early intervention and selection of appropriate treatments to improve disease outcome and overall survival rates of subjects. For example, an intensified chemotherapy can be selected for subjects, in the event their corresponding samples are predictive of disease relapse. In another example, a biological sample of a subject who had completed an initial treatment can be sequenced to identify viral DNA that is predictive of disease relapse. In such example, alternative treatment regimen (e.g., a higher dose) and/or a different treatment can be selected for the subject, as the subject's cancer may have been resistant to the initial treatment.

The embodiments may also include treating the subject in response to determining a classification of relapse of the pathology. For example, if the prediction corresponds to a loco-regional failure, surgery can be selected as a possible treatment. In another example, if the prediction corresponds to a distant metastasis, chemotherapy can be additionally selected as a possible treatment. In some embodiments, the treatment includes surgery, radiation therapy, chemotherapy, immunotherapy, targeted therapy, hormone therapy, stem cell transplant, or precision medicine. Based on the determined classification of relapse, a treatment plan can be developed to decrease the risk of harm to the subject and increase overall survival rate. Embodiments may further include treating the subject according to the treatment plan.

C. Types of Treatments

Embodiments may further include treating the pathology in the patient after determining a classification for the subject. Treatment can be provided according to a determined level of pathology, the fractional concentration of clinically-relevant DNA, or a tissue of origin. For example, an identified mutation can be targeted with a particular drug or chemotherapy. The tissue of origin can be used to guide a surgery or any other form of treatment. And, the level of the pathology can be used to determine how aggressive to be with any type of treatment, which may also be determined based on the level of pathology. A pathology (e.g., cancer) may be treated by chemotherapy, drugs, diet, therapy, and/or surgery. In some embodiments, the more the value of a parameter (e.g., amount or size) exceeds the reference value, the more aggressive the treatment may be.

Treatment may include resection. As an example, for bladder cancer, treatments may include transurethral bladder tumor resection (TURBT). This procedure is used for diagnosis, staging and treatment. During TURBT, a surgeon inserts a cystoscope through the urethra into the bladder. The tumor is then removed using a tool with a small wire loop, a laser, or high-energy electricity. For patients with non-muscle invasive bladder cancer (NMIBC), TURBT may be used for treating or eliminating the cancer. Another treatment may include radical cystectomy and lymph node dissection. Radical cystectomy is the removal of the whole bladder and possibly surrounding tissues and organs. Treatment may also include urinary diversion. Urinary diversion is when a physician creates a new path for urine to pass out of the body when the bladder is removed as part of treatment.

Treatment may include chemotherapy, which is the use of drugs to destroy cancer cells, usually by keeping the cancer cells from growing and dividing. The drugs may involve, for example but are not limited to, mitomycin-C (available as a generic drug), gemcitabine (Gemzar), and thiotepa (Tepadina) for intravesical chemotherapy. The systemic chemotherapy may involve, for example but not limited to, gemcitabine, methotrexate (Rheumatrex, Trexall), vinblastine (Velban), doxorubicin, and cisplatin.

In some embodiments, treatment may include immunotherapy. Immunotherapy may include immune checkpoint inhibitors that block a protein called PD-1. Inhibitors may include but are not limited to atezolizumab (Tecentriq), nivolumab (Opdivo), avelumab (Bavencio), durvalumab (Imfinzi), and pembrolizumab (Keytruda).

Treatment embodiments may also include targeted therapy. Targeted therapy is a treatment that targets the cancer's specific genes and/or proteins that contributes to cancer growth and survival. For example, erdafitinib is a drug given orally that is approved to treat people with locally advanced or metastatic urothelial carcinoma with FGFR3 or FGFR2 genetic mutations that has continued to grow or spread of cancer cells.

Some treatments may include radiation therapy. Radiation therapy can include the use of high-energy photons (e.g., x-rays) or other particles to destroy cancer cells. In addition to each individual treatment, combinations of these treatments described herein may be used. In some embodiments, when the value of the parameter exceeds a threshold value, which itself exceeds a reference value, a combination of the treatments may be used. Information on treatments in the references are incorporated herein by reference.

XIII. Example Systems

Figure 127:
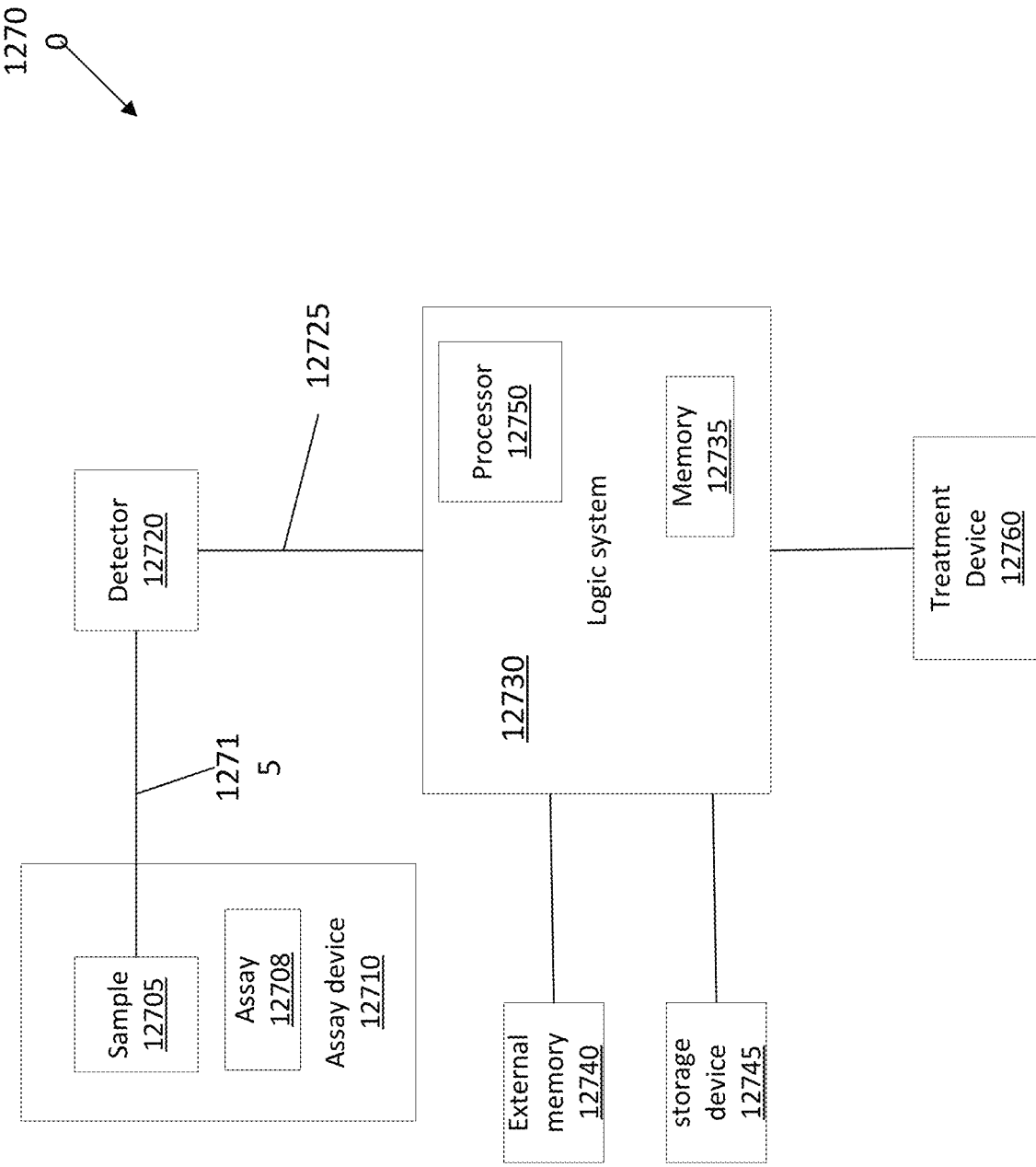

FIG. 127 illustrates a measurement system 12700 according to an embodiment of the present disclosure. The system as shown includes a sample 12705, such as cell-free DNA molecules within an assay device 12710, where an assay 12708 can be performed on sample 12705. For example, sample 12705 can be contacted with reagents of assay 12708 to provide a signal of a physical characteristic 12715 (e.g., sequence information of a cell-free DNA molecule). An example of an assay device can be a flow cell that includes probes and/or primers of an assay or a tube through which a droplet moves (with the droplet including the assay). Physical characteristic 12715 (e.g., a fluorescence intensity, a voltage, or a current), from the sample is detected by detector 12720. Detector 12720 can take a measurement at intervals (e.g., periodic intervals) to obtain data points that make up a data signal. In one embodiment, an analog-to-digital converter converts an analog signal from the detector into digital form at a plurality of times. Assay device 12710 and detector 12720 can form an assay system, e.g., a sequencing system that performs sequencing according to embodiments described herein. A data signal 12725 is sent from detector 12720 to logic system 12730. As an example, data signal 12725 can be used to determine sequences and/or locations in a reference genome of DNA molecules. Data signal 12725 can include various measurements made at a same time, e.g., different colors of fluorescent dyes or different electrical signals for different molecule of sample 12705, and thus data signal 12725 can correspond to multiple signals. Data signal 12725 may be stored in a local memory 12735, an external memory 12740, or a storage device 12745.

Logic system 12730 may be, or may include, a computer system, ASIC, microprocessor, graphics processing unit (GPU), etc. It may also include or be coupled with a display (e.g., monitor, LED display, etc.) and a user input device (e.g., mouse, keyboard, buttons, etc.). Logic system 12730 and the other components may be part of a stand-alone or network connected computer system, or they may be directly attached to or incorporated in a device (e.g., a sequencing device) that includes detector 12720 and/or assay device 12710. Logic system 12730 may also include software that executes in a processor 12750. Logic system 12730 may include a computer readable medium storing instructions for controlling measurement system 12700 to perform any of the methods described herein. For example, logic system 12730 can provide commands to a system that includes assay device 12710 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Measurement system 12700 may also include a treatment device 12760, which can provide a treatment to the subject. Treatment device 12760 can determine a treatment and/or be used to perform a treatment. Examples of such treatment can include surgery, radiation therapy, chemotherapy, immunotherapy, targeted therapy, hormone therapy, and stem cell transplant. Logic system 12730 may be connected to treatment device 12760, e.g., to provide results of a method described herein. The treatment device may receive inputs from other devices, such as an imaging device and user inputs (e.g., to control the treatment, such as controls over a robotic system).

Figure 128:
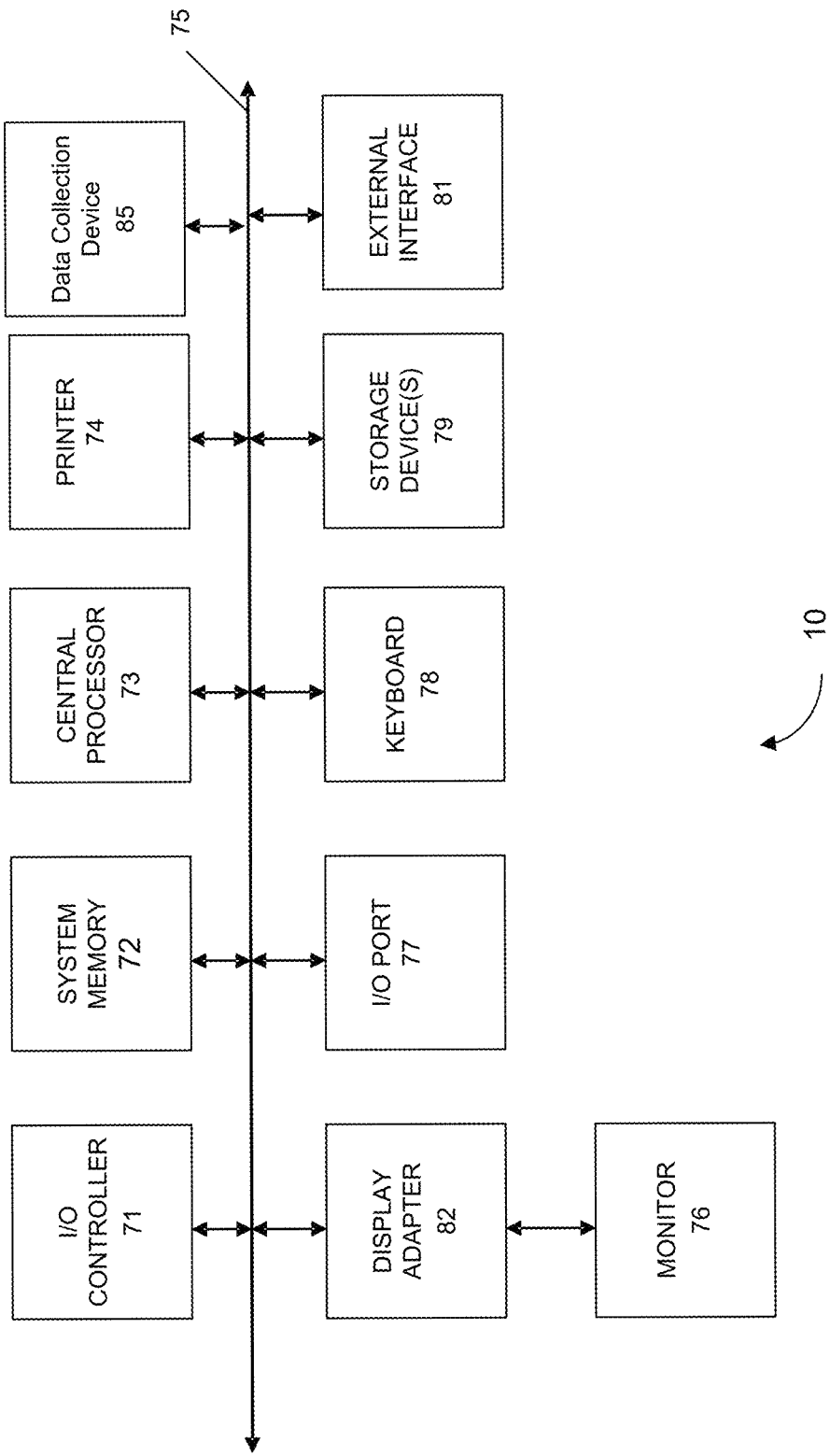

Any of the computer systems mentioned herein may utilize any suitable number of subsystems. Examples of such subsystems are shown in FIG. 128 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 128 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire©). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software stored in a memory with a generally programmable processor in a modular or integrated manner, and thus a processor can include memory storing software instructions that configure hardware circuitry, as well as an FPGA with configuration instructions or an ASIC. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such devices. In addition, the order of operations may be re-arranged. A process can be terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Any operations performed with a processor (e.g., aligning, determining, comparing, computing, calculating) may be performed in real-time. The term "real-time" may refer to computing operations or processes that are completed within a certain time constraint. The time constraint may be 1 minute, 1 hour, 1 day, or 7 days. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The claims may be drafted to exclude any element which may be optional. As such, this statement is intended to serve as antecedent basis for use of such exclusive terminology as "solely", "only", and the like in connection with the recitation of claim elements, or the use of a "negative" limitation.

All patents, patent applications, publications, and descriptions mentioned herein are incorporated by reference in their entirety for all purposes. None is admitted to be prior art. Where a conflict exists between the instant application and a reference provided herein, the instant application shall dominate.

What is claimed is:

1. A method of analyzing a biological sample of a subject to determine a level of a pathology, wherein the pathology is a cancer, in the biological sample of the subject, the biological sample including cell-free DNA, the method comprising performing, by a computer system:
   receiving, over a network connection or from a computer-readable medium, sequence reads obtained from an assay performed on a plurality of cell-free DNA molecules from the biological sample to obtain sequence reads, wherein the sequence reads include ending sequences corresponding to ends of the plurality of cell-free DNA molecules;
   for each of the plurality of cell-free DNA molecules, determining a sequence motif for each of one or more ends of the cell-free DNA molecule, wherein an end of a cell-free DNA molecule has a first position at an outermost position, a second position that is next to the first position, and a third position that is next to the second position, wherein the plurality of cell-free DNA molecules includes at least 10,000 cell-free DNA molecules;
   determining a first set of amounts of a first set of end sequence motifs of the plurality of cell-free DNA molecules, wherein:
      each of the first set of end sequence motifs has C at the first position and G at the second position, or
      each of the first set of end sequence motifs has C at the second position and G at the third position;
   generating a feature vector including the first set of amounts, the feature vector generated using end sequence motifs only selected from a group consisting of (1) end sequence motifs having C at the first position and G at the second position and (2) end sequence motifs having C at the second position and G at the third position; inputting the feature vector into a machine learning model, wherein the machine learning model is trained using cell-free DNA molecules in training samples having known classifications;
   determining, using the machine learning model and the feature vector, a probability for the level of the pathology;
   determining a classification of the level of the cancer for the subject based on a comparison of the probability to a cutoff value, wherein the classification is that the subject has the cancer; and
   administering a treatment to the subject, wherein the treatment includes radiation therapy, immunotherapy, chemotherapy, hormone therapy, stem cell transplant, or surgery to treat the cancer.

2. The method of claim 1, further comprising measuring a size of each of the plurality of cell-free DNA molecules, wherein the set of first amounts is determined for a first group of cell-free DNA molecules that are within a first size range.

3. The method of claim 2, wherein the first size range corresponds to sizes that are less than a size cutoff.

4. The method of claim 2, wherein the first size range corresponds to sizes that are greater than a first size cutoff.

5. The method of claim 4, further comprising:
   determining a second set of amounts of a second set of end sequence motifs of the plurality of cell-free DNA molecules, wherein:
      the second set of end sequence motifs have C at the first position and G at the second position, or
      the second set of end sequence motifs have C at the second position and G at the third position,
   wherein the second set of amounts is determined for a second group of cell-free DNA molecules that are within a second size range corresponding to sizes that are less than a second size cutoff, and wherein the classification is determined using the set of first amounts and the set of second amounts.

6. The method of claim 5, wherein the set of first amounts is determined using the first set of end sequence motifs having C at the first position and G at the second position, and wherein the set of second amounts is determined using the second set of end sequence motifs having C at the first position and G at the second position, the method further comprising:
   determining a third set of amounts of the first group of cell-free DNA molecules having a third set of end sequence motifs with C at the second position and G at the third position, and
   determining a fourth set of amounts of the second group of cell-free DNA molecules having a fourth set of end sequence motifs with C at the second position and G at the third position, wherein the classification is further determined using the third set of amounts and the fourth set of amounts.

7. The method of claim 1, wherein the first set of amounts is determined for a first group of cell-free DNA molecules that are each located within one or more regions that are each 5hmC-enriched or each 5hmC-depleted for a particular tissue type, and wherein the pathology is of the particular tissue type.

8. The method of claim 7, wherein the particular tissue type is HCC cancer tissue.

9. The method of claim 7, wherein the first group of cell-free DNA molecules are each located within the one or more regions that are each 5hmC-enriched, the method further comprising:
determining a second set of amounts of the first set of end sequence motifs of the plurality of cell-free DNA molecules that are each located within one or more regions that are each 5hmC-depleted for the particular tissue type, wherein the classification is determined using the first set of amounts and the second set of amounts.

10. The method of claim 1, wherein the first set of amounts is determined for a first group of cell-free DNA molecules that are each located within one or more regions that are each hypermethylated or hypomethylated for a particular tissue type, and wherein the pathology is of the particular tissue type.

11. The method of claim 1, wherein the plurality of cell-free DNA molecules are from a first region of a plurality of regions of a reference genome, and wherein a comparison of one or more of the first set of amounts to a reference value indicates whether the one or more of the first set of amounts for the first region is aberrant, the method further comprising:
determining a number of the plurality of regions that are aberrant; and
comparing the number of aberrant regions to a threshold to determine the classification of the level of the pathology.

12. The method of claim 11, wherein determining the number of the plurality of regions that are aberrant comprises:
for each of the plurality of regions, comparing a respective amount of the first set of end sequence motifs to a region-specific reference value.

13. The method of claim 1, wherein the plurality of cell-free DNA molecules are from one or more particular regions of a reference genome, and wherein the pathology is in the one or more particular regions.

14. The method of claim 13, wherein at least one of the one or more particular regions corresponds to a particular genotype or haplotype comprising one or more alleles.

15. The method of claim 13, wherein the level of the pathology includes a copy number aberration.

16. The method of claim 1, wherein the first set of end sequence motifs includes CGN, where N includes any nucleotide at the third position.

17. The method of claim 1, wherein the first set of end sequence motifs have C at the first position and G at the second position, the method further comprising:
determining a second set of amounts of a second set of end sequence motifs that have C at the second position and G at the third position.

18. The method of claim 17, wherein the second set of end sequence motifs includes NCG, where N includes any nucleotide at the first position.

19. The method of claim 1, wherein the first set of end sequence motifs have C at the first position and G at the second position, the method further comprising:
determining a respective amount of each 3-mer end sequence motif that has a C at the first position and that has G at the second position, thereby determining the first set of amounts.

20. The method of claim 19, further comprising:
determining a respective additional amount of each 3-mer end sequence motif that has a C at the second position and that has G at the third position, thereby determining respective additional amounts, wherein the feature vector includes the respective additional amounts.

21. The method of claim 1, wherein the first set of end sequence motifs have C at the second position and G at the third position, the method further comprising:
determining a respective amount of each 3-mer end sequence motif that has a C at the second position and that has G at the third position, thereby determining the first set of amounts.

22. The method of claim 1, further comprising:
training the machine learning model using training feature vectors determined from the training samples having the known classifications.

23. The method of claim 1, further comprising:
performing the assay using probes, wherein each of the probes include a common adaptor portion and a targeted sequence portion.

24. The method of claim 23, wherein the targeted sequence portions are selected from CGCCTGT, CGGGAGG, CGGCCTC, CGAGACC, CGCCCAG, CGTGAGC, CGTGGTG, CGGCTCA, CGATCTC, CGGTGGC, ACGCCTGT, TCGGCCTC, TCGAGACC, GCGTGAGC, TCGGCTCA, GCGTGGTG, CCGTCTCT, TCGGGAGG, TCGCTTGA, and CCGCCTCC.

25. The method of claim 10, wherein the feature vector includes an amount for each of the following: CGA, CGT, CGC, CGC, ACG, TCG, CCG, and GCG.

26. The method of claim 1, wherein the method is performed within one hour.

* * * * *

SEQUENCE LISTING

```
Sequence total quantity: 14
SEQ ID NO: 1        moltype = DNA  length = 11
FEATURE             Location/Qualifiers
source              1..11
                    mol_type = other DNA
                    organism = synthetic construct
SEQUENCE: 1
atctgcgagt a                                                        11

SEQ ID NO: 2        moltype = DNA  length = 11
FEATURE             Location/Qualifiers
source              1..11
                    mol_type = other DNA
```

```
                                organism = synthetic construct
SEQUENCE: 2
ttactcgcag a                                                               11

SEQ ID NO: 3                    moltype = DNA   length = 18
FEATURE                         Location/Qualifiers
source                          1..18
                                mol_type = other DNA
                                organism = synthetic construct
SEQUENCE: 3
ccactgcact ccagcctg                                                        18

SEQ ID NO: 4                    moltype = DNA   length = 19
FEATURE                         Location/Qualifiers
source                          1..19
                                mol_type = other DNA
                                organism = synthetic construct
SEQUENCE: 4
ctcttccgat ctcgcctgt                                                       19

SEQ ID NO: 5                    moltype = DNA   length = 20
FEATURE                         Location/Qualifiers
source                          1..20
                                mol_type = other DNA
                                organism = synthetic construct
SEQUENCE: 5
ctcttccgat cttcgcttga                                                      20

SEQ ID NO: 6                    moltype = DNA   length = 11
FEATURE                         Location/Qualifiers
source                          1..11
                                mol_type = other DNA
                                organism = synthetic construct
SEQUENCE: 6
atgaccgagt a                                                               11

SEQ ID NO: 7                    moltype = DNA   length = 11
FEATURE                         Location/Qualifiers
source                          1..11
                                mol_type = other DNA
                                organism = synthetic construct
SEQUENCE: 7
atgacatcgt a                                                               11

SEQ ID NO: 8                    moltype = DNA   length = 11
FEATURE                         Location/Qualifiers
source                          1..11
                                mol_type = other DNA
                                organism = synthetic construct
SEQUENCE: 8
gtactcggtc a                                                               11

SEQ ID NO: 9                    moltype = DNA   length = 11
FEATURE                         Location/Qualifiers
source                          1..11
                                mol_type = other DNA
                                organism = synthetic construct
SEQUENCE: 9
ggacacggat g                                                               11

SEQ ID NO: 10                   moltype = DNA   length = 11
FEATURE                         Location/Qualifiers
source                          1..11
                                mol_type = other DNA
                                organism = synthetic construct
SEQUENCE: 10
ccatccgtgt c                                                               11

SEQ ID NO: 11                   moltype = DNA   length = 11
FEATURE                         Location/Qualifiers
source                          1..11
                                mol_type = other DNA
                                organism = synthetic construct
SEQUENCE: 11
ccatccgtgt c                                                               11

SEQ ID NO: 12                   moltype = DNA   length = 11
FEATURE                         Location/Qualifiers
source                          1..11
```

```
                        mol_type = other DNA
                        organism = synthetic construct
SEQUENCE: 12
ttactcgcag a                                                                11

SEQ ID NO: 13           moltype = DNA   length = 13
FEATURE                 Location/Qualifiers
source                  1..13
                        mol_type = other DNA
                        organism = synthetic construct
SEQUENCE: 13
cgcatcgatg cgt                                                              13

SEQ ID NO: 14           moltype = DNA   length = 218
FEATURE                 Location/Qualifiers
source                  1..218
                        mol_type = other DNA
                        organism = synthetic construct
SEQUENCE: 14
gggaggccga ggtgggtgga tcacctgagg tcaggagttc aagaccagcc tggccaacat           60
ggtgaaaccc cgtctctact aaaaatacaa aaattagccg ggcgtggtgg cgcgcgcctg          120
taatcccagc tactcgggag gctgaggcag gagaatcgct tgaacccggg aggtggaggt          180
tgcagtgagc cgagatcgcg ccactgcact ccagcctg                                  218
```